United States Patent
Ren et al.

(10) Patent No.: US 10,117,411 B2
(45) Date of Patent: *Nov. 6, 2018

(54) MAIZE CYTOPLASMIC MALE STERILITY (CMS) C-TYPE RESTORER RF4 GENE, MOLECULAR MARKERS AND THEIR USE

(75) Inventors: Ruihua Ren, Westfield, IN (US); Bruce A. Nagel, Beaver Dam, WI (US); Siva P. Kumpatla, Carmel, IN (US); Peizhong Zheng, Westfield, IN (US); Gary L. Cutter, Normal, IL (US); Thomas W. Greene, West Des Moines, IA (US); Steven A. Thompson, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 641 days.

This patent is subject to a terminal disclaimer.

(21) Appl. No.: 13/244,049

(22) Filed: Sep. 23, 2011

(65) Prior Publication Data

US 2012/0090047 A1    Apr. 12, 2012

Related U.S. Application Data

(60) Provisional application No. 61/390,526, filed on Oct. 6, 2010.

(51) Int. Cl.
| | | |
|---|---|---|
| *A01H 5/10* | (2018.01) | |
| *A01H 6/46* | (2018.01) | |
| *C07K 14/415* | (2006.01) | |
| *C12N 15/82* | (2006.01) | |
| *C12Q 1/6895* | (2018.01) | |
| *A01H 1/02* | (2006.01) | |
| *C12Q 1/68* | (2018.01) | |

(52) U.S. Cl.
CPC ......... *A01H 6/4684* (2018.05); *C07K 14/415* (2013.01); *C12N 15/8289* (2013.01); *C12Q 1/6895* (2013.01); *A01H 1/02* (2013.01); *A01H 5/10* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2,753,663 | A | 7/1956 | Jones et al. |
| 3,710,511 | A | 1/1973 | Patterson |
| 4,569,152 | A | 2/1986 | Gracen et al. |
| 4,658,085 | A | 4/1987 | Beversdorf et al. |
| 5,254,802 | A | 10/1993 | Hoekstra et al. |
| 5,530,191 | A | 6/1996 | Maliga |
| 5,624,842 | A | 4/1997 | Okuhara et al. |
| 5,644,066 | A | 7/1997 | Sakai et al. |
| 5,684,242 | A | 11/1997 | Schnable et al. |
| 5,981,833 | A | 11/1999 | Wise et al. |
| 6,392,127 | B1 | 5/2002 | Charne et al. |
| 6,951,970 | B2 | 10/2005 | Brown |
| 7,017,375 | B1 | 3/2006 | Chen |
| 7,071,375 | B2 | 7/2006 | Brown et al. |
| 7,164,058 | B2 | 1/2007 | Hanson et al. |
| 7,314,971 | B2 | 1/2008 | Brown et al. |
| 7,411,117 | B2 * | 8/2008 | Bohning .................... 800/320.1 |
| 7,612,251 | B2 | 11/2009 | Albertsen et al. |
| 8,471,117 | B1 * | 6/2013 | Johnson et al. ........... 800/320.1 |
| 2006/0253931 | A1 | 11/2006 | Komori et al. |
| 2008/0229439 | A1 | 9/2008 | La Rosa et al. |
| 2009/0087878 | A9 | 4/2009 | La Rosa et al. |

FOREIGN PATENT DOCUMENTS

| | | |
|---|---|---|
| CN | 1148869 | 4/1997 |
| CN | 1514017 | 7/2004 |
| RU | 2139347 | 10/1999 |
| WO | 199854340 | 12/1998 |

OTHER PUBLICATIONS

Puchta et al. Trends in Plant Science 1(10): 340-348 (Oct. 1996).*
Beckett J. B., Classification of male-sterile cytoplasms in maize (*Zea mays* L.), Crip Science, Sep.-Oct. 1971, pp. 724-727, vol. 11.
Cui, Xiangqin et al., "The r12 nuclear restorer gene of male-sterile t-cytoplasm maize," Science, May 31, 1996, pp. 1334-1336, vol. 272.
Dewey, R.E., et al., "Chimeric mitochondrial genes express in the C male-sterile cytoplasm of maize," Curre Genet, 1991, pp. 475-482, vol. 20.
Has et al., "The use of cytoplasmic male-sterility in maize seed production," http://ww.maizegdb.rog/mnl/77/07has.html, accessed Jun. 17, 2010, 3 pages.
Havey, Michael J., "The use of cytoplasmic male sterility for hybrid seed production," USDA-ARS, Department of Horticulture, 2005, University of Wisconsin, 1575 Linden Drive, Madison, WI, pp. 623-634.
Hu, Y.M., et al. "identification and mapping of RF-I an inhibitor of the Rf5 restorer gene for CMS-C in maize (*Zea mays* L.)," Theor Appl Genet, 2006, pp. 357-360, vol. 113.
Ignjatovic-Micic, Dragana, et al., "Identification of sterile cytoplasm (CMS) in maize by using specific mtDNA primers," Genetika, 2006, pp. 227-233, vol. 38, No. 3.

(Continued)

*Primary Examiner* — David T Fox
(74) *Attorney, Agent, or Firm* — Magleby Cataxinos & Greenwood

(57) ABSTRACT

This disclosure concerns high-resolution mapping and candidate gene cloning of Rf4, a maize restorer of fertility gene that restores fertility to C-type cytoplasmic male sterility. The disclosure also relates to molecular markers that are tightly-linked to, or reside within, the Rf4 gene. In some embodiments, methods are provided whereby hybrid seeds may be produced from crosses of a male plant comprising nucleic acid molecular markers that are linked to or that reside within the Rf4 gene and a female plant carrying C-type CMS.

19 Claims, 30 Drawing Sheets
Specification includes a Sequence Listing.

(56) References Cited

OTHER PUBLICATIONS

Kheyr-Pour et al., "Genetics of fertility restoration in the c-group of cytoplasmic male sterility in maize," Genetics, Jun. 1981, pp. 379-388, vol. 98.
Sisco, Paul H., :Duplications complicate genetic mapping of r14, a restorer gene for cms-c cytoplasmic male sterility in corn, Crop Science, Sep.-Oct. 1991, pp. 1264-1266, vol. 31.
Sotchenko, V.S., et al., "C-type cytoplasmic male sterility in corn," Russian Agricultural Sciences, 2007 pp. 83-86, vol. 33, No. 2.
Vidakovic, M., et al., "Complementary genes Rf4, Rf5 and Rf6 are not the unique genetic system for fertility restoration in cmsC of maize (Zea mays L.)," http://www.agron.missouri.edu/nml/71/19vidakovic.html, accessed Jun. 17, 2010, Belgrade, Yugoslavia, 2 pages.
Kohls S. et al:: "Fine-mapping of r14, a major restorer-of-fertility gene for c-type cytoplasmic male sterility in maize", Program and Abstracts of the 52nd Annual Maize Genetics Conference, Mar. 18, 2010-Mar. 21, 2010, Retrieved from the Internet: URL:http://www.maizegdb.orgjmaize meeting/2010/52nd Maize Genetics Conf.pdf•, p. 137, abstract No. 192.
Kohls, Susanne: "Unraveling genetic factors controlling the restoration of fertility of C-type cytoplasmic male sterility in maize", A dissertation submitted to ETH Zurich URL:http://e-collection.library.ethz.chjes, 2010.
Tang, Ji-hua et al: "Mapping of the main 1-7, restoring gene (Rf4)of C-cytoplasmic male 25-29 sterility in maize with RFLP", CNKI—China National Knowledge Infrastructure J.Henan Agric. Univ., Feb. 2001 (Feb. 2001), Retrieved from the Internet: URL:http://en.cnki.com.cnjArticle en/CJFDT OTAL-NNXB200102000.htm abstract.
International Search Report for PCT/US2011/053304, dated Jun. 26, 2012.
Written Opinion for PCT/US2011/053304, dated Jun. 26, 2012.
Kohls, et al., "QTL involved in the partial restoration of male fertility of C-type cytoplasmic male sterility in maize,"Theoretical and Applied Genetics, Apr. 9, 2011, pp. 327-338, vol. 123 (2).
Frankel, A.E., et al., "Characterization of diphtheria fusion proteins targeted to the human interleukin-3 receptor," published in Protein Eng., 2000, vol. 13, No. 8, pp. 575-581.
Genbank Accession No. B1064392.1, Feb. 21, 2009.
Jing, Ranchun et al., "Mapping fertility-restoring genes of rice WA cytoplasmic male sterility using SSLP markers," pp. 167-171, Bot.Bull.Acad.Sin., vol. 42, (2001).
Kaser-Schneider, Olivier, "physiological and agronomic traits of cytoplasmic male sterility in maize (Zea Myas, L) and its molecular discrimination," Ph.D.thesis, Swiss. Fed.Inst.Tech.Zurich (2002).
Trinidad Sanches Martin Biotechnology, "Plantas Transgenicas" Jun. 2008, 39 pages.
Polymorphic corn DAN Sequence, Seq ID No. 9704, EBI accession No. GSN:AFK75269, database No. AFK75269, Oct. 4, 2007.
Gupta, et al., "Single nucleotide polymorphisms: A new paradigm for molecular marker technology and DNA polymorphism detection with emphasis on their use in plants," Current Science, vol. 80, No. 4, Feb. 25, 2001, Department of Agricultural Botany, Ch. Charan Singh University, Meerut, India, 12 Pages.

\* cited by examiner

Fig. 1

| New DAS name | Seq. No. | Accession | Clone name | Target Seq. Acc. Num | Chromosome | Chr. start | Chr. end | Contig | Contig. start | Contig. end |
|---|---|---|---|---|---|---|---|---|---|---|
| DAS-PZ-33865 | 41 | AC1678693 | c0011P19 | AC1678693 | Chr. 5 | 33338400 | 35329900 | ctg326 | 33340600 | 35329900 |
| DAS-PZ-48438 | 42 | AC1678693 | c0011P19 | AC1678693 | Chr. 5 | 33338400 | 35329900 | ctg326 | 33340600 | 35329900 |
| Mxt17-19804 | 43 | c0011P19 | IMPROVED | AC1678693 | Chr. 5 | 33338400 | 35329900 | ctg326 | 33340600 | 35329900 |
| DAS-PZ-28255 | 44 | AC1937693 | c0165M06 | AC1937693 | Chr. 5 | 34833800 | 36788900 | ctg326 | 34833800 | 36789900 |
| DAS-PZ-32760 | 45 | AC1937693 | c0165M06 | AC1937693 | Chr. 5 | 34833800 | 36788900 | ctg326 | 34833800 | 36789900 |
| MAAGI_1032267-1 | 46 | AC1937693 | IMPROVED | AC1937693 | Chr. 5 | 34833800 | 36788900 | ctg326 | 34833800 | 36789900 |
| MAAGI_1032267-5 | 47 | c0165M06 | IMPROVED | AC1937693 | Chr. 5 | 34833800 | 36788900 | ctg326 | 34833800 | 36789900 |
| DAS-PZ-24642 | 48 | AC1994012 | c0223E18 | AC1994012 | Chr. 5 | 36944800 | 38318800 | ctg326 | 36944800 | 38318800 |
| DAS-PZ-2819 | 49 | AC1994012 | c0223E18 | AC1994012 | Chr. 5 | 36944800 | 38318800 | ctg326 | 36944800 | 38318800 |
| DAS-PZ-33147 | 50 | AC1994012 | c0223E18 | AC1994012 | Chr. 5 | 36944800 | 38318800 | ctg326 | 36944800 | 38318800 |
| DAS-PZ-3369 | 51 | AC1994012 | c0223E18 | AC1994012 | Chr. 5 | 36944800 | 38318800 | ctg326 | 36946800 | 38318800 |
| DAS-PZ-35458 | 52 | AC1994012 | c0223E18 | AC1994012 | Chr. 8, 3 and 3 | 36946600 | 38318800 | ctg326 | 36946600 | 38318800 |
| DAS-PZ-39708 | 53 | AC1994012 | c0223E18 | AC1994012 | Chr. 8, 3 and 3 | 36946600 | 38318800 | ctg326 | 36946600 | 38318800 |
| DAS-PZ-46195 | 54 | AC1994012 | c0223E18 | AC1994012 | Chr. 8, 3 and 3 | 36946600 | 38318800 | ctg326 | 36946600 | 38318800 |
| DAS-PZ-46197 | 55 | AC1994012 | c0223E18 | AC1994012 | Chr. 8 and 3 | 36946600 | 38318800 | ctg326 | 36946600 | 38318800 |
| DAS-PZ-19268 | 56 | AC1984753 | b0688N07 | AC1984753 | Chr. 8 | 37626800 | 38692200 | ctg326 | 37626800 | 39592200 |
| DAS-PZ-40368 | 57 | AC1984753 | b0688N07 | AC1984753 | Chr. 6,3,2,4 | 37626800 | 38692200 | ctg326 | 37626800 | 39592200 |
| DAS-PZ-40389 | 58 | AC1984753 | b0688N07 | AC1984753 | Chr. 8 | 37626800 | 38692200 | ctg326 | 37626800 | 39592200 |
| DAS-PZ-40370 | 59 | AC1984753 | b0688N07 | AC1984753 | Chr. 8 | 37626800 | 38692200 | ctg326 | 37626800 | 39592200 |
| DAS-PZ-8850 | 60 | AC1984753 | b0688N07 | AC1984753 | Chr. 8 | 37626800 | 38692200 | ctg326 | 37626800 | 39592200 |
| DAS-PZ-10551 | 61 | AC2133892 | c0082M02 | AC2133892 | Chr. 8 | 39347700 | 41209900 | ctg326 | 39347700 | 41209900 |
| DAS-PZ-15463 | 62 | AC2133892 | c0082M02 | AC2133892 | Chr. 8 and 3 | 39347700 | 41209900 | ctg326 | 39347700 | 41209900 |
| DAS-PZ-1629 | 63 | AC2133892 | c0082M02 | AC2133892 | Chr. 8 | 39347700 | 41209900 | ctg326 | 39347700 | 41209900 |
| DAS-PZ-17902 | 64 | AC2133892 | c0082M02 | AC2133892 | Chr. 8 | 39347700 | 41209900 | ctg326 | 39347700 | 41209900 |
| DAS-PZ-23502 | 65 | AC2133892 | c0082M02 | AC2133892 | Chr. 8 | 39347700 | 41209900 | ctg326 | 39347700 | 41209900 |
| DAS-PZ-31707 | 66 | AC2133892 | c0082M02 | AC2133892 | Chr. 8 and 3 | 39347700 | 41209900 | ctg326 | 39347700 | 41209900 |
| DAS-PZ-3960 | 67 | AC2133892 | c0082M02 | AC2133892 | Chr. 8 and 3 | 39347700 | 41209900 | ctg326 | 39347700 | 41209900 |
| DAS-PZ-3961 | 68 | AC2133892 | c0082M02 | AC2133892 | Chr. 8 and 3 | 39347700 | 41209900 | ctg326 | 39347700 | 41209900 |
| DAS-PZ-10789 | 69 | AC2038653 | c0157J07 | AC2038653 | Chr. 8 | 3964100 | 41258600 | ctg326 | 39641100 | 41258600 |
| DAS-PZ-107801 | 70 | AC2038653 | c0157J07 | AC2038653 | Chr. 8 | 39641100 | 41258600 | ctg326 | 39641100 | 41258600 |
| DAS-PZ-29637 | 71 | AC2038653 | c0157J07 | AC2038653 | Chr. 9 and 3 | 39641100 | 41258600 | ctg326 | 39641100 | 41258600 |
| DAS-PZ-20828 | 72 | AC2038653 | c0157J07 | AC2038653 | Chr. 8 | 39641100 | 41258600 | ctg326 | 39641100 | 41258600 |
| DAS-PZ-3860 | 73 | AC2038653 | c0157J07 | AC2038653 | Chr. 8 | 39641100 | 41258600 | ctg326 | 39641100 | 41258600 |
| DAS-PZ-12630 | 74 | AC2179852 | b0230Q19 | AC2179852 | Chr. 8,3,2,1,4,5,6,7,8,9,10 | 41111100 | 42042200 | ctg326 | 41111100 | 43042200 |
| DAS-PZ-12863 | 75 | AC2179852 | b0230Q19 | AC2179852 | Chr. 8,3,2,1,4,5,6,7,8,9,10 | 41111100 | 42042200 | ctg326 | 41111100 | 43042200 |
| DAS-PZ-24436 | 76 | AC2179852 | b0230Q19 | AC2179852 | Chr. 8 | 41111100 | 42042200 | ctg326 | 41111100 | 43042200 |
| DAS-PZ-34812 | 77 | AC2179852 | b0230Q19 | AC2179852 | Chr. 8 and 2 | 41111100 | 42042200 | ctg326 | 41111100 | 43042200 |
| DAS-PZ-41230 | 78 | AC2179852 | b0230Q19 | AC2179852 | Chr. 8, 9, 2 | 41111100 | 42042200 | ctg326 | 41111100 | 43042200 |
| DAS-PZ-41231 | 79 | AC2179852 | b0230Q18 | AC2179852 | Chr. 8, 9, 2 | 41111100 | 42042200 | ctg326 | 41111100 | 43042200 |
| DAS-PZ-41232 | 80 | AC2179852 | b0230Q19 | AC2179852 | Chr. 8 | 41111100 | 42042200 | ctg326 | 41111100 | 43042200 |

Fig. 1 Cont.

| New DAS name | Seq. No. | Accession | Clone name | Target Seq. Acc. Num | Chromosome | Chr_start | Chr_end | Contig | Contig_start | Contig_end |
|---|---|---|---|---|---|---|---|---|---|---|
| DAS-PZ-43023 | 81 | AC217985.2 | b0230O19 | AC217985.3 | Chr. 6, 2, 10 | 4111100 | 4204200 | ctg328 | 4111100 | 4204200 |
| DAS-PZ-9492 | 82 | AC217985.2 | b0230O19 | AC217985.2 | Chr. 6 | 4111100 | 4204200 | ctg328 | 4111100 | 4204200 |
| DAS-PZ-28070 | 83 | AC213375.3 | c0201P10 | AC213375.4 | Chr. 6 and 2 | 4184800 | 4370800 | ctg328 | 4184800 | 4370800 |
| DAS-PZ-35275 | 84 | AC213375.3 | c0201P10 | AC213375.4 | Chr. 6 and 3 | 4184800 | 4370800 | ctg328 | 4184800 | 4370800 |
| DAS-PZ-33034 | 85 | AC213375.3 | c0201P10 | AC213375.4 | Chr. 6, 4, 2 | 4184800 | 4370800 | ctg328 | 4184800 | 4370800 |
| DAS-PZ-4516 | 86 | AC213375.3 | c0201P10 | AC213375.3 | Chr. 6 | 4184800 | 4370800 | ctg328 | 4184800 | 4370800 |
| DAS-PZ-4517 | 87 | AC213375.3 | c0201P10 | AC213375.3 | Chr. 6 | 4184800 | 4370800 | ctg328 | 4184800 | 4370800 |
| PZA02174-2 | 88 | c0118C06 | IMPROVED | AC208992.3 | Chr. 8 | 4657000 | 4844400 | ctg328 | 4557000 | 4684400 |
| DAS-PZ-28925 | 89 | AC199118.3 | c0240G02 | AC199118.3 | Chr. 8 | 4743200 | 4870600 | ctg328 | 4743200 | 4870600 |
| DAS-PZ-35508 | 90 | AC199118.3 | c0240G02 | AC199118.3 | Chr. 8 | 4743200 | 4870600 | ctg328 | 4743200 | 4870600 |
| DAS-PZ-35762 | 91 | AC199118.3 | c0240G02 | AC199118.3 | Chr. 8 | 4743200 | 4870600 | ctg328 | 4743200 | 4870600 |
| DAS-PZ-9101 | 92 | AC199118.3 | c0240G02 | AC199118.3 | Chr. 8 | 4743200 | 4870600 | ctg328 | 4743200 | 4870600 |
| DAS-PZ-9102 | 93 | AC199118.3 | c0240G02 | AC199118.3 | Chr. 8 | 4743200 | 4870600 | ctg328 | 4743200 | 4870600 |
| DAS-PZ-9523 | 94 | AC199118.3 | c0240G02 | AC199118.3 | Chr. 8 | 4743200 | 4870600 | ctg328 | 4743200 | 4870600 |
| DAS-PZ-9524 | 95 | AC199118.3 | c0240G02 | AC199118.3 | Chr. 8 | 4743200 | 4870600 | ctg328 | 4743200 | 4870600 |
| KG-2620258 | 96 | | | | ? | | | | | |
| PZA01800-2 | 97 | | | | Chr. 8,3,10,9,2 | | | | | |
| MAGI_9625 | 98 | | | | Chr. 8 | | | | | |
| KG-2528474 | 99 | | | | Chr. 8 | | | | | |
| KG-2528419 | 100 | | | | | | | | | |
| CSNP-13 | 101 | | | | Chr. 9 and 3 | | | | | |

Fig. 1 Cont.

| Locus_Name | Seq. No. | Chromosome | Start Seq | Stop Seq | Map Status |
|---|---|---|---|---|---|
| PZE-108000002 | 102 | Maize_Chr8 | 12507 | 12607 | U |
| PZE-108000026 | 103 | Maize_Chr8 | 65463 | 65563 | U |
| PZE-108000053 | 104 | Maize_Chr8 | 85975 | 86075 | U |
| PZE-108000086 | 105 | Maize_Chr8 | 98418 | 98518 | U |
| PZE-108000099 | 106 | Maize_Chr8 | 168159 | 168259 | U |
| PZE-108000100 | 107 | Maize_Chr8 | 169431 | 169531 | U |
| PZE-108000106 | 108 | Maize_Chr8 | 173646 | 173746 | U |
| PZE-108000113 | 109 | Maize_Chr8 | 174208 | 174308 | U |
| PZE-108000118 | 110 | Maize_Chr8 | 213624 | 213724 | U |
| PZE-108000123 | 111 | Maize_Chr8 | 218420 | 218520 | U |
| PZE-108000127 | 112 | Maize_Chr8 | 228388 | 228488 | U |
| PZE-108000136 | 113 | Maize_Chr8 | 266270 | 266370 | U |
| PZE-108000168 | 114 | Maize_Chr8 | 272561 | 272661 | U |
| PZE-108000210 | 115 | Maize_Chr8 | 274252 | 274352 | U |
| PZE-108000244 | 116 | Maize_Chr8 | 276396 | 276496 | U |
| PZE-108000284 | 117 | Maize_Chr8 | 298949 | 299049 | U |
| PZE-108000285 | 118 | Maize_Chr8 | 307247 | 307347 | U |
| PZE-108000294 | 119 | Maize_Chr8 | 318527 | 318627 | U |
| PZE-108000300 | 120 | Maize_Chr8 | 321922 | 322022 | U |
| PZE-108000337 | 121 | Maize_Chr8 | 358426 | 358526 | U |
| PZE-108000348 | 122 | Maize_Chr8 | 358818 | 358918 | U |
| PZE-108000353 | 123 | Maize_Chr8 | 374494 | 374594 | U |
| PZE-108000355 | 124 | Maize_Chr8 | 376366 | 376466 | U |
| PZE-108000371 | 125 | Maize_Chr8 | 377780 | 377880 | U |
| PZE-108000378 | 126 | Maize_Chr8 | 398865 | 398965 | U |
| PZE-108000388 | 127 | Maize_Chr8 | 400836 | 400936 | U |
| PZE-108000393 | 128 | Maize_Chr8 | 465852 | 465952 | U |
| PZE-108000406 | 129 | Maize_Chr8 | 488886 | 488986 | U |
| PZE-108000414 | 130 | Maize_Chr8 | 490555 | 490655 | U |
| PZE-108000422 | 131 | Maize_Chr8 | 506556 | 506656 | U |
| PZE-108000438 | 132 | Maize_Chr8 | 544911 | 545011 | U |
| PZE-108000456 | 133 | Maize_Chr8 | 547852 | 547952 | U |
| PZE-108000459 | 134 | Maize_Chr8 | 564822 | 564922 | U |
| PZE-108000460 | 135 | Maize_Chr8 | 601360 | 601460 | U |
| PZE-108000476 | 136 | Maize_Chr8 | 630247 | 630347 | U |
| PZE-108000510 | 137 | Maize_Chr8 | 638782 | 638882 | U |
| PZE-108000524 | 138 | Maize_Chr8 | 640185 | 640285 | U |
| PZE-108000555 | 139 | Maize_Chr8 | 641348 | 641448 | U |
| PZE-108000560 | 140 | Maize_Chr8 | 661179 | 661279 | U |
| PZE-108000573 | 141 | Maize_Chr8 | 672526 | 672626 | U |
| PZE-108000586 | 142 | Maize_Chr8 | 679350 | 679450 | U |
| PZE-108000604 | 143 | Maize_Chr8 | 690369 | 690469 | U |
| PZE-108000636 | 144 | Maize_Chr8 | 735216 | 735316 | U |
| PZE-108000856 | 145 | Maize_Chr8 | 759595 | 759695 | U |
| PZE-108000865 | 146 | Maize_Chr8 | 759988 | 760088 | U |
| PZE-108000696 | 147 | Maize_Chr8 | 764270 | 764370 | U |
| PZE-108000698 | 148 | Maize_Chr8 | 799806 | 799906 | U |
| PZE-108000703 | 149 | Maize_Chr8 | 800126 | 800226 | U |
| PZE-108000710 | 150 | Maize_Chr8 | 810431 | 810531 | U |
| PZE-108000714 | 151 | Maize_Chr8 | 811543 | 811643 | U |
| PZE-108000731 | 152 | Maize_Chr8 | 819485 | 819585 | U |
| PZE-108000733 | 153 | Maize_Chr8 | 820267 | 820367 | U |
| PZE-108000747 | 154 | Maize_Chr8 | 820997 | 821097 | U |
| PZE-108000757 | 155 | Maize_Chr8 | 825368 | 825468 | U |
| PZE-108000791 | 156 | Maize_Chr8 | 838718 | 838818 | U |

Fig. 1 Cont.

| Locus_Name | Seq. No. | Chromosome | Start Seq | Stop Seq | Map Status |
|---|---|---|---|---|---|
| PZE-108000805 | 157 | Maize_Chr8 | 839134 | 839234 | U |
| PZE-108000834 | 158 | Maize_Chr8 | 857577 | 857677 | U |
| PZE-108000882 | 159 | Maize_Chr8 | 858925 | 859025 | U |
| PZE-108000891 | 160 | Maize_Chr8 | 861795 | 861895 | U |
| PZE-108000911 | 161 | Maize_Chr8 | 866937 | 867037 | U |
| PZE-108000923 | 162 | Maize_Chr8 | 867548 | 867648 | U |
| PZE-108000933 | 163 | Maize_Chr8 | 894628 | 894728 | U |
| PZE-108000971 | 164 | Maize_Chr8 | 896626 | 896726 | U |
| PZE-108000982 | 165 | Maize_Chr8 | 923932 | 924032 | U |
| PZE-108001034 | 166 | Maize_Chr8 | 926427 | 926527 | U |
| PZE-108001108 | 167 | Maize_Chr8 | 927943 | 928043 | U |
| PZE-108001117 | 168 | Maize_Chr8 | 950690 | 950790 | U |
| PZE-108001142 | 169 | Maize_Chr8 | 953114 | 953214 | U |
| PZE-108001167 | 170 | Maize_Chr8 | 1013872 | 1013972 | U |
| PZE-108001169 | 171 | Maize_Chr8 | 1014113 | 1014213 | U |
| PZE-108001173 | 172 | Maize_Chr8 | 1031905 | 1032005 | U |
| PZE-108001193 | 173 | Maize_Chr8 | 1052064 | 1052164 | U |
| PZE-108001215 | 174 | Maize_Chr8 | 1054184 | 1054284 | U |
| PZE-108001221 | 175 | Maize_Chr8 | 1057032 | 1057132 | U |
| PZE-108001233 | 176 | Maize_Chr8 | 1070992 | 1071092 | U |
| PZE-108001258 | 177 | Maize_Chr8 | 1072032 | 1072132 | U |
| PZE-108001268 | 178 | Maize_Chr8 | 1072909 | 1073009 | U |
| PZE-108001287 | 179 | Maize_Chr8 | 1075651 | 1075751 | U |
| PZE-108001305 | 180 | Maize_Chr8 | 1107939 | 1108039 | U |
| PZE-108001316 | 181 | Maize_Chr8 | 1146167 | 1146267 | U |
| PZE-108001333 | 182 | Maize_Chr8 | 1204529 | 1204629 | U |
| PZE-108001344 | 183 | Maize_Chr8 | 1206254 | 1206354 | U |
| PZE-108001364 | 184 | Maize_Chr8 | 1315005 | 1315105 | U |
| PZE-108001372 | 185 | Maize_Chr8 | 1328960 | 1329060 | U |
| PZE-108001383 | 186 | Maize_Chr8 | 1332613 | 1332713 | U |
| PZE-108001390 | 187 | Maize_Chr8 | 1337714 | 1337814 | U |
| PZE-108001398 | 188 | Maize_Chr8 | 1338309 | 1338409 | U |
| PZE-108001410 | 189 | Maize_Chr8 | 1340504 | 1340604 | U |
| PZE-108001439 | 190 | Maize_Chr8 | 1359173 | 1359273 | U |
| PZE-108001457 | 191 | Maize_Chr8 | 1433868 | 1433968 | U |
| PZE-108001489 | 192 | Maize_Chr8 | 1440947 | 1441047 | U |
| PZE-108001500 | 193 | Maize_Chr8 | 1440980 | 1441080 | U |
| PZE-108001509 | 194 | Maize_Chr8 | 1499701 | 1499801 | U |
| PZE-108001517 | 195 | Maize_Chr8 | 1500924 | 1501024 | U |
| PZE-108001539 | 196 | Maize_Chr8 | 1504306 | 1504406 | U |
| PZE-108001548 | 197 | Maize_Chr8 | 1504526 | 1504626 | U |

| 344-4313 | 344-4117 | 316-3877 | 083-0786 | 286-3040 | 468-4977 | 468-5048 | S-378 | 344-4110 | 316-3929 | 030-0304 | 316-4001 | B73 physical position (bp) | Marker |
|---|---|---|---|---|---|---|---|---|---|---|---|---|---|
| H | H | H | H | H | A | A | A | A | A | A | A | 8885 | DAS-CMS1 |
| H | H | H | H | H | A | A | A | A | A | A | A | 11684 | DAS-CMS3 |
| H | H | H | H | H | A | A | A | A | A | A | A | 15309 | DAS-CMS5 |
| H | H | H | H | H | A | A | A | A | A | A | A | 15639 | DAS-CMS6 |
| H | H | H | A | H | A | A | A | A | A | A | A | 22230 | DAS-CMS7 |
| H | H | H | A | H | A | A | A | A | A | A | A | 22266 | DAS-CMS8 |
| H | H | H | A | A | H | A | A | A | A | A | A | 65438 | DAS-CMS12 |
| H | H | H | A | A | H | A | A | A | A | A | A | 66993 | DAS-CMS13 |
| H | H | H | A | A | H | A | A | A | A | A | A | 85667 | DAS-CMS14 |
| H | H | H | A | A | H | A | A | A | A | A | A | 85782 | DAS-CMS15 |
| H | H | H | A | A | H | A | A | A | A | A | A | 86079 | DAS-CMS16 |
| H | H | H | A | A | H | A | A | A | A | A | A | 86247 | DAS-CMS19 | ⬅
| H | H | H | A | A | H | A | A | A | A | A | A | 96248 | DAS-CMS21 |
| H | H | H | A | A | H | A | A | A | A | A | A | 97087 | DAS-CMS22 |
| H | H | H | A | A | H | A | A | A | A | A | A | 97177 | DAS-CMS23 |
| H | H | H | A | A | H | A | A | A | A | A | A | 97673 | DAS-CMS28 |
| H | H | H | A | A | H | A | A | A | A | A | A | 97827 | DAS-CMS29 |
| H | H | H | A | A | H | A | A | A | A | A | A | 97962 | DAS-CMS30 |
| H | H | H | A | A | H | A | A | A | A | A | A | 98188 | DAS-CMS31 | ⬅
| H | H | H | A | A | H | A | A | A | A | A | A | 98393 | DAS-CMS32 |
| H | H | H | A | A | A | A | A | A | A | A | A | 98468 | PZE-108000086 |
| H | H | H | A | A | A | A | A | A | A | A | A | 98489 | DAS-CMS33 |
| H | H | H | A | A | A | A | H | H | A | A | A | 174258 | PZE-108000113 |
| H | H | H | A | A | A | A | H | H | A | A | A | 218470 | PZE-108000123 |
| H | H | H | A | A | A | A | H | H | A | A | A | 307297 | PZE-108000285 |
| H | H | H | A | A | A | A | H | H | A | A | A | 318577 | PZE-108000294 |
| H | H | H | A | A | A | A | H | H | A | A | A | 321972 | PZE-108000300 |
| H | A | A | A | A | A | A | H | H | H | H | A | 374544 | PZE-108000353 |
| A | A | A | A | A | A | A | H | H | H | H | H | 398915 | PZE-108000378 |
| A | A | A | A | A | A | A | H | H | H | H | H | 564872 | PZE-108000459 |
| F | F | F | S | F | F | S | S | S | S | S | S | | Fertility |

Fig. 5

```
B73  rf4-bHLH    (SEQ ID NO:218)   (1)  GGCAAGCTAATGGGGTACATATGGA
BE4207 rf4-bHLH  (SEQ ID NO:218)   (1)  GGCAAGCTAATGGGGTACATATGGA
B104 bHLH        (SEQ ID NO:219)   (1)  GGCAAGCTAATGGGGTACATATGGA
XJH58 Rf4-bHLH   (SEQ ID NO:220)   (1)  GGCAAGCTAATGGGGTACATATGGA
BE9515 Rf4-bHLH  (SEQ ID NO:220)   (1)  GGCAAGCTAATGGGGTACATATGGA
MLW03 Rf4-bHLH   (SEQ ID NO:220)   (1)  GGCAAGCTAATGGGGTACATATGGA

(26)   AGGAGGAAACCAAGTCGATCGTCGTCGTAGCATGTCGGTGTGGGTACTACACTACAC
(26)   AGGAGGAAACCAAGTCGATCGTCGTCGTAGCATGTCGGTGTGGGTACTACACTACAC
(26)   AGGAGGAAACCAAGTCGATCGTCGTCGTAGCATGTCGGTGTGGGTACTACACTACAC
(26)   AGGAGGAAACCAAGTCGATCGTCGTCGTAGCATGTCGGTGTGGGTACTACACTACAC
(26)   AGGAGGAAACCAAGTCGATCGTCGTCGTAGCATGTCGGTGTGGGTACTACACTACAC
(26)   AGGAGGAAACCAAGTCGATCGTCGTCGTAGCATGTCGGTGTGGGTACTACACTACAC

(83)   ACACATATACATGGGCAACGCAAGGCCACCTTTCTGAATCCTGCATGAGCGTGTACC
(83)   ACACATATACATGGGCAACGCAAGGCCACCTTTCTGAATCCTGCATGAGCGTGTACC
(83)   ACACATATACATGGGCAACGCAAGGCCACCTTTCTGAATCCTGCATGAGCGTGTACC
(83)   ACACATATACATGGGCAACGCAAGGCCACCTTTCTGAATCCTGCATGAGCGTGTACC
(83)   ACACATATACATGGGCAACGCAAGGCCACCTTTCTGAATCCTGCATGAGCGTGTACC
(83)   ACACATATACATGGGCAACGCAAGGCCACCTTTCTGAATCCTGCATGAGCGTGTACC (140)  ACTAGAATTGTCAGTGTGTGCGGTGTATGGCAGGTTTTTGGTTCGGCAAGTGGGGCC
(140)  ACTAGAATTGTCAGTGTGTGCGGTGTATGGCAGGTTTTTGGTTCGGCAAGTGGGGCC
(140)  ACTAGAATTGTCAGTGTGTGCGGTGTATGGCAGGTTTTTGGTTCGGCAAGTGGGGCC
(140)  ACTAGAATTGTCAGTGTGTGCGGTGTATGGCAGGTTTTTGGTTCGGCAAGTGGGGCC
(140)  ACTAGAATTGTCAGTGTGTGCGGTGTATGGCAGGTTTTTGGTTCGGCAAGTGGGGCC
(140)  ACTAGAATTGTCAGTGTGTGCGGTGTATGGCAGGTTTTTGGTTCGGCAAGTGGGGCC (197)  CTCCGGGGAGGAATCTCAGTAACAAACCGCTCTTCTGAAAAGGTCAGCCATCCCCGG
(197)  CTCCGGGGAGGAATCTCAGTAACAAACCGCTCTTCTGAAAAGGTCAGCCATCCCCGG
(197)  CTCCGGGGAGGAATCTCAGTAACAAACCGCTCTTCTGAAAAGGTCAGCCATCCCCGG
(197)  CTCCGGGGAGGAATCTCAGTAACAAACCGCTCTTCTGAAAAGGTCAGCCATCCCCGG
(197)  CTCCGGGGAGGAATCTCAGTAACAAACCGCTCTTCTGAAAAGGTCAGCCATCCCCGG
(197)  CTCCGGGGAGGAATCTCAGTAACAAACCGCTCTTCTGAAAAGGTCAGCCATCCCCGG (254)  TCCGGTCCGGTGATGTCGTCGCTGTCGCTCTGCTAGCTTGCTGCCGATCCCCCCCCC
(254)  TCCGGTCCGGTGATGTCGTCGCTGTCGCTCTGCTAGCTTGCTGCCGATCCCCCCCCC
(254)  TCCGGTCCGGTGATGTCGTCGCTGTCGCTCTGCTAGCTTGCTGCCGATCCCCCCCCC
(254)  TCCGGTCCGGTGATGTCGTCGCTGTCGCTCTGCTAGCTTGCTGCCGATCCCCCCCCC
(254)  TCCGGTCCGGTGATGTCGTCGCTGTCGCTCTGCTAGCTTGCTGCCGATCCCCCCCCC
(254)  TCCGGTCCGGTGATGTCGTCGCTGTCGCTCTGCTAGCTTGCTGCCGATCCCCCCCCC
```

Fig. 7

```
(311)  CCCCCCCCCCCTTCTTCTCTCTACCCCTCCCTCCACCTCATAAATACTTAGTTTAAT
(311)  CCCCCCCCCCCTTCTTCTCTCTACCCCTCCCTCCACCTCATAAATACTTAGTTTAAT
(311)  ----------TTCTTCTCTCTACCCCTCCCTCCACCTCATAAATACTTAGTTTAAT
(311)  CCCCCCCCCCCTTCTTCTCTCTACCCCTCCCTCCACCTCATAAATACTTAGTTTAAT
(311)  CCCCCCCCCCCTTCTTCTCTCTACCCCTCCCTCCACCTCATAAATACTTAGTTTAAT
(311)  CCCCCCCCCCCTTCTTCTCTCTACCCCTCCCTCCACCTCATAAATACTTAGTTTAAT (368)  AACCTTGCACTGCCGCAGTAGCCCTTAACTGCTGCTATCTATCTCTTTTCTGAAGGA
(368)  AACCTTGCACTGCCGCAGTAGCCCTTAACTGCTGCTATCTATCTCTTTTCTGAAGGA
(357)  AACCTTGCACTGCCGCAGTAGCCCTTAACTGCTGCTATCTATCTCTTTTCTGAAGGA
(368)  AACCTTGCACTGCCGCAGTAGCCCTTAACTGCTGCTATCTATCTCTTTTCTGAAGGA
(368)  AACCTTGCACTGCCGCAGTAGCCCTTAACTGCTGCTATCTATCTCTTTTCTGAAGGA
(368)  AACCTTGCACTGCCGCAGTAGCCCTTAACTGCTGCTATCTATCTCTTTTCTGAAGGA (425)  AAAAAAAGGTTTGATACTCCTCTACCTAGCTAGTCCTGCATGCCGCTAATGTGCGTC
(425)  AAAAAAAGGTTTGATACTCCTCTACCTAGCTAGTCCTGCATGCCGCTAATGTGCGTC
(414)  AAAAAAAGGTTTGATACTCCTCTACCTAGCTAGTCCTGCATGCCGCTAATGTGCGTC
(425)  AAAAAAAGGTTTGATACTCCTCTACCTAGCTAGTCCTGCATGCCGCTAATGTGCGTC
(425)  AAAAAAAGGTTTGATACTCCTCTACCTAGCTAGTCCTGCATGCCGCTAATGTGCGTC
(425)  AAAAAAAGGTTTGATACTCCTCTACCTAGCTAGTCCTGCATGCCGCTAATGTGCGTC (482)  TTGCCTGTTTATTTGTTCTTAATAAGGGCTGCCTATCTATTATATTTTGCACCTGTT
(482)  TTGCCTGTTTATTTGTTCTTAATAAGGGCTGCCTATCTATTATATTTTGCACCTGTT
(471)  TTGCCTGTTTATTTGTTCTTAATAAGGGCTGCCTATCTATTATATTTTGCACCTGTT
(482)  TTGCCTGTTTATTTGTTCTTAATAAGGGCTGCCTATCTATTATATTTTGCACCTGTT
(482)  TTGCCTGTTTATTTGTTCTTAATAAGGGCTGCCTATCTATTATATTTTGCACCTGTT
(482)  TTGCCTGTTTATTTGTTCTTAATAAGGGCTGCCTATCTATTATATTTTGCACCTGTT
                                            * (DAS-CMS21)
(539)  TTGCTGTGTTCTTGGTAACTAGCTTAATTCCTTCGCCTACAATCGTCAAATCCCCCC
(539)  TTGCTGTGTTCTTGGTAACTAGCTTAATTCCTTCGCCTACAATCGTCAAATCCCCCC
(528)  TTGCTGTGTTCTTGGTAACTAGCTTAATTCCTTTGCCTACAATCGTCAAATCCCCCC
(539)  TTGCTGTGTTCTTGGTAACTAGCTTAATTCCTTTGCCTACAATCGTCAAATCCCCCC
(539)  TTGCTGTGTTCTTGGTAACTAGCTTAATTCCTTTGCCTACAATCGTCAAATCCCCCC
(539)  TTGCTGTGTTCTTGGTAACTAGCTTAATTCCTTTGCCTACAATCGTCAAATCCCCCC (596)  CATCATCAGTCAGATGAACTTTTGATCGAATTGAAGTTGTTCTTCTAATTCGGCCCC
(596)  CATCATCAGTCAGATGAACTTTTGATCGAATTGAAGTTGTTCTTCTAATTCGGCCCC
(585)  CATCATCAGTCAGATGAACTTTTGATCGAATTGAAGTTGTTCTTCTAATTCGGCCCC
(596)  CATCATCAGTCAGATGAACTTTTGATCGAATTGAAGTTGTTCTTCTAATTCGGCCCC
(596)  CATCATCAGTCAGATGAACTTTTGATCGAATTGAAGTTGTTCTTCTAATTCGGCCCC
(596)  CATCATCAGTCAGATGAACTTTTGATCGAATTGAAGTTGTTCTTCTAATTCGGCCCC
```

Fig. 7 Cont.

```
(653)  AGCAGCGCCCATGCATCTGGTTTTATTTGCTTTCTGTTGGGTATAATATGCAAGACC
(653)  AGCAGCGCCCATGCATCTGGTTTTATTTGCTTTCTGTTGGGTATAATATGCAAGACC
(642)  AGCAGCGCCCATGCATCTGGTTTTATTTGCTTTCTGTTGGGTATAATATGCAAGACC
(653)  AGCAGCGCCCATGCATCTGGTTTTATTTGCTTTCTGTTGGGTATAATATGCAAGACC
(653)  AGCAGCGCCCATGCATCTGGTTTTATTTGCTTTCTGTTGGGTATAATATGCAAGACC
(653)  AGCAGCGCCCATGCATCTGGTTTTATTTGCTTTCTGTTGGGTATAATATGCAAGACC (710)  TTTTGTTGCTAGGGCAAGGCTGCAACCACATGCGTGTACTGAACTCATGATGTAACT
(710)  TTTTGTTGCTAGGGCAAGGCTGCAACCACATGCGTGTACTGAACTCATGATGTAACT
(699)  TTTTGTTGCTAGGGCAAGGCTGCAACCACATGCGTGTACTGAACTCATGATGTAACT
(710)  TTTTGTTGCTAGGGCAAGGCTGCAACCACATGCGTGTACTGAACTCATGATGTAACT
(710)  TTTTGTTGCTAGGGCAAGGCTGCAACCACATGCGTGTACTGAACTCATGATGTAACT
(710)  TTTTGTTGCTAGGGCAAGGCTGCAACCACATGCGTGTACTGAACTCATGATGTAACT (767)  CATCCTTTTTGTTTGCTCACAGAATCACTACTCTACTGCACTTCCTTTTCATCCGAT
(767)  CATCCTTTTTGTTTGCTCACAGAATCACTACTCTACTGCACTTCCTTTTCATCCGAT
(756)  CATCCTTTTTGTTTGCTCACAGAATCACTACTCTACTGCACTTCCTTTTCATCCGAT
(767)  CATCCTTTTTGTTTGCTCACAGAATCACTACTCTACTGCACTTCCTTTTCATCCGAT
(767)  CATCCTTTTTGTTTGCTCACAGAATCACTACTCTACTGCACTTCCTTTTCATCCGAT
(767)  CATCCTTTTTGTTTGCTCACAGAATCACTACTCTACTGCACTTCCTTTTCATCCGAT (824)  CCGCAATCTTTTTTTTCTTTTACATGCTTTAGTTTTCTCTCTTTCTTGATTACAAAC
(824)  CCGCAATCTTTTTTTTCTTTTACATGCTTTAGTTTTCTCTCTTTCTTGATTACAAAC
(813)  CCGCAATCTTTTTTTTCTTTTACATGCTTTAGTTTTCTCTCTTTCTTGATTACAAAC
(824)  CCGCAATCTTTTTTTTCTTTTACATGCTTTAGTTTTCTCTCTTTCTTGATTACAAAC
(824)  CCGCAATCTTTTTTTTCTTTTACATGCTTTAGTTTTCTCTCTTTCTTGATTACAAAC
(824)  CCGCAATCTTTTTTTTCTTTTACATGCTTTAGTTTTCTCTCTTTCTTGATTACAAAC (881)  ATGATTACTGGAACTTTCTTAGGCTGCCTTCCCCTTCCTTGGATCTGCTTTAGTTTT
(881)  ATGATTACTGGAACTTTCTTAGGCTGCCTTCCCCTTCCTTGGATCTGCTTTAGTTTT
(870)  ATGATTACTGGAACTTTCTTAGGCTGCCTTCCCCTTCCTTGGATCTGCTTTAGTTTT
(881)  ATGATTACTGGAACTTTCTTAGGCTGCCTTCCCCTTCCTTGGATCTGCTTTAGTTTT
(881)  ATGATTACTGGAACTTTCTTAGGCTGCCTTCCCCTTCCTTGGATCTGCTTTAGTTTT
(881)  ATGATTACTGGAACTTTCTTAGGCTGCCTTCCCCTTCCTTGGATCTGCTTTAGTTTT (938)  CTTTTTTGGGCTACCGCGCGCGGCTTATTTGAGTTTATCACTTGCTGCATATACATA
(938)  CTTTTTTGGGCTACCGCGCGCGGCTTATTTGAGTTTATCACTTGCTGCATATACATA
(927)  CTTTTTTGGGCTACCGCGCGCGGCTTATTTGAGTTTATCACTTGCTGCATATACATA
(938)  CTTTTTTGGGCTACCGCGCGCGGCTTATTTGAGTTTATCACTTGCTGCATATACATA
(938)  CTTTTTTGGGCTACCGCGCGCGGCTTATTTGAGTTTATCACTTGCTGCATATACATA
(938)  CTTTTTTGGGCTACCGCGCGCGGCTTATTTGAGTTTATCACTTGCTGCATATACATA
```

Fig. 7 Cont.

```
  (995) ATATATATATACATGCATGCGATGGCGTTCATGTTACTCAACTACAGATCTGTTTCT
  (995) ATATATATATACATGCATGCGATGGCGTTCATGTTACTCAACTACAGATCTGTTTCT
  (984) ATATATATATACATGCATGCGATGGCGTTCATGTTACTCAACTACAGATCTGTTTCT
  (995) ATATATATATACATGCATGCGATGGCGTTCATGTTACTCAACTACAGATCTGTTTCT
  (995) ATATATATATACATGCATGCGATGGCGTTCATGTTACTCAACTACAGATCTGTTTCT
  (995) ATATATATATACATGCATGCGATGGCGTTCATGTTACTCAACTACAGATCTGTTTCT
                                                         START (1052) GTTCGTGTGTTTCAGTTCAGCGCGCAGTTAAGCATAGCAGGACGACCACGACGATGT
 (1052) GTTCGTGTGTTTCAGTTCAGCGCGCAGTTAAGCATAGCAGGACGACCACGACGATGT
 (1041) GTTCGTGTGTTTCAGTTCAGCGCGCAGTTAAGCATAGCAGGACGACCACGACGATGT
 (1052) GTTCGTGTGTTTCAGTTCAGCGCGCAGTTAAGCATAGCAGGACGACCACGACGATGT
 (1052) GTTCGTGTGTTTCAGTTCAGCGCGCAGTTAAGCATAGCAGGACGACCACGACGATGT
 (1052) GTTCGTGTGTTTCAGTTCAGCGCGCAGTTAAGCATAGCAGGACGACCACGACGATGT (1109) ATCACCCGCAGTGCGAGCTCCTGACGATGGCGCACGAAACGCCGGACCTGGACGCCG
 (1109) ATCACCCGCAGTGCGAGCTCCTGACGATGGCGCACGAAACGCCGGACCTGGACGCCG
 (1098) ATCACCCGCAGTGCGAGCTCCTGACGATGGCGCACGAAACGCCGGACCTGGACGCCG
 (1109) ATCACCCGCAGTGCGAGCTCCTGACGATGGCGCACGAAACGCCGGACCTGGACGCCG
 (1109) ATCACCCGCAGTGCGAGCTCCTGACGATGGCGCACGAAACGCCGGACCTGGACGCCG
 (1109) ATCACCCGCAGTGCGAGCTCCTGACGATGGCGCACGAAACGCCGGACCTGGACGCCG (1166) GCCAGCCGCACCTAACCGTCTCCGGCGTCGCCAGCATCCCGGCAGAGCTGAGCTTCC
 (1166) GCCAGCCGCACCTAACCGTCTCCGGCGTCGCCAGCATCCCGGCAGAGCTGAGCTTCC
 (1155) GCCAGCCGCACCTAACCGTCTCCGGCGTCGCCAGCATCCCGGCAGAGCTGAGCTTCC
 (1166) GCCAGCCGCACCTAACCGTCTCCGGCGTCGCCAGCATCCCGGCAGAGCTGAGCTTCC
 (1166) GCCAGCCGCACCTAACCGTCTCCGGCGTCGCCAGCATCCCGGCAGAGCTGAGCTTCC
 (1166) GCCAGCCGCACCTAACCGTCTCCGGCGTCGCCAGCATCCCGGCAGAGCTGAGCTTCC (1223) ACCTGCTGCACTCGCTCGACGCCGCGGCGGCGGTCAATCCCGTCACGGCGCCGCCGC
 (1223) ACCTGCTGCACTCGCTCGACGCCGCGGCGGCGGTCAATCCCGTCACGGCGCCGCCGC
 (1212) ACCTGCTGCACTCGCTCGACGCCGCGGCGGCGGTCAATCCCGTCACGGCGCCGCCGC
 (1223) ACCTGCTGCACTCGCTCGACGCCGCGGCGGCGGTCAATCCCGTCACGGCGCCGCCGC
 (1223) ACCTGCTGCACTCGCTCGACGCCGCGGCGGCGGTCAATCCCGTCACGGCGCCGCCGC
 (1223) ACCTGCTGCACTCGCTCGACGCCGCGGCGGCGGTCAATCCCGTCACGGCGCCGCCGC (1280) AGTCCACCATCGACTACTTCCTCGGCGGCGCCGATCCCCACCAGCAGGCCATGCAGT
 (1280) AGTCCACCATCGACTACTTCCTCGGCGGCGCCGATCCCCACCAGCAGGCCATGCAGT
 (1269) AGTCCACCATCGACTACTTCCTCGGCGGCGCCGATCCCCACCAGCAGGCCATGCAGT
 (1280) AGTCCACCATCGACTACTTCCTCGGCGGCGCCGATCCCCACCAGCAGGCCATGCAGT
 (1280) AGTCCACCATCGACTACTTCCTCGGCGGCGCCGATCCCCACCAGCAGGCCATGCAGT
 (1280) AGTCCACCATCGACTACTTCCTCGGCGGCGCCGATCCCCACCAGCAGGCCATGCAGT
```

Fig. 7 Cont.

```
(1337) ACGAGCCGCTGCCGCCCGCCGCGGGCGGCCACCACCAGTACACCATGGACATGTTCC
(1337) ACGAGCCGCTGCCGCCCGCCGCGGGCGGCCACCACCAGTACACCATGGACATGTTCC
(1326) ACGAGCCGCTGCCGCCCGCCGCGGGCGGCCACCACCAGTACACCATGGACATGTTCC
(1337) ACGAGCCGCTGCCGCCCGCCGCGGGCGGCCACCACCAGTACACCATGGACATGTTCC
(1337) ACGAGCCGCTGCCGCCCGCCGCGGGCGGCCACCACCAGTACACCATGGACATGTTCC
(1337) ACGAGCCGCTGCCGCCCGCCGCGGGCGGCCACCACCAGTACACCATGGACATGTTCC
                         * (DAS-CMS22)
(1394) GCGACTACTGCGACGGCCACTACCCCACCGCCGAGCCGTACATCCGCGGGACAATGA
(1394) GCGACTACTGCGACGGCCACTACCCCACCGCCGAGCCGTACATCCGCGGGACAATGA
(1383) GCGACTACTGCGACGGCCACTACCCCACCGCCGAGCCGTACATCCGCGGGACAATGA
(1394) GCGACTACTGCGACGGCAACTACCCCACCGCCGAGCCGTACATCCGCGGGACAATGA
(1394) GCGACTACTGCGACGGCAACTACCCCACCGCCGAGCCGTACATCCGCGGGACAATGA
(1394) GCGACTACTGCGACGGCAACTACCCCACCGCCGAGCCGTACATCCGCGGGACAATGA
                                        (DAS-CMS23) ***
(1451) CTGGAGCCCTCGTGTTCGGGGCCACCGACGACGACGACTCGGCCGCTGCC---TACA
(1451) CTGGAGCCCTCGTGTTCGGGGCCACCGACGACGACGACTCGGCCGCTGCC---TACA
(1440) CTGGAGCCCTCGTGTTCGGGGCCACCGACGACGACGACTCGGCCGCTGCC---TACA
(1451) CTGGAGCCCTCGTGTTCGGGGCCACCGACGACGACGACTCGGCCGCTGCCGCCTACA
(1451) CTGGAGCCCTCGTGTTCGGGGCCACCGACGACGACGACTCGGCCGCTGCCGCCTACA
(1451) CTGGAGCCCTCGTGTTCGGGGCCACCGACGACGACGACTCGGCCGCTGCCGCCTACA (1505) TGCCCGGGGGGCACTTTGAGACCTCCCCGCCGCCGCCACGCGCCACCGGCCGCGGCA
(1505) TGCCCGGGGGGCACTTTGAGACCTCCCCGCCGCCGCCACGCGCCACCGGCCGCGGCA
(1494) TGCCCGGGGGGCACTTTGAGACCTCCCCGCCGCCGCCACGCGCCACCGGCCGCGGCA
(1508) TGCCCGGGGGGCACTTTGAGACCTCCCCGCCGCCGCCACGCGCCACCGGCCGCGGCA
(1508) TGCCCGGGGGGCACTTTGAGACCTCCCCGCCGCCGCCACGCGCCACCGGCCGCGGCA
(1508) TGCCCGGGGGGCACTTTGAGACCTCCCCGCCGCCGCCACGCGCCACCGGCCGCGGCA (1562) GGAAGCGGGGCAGGGCGCTGGGCGGCGGCTTCCATGCTGTGCTGGCCAACGGCGTCG
(1562) GGAAGCGGGGCAGGGCGCTGGGCGGCGGCTTCCATGCTGTGCTGGCCAACGGCGTCG
(1551) GGAAGCGGGGCAGGGCGCTGGGCGGCGGCTTCCATGCTGTGCTGGCCAACGGCGTCG
(1565) GGAAGCGGGGCAGGGCGCTGGGCGGCGGCTTCCATGCTGTGCTGGCCAACGGCGTCG
(1565) GGAAGCGGGGCAGGGCGCTGGGCGGCGGCTTCCATGCTGTGCTGGCCAACGGCGTCG
(1565) GGAAGCGGGGCAGGGCGCTGGGCGGCGGCTTCCATGCTGTGCTGGCCAACGGCGTCG
                                    (DAS-CMS24) *
(1619) AGAAGAAGGAGAAGCAGCGCCGGCTGCGGCTCACCGAGAAGTACACCGCCCTCATGC
(1619) AGAAGAAGGAGAAGCAGCGCCGGCTGCGGCTCACCGAGAAGTACACCGCCCTCATGC
(1608) AGAAGAAGGAGAAGCAGCGCCGGCTGCGGCTCACCGAGAAGTACACCGCCCTCATGC
(1622) AGAAGAAGGAGAAGCAGCGCCGGCTGCGGCTCACCGAGAAGTTTACGGCCCTCATGC
(1622) AGAAGAAGGAGAAGCAGCGCCGGCTGCGGCTCACCGAGAAGTTTACGGCCCTCATGC
(1622) AGAAGAAGGAGAAGCAGCGCCGGCTGCGGCTCACCGAGAAGTTTACGGCCCTCATGC
```

Fig. 7 Cont.

```
                          * (DAS-CMS25)
(1676) ACCTCATACCCAACGTTACAAAGGTCGTAC--------------CAAATCCT
(1676) ACCTCATACCCAACGTTACAAAGGTCGTAC--------------CAAATCCT
(1665) ACCTCATACCCAACGTTACAAAGGTCGTAC--------------CAAATCCT
(1679) ACCTCATACCCAACGTTACGAAGGTCGTACGGCGTACTTGCGCGCGGACCAAATCCT
(1679) ACCTCATACCCAACGTTACGAAGGTCGTACGGCGTACTTGCGCGCGGACCAAATCCT
(1679) ACCTCATACCCAACGTTACGAAGGTCGTACGGCGTACTTGCGCGCGGACCAAATCCT
                          * (DAS-CMS26)
(1714) CCTCTTATGTTCGTC---CATCGTTTCAAATTAAGTTAAAAAATTAATTCACGGTTC
(1714) CCTCTTATGTTCGTC---CATCGTTTCAAATTAAGTTAAAAAATTAATTCACGGTTC
(1703) CCTCTTATGTTCGTC---CATCGTTTCAAATTAAGTTAAAAAATTAATTCACGGTTC
(1736) CCTCTTATGTTCGTCGTCCATCGTCTCAAATTAA-------------TTCACGGTTC
(1736) CCTCTTATGTTCGTCGTCCATCGTCTCAAATTAA-------------TTCACGGTTC
(1736) CCTCTTATGTTCGTCGTCCATCGTCTCAAATTAA-------------TTCACGGTTC
                        *** (DAS-CMS27)
(1768) TTGTTGTT---TATTTTTTGCGCACTGCAGACTGATAGGGCGACGGTGATCTCGGAC
(1768) TTGTTGTT---TATTTTTTGCGCACTGCAGACTGATAGGGCGACGGTGATCTCGGAC
(1757) TTGTTGTT---TATTTTTTGCGCACTGCAGACTGATAGGGCGACGGTGATCTCGGAC
(1780) TTGTTGTTCTTTATTTTTTGCGCACTGCAGACTGATAGGGCGACGGTGATCTCGGAC
(1780) TTGTTGTTCTTTATTTTTTGCGCACTGCAGACTGATAGGGCGACGGTGATCTCGGAC
(1780) TTGTTGTTCTTTATTTTTTGCGCACTGCAGACTGATAGGGCGACGGTGATCTCGGAC (1822) GCGATCGAGTACATCCAGGAGCTGGGGAGGACGGTGGAGGAGCTGACGCTGCTGGTG
(1822) GCGATCGAGTACATCCAGGAGCTGGGGAGGACGGTGGAGGAGCTGACGCTGCTGGTG
(1811) GCGATCGAGTACATCCAGGAGCTGGGGAGGACGGTGGAGGAGCTGACGCTGCTGGTG
(1837) GCGATCGAGTACATCCAGGAGCTGGGGAGGACGGTGGAGGAGCTGACGCTGCTGGTG
(1837) GCGATCGAGTACATCCAGGAGCTGGGGAGGACGGTGGAGGAGCTGACGCTGCTGGTG
(1837) GCGATCGAGTACATCCAGGAGCTGGGGAGGACGGTGGAGGAGCTGACGCTGCTGGTG (1879) GAGAAGAAGCGGCGCCGGAGGGAGCTGCAGGGGGACGTCGTGGACGCGGCGCCGGCT
(1879) GAGAAGAAGCGGCGCCGGAGGGAGCTGCAGGGGGACGTCGTGGACGCGGCGCCGGCT
(1868) GAGAAGAAGCGGCGCCGGAGGGAGCTGCAGGGGGACGTCGTGGACGCGGCGCCGGCT
(1894) GAGAAGAAGCGGCGCCGGAGGGAGCTGCAGGGGGACGTCGTGGACGCGGCGCCGGCT
(1894) GAGAAGAAGCGGCGCCGGAGGGAGCTGCAGGGGGACGTCGTGGACGCGGCGCCGGCT
(1894) GAGAAGAAGCGGCGCCGGAGGGAGCTGCAGGGGGACGTCGTGGACGCGGCGCCGGCT (1936) GCGGTGGTTGCTGCCGCCGGTGAGGCGGAGAGCTCGGAGGGCGAGGTGGCTCCTCCG
(1936) GCGGTGGTTGCTGCCGCCGGTGAGGCGGAGAGCTCGGAGGGCGAGGTGGCTCCTCCG
(1925) GCGGTGGTTGCTGCCGCCGGTGAGGCGGAGAGCTCGGAGGGCGAGGTGGCTCCTCCG
(1951) GCGGTGGTTGCTGCCGCCGGTGAGGCGGAGAGCTCGGAGGGCGAGGTGGCTCCTCCG
(1951) GCGGTGGTTGCTGCCGCCGGTGAGGCGGAGAGCTCGGAGGGCGAGGTGGCTCCTCCG
(1951) GCGGTGGTTGCTGCCGCCGGTGAGGCGGAGAGCTCGGAGGGCGAGGTGGCTCCTCCG
```

Fig. 7 Cont.

```
                * (DAS-CMS28)
(1993)  CCGCCGGCCGTGCCGCGGCAGCCGATCCGGAGCACGTACATCCAGCGGCGGAGCAAG
(1993)  CCGCCGGCCGTGCCGCGGCAGCCGATCCGGAGCACGTACATCCAGCGGCGGAGCAAG
(1982)  CCGCCGGCCGTGCCGCGGCAGCCGATCCGGAGCACGTACATCCAGCGGCGGAGCAAG
(2008)  CCGCTGGCCGTGCCGCGGCAGCCGATCCGGAGCACGTACATCCAGCGGCGGAGCAAG
(2008)  CCGCTGGCCGTGCCGCGGCAGCCGATCCGGAGCACGTACATCCAGCGGCGGAGCAAG
(2008)  CCGCTGGCCGTGCCGCGGCAGCCGATCCGGAGCACGTACATCCAGCGGCGGAGCAAG (2050)  GACACGTCCGTGGACGTGCGGATCGTGGAGGAGGACGTGAACATCAAGCTCACCAAG
(2050)  GACACGTCCGTGGACGTGCGGATCGTGGAGGAGGACGTGAACATCAAGCTCACCAAG
(2039)  GACACGTCCGTGGACGTGCGGATCGTGGAGGAGGACGTGAACATCAAGCTCACCAAG
(2065)  GACACGTCCGTGGACGTGCGGATCGTGGAGGAGGACGTGAACATCAAGCTCACCAAG
(2065)  GACACGTCCGTGGACGTGCGGATCGTGGAGGAGGACGTGAACATCAAGCTCACCAAG
(2065)  GACACGTCCGTGGACGTGCGGATCGTGGAGGAGGACGTGAACATCAAGCTCACCAAG
                                                  * (DAS-CMS29)
(2107)  CGCCGGCGCGACGGGTGCCTCGCAGCCGCGTCGCGCGCGCTGGATGACCTCCGCCTT
(2107)  CGCCGGCGCGACGGGTGCCTCGCAGCCGCGTCGCGCGCGCTGGATGACCTCCGCCTT
(2096)  CGCCGGCGCGACGGGTGCCTCGCAGCCGCGTCGCGCGCGCTGGATGACCTCCGCCTT
(2122)  CGCCGGCGCGACGGGTGCCTCGCAGCCGCGTCGCGCGCGCTGGACGACCTCCGCCTT
(2122)  CGCCGGCGCGACGGGTGCCTCGCAGCCGCGTCGCGCGCGCTGGACGACCTCCGCCTT
(2122)  CGCCGGCGCGACGGGTGCCTCGCAGCCGCGTCGCGCGCGCTGGACGACCTCCGCCTT (2164)  GACCTCGTCCACCTCTCCGGCGGCAAGATCGGTGACTGTCAAATCTACATGTTCAAC
(2164)  GACCTCGTCCACCTCTCCGGCGGCAAGATCGGTGACTGTCAAATCTACATGTTCAAC
(2153)  GACCTCGTCCACCTCTCCGGCGGCAAGATCGGTGACTGTCAAATCTACATGTTCAAC
(2179)  GACCTCGTCCACCTCTCCGGCGGCAAGATCGGTGACTGTCAAATCTACATGTTCAAC
(2179)  GACCTCGTCCACCTCTCCGGCGGCAAGATCGGTGACTGTCAAATCTACATGTTCAAC
(2179)  GACCTCGTCCACCTCTCCGGCGGCAAGATCGGTGACTGTCAAATCTACATGTTCAAC (2221)  ACCAAGGTACATACGAATACGATACGTAGCCATTGATCGATCTGTAATTCTGTAGCC
(2221)  ACCAAGGTACATACGAATACGATACGTAGCCATTGATCGATCTGTAATTCTGTAGCC
(2210)  ACCAAGGTACATACGAATACGATACGTAGCCATTGATCGATCTGTAATTCTGTAGCC
(2236)  ACCAAGGTACATACGAATACGATACGTAGCCATTGATCGATCTGTAATTCTGTAGCC
(2236)  ACCAAGGTACATACGAATACGATACGTAGCCATTGATCGATCTGTAATTCTGTAGCC
(2236)  ACCAAGGTACATACGAATACGATACGTAGCCATTGATCGATCTGTAATTCTGTAGCC
        ************* (DAS-CMS30)
(2278)  TGACGATT-------------CCGAGGTTTCTG---------------GT
(2278)  TGACGATT-------------CCGAGGTTTCTG---------------GT
(2267)  TGACGATT-------------CCGAGGTTTCTG---------------GT
(2293)  TGACGATTTCATGCATTACTTTTCCGAGGTTTCTGTGCTATACTACCTAACCTAGGT
(2293)  TGACGATTTCATGCATTACTTTTCCGAGGTTTCTGTGCTATACTACCTAACCTAGGT
(2293)  TGACGATTTCATGCATTACTTTTCCGAGGTTTCTGTGCTATACTACCTAACCTAGGT
```

Fig. 7 Cont.

```
(2300)  GCTAAAAAATGCATCTTTTTTTCTCAGATGACAATGCTTTCTGTCTTTGTTCACCGC
(2300)  GCTAAAAAATGCATCTTTTTTTCTCAGATGACAATGCTTTCTGTCTTTGTTCACCGC
(2289)  GCTAAAAAATGCATCTTTTTTTCTCAGATGACAATGCTTTCTGTCTTTGTTCACCGC
(2350)  GCTAAAAAATGCACCTTTTTTTCTCAGATGACAATGCTTTCTGTCTTTGTTCACCGC
(2350)  GCTAAAAAATGCACCTTTTTTTCTCAGATGACAATGCTTTCTGTCTTTGTTCACCGC
(2350)  GCTAAAAAATGCACCTTTTTTTCTCAGATGACAATGCTTTCTGTCTTTGTTCACCGC (2357)  AGATTCACAAGGGGTCTTCAGTGTTTGCGAGTGCAGTGGCCGGTAGGCTGATGGAAG
(2357)  AGATTCACAAGGGGTCTTCAGTGTTTGCGAGTGCAGTGGCCGGTAGGCTGATGGAAG
(2346)  AGATTCACAAGGGGTCTTCAGTGTTTGCGAGTGCAGTGGCCGGTAGGCTGATGGAAG
(2407)  AGATTCACAAGGGGTCTTCAGTGTTTGCGAGTGCAGTGGCCGGTAGGCTGATGGAAG
(2407)  AGATTCACAAGGGGTCTTCAGTGTTTGCGAGTGCAGTGGCCGGTAGGCTGATGGAAG
(2407)  AGATTCACAAGGGGTCTTCAGTGTTTGCGAGTGCAGTGGCCGGTAGGCTGATGGAAG
                                  STOP
(2414)  TGGTGGACGAGTACTAGGCTACCATGCACTTGAATTTCTAGCTAGCTCTACGTACCG
(2414)  TGGTGGACGAGTACTAGGCTACCATGCACTTGAATTTCTAGCTAGCTCTACGTACCG
(2403)  TGGTGGACGAGTACTAGGCTACCATGCACTTGAATTTCTAGCTAGCTCTACGTACCG
(2464)  TGGTGGACGAGTACTAGGCTACCATGCACTTGAATTTCTAGCTAGCTCTACGTACCG
(2464)  TGGTGGACGAGTACTAGGCTACCATGCACTTGAATTTCTAGCTAGCTCTACGTACCG
(2464)  TGGTGGACGAGTACTAGGCTACCATGCACTTGAATTTCTAGCTAGCTCTACGTACCG
                                                * (DAS-CMS31)
(2471)  CGCTGCTATGAATCTAGCTATAGCGTTTCTTGGATGAAAGACTAGTTAGTTGTTACC
(2471)  CGCTGCTATGAATCTAGCTATAGCGTTTCTTGGATGAAAGACTAGTTAGTTGTTACC
(2460)  CGCTGCTATGAATCTAGCTATAGCGTTTCTTGGATGAAAGACTAGTTAGTTGTTACC
(2521)  CGCTGCTATGAATCTAGCTATAGCGTTTCTTGGATGAAAGAATAGTTAGTTGTTACC
(2521)  CGCTGCTATGAATCTAGCTATAGCGTTTCTTGGATGAAAGAATAGTTAGTTGTTACC
(2521)  CGCTGCTATGAATCTAGCTATAGCGTTTCTTGGATGAAAGAATAGTTAGTTGTTACC (2528)  TTCTATCTTTGCTTCAATTAAATCCGCTTGCTCGTTACAGACTGAGTTTGTTTCTAA
(2528)  TTCTATCTTTGCTTCAATTAAATCCGCTTGCTCGTTACAGACTGAGTTTGTTTCTAA
(2517)  TTCTATCTTTGCTTCAATTAAATCCGCTTGCTCGTTACAGACTGAGTTTGTTTCTAA
(2578)  TTCTATCTTTGCTTCAATTAAATCCGCTTGCTCGTTACAGACTGAGTTTGTTTCTAA
(2578)  TTCTATCTTTGCTTCAATTAAATCCGCTTGCTCGTTACAGACTGAGTTTGTTTCTAA
(2578)  TTCTATCTTTGCTTCAATTAAATCCGCTTGCTCGTTACAGACTGAGTTTGTTTCTAA (2585)  ATGTCAAGGTTGTTTTGGTCAAATTGAATAAATTGGCACACTGGCCTGTGAGGTTAT
(2585)  ATGTCAAGGTTGTTTTGGTCAAATTGAATAAATTGGCACACTGGCCTGTGAGGTTAT
(2574)  ATGTCAAGGTTGTTTTGGTCAAATTGAATAAATTGGCACACTGGCCTGTGAGGTTAT
(2635)  ATGTCAAGGTTGTTTTGGTCAAATTGAATAAATTGGCACACTGGCCTGTGAGGTTAT
(2635)  ATGTCAAGGTTGTTTTGGTCAAATTGAATAAATTGGCACACTGGCCTGTGAGGTTAT
(2635)  ATGTCAAGGTTGTTTTGGTCAAATTGAATAAATTGGCACACTGGCCTGTGAGGTTAT
```

Fig. 7 Cont.

```
(2642)  TATATATATTTATGTGT-TTATTACTGGTCTATTAATTTGTCTTATTATTAATGTAT
(2642)  TATATATATTTATGTGT-TTATTACTGGTCTATTAATTTGTCTTATTATTAATGTAT
(2631)  TATATATATTTATGTGT-TTATTACTGGTCTATTAATTTGTCCTATTATTAATGTAT
(2692)  TATAT-----TTATGTGTATTATTACTGGTCTATCAATTTGTCCTATTATT---GTAT
(2692)  TATAT-----TTATGTGTATTATTACTGGTCTATCAATTTGTCCTATTATT---GTAT
(2692)  TATAT-----TTATGTGTATTATTACTGGTCTATCAATTTGTCCTATTATT---GTAT
                   * (DAS-CMS32)
(2698)  TGCCTGTCAAGGAATAAATGGTATGATGACCATATTTATGCATAGATAGGATCGGAT
(2698)  TGCCTGTCAAGGAATAAATGGTATGATGACCATATTTATGCATAGATAGGATCGGAT
(2687)  TGCCTGTCAAGGAATAAATGATATGATGACCATATTTATGCATAGATAGGA-----T
(2742)  TGCCTGTCAAGGAATAAATTGTATGATGACTATATTTATGCATAGATAGGA-----T
(2742)  TGCCTGTCAAGGAATAAATTGTATCATCACTATATTTATGCATAGATAGGA-----T
(2742)  TGCCTGTCAAGGAATAAATTGTATGATGACTATATTTATGCATAGATAGGA-----T (2755)  GAGTAGGTTCACTTGCTTGAGTTCACCGGTATAATTCGGG------ATACATCTGG
(2755)  GAGTAGGTTCACTTGCTTGAGTTCACCGGTATAATTCGGG------ATACATCTGG
(2739)  GAGTAGGTTCACTTGCTTGAGTTCACCGGTATAATTCTGG------ATACATCTGG
(2794)  GAGTAGGTTCACTTGCTTGAGTTCACCGGTATAATTCTGGTTTCTGGATACATCTGG
(2794)  GAGTAGGTTCACTTGCTTGAGTTCACCGGTATAATTCTGGTTTCTGGATACATCTGG
(2794)  GAGTAGGTTCACTTGCTTGAGTTCACCGGTATAATTCTGGTTTCTGGATACATCTGG
                   * (DAS-CMS33)
(2805)  TTAGGTCATCCTTTGGTCAGCTGCCCGCAAGCTTAACTCCGTGCGATATACAATATA
(2805)  TTAGGTCATCCTTTGGTCAGCTGCCCGCAAGCTTAACTCCGTGCGATATACAATATA
(2789)  TTAGGTCATCCTTTGGTCAGCTGCCCGCAA--------CGTGCGATATACAATATA
(2851)  TTAGGTCAGCCTTTGGTCAGCTGCCCGCAAGCTTAACTCCGTGCGATATACACTATA
(2851)  TTAGGTCAGCCTTTGGTCAGCTGCCCGCAAGCTTAACTCCGTGCGATATACACTATA
(2851)  TTAGGTCAGCCTTTGGTCAGCTGCCCGCAAGCTTAACTCCGTGCGATATACACTATA (2862)  CAGATTTTATTATGGTTTTCCCTGAACCTTCGTGACTAACTATGTTATCATTTTTA
(2862)  CAGATTTTATTATGGTTTTCCCTGAACCTTCGTGACTAACTATGTTATCATTTTTA
(2837)  CATATTTTATTATGTTTTT---------TTCGTGACTAACTATGTTATCATTTTTA
(2908)  CAAATTTTATTATGTTTTT---------TTCGTGACTAACTATGTTATCATTTTTA
(2908)  CAAATTTTATTATGTTTTT---------TTCGTGACTAACTATGTTATCATTTTTA
(2908)  CAAATTTTATTATGTTTTT---------TTCGTGACTAACTATGTTATCATTTTTA (2919)  TAGCTTTATAGTCTACAAACTGTTTTATACTCAGCTTGATAAGTACATTCTGGTTTG
(2919)  TAGCTTTATAGTCTACAAACTGTTTTATACTCAGCTTGATAAGTACATTCTGGTTTG
(2884)  TAGCTTTATAGTCTACAAACTGTTTTATACTCAGCTTGATAAGTACATTCTGGTTTG
(2955)  TAGCTTTATAGTCTACAAACTGTTTTATACTCAGCTTGATAAGTACATTCTGGTTTG
(2955)  TAGCTTTATAGTCTACAAACTGTTTTATACTCAGCTTGATAAGTACATTCTGGTTTG
(2955)  TAGCTTTATAGTCTACAAACTGTTTTATACTCAGCTTGATAAGTACATTCTGGTTTG
```

Fig. 7 Cont.

```
              * (DAS-CMS34)
   (2976)  GACGATGG-TTTTTTTTTCTTGCAAAA-TGAATTTGTCTTCAGCCTTTACGACTACA
   (2976)  GACGATGG-TTTTTTTTTCTTGCAAAA-TGAATTTGTCTTCAGCCTTTACGACTACA
   (2941)  GACGAT-----TTTTTTTTCTTGCAAAAATGAATTTGTCTTCAGCCTTTACGACTACA
   (3012)  GACGATGGTTTTTTTTTCTTGCAAAAATGAATTTGTCTTCAGCCTTTACGACTACA
   (3012)  GACGATGGTTTTTTTTTCTTGCAAAAATGAATTTGTCTTCAGCCTTTACGACTACA
   (3012)  GACGATGGTTTTTTTTTCTTGCAAAAATGAATTTGTCTTCAGCCTTTACGACTACA (3031)  TACAGTTTAGTT---------------TGTATTAATTGATACCGGAAGATCAGATT
   (3031)  TACAGTTTAGTT---------------TGTATTAATTGATACCGGAAGATCAGATT
   (2994)  TACAGTTTAGTTCTTAGAGTATCTCATCTGTATTAATTGATACCGGAAGA---GATT
   (3069)  TACAGTTTAGTT---------------TGTATTAATTGATACCAGAAGATCAGATT
   (3069)  TACAGTTTAGTT---------------TGTATTAATTGATACCAGAAGATCAGATT
   (3069)  TACAGTTTAGTT---------------TGTATTAATTGATACCAGAAGATCAGATT (3072)  CGGACCACATATAAACAAGGAATATATAGCACGTACTCGCTGAACCTTAAATATAGT
   (3072)  CGGACCACATATAAACAAGGAATATATAGCACGTACTCGCTGAACCTTAAATATAGT
   (3048)  CGGGCCACATATAAACAAGGAATATATAGCACGTACTCGCTGAACCTTAAATATAGT
   (3110)  CGGACCACATATAAACAAGGAATATATAGCACGTACTCGCTGAACCTTAAATATAGT
   (3110)  CGGACCACATATAAACAAGGAATATATAGCACGTACTCGCTGAACCTTAAATATAGT
   (3110)  CGGACCACATATAAACAAGGAATATATAGCACGTACTCGCTGAACCTTAAATATAGT (3129)  CAGGAAAATAGAGGGTTAACTAAACCGATCCAGAAACCAATTACATTGATATTGACT
   (3129)  CAGGAAAATAGAGGGTTAACTAAACCGATCCAGAAACCAATTACATTGATATTGACT
   (3105)  CAGGAACATAGAGGGTTAACTAAACCGATCCAGAAACCAATTACATTGATATTGACT
   (3167)  CAGGAACATAGAGGGTTAACTAAACCGATCCAGAAACCAATTACATTGATATTGACT
   (3167)  CAGGAACATAGAGGGTTAACTAAACCGATCCAGAAACCAATTACATTGATATTGACT
   (3167)  CAGGAACATAGAGGGTTAACTAAACCGATCCAGAAACCAATTACATTGATATTGACT (3186)  CTATTCTTCGTT
   (3186)  CTATTCTTCGTT
   (3162)  CTATTCTTCGTT
   (3224)  CTATTCTTCGTT
   (3224)  CTATTCTTCGTT
   (3224)  CTATTCTTCGTT
```

Fig. 7 Cont.

```
B73 rf4-bHLH cDNA       (SEQ ID NO:221)   (1)  CTCTGCTAGCTTGCTGCCGA
BE4207 rf4-bHLH cDNA    (SEQ ID NO:221)   (1)  CTCTGCTAGCTTGCTGCCGA
B104 bHLH cDNA          (SEQ ID NO:222)   (1)  CTCTGCTAGCTTGCTGCCGA
XJN58 Rf4-bHLH cDNA     (SEQ ID NO:223)   (1)  CTCTGCTAGCTTGCTGCCGA
BE9515 Rf4-bHLH cDNA    (SEQ ID NO:223)   (1)  CTCTGCTAGCTTGCTGCCGA
MLW03 Rf4-bHLH cDNA     (SEQ ID NO:223)   (1)  CTCTGCTAGCTTGCTGCCGA

(21)    TCCCCCCCCCCCCCCCCCCCCTTCTTCTCTCTACCCCTCCCTCCACCTCATAAATAC
(21)    TCCCCCCCCCCCCCCCCCCCCTTCTTCTCTCTACCCCTCCCTCCACCTCATAAATAC
(21)    TCCCCCCCCCC------------TTCTTCTCTCTACCCCTCCCTCCACCTCATAAATAC
(21)    TCCCCCCCCCCCCCCCCCCCCTTCTTCTCTCTACCCCTCCCTCCACCTCATAAATAC
(21)    TCCCCCCCCCCCCCCCCCCCCTTCTTCTCTCTACCCCTCCCTCCACCTCATAAATAC
(21)    TCCCCCCCCCCCCCCCCCCCCTTCTTCTCTCTACCCCTCCCTCCACCTCATAAATAC

(78)    TTAGTTTAATAACCTTGCACTGCCGCAGTAGCCCTTAACTGCTGCTATCTATCTCTT
(78)    TTAGTTTAATAACCTTGCACTGCCGCAGTAGCCCTTAACTGCTGCTATCTATCTCTT
(67)    TTAGTTTAATAACCTTGCACTGCCGCAGTAGCCCTTAACTGCTGCTATCTATCTCTT
(78)    TTAGTTTAATAACCTTGCACTGCCGCAGTAGCCCTTAACTGCTGCTATCTATCTCTT
(78)    TTAGTTTAATAACCTTGCACTGCCGCAGTAGCCCTTAACTGCTGCTATCTATCTCTT
(78)    TTAGTTTAATAACCTTGCACTGCCGCAGTAGCCCTTAACTGCTGCTATCTATCTCTT (135)   TTCTGAAGGAAAAAAAAGTTCAGCGCGCAGTTAAGCATAGCAGGACGACCACGACGA
(135)   TTCTGAAGGAAAAAAAAGTTCAGCGCGCAGTTAAGCATAGCAGGACGACCACGACGA
(124)   TTCTGAAGGAAAAAAAAGTTCAGCGCGCAGTTAAGCATAGCAGGACGACCACGACGA
(135)   TTCTGAAGGAAAAAAAAGTTCAGCGCGCAGTTAAGCATAGCAGGACGACCACGACGA
(135)   TTCTGAAGGAAAAAAAAGTTCAGCGCGCAGTTAAGCATAGCAGGACGACCACGACGA
(135)   TTCTGAAGGAAAAAAAAGTTCAGCGCGCAGTTAAGCATAGCAGGACGACCACGACGA
                                                              START
(192)   TGTATCACCCGCAGTGCGAGCTCCTGACGATGGCGCACGAAACGCCGGACCTGGACG
(192)   TGTATCACCCGCAGTGCGAGCTCCTGACGATGGCGCACGAAACGCCGGACCTGGACG
(181)   TGTATCACCCGCAGTGCGAGCTCCTGACGATGGCGCACGAAACGCCGGACCTGGACG
(192)   TGTATCACCCGCAGTGCGAGCTCCTGACGATGGCGCACGAAACGCCGGACCTGGACG
(192)   TGTATCACCCGCAGTGCGAGCTCCTGACGATGGCGCACGAAACGCCGGACCTGGACG
(192)   TGTATCACCCGCAGTGCGAGCTCCTGACGATGGCGCACGAAACGCCGGACCTGGACG (249)   CCGGCCAGCCGCACCTAACCGTCTCCGGCGTCGCCAGCATCCCGGCAGAGCTGAGCT
(249)   CCGGCCAGCCGCACCTAACCGTCTCCGGCGTCGCCAGCATCCCGGCAGAGCTGAGCT
(238)   CCGGCCAGCCGCACCTAACCGTCTCCGGCGTCGCCAGCATCCCGGCAGAGCTGAGCT
(249)   CCGGCCAGCCGCACCTAACCGTCTCCGGCGTCGCCAGCATCCCGGCAGAGCTGAGCT
(249)   CCGGCCAGCCGCACCTAACCGTCTCCGGCGTCGCCAGCATCCCGGCAGAGCTGAGCT
(249)   CCGGCCAGCCGCACCTAACCGTCTCCGGCGTCGCCAGCATCCCGGCAGAGCTGAGCT
```

Fig. 8

```
(306)  TCCACCTGCTGCACTCGCTCGACGCCGCGGCGGCGGTCAATCCCGTCACGGCGCCGC
(306)  TCCACCTGCTGCACTCGCTCGACGCCGCGGCGGCGGTCAATCCCGTCACGGCGCCGC
(295)  TCCACCTGCTGCACTCGCTCGACGCCGCGGCGGCGGTCAATCCCGTCACGGCGCCGC
(306)  TCCACCTGCTGCACTCGCTCGACGCCGCGGCGGCGGTCAATCCCGTCACGGCGCCGC
(306)  TCCACCTGCTGCACTCGCTCGACGCCGCGGCGGCGGTCAATCCCGTCACGGCGCCGC
(306)  TCCACCTGCTGCACTCGCTCGACGCCGCGGCGGCGGTCAATCCCGTCACGGCGCCGC (363)  CGCAGTCCACCATCGACTACTTCCTCGGCGGCGCCGATCCCCACCAGCAGGCCATGC
(363)  CGCAGTCCACCATCGACTACTTCCTCGGCGGCGCCGATCCCCACCAGCAGGCCATGC
(352)  CGCAGTCCACCATCGACTACTTCCTCGGCGGCGCCGATCCCCACCAGCAGGCCATGC
(363)  CGCAGTCCACCATCGACTACTTCCTCGGCGGCGCCGATCCCCACCAGCAGGCCATGC
(363)  CGCAGTCCACCATCGACTACTTCCTCGGCGGCGCCGATCCCCACCAGCAGGCCATGC
(363)  CGCAGTCCACCATCGACTACTTCCTCGGCGGCGCCGATCCCCACCAGCAGGCCATGC (420)  AGTACGAGCCGCTGCCGCCCGCCGCGGGCGGCCACCACCAGTACACCATGGACATGT
(420)  AGTACGAGCCGCTGCCGCCCGCCGCGGGCGGCCACCACCAGTACACCATGGACATGT
(409)  AGTACGAGCCGCTGCCGCCCGCCGCGGGCGGCCACCACCAGTACACCATGGACATGT
(420)  AGTACGAGCCGCTGCCGCCCGCCGCGGGCGGCCACCACCAGTACACCATGGACATGT
(420)  AGTACGAGCCGCTGCCGCCCGCCGCGGGCGGCCACCACCAGTACACCATGGACATGT
(420)  AGTACGAGCCGCTGCCGCCCGCCGCGGGCGGCCACCACCAGTACACCATGGACATGT
                  *  (DAS-CMS22)
(477)  TCCGCGACTACTGCGACGGCCACTACCCCACCGCCGAGCCGTACATCCGCGGGACAA
(477)  TCCGCGACTACTGCGACGGCCACTACCCCACCGCCGAGCCGTACATCCGCGGGACAA
(466)  TCCGCGACTACTGCGACGGCCACTACCCCACCGCCGAGCCGTACATCCGCGGGACAA
(477)  TCCGCGACTACTGCGACGGCAACTACCCCACCGCCGAGCCGTACATCCGCGGGACAA
(477)  TCCGCGACTACTGCGACGGCAACTACCCCACCGCCGAGCCGTACATCCGCGGGACAA
(477)  TCCGCGACTACTGCGACGGCAACTACCCCACCGCCGAGCCGTACATCCGCGGGACAA
                                            (DAS-CMS23)  ***
(534)  TGACTGGAGCCCTCGTGTTCGGGGCCACCGACGACGACGACTCGGCCGCTGCC--GT
(534)  TGACTGGAGCCCTCGTGTTCGGGGCCACCGACGACGACGACTCGGCCGCTGCC--GT
(523)  TGACTGGAGCCCTCGTGTTCGGGGCCACCGACGACGACGACTCGGCCGCTGCC--GT
(534)  TGACTGGAGCCCTCGTGTTCGGGGCCACCGACGACGACGACTCGGCCGCTGCCGCCT
(534)  TGACTGGAGCCCTCGTGTTCGGGGCCACCGACGACGACGACTCGGCCGCTGCCGCCT
(534)  TGACTGGAGCCCTCGTGTTCGGGGCCACCGACGACGACGACTCGGCCGCTGCCGCCT (585)  ACATGCCCGGGGGGCACTTTGAGACCTCCCCGCCGCCGCCACGCGCCACCGGCCGCG
(585)  ACATGCCCGGGGGGCACTTTGAGACCTCCCCGCCGCCGCCACGCGCCACCGGCCGCG
(574)  ACATGCCCGGGGGGCACTTTGAGACCTCCCCGCCGCCGCCACGCGCCACCGGCCGCG
(588)  ACATGCCCGGGGGGCACTTTGAGACCTCCCCGCCGCCGCCACGCGCCACCGGCCGCG
(588)  ACATGCCCGGGGGGCACTTTGAGACCTCCCCGCCGCCGCCACGCGCCACCGGCCGCG
(588)  ACATGCCCGGGGGGCACTTTGAGACCTCCCCGCCGCCGCCACGCGCCACCGGCCGCG
```

Fig. 8 Cont.

```
(642)  GCAGGAAGCGGGGCAGGGCGCTGGGCGGCGGCTTCCATGCTGTGCTGGCCAACGGCG
(642)  GCAGGAAGCGGGGCAGGGCGCTGGGCGGCGGCTTCCATGCTGTGCTGGCCAACGGCG
(631)  GCAGGAAGCGGGGCAGGGCGCTGGGCGGCGGCTTCCATGCTGTGCTGGCCAACGGCG
(645)  GCAGGAAGCGGGGCAGGGCGCTGGGCGGCGGCTTCCATGCTGTGCTGGCCAACGGCG
(645)  GCAGGAAGCGGGGCAGGGCGCTGGGCGGCGGCTTCCATGCTGTGCTGGCCAACGGCG
(645)  GCAGGAAGCGGGGCAGGGCGCTGGGCGGCGGCTTCCATGCTGTGCTGGCCAACGGCG
                                          (DAS-CMS34)  *
(699)  TCGAGAAGAAGGAGAAGCAGCGCCGGCTGCGGCTCACCGAGAAGTACACCGCCCTCA
(699)  TCGAGAAGAAGGAGAAGCAGCGCCGGCTGCGGCTCACCGAGAAGTACACCGCCCTCA
(688)  TCGAGAAGAAGGAGAAGCAGCGCCGGCTGCGGCTCACCGAGAAGTACACCGCCCTCA
(702)  TCGAGAAGAAGGAGAAGCAGCGCCGGCTGCGGCTCACCGAGAAGTTTACGGCCCTCA
(702)  TCGAGAAGAAGGAGAAGCAGCGCCGGCTGCGGCTCACCGAGAAGTTTACGGCCCTCA
(702)  TCGAGAAGAAGGAGAAGCAGCGCCGGCTGCGGCTCACCGAGAAGTTTACGGCCCTCA
                 *  (DAS-CMS29)
(756)  TGCACCTCATACCCAACGTTACAAAGACTGATAGGGCGACGGTGATCTCGGACGCGA
(756)  TGCACCTCATACCCAACGTTACAAAGACTGATAGGGCGACGGTGATCTCGGACGCGA
(745)  TGCACCTCATACCCAACGTTACAAAGACTGATAGGGCGACGGTGATCTCGGACGCGA
(759)  TGCACCTCATACCCAACGTTACGAAGACTGATAGGGCGACGGTGATCTCGGACGCGA
(759)  TGCACCTCATACCCAACGTTACGAAGACTGATAGGGCGACGGTGATCTCGGACGCGA
(759)  TGCACCTCATACCCAACGTTACGAAGACTGATAGGGCGACGGTGATCTCGGACGCGA (813)  TCGAGTACATCCAGGAGCTGGGGAGGACGGTGGAGGAGCTGACGCTGCTGGTGGAGA
(813)  TCGAGTACATCCAGGAGCTGGGGAGGACGGTGGAGGAGCTGACGCTGCTGGTGGAGA
(802)  TCGAGTACATCCAGGAGCTGGGGAGGACGGTGGAGGAGCTGACGCTGCTGGTGGAGA
(816)  TCGAGTACATCCAGGAGCTGGGGAGGACGGTGGAGGAGCTGACGCTGCTGGTGGAGA
(816)  TCGAGTACATCCAGGAGCTGGGGAGGACGGTGGAGGAGCTGACGCTGCTGGTGGAGA
(816)  TCGAGTACATCCAGGAGCTGGGGAGGACGGTGGAGGAGCTGACGCTGCTGGTGGAGA (870)  AGAAGCGGCGCCGGAGGGAGCTGCAGGGGGACGTCGTGGACGCGGCGCCGGCTGCGG
(870)  AGAAGCGGCGCCGGAGGGAGCTGCAGGGGGACGTCGTGGACGCGGCGCCGGCTGCGG
(859)  AGAAGCGGCGCCGGAGGGAGCTGCAGGGGGACGTCGTGGACGCGGCGCCGGCTGCGG
(873)  AGAAGCGGCGCCGGAGGGAGCTGCAGGGGGACGTCGTGGACGCGGCGCCGGCTGCGG
(873)  AGAAGCGGCGCCGGAGGGAGCTGCAGGGGGACGTCGTGGACGCGGCGCCGGCTGCGG
(873)  AGAAGCGGCGCCGGAGGGAGCTGCAGGGGGACGTCGTGGACGCGGCGCCGGCTGCGG (927)  TGGTTGCTGCCGCCGGTGAGGCGGAGAGCTCGGAGGGCGAGGTGGCTCCTCCGCCGC
(927)  TGGTTGCTGCCGCCGGTGAGGCGGAGAGCTCGGAGGGCGAGGTGGCTCCTCCGCCGC
(916)  TGGTTGCTGCCGCCGGTGAGGCGGAGAGCTCGGAGGGCGAGGTGGCTCCTCCGCCGC
(930)  TGGTTGCTGCCGCCGGTGAGGCGGAGAGCTCGGAGGGCGAGGTGGCTCCTCCGCCGC
(930)  TGGTTGCTGCCGCCGGTGAGGCGGAGAGCTCGGAGGGCGAGGTGGCTCCTCCGCCGC
(930)  TGGTTGCTGCCGCCGGTGAGGCGGAGAGCTCGGAGGGCGAGGTGGCTCCTCCGCCGC
```

Fig. 8 Cont.

```
          * (DAS-CMS28)
 (984)  CGGCCGTGCCGCGGCAGCCGATCCGGAGCACGTACATCCAGCGGCGGAGCAAGGACA
 (984)  CGGCCGTGCCGCGGCAGCCGATCCGGAGCACGTACATCCAGCGGCGGAGCAAGGACA
 (973)  CGGCCGTGCCGCGGCAGCCGATCCGGAGCACGTACATCCAGCGGCGGAGCAAGGACA
 (987)  TGGCCGTGCCGCGGCAGCCGATCCGGAGCACGTACATCCAGCGGCGGAGCAAGGACA
 (987)  TGGCCGTGCCGCGGCAGCCGATCCGGAGCACGTACATCCAGCGGCGGAGCAAGGACA
 (987)  TGGCCGTGCCGCGGCAGCCGATCCGGAGCACGTACATCCAGCGGCGGAGCAAGGACA (1041)  CGTCCGTGGACGTGCGGATCGTGGAGGAGGACGTGAACATCAAGCTCACCAAGCGCC
(1041)  CGTCCGTGGACGTGCGGATCGTGGAGGAGGACGTGAACATCAAGCTCACCAAGCGCC
(1030)  CGTCCGTGGACGTGCGGATCGTGGAGGAGGACGTGAACATCAAGCTCACCAAGCGCC
(1044)  CGTCCGTGGACGTGCGGATCGTGGAGGAGGACGTGAACATCAAGCTCACCAAGCGCC
(1044)  CGTCCGTGGACGTGCGGATCGTGGAGGAGGACGTGAACATCAAGCTCACCAAGCGCC
(1044)  CGTCCGTGGACGTGCGGATCGTGGAGGAGGACGTGAACATCAAGCTCACCAAGCGCC
                                                    * (DAS-CMS29)
(1098)  GGCGCGACGGGTGCCTCGCAGCCGCGTCGCGCGCGCTGGATGACCTCCGCCTTGACC
(1098)  GGCGCGACGGGTGCCTCGCAGCCGCGTCGCGCGCGCTGGATGACCTCCGCCTTGACC
(1087)  GGCGCGACGGGTGCCTCGCAGCCGCGTCGCGCGCGCTGGATGACCTCCGCCTTGACC
(1101)  GGCGCGACGGGTGCCTCGCAGCCGCGTCGCGCGCGCTGGACGACCTCCGCCTTGACC
(1101)  GGCGCGACGGGTGCCTCGCAGCCGCGTCGCGCGCGCTGGACGACCTCCGCCTTGACC
(1101)  GGCGCGACGGGTGCCTCGCAGCCGCGTCGCGCGCGCTGGACGACCTCCGCCTTGACC (1155)  TCGTCCACCTCTCCGGCGGCAAGATCGGTGACTGTCAAATCTACATGTTCAACACCA
(1155)  TCGTCCACCTCTCCGGCGGCAAGATCGGTGACTGTCAAATCTACATGTTCAACACCA
(1144)  TCGTCCACCTCTCCGGCGGCAAGATCGGTGACTGTCAAATCTACATGTTCAACACCA
(1158)  TCGTCCACCTCTCCGGCGGCAAGATCGGTGACTGTCAAATCTACATGTTCAACACCA
(1158)  TCGTCCACCTCTCCGGCGGCAAGATCGGTGACTGTCAAATCTACATGTTCAACACCA
(1158)  TCGTCCACCTCTCCGGCGGCAAGATCGGTGACTGTCAAATCTACATGTTCAACACCA (1212)  AGATTCACAAGGGGTCTTCAGTGTTTGCGAGTGCAGTGGCCGGTAGGCTGATGGAAG
(1212)  AGATTCACAAGGGGTCTTCAGTGTTTGCGAGTGCAGTGGCCGGTAGGCTGATGGAAG
(1201)  AGATTCACAAGGGGTCTTCAGTGTTTGCGAGTGCAGTGGCCGGTAGGCTGATGGAAG
(1215)  AGATTCACAAGGGGTCTTCAGTGTTTGCGAGTGCAGTGGCCGGTAGGCTGATGGAAG
(1215)  AGATTCACAAGGGGTCTTCAGTGTTTGCGAGTGCAGTGGCCGGTAGGCTGATGGAAG
(1215)  AGATTCACAAGGGGTCTTCAGTGTTTGCGAGTGCAGTGGCCGGTAGGCTGATGGAAG
                      STOP
(1269)  TGGTGGACGAGTACTAGGCTACCATGCACTTGAATTTCTAGCTAGCTCTACGTACCG
(1269)  TGGTGGACGAGTACTAGGCTACCATGCACTTGAATTTCTAGCTAGCTCTACGTACCG
(1258)  TGGTGGACGAGTACTAGGCTACCATGCACTTGAATTTCTAGCTAGCTCTACGTACCG
(1272)  TGGTGGACGAGTACTAGGCTACCATGCACTTGAATTTCTAGCTAGCTCTACGTACCG
(1272)  TGGTGGACGAGTACTAGGCTACCATGCACTTGAATTTCTAGCTAGCTCTACGTACCG
(1272)  TGGTGGACGAGTACTAGGCTACCATGCACTTGAATTTCTAGCTAGCTCTACGTACCG
```

Fig. 8 Cont.

* (DAS-CMS31)
(1326) CGCTGCTATGAATCTAGCTATAGCGTTTCTTGGATGAAAGACTAGTTAGTTGTTACC
(1326) CGCTGCTATGAATCTAGCTATAGCGTTTCTTGGATGAAAGACTAGTTAGTTGTTACC
(1315) CGCTGCTATGAATCTAGCTATAGCGTTTCTTGGATGAAAGACTAGTTAGTTGTTACC
(1329) CGCTGCTATGAATCTAGCTATAGCGTTTCTTGGATGAAAGAATAGTTAGTTGTTACC
(1329) CGCTGCTATGAATCTAGCTATAGCGTTTCTTGGATGAAAGAATAGTTAGTTGTTACC
(1329) CGCTGCTATGAATCTAGCTATAGCGTTTCTTGGATGAAAGAATAGTTAGTTGTTACC (1383) TTCTATCTTTGCTTCAATTAAATCCGCTTGCTCGTTACAGACTGAGTTTGTTTCTAA
(1383) TTCTATCTTTGCTTCAATTAAATCCGCTTGCTCGTTACAGACTGAGTTTGTTTCTAA
(1372) TTCTATCTTTGCTTCAATTAAATCCGCTTGCTCGTTACAGACTGAGTTTGTTTCTAA
(1386) TTCTATCTTTGCTTCAATTAAATCCGCTTGCTCGTTACAGACTGAGTTTGTTTCTAA
(1386) TTCTATCTTTGCTTCAATTAAATCCGCTTGCTCGTTACAGACTGAGTTTGTTTCTAA
(1386) TTCTATCTTTGCTTCAATTAAATCCGCTTGCTCGTTACAGACTGAGTTTGTTTCTAA (1443) ATGTCAAGGTTGTTTTGGTCAAATTGAATAAATTGGCACACTGGCCTGTGAGG
(1443) ATGTCAAGGTTGTTTTGGTCAAATTGAATAAATTGGCACACTGGCCTGTGAGG
(1443) ATGTCAAGGTTGTTTTGGTCAAATTGAATAAATTGGCACACTGGCCTGTGAGG
(1443) ATGTCAAGGTTGTTTTGGTCAAATTGAATAAATTGGCACACTGGCCTGTGAGG
(1443) ATGTCAAGGTTGTTTTGGTCAAATTGAATAAATTGGCACACTGGCCTGTGAGG
(1443) ATGTCAAGGTTGTTTTGGTCAAATTGAATAAATTGGCACACTGGCCTGTGAGG

Fig. 8 Cont.

```
B73 rf4-bHLH    (SEQ ID NO:224)  (1)  MYHPQCELLTMAHETPDLDAGQPHLTVS
BE4207 rf4-bHLH (SEQ ID NO:224)  (1)  MYHPQCELLTMAHETPDLDAGQPHLTVS
B104 bHLH       (SEQ ID NO:224)  (1)  MYHPQCELLTMAHETPDLDAGQPHLTVS
XJH58 Rf4-bHLH  (SEQ ID NO:225)  (1)  MYHPQCELLTMAHETPDLDAGQPHLTVS
BE9515 Rf4-bHLH (SEQ ID NO:225)  (1)  MYHPQCELLTMAHETPDLDAGQPHLTVS
MLW03 Rf4-bHLH  (SEQ ID NO:225)  (1)  MYHPQCELLTMAHETPDLDAGQPHLTVS

(29)  GVASIPAELSFHLLHSLDAAAAVNPVTAPPQSTIDYFLGGADPHQQAMQYEPLPPAA
               (29)  GVASIPAELSFHLLHSLDAAAAVNPVTAPPQSTIDYFLGGADPHQQAMQYEPLPPAA
               (29)  GVASIPAELSFHLLHSLDAAAAVNPVTAPPQSTIDYFLGGADPHQQAMQYEPLPPAA
               (29)  GVASIPAELSFHLLHSLDAAAAVNPVTAPPQSTIDYFLGGADPHQQAMQYEPLPPAA
               (29)  GVASIPAELSFHLLHSLDAAAAVNPVTAPPQSTIDYFLGGADPHQQAMQYEPLPPAA
               (29)  GVASIPAELSFHLLHSLDAAAAVNPVTAPPQSTIDYFLGGADPHQQAMQYEPLPPAA
                                  * (DAS-CMS22)              * (DAS-CMS23)
               (86)  GGHHQYTMDMFRDYCDGHYPTAEPYIRGTMTGALVFGATDDDDS-AAAYMPGGHFET
               (86)  GGHHQYTMDMFRDYCDGHYPTAEPYIRGTMTGALVFGATDDDDS-AAAYMPGGHFET
               (86)  GGHHQYTMDMFRDYCDGHYPTAEPYIRGTMTGALVFGATDDDDS-AAAYMPGGHFET
               (86)  GGHHQYTMDMFRDYCDGNYPTAEPYIRGTMTGALVFGATDDDDSAAAAYMPGGHFET
               (86)  GGHHQYTMDMFRDYCDGNYPTAEPYIRGTMTGALVFGATDDDDSAAAAYMPGGHFET
               (86)  GGHHQYTMDMFRDYCDGNYPTAEPYIRGTMTGALVFGATDDDDSAAAAYMPGGHFET
                            NLS                          bHLH Domain
              (142)  SPPPPRATGRGRKRGRALGGGFHAVLANGVEKKEKQRRLRLTEKYTALMHLIPNVTK
              (142)  SPPPPRATGRGRKRGRALGGGFHAVLANGVEKKEKQRRLRLTEKYTALMHLIPNVTK
              (142)  SPPPPRATGRGRKRGRALGGGFHAVLANGVEKKEKQRRLRLTEKYTALMHLIPNVTK
              (143)  SPPPPRATGRGRKRGRALGGGFHAVLANGVEKKEKQRRLRLTEKFTALMHLIPNVTK
              (143)  SPPPPRATGRGRKRGRALGGGFHAVLANGVEKKEKQRRLRLTEKFTALMHLIPNVTK
              (143)  SPPPPRATGRGRKRGRALGGGFHAVLANGVEKKEKQRRLRLTEKFTALMHLIPNVTK
                                                  NLS
              (199)  TDRATVISDAIEYIQELGRTVEELTLLVEKKRERRELQGDVVDAAPAAVVAAAGEAE
              (199)  TDRATVISDAIEYIQELGRTVEELTLLVEKKRERRELQGDVVDAAPAAVVAAAGEAE
              (199)  TDRATVISDAIEYIQELGRTVEELTLLVEKKRERRELQGDVVDAAPAAVVAAAGEAE
              (200)  TDRATVISDAISYIQELGRTVEELTLLVEKKRRRELQGDVVDAAPAAVVAAAGEAE
              (200)  TDRATVISDAIEYIQELGRTVEELTLLVEKKRRRELQGDVVDAAPAAVVAAAGEAE
              (200)  TDRATVISDAIEYIQELGRTVEELTLLVEKKRRRELQGDVVDAAPAAVVAAAGEAE
                           * (DAS-CMS28)
              (256)  SSEGEVAPPPPAVPRQPIRSTYIQRRSKDTSVDVRIVEEDVNIKLTKRRRDGCLAAA
              (256)  SSEGEVAPPPPAVPRQPIRSTYIQRRSKDTSVDVRIVEEDVNIKLTKRRRDGCLAAA
              (256)  SSEGEVAPPPPAVPRQPIRSTYIQRRSKDTSVDVRIVEEDVNIKLTKRRRDGCLAAA
              (257)  SSEGEVAPPPLAVPRQPIRSTYIQRRSKDTSVDVRIVEEDVNIKLTKRRRDGCLAAA
              (257)  SSEGEVAPPPLAVPRQPIRSTYIQRRSKDTSVDVRIVEEDVNIKLTKRRRDGCLAAA
              (257)  SSEGEVAPPPLAVPRQPIRSTYIQRRSKDTSVDVRIVEEDVNIKLTKRRRDGCLAAA
```

Fig. 9

```
(313)  SRALDDLRLDLVHLSGGKIGDCQIYMFNTKIHKGSSVFASAVAGRLMEVVDEY
(313)  SRALDDLRLDLVHLSGGKIGDCQIYMFNTKIHKGSSVFASAVAGRLMEVVDEY
(313)  SRALDDLRLDLVHLSGGKIGDCQIYMFNTKIHKGSSVFASAVAGRLMEVVDEY
(314)  SRALDDLRLDLVHLSGGKIGDCQIYMFNTKIHKGSSVFASAVAGRLMEVVDEY
(314)  SRALDDLRLDLVHLSGGKIGDCQIYMFNTKIHKGSSVFASAVAGRLMEVVDEY
(314)  SRALDDLRLDLVHLSGGKIGDCQIYMFNTKIHKGSSVFASAVAGRLMEVVDEY
```

Fig. 9 Cont.

```
XJH58 Rf4-bHLH      (SEQ ID NO:225)  (1) MYHPQCELLTMAHETPDLDAG--QP
BE4207 rf4-bHLH     (SEQ ID NO:224)  (1) MYHPQCELLTMAHETPDLDAG--QP
BRADI2G11260 bHLH   (SEQ ID NO:226)  (1) MYHPQCELL-MPHESLDMDAVVGQS
Sb03g011940 bHLH    (SEQ ID NO:227)  (1) MYHPQCELL-MAHEAQDLDAAGQPH
Os01g11870 bHLH     (SEQ ID NO:228)  (1) MYHPQCELL-MPLESLEMD--VGQS

(24)  HLTVSGVA-SIPAELSFHLLHSLDAAAAVNPVTAFP---QSTIDYFL--GGADPHQ-
 (24)  HLTVSGVA-SIPAELSFHLLHSLDAAAAVNPVTAFP---QSTIDYFL--GGADPHQ-
 (25)  HLAASGVS-AIPAELNFHLLHHSFVDTAASP------QPPTVDYFFGGTD---PPP
 (25)  HLAVSGVAGSIPAELSFHLLHSLDATAAVNNSVTP----QSTIDYFLGVGGADPHQP
 (23)  HLAAAVAA-AMPQELNFHLLHSLDAAAAAASSTAASASSSQPTVDYFFGGADQQPPFP
                                  *   (N/H)
 (74)  QAMQYEPLPPAAGGHHQYTMDMFRDYCD------GNYPTAEPYIRG-----TMTGA
 (74)  QAMQYEPLPPAAGGHHQYTMDMFRDYCD------GHYPTAEPYIRG-----TMTGA
 (71)  AAVQFPQL---AATNHH-AMSMLRDYY------GQQYPAETYLRGGFRTTTGSGG
 (78)  AALQYEPLPPPGG-HHQHTMNMLRDYCSNGGG--GGHYPTAEPYLRG-----TPTGA
 (79)  AAMQYDQL----AAPHHHQTVAMLRDYYGGRYPPAAAAAAATEAYFRGGP-RTAGSSS
                   *   (A/-)
(119)  LVFGATDDDDRAAAAYMPGGHFETSPPPPRATGEGRKRGRALGGGFHAVLANGVEKK
(119)  LVFGATDDDDS-AAAYMPGGHFETSPPPPRATGEGRKRGRALGGGFHAVLANGVEKK
(116)  LVFGVAHDDES---AAYNMVGPFVESSPTTRAAG-GGRKRNRGSRAAGGPANGGVEKK
(128)  LVFGATDDDSS-AAAYMPGGPFVETSPPPRATG-GRKRGRALGGGFHAGLANGVEKK
(132)  LVFGPADDDES-----APMVGPFE-SSPTPRSGG-GRKRSRATAGFHGGGPANGVEKK
                   *   (F/Y)
(176)  EKQRRLRLTEKFTALMHLIPNVTKTDRATVISDAIEYIQELGRTVEELTLLVEKKRR
(175)  EKQRRLRLTEKYTALMHLIPNVTKTDRATVISDAIEYIQELGRTVEELTLLVEKKRR
(170)  EKQRRLRLTEKYTALMLLIPNRTKEDRATVISDAIEYIQELGRTVEELTLLVQKKRR
(183)  EKQRQELTEKYTALMHLIPNVTKPDRATVISDAIEYIQELGRTVEELTLLVEKKRR
(182)  EKQERDRLTEKYNALMLLIPNRTKEDRATVISDAIEYIQELGRTVEELTLLVEKKRR
                                                   (L/P) *
(233)  RE------ELQGDVVDAAPAAVVAAAG----EAESSE-------GEVAPPPE---AV
(232)  RE------ELQGDVVDAAPAAVVAAAG----EAESSE-------GEVAPPPE---AV
(227)  RNGAGEHHLHQGDVVDAAPAVGAAGELVLAAESSEG--------EVQAPLAAL---
(240)  RR------ELQGDVVDAAPTAVVVAAAATGGEAESSE-------GEVAPPPPPAAV
(239)  RR------EMQGDVVDAATSSVVAGMDQAAE-SSEGEVMAAAAMGAVAPPPRQ---

(270)  PKQPIRSTYIQRRSKDTSVDVRIVEEDVNIKLTKERRDGCLAAASRALDDLRLDLVH
(269)  PRQPIRSTYIQRRSKDTSVDVRIVEEDVNIKLTKERRDGCLAAASRALDDLRLDLVH
(272)  --QPIRSTYIQRRSKETFVDVRIVEDEVNIKLTKERRDGCLAAASRALDDLRLDLVH
(284)  QRQPIRSTYIQRRSKDTSVDVRIVEEDVNIKLTKRRRDGCLAAASRALDDLRLDLVH
(285)  --APIRSTYIQRRSKETFVDVRIVEDDVNIKLTKRRRDGCLAAASRALDDLRLDLVH
```

Fig. 11

```
(327)  LSGGKIGDCQIYMFNTKIHKGSSVFASAVAGRLMEVVDEY
(326)  LSGGKIGDCQIYMFNTKIHKGSSVFASAVAGRLMEVVDEY
(327)  LSGGKIGDCHIYMFNTKIHQGSPVFASAVASKLIEVVDEY
(341)  LSGGKIGDCHIYMFNTKIHKGSSVFASAVASRLMEVVDEY
(340)  LSGGKIGDCHIYMFNTKIHSGSPVFASAVASRLIEVVDEY
```

Fig. 11 Cont.

ized as CMS-T (Texas), CMS-S (USDA) and CMS-C (Charrua). Beckett (1971). In the CMS-T group, two dominant genes, Rf1 and Rf2, which are located on chromosomes 3 and 9, respectively, are required for the restoration of pollen fertility. Duvick (1965) Adv. Genetics 13:1-56. The S-cytoplasm is restored by a single gene, Rf3, which has been mapped on chromosome 2. Laughnan and Gabay (1978) "Nuclear and cytoplasmic
MAIZE CYTOPLASMIC MALE STERILITY (CMS) C-TYPE RESTORER RF4 GENE, MOLECULAR MARKERS AND THEIR USE

CROSS-REFERENCE TO RELATED APPLICATIONS

This application claims benefit to U.S. Provisional Patent Application No. 61/390,526, filed Oct. 6, 2010. The contents of the entirety of each of the foregoing are hereby incorporated herein by this reference.

FIELD OF THE DISCLOSURE

The present disclosure relates to plant fertility genes. In some embodiments, the disclosure relates to Rf4, a maize restorer of fertility gene. In particular embodiments, the disclosure relates to compositions and methods for restoring fertility to C-type cytoplasmic male sterility (CMS-C), for example, by using molecular markers linked to, or residing within, the Rf4 gene. Particular embodiments relate to methods for using particular nucleic acid sequences to identify plants that contain restorer of fertility to CMS-C, and for hybrid seed production. Some particular embodiments relate to polypeptides associated with restoration of fertility to CMS-C.

BACKGROUND

The development of hybrid plant breeding has made possible considerable advances in quality and quantity of crops produced. Increased yield and the combination of desirable characteristics, such as resistance to disease and insects, heat and drought tolerance, and variations in plant composition are all possible, in part, due to hybridization procedures. Hybridization procedures rely on the contribution of pollen from a male parent plant to a female parent plant to produce the resulting hybrid.

Plants may self-pollinate if pollen from one flower is transferred to the same or another flower of the same plant. Plants may cross-pollinate if the pollen originates in a flower from a different plant. Maize plants (*Zea mays*) may be bred by both self-pollination and cross-pollination techniques. Maize plants have male flowers, which are located on the tassel, and female flowers, which are located on the ear of the same plant. Natural pollination in maize occurs when pollen from the tassels reaches the silks that are found at the tops of the incipient ears. The development of maize hybrids relies upon male sterility systems.

The development of maize hybrids requires the development of homozygous inbred lines, the crossing of these lines, and the evaluation of the crosses. Pedigree breeding and recurrent selection are two breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics absent in one, or complementing the other. The new inbred plants are crossed with other inbred lines and the hybrids from these crosses are evaluated to determine which are desirable. The hybrid progeny from the first generation are designated $F_1$. In the development of hybrids, only the $F_1$ hybrids are sought. The $F_1$ hybrid is typically more vigorous than its inbred parents. This hybrid vigor, termed heterosis, typically leads to, for example, increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from foreign maize pollen, the ears of the female inbred will be fertilized only with pollen from the male inbred. The resulting seed is hybrid $F_1$ seed.

Manual detasseling is labor-intensive and costly. Manual detasseling is also often ineffective, for example, because environmental variation in plant development can result in plants tasseling after manual detasseling of the female parent plant is completed, or because a detasseler might not completely remove the tassel of a female inbred plant. If detasseling is ineffective, the female plant will successfully shed pollen and some female plants will be self-pollinated. This will result in seed of the female inbred being harvested along with the hybrid seed which is normally produced. Female inbred see is not as productive as $F_1$ seed. In addition, the presence of female inbred seed can represent a germplasm security risk for the producer of the hybrid seed.

A female inbred plant can also be mechanically detasseled by a machine. Mechanical detasseling is approximately as reliable as hand detasseling, but is faster and less expensive. However, most detasseling machines produces more damage to the plants than hand detasseling. Thus, no form of detasseling is presently entirely satisfactory.

Genetic male sterility is an alternative method that may be used in hybrid seed production. The laborious detasseling process can be avoided in some genotypes by using cytoplasmic male-sterile (CMS) inbred plants. In the absence of a fertility restorer gene, plants of a CMS inbred are male sterile as a result of factors resulting from the cytoplasmic, as opposed to the nuclear genome. Therefore, the characteristic of male sterility is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to ensure cytoplasmic diversity.

Drawbacks to CMS as a system for the production of hybrid seed include the association of specific variants to CMS with susceptibility to certain crop diseases. See, e.g., Beckett (1971) Crop Science 11:724-6. This problem has specifically discouraged the use of the CMS-T variant in the production of hybrid maize seed, and has had a negative impact on the use of CMS in maize in general.

Cytoplasmic male sterility (CMS) is the maternally inherited inability to produce functional pollen. More than 40 sources of CMS have been found and classified into three major groups by differential fertility restoration reactions in maize. These groups are designated as CMS-T (Texas), CMS-S (USDA) and CMS-C (Charrua). Beckett (1971). In the CMS-T group, two dominant genes, Rf1 and Rf2, which are located on chromosomes 3 and 9, respectively, are required for the restoration of pollen fertility. Duvick (1965) Adv. Genetics 13:1-56. The S-cytoplasm is restored by a single gene, Rf3, which has been mapped on chromosome 2. Laughnan and Gabay (1978) "Nuclear and cytoplasmic mutations to fertility in S male-sterile maize," in *Maize Breeding and Genetics*, pp. 427-446.

Compared to CMS-T and CMS-S, the fertility restoration of CMS-C has been found to be very complex in previous analyses. Duvick (1972), "Potential usefulness of new cytoplasmic male sterile and sterility system," in *Proceeding of the 27th annual corn and sorghum research conference*, pp. 197-201, found that full restoration of fertility in CMS-C is controlled by a dominant allele of Rf4 gene. Khey-Pour et al. (1981) also found this gene to be sufficient for CMS-C restoration. However, Josephson et al. (1978), "Genetics and inheritance of fertility restoration of male sterile cytoplasms in corn," in *Proceedings of the 33rd corn and sorghum research conference* 7:13, proposed that full restoration of fertility in CMS-C was conditioned by the complementary action of the dominant alleles of two genes, Rf4 and Rf5, which have since been mapped to chromosomes 8 and 5, respectively. Sisco (1991) Crop Sci. 31:1263-6. Meanwhile, Chen et al. (1979) Acta Agronom. Sin. 5(4):21-28, considered that two dominant restorer genes in CMS-C had duplicate functions. Further complicating the system, Vidakovic (1988), Maydica 33:51-65, demonstrated the existence of three dominant and complementary genes for full restoration of fertility in CMS-C, adding the gene, Rf6. Vidakovic et al., (1997a) Maize Genet. Coop. News Lett. 71:10; (1997b) Maydica 42:313-6, later reported these complementary genes, Rf4, Rf5, and Rf6, were indeed not the sole genetic systems for fertility restoration in CMS-C of maize. Thus, the fertility restoration mechanisms of CMS-C remain unresolved. As a result, it is difficult to select restorer lines for some genotypic sterile lines.

Molecular markers are particularly useful for accelerating the process of introducing a gene or quantitative trait loci (QTL) into an elite cultivar or breeding line via backcrossing. Markers linked to the gene can be used to select plants possessing the desired trait, and markers throughout the genome can be used to select plants that are genetically similar to the recurrent parent (Young and Tanksley (1989) Theor. Appl. Genet. 77:95-101; Hospital et al. (1992) Genetics 132:1199-210).

Most of the plant fertility restorer genes have been cloned via a map-based cloning strategy. To date, nine Rf genes have been isolated from several plant species including maize (*Zea Mays* L.) (Cui et al. (1996) Science 272:1334-6; Liu et al. (2001) Plant Cell 13:1063-78), Petunia (*Petunia hybrida*) (Bentolila et al. (2002) Proc. Natl. Acad. Sci. USA 99:10887-92, radish (*Raphanus sativus* L.) (Brown et al. (2003) Plant J. 35:262-72; Desloire et al. (2003) EMBO Rep. 4:1-7; Koizuka et al. (2003) Plant J. 34:407-15), sorghum (*Sorghum bicolor* L.) (Klein et al. (2005) Theor. Appl. Genet. 111:994-1012), rice (*Oryza sativa* L.) (Kazama and Toriyama (2003) FEBS Lett. 544:99-102; Akagi et al. (2004) Theor. Appl. Genet. 108:1449-57; Komori et al. (2004) Plant J. 37:315-25; Wang et al. (2006) Plant Cell 18:676-87; and Fujii and Toriyama (2009) Proc. Natl. Acad. Sci. USA 106(23):9513-8), and monkey flower (*Mimulus guttatus*) (Barr and Fishman (2010) Genetics 184:455-65).

All of the identified restorer genes, except for Rf2 in maize and Rf17 in rice, encode different pentatricopeptide repeat (PPR) proteins. Plant genomes encode several hundred PPR proteins with many of them involved in regulating organelle gene expression. Lurin et al. (2004) Plant Cell 16:2089-103; and Schmitz-Linneweber and Small (2008) Trends Plant Sci. 12:663-70. A PPR protein contains 2 to 27 repeats of 35 amino acids, called PPR motifs. Small and Peeters, (2000) Trends Biochem. Sci. 25(2):46-7. PPR proteins are predicted to bind to RNA (Delannoy et al. (2007) Biochemical Society Transactions 35:1643-7), and many PPR proteins are targeted to mitochondria where the CMS-associated genes and products are located. Lurin et al. (2004), supra. Evidence suggest that PPR proteins bind directly to CMS transcripts. Akagi et al. (2004), supra; Gillman et al. (2007) Plant J. 49:217-27; and Kazama et al. (2008) Plant J. 55:619-28. Rf proteins reduce the expression of CMS-associated transcripts by changing their processing patterns (Kazama & Toriyama (2003), supra), decreasing RNA stability (Wang et al. (2006), supra; and Ohta et al. (2010) Plant Cell Rep. 29:359-69), or preventing them from being translated (Kazama et al. (2008), supra).

Additional information regarding restorer of fertility genes from maize, rice, petunia, and radish may be found in U.S. Patent Application Ser. No. US2006/0253931, and in U.S. Pat. Nos. 5,981,833; 5,624,842; 4,569,152; 6,951,970; 6,392,127; 7,612,251; 7,314,971; 7,017,375; 7,164,058; and 5,644,066.

BRIEF SUMMARY OF THE DISCLOSURE

Described herein is the mapping of the maize Rf4 locus to a small 12-kb region located on the top of chromosome 8. Within this region, the only likely candidate for Rf4 is a gene encoding a bHLH transcription factor. By cloning of the Rf4-bHLH locus from CMS-C, non-restorer and restorer lines, a number of sequence variations were identified. At the protein level, the CMS-C line and non-restorer lines all have the same sequence, and are different from the restorer allele (also identical to each other) by 4 amino-acid changes, including a conserved, hydrophilic tyrosine residue within the bHLH domain ($Y_{186}$) that is changed to a hydrophobic phenylalanine residue ($F_{187}$) in the restorer line.

The maize Rf4 gene and its encoded polypeptide are identified herein, and nucleic acid molecules comprising the sequence of the Rf4 gene are additionally described. Surprisingly, the Rf4 gene is not a pentatricopeptide repeat (PPR) protein gene, as are nearly all other fertility restorer genes. Furthermore, fertility restoration in the CMS-C/Rf4 system germplasm of the present invention is demonstrated to be controlled by Rf4 as a single dominant restorer gene, which was unexpected due to the recent work of several groups. See, supra. The hydrophilic tyrosine residue within the bHLH domain of maize rf4-bHLH($Y_{186}$), which is changed to a hydrophobic phenylalanine residue ($F_{187}$) in restorer lines, is conserved among monocots. Thus, the identification of the Rf4 gene and Rf4 gene markers may greatly facilitate the development and deployment of the CMS-C fertility restoration trait broadly in plant germplasm.

In embodiments, mutation of the conserved tyrosine residue at position 186 of rf4-bHLH to a hydrophobic amino acid residue (e.g., phenylalanine) is responsible for the restorer phenotype in the Rf4-bHLH polypeptide. Thus, maize Rf4-bHLH genes or orthologs of maize Rf4-bHLH genes that encode a hydrophobic amino acid residue at that position (as identified by sequence alignment) are described herein, where these genes contribute to a restorer of CMS-C phenotype when introduced into a plant.

Described herein are nucleic acid molecular markers that are linked to (e.g., linked; tightly linked; or extremely tightly linked) or that reside within the maize Rf4 gene. In some embodiments, markers that are linked to (e.g., linked; tightly linked; or extremely tightly linked) or that reside within the maize Rf4 gene, or the maize Rf4 gene sequence itself, may be used to introduce the maize Rf4 gene into organisms, for example, plants (e.g., maize and other monocots).

Also described herein are methods of using nucleic acid molecular markers that are linked to or that reside within the Rf4 gene, for example and without limitation, to identify plants with a functional restorer gene for C-type CMS; to introduce Rf4 to new plant genotypes (e.g., through marker-assisted breeding or genetic transformation); and to produce hybrid seeds from crosses of a male plant comprising nucleic acid molecular markers that are linked to or that reside within the Rf4 gene and a female plant carrying C-type CMS. Plants comprising the Rf4 functional restorer gene for C-type CMS produced by crossing a first parent plant comprising the functional restorer gene with a second parent plant will comprise genetic markers inherited from the first parent plant. For example, in embodiments where a plant comprising the Rf4 functional restorer gene has male restorer line XJH58 as a parent, the plant may comprise particular genetic markers from the XHJ58, particularly on chromosome 8, wherein the Rf4 functional restorer gene has been fine mapped herein.

Further described are means for restoring fertility to CMS-C corn, and means for identifying plants carrying a gene for restoring fertility to CMS-C corn. In some examples, a means for restoring fertility to CMS-C corn may be a marker that is linked (e.g., linked; tightly linked; or extremely tightly linked) or that resides within the maize Rf4 gene. In some examples, a means for identifying plants carrying a gene for restoring fertility to CMS-C corn may be a probe that specifically hybridizes to a marker that is linked (e.g., linked; tightly linked; or extremely tightly linked) or that resides within the maize Rf4 gene.

Also described herein are methods whereby hybrid seeds may be produced from crosses of a male plant comprising nucleic acid molecular markers that are linked to (e.g., linked; tightly linked; or extremely tightly linked) or that reside within the maize Rf4 gene and a female plant carrying C-type CMS. The production of such hybrid seed may result in a cost savings due to elimination of hand or mechanical detasseling, and may further increase seed yield.

Further described are methods of using nucleic acid molecules disclosed herein to identify homologous Rf4 sequences from plant species other than maize (e.g., by sequence comparison). In some embodiments, the CMS-C/Rf4 system for hybrid seed production is engineered in plant species other than maize.

BRIEF DESCRIPTION OF THE FIGURES

Figure 1:
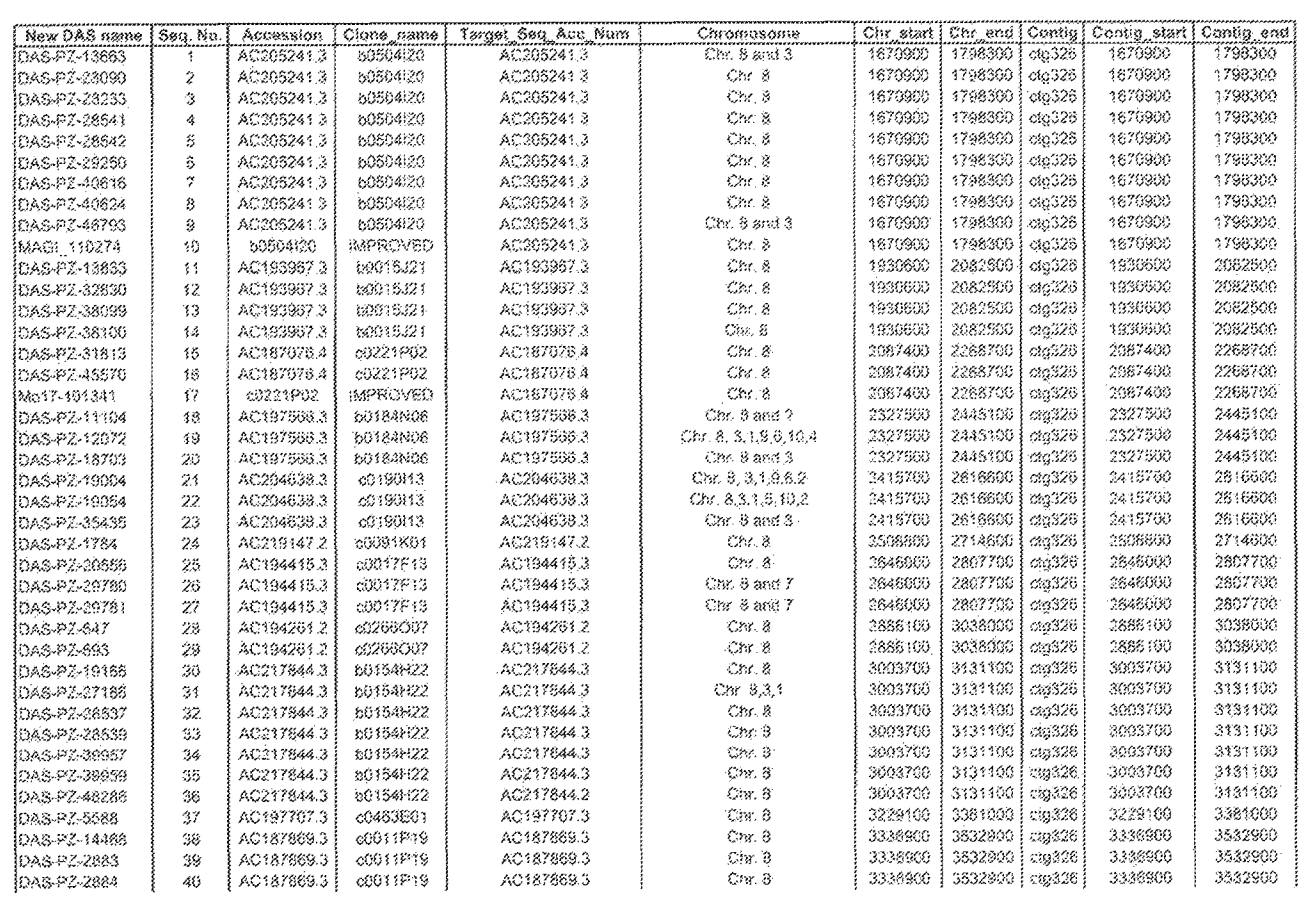

FIG. 1 includes 197 SNP markers determined to be within the Rf4 gene region and their physical map positions.

FIG. 2 includes a representation of thirty-four randomly selected recombinant plants, with their phenotypic data and corresponding genetic data for 27 SNP markers.

FIG. 3 includes a representation of the relative positions of SNP markers for the Rf4 gene and genes within a 1.5 Mb region on chromosome 8.

FIG. 4 includes a representation of the relative positions of SNP markers for the Rf4 gene and genes within a 0.56 Mb region and a 100 kb region on chromosome 8.

FIG. 5 includes a representation of the fine mapping of Rf4 to a 12-kb region. Letters indicate genotypes: A=homozygous for BE4207 (CMS); H=Heterozygous. Arrows indicate Rf4 left and right border markers, and the two most critical recombinant plants.

FIG. 7 includes sequence alignments of Rf4-bHLH from the following maize genotypes: B73; BE4207; B104; XJH58; BE9515; and MLW03. Translation START, STOP, and marker positions for DAS-CMS21 through DAS-CMS34 located within the gene are labeled. The locations of SNPs and InDels are shaded.

FIG. 8 includes predicted sequence alignments of Rf4-bHLH cDNA from the following maize genotypes: B73; BE4207; B104; XJH58; BE9515; and MLW03. Translation START, STOP, and marker positions for DAS-CMS22-25, 28-29, and 31 located within the cDNAs are labeled.

FIG. 9 includes predicted Rf4-bHLH protein sequence alignments. The locations of the conserved bHLH domain, nuclear localization signals (NLS), and corresponding marker positions for DAS-CMS22, 23, and 28 are labeled. The Tyr to Phe substitution in the bHLH domain is caused by the AC to TT dinucleotide substitution at position 747 (of the B73 predicted cDNA sequence), nearly adjacent to marker DAS-CMS24 (see FIG. 8 and polymorphism ID 54 in Table 3).

SEQUENCE LISTING

Figure 6:
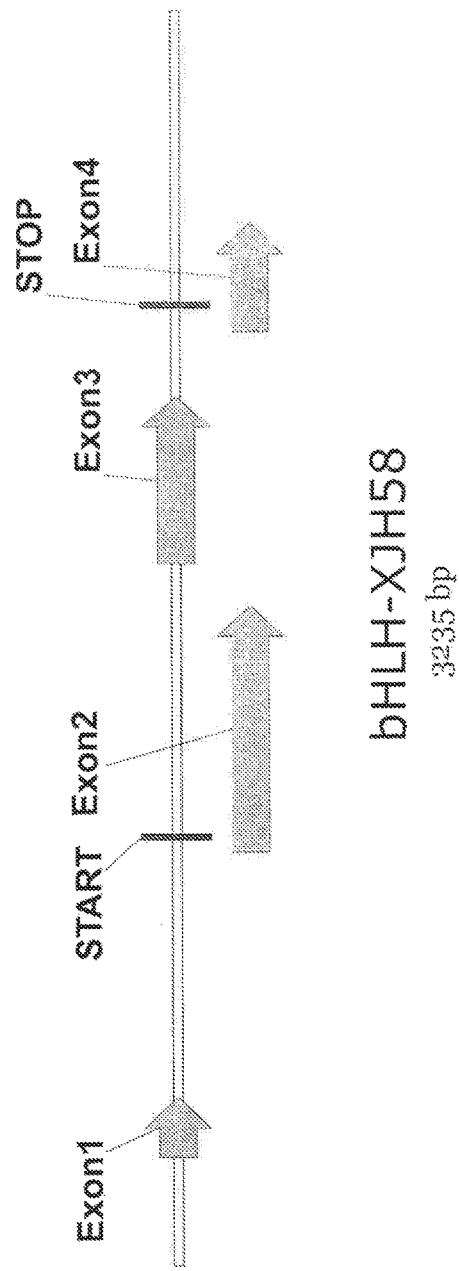
FIG. 6 includes a cartoon depiction of the genomic structure of an Rf4-bHLH allele, showing an entire coding region (START to STOP—1.38 kb), a 1.1 kb 5'UTR/Promoter, and a 0.75 kb 3' UTR/Terminator.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. For simplicity, when describing a gene or locus, the gene may be described by the mutant form of the gene (e.g., Rf4, as opposed to rf4), even though the actual sequence may be the wild-type form of the gene at the corresponding genomic location. Nonetheless, it will be understood that both alleles have different sequences, and it will be clear from the context precisely which allele is meant. In the accompanying sequence listing:

SEQ ID NOs:1-197 show exemplary nucleotide sequences of markers that are linked to (e.g., linked; tightly linked; or extremely tightly linked) or that reside within the maize Rf4 gene.

SEQ ID NOs:198-211 show nucleotide sequences within a region of approximately 0.56 Mb on the top of maize chromosome 8, to which the Rf4 allele was initially mapped. SEQ ID NO:203 is the Rf4-bHLH allele.

SEQ ID NOs:212-216 represent exemplary nucleotide sequence differences between CMS (BE4207) and restorer (XJH58) maize lines.

SEQ ID NO:217 shows the nucleotide sequence of the approximately 12-kb interval from maize variety B73 to which the Rf4 allele was fine-mapped.

SEQ ID NO:218 shows the nucleotide sequence of a rf4-bHLH allele from maize varieties B73 and BE4207.

SEQ ID NO:219 shows the nucleotide sequence of a bHLH allele from maize variety B104.

SEQ ID NO:220 shows the nucleotide sequence of a Rf4-bHLH allele from maize varieties XJH58, BE9515, and MLW03.

SEQ ID NO:221 shows the nucleotide sequence of a predicted rf4-bHLH cDNA from maize varieties B73 and B4207.

SEQ ID NO:222 shows the nucleotide sequence of a predicted bHLH cDNA from maize variety B104.

SEQ ID NO:223 shows the nucleotide sequence of a predicted Rf4-bHLH cDNA from maize varieties XJH58, BE9515, and MLW03.

SEQ ID NO:224 shows the amino acid sequence of a predicted maize rf4-bHLH polypeptide.

SEQ ID NO:225 shows the amino acid sequence of a predicted maize Rf4-bHLH polypeptide.

SEQ ID NO:226 shows the amino acid sequence of a predicted *Brachypodium distachyon* rf4-bHLH polypeptide.

SEQ ID NO:227 shows the amino acid sequence of a predicted *Sorghum bicolor* rf4-bHLH polypeptide.

SEQ ID NO:228 shows the amino acid sequence of a predicted *Oryza sativa* rf4-bHLH polypeptide.

SEQ ID NOs:229 and 230 show predicted nuclear localization signals (NLSs) in Rf4-bHLH.

DETAILED DESCRIPTION

I. Overview of Several Embodiments

Described herein are particular embodiments of genes impacting male fertility in plants, maize Rf4, and tightly-linked genetic markers thereof, which can be useful in a variety of systems to control male fertility. Furthermore, the polymorphism inherent in the disclosed tightly-linked genetic markers allows the plant breeder to follow the particular allele of the gene, Rf4 or rf4, in a segregating population. The Rf4 gene was initially mapped to chromosome 8 in three populations derived from crosses of four maize cultivars: BE4207×BE9515; BE4207×MLW03F; and BE4207×XJH58. Fine mapping and map-based cloning was demonstrated by way of example in population BE4207×XJH58, eventually locating the Rf4 gene within about 12 kb.

The restoration of the cytoplasmic male sterility (CMS) has been a common agriculture practice in the production of hybrid seed for many years. The use of the fertility restorer gene (Rf) with the cytoplasmic male sterility simplifies seed production programs and reduces the overall costs by totally eliminating manual and machine detasseling. However, the full benefits of applications of the genetics of fertility restoration for C-type cytoplasmic male sterility in corn to hybrid seed production have not been realized, because previous studies of the genetics of fertility restoration for C-type cytoplasmic male sterility in corn have produced conflicting results.

In view of the practical importance of cytoplasmic male sterility and pollen fertility restoration in maize hybrid seed production, and the necessity of cytoplasm source diversification, fine mapping of the maize Rf4 restorer gene for CMS-C to a very small region by using molecular markers with a KASPar™ genotyping technique and the identification of the maize Rf4 gene through map-based cloning are described. It was discovered that Rf4 is a single dominant restorer gene for CMS-C in three maize inbreds: BE9515, MLW03 and XJH58.

Rf4 was first mapped using SSR and SNP markers to a region of approximately 5.0 Mb, starting from the SSR marker umc-1075 to the top of the short arm of chromosome 8. A BE4207×XJH58 $F_2$ validation population with 500 individuals was created and scored for fertility in the field. A total of 197 SNP markers were screened with the validation population and 104 recombinants were identified within the 5.0 Mb region. By comparing the phenotypic scores and the genotype data for the informative recombinant lines, the maize Rf4 gene was positively identified within a region of approximately 0.56 Mb (14 genes), and likely within 100 kb (6 genes).

Thus, use of embodiments of the methods disclosed herein demonstrated that the Rf4 gene is selected from the group consisting of GRMZM2G122853 (SEQ ID NO:198); AC187051.4_FG005 (SEQ ID NO:199); GRMZM2G122851 (SEQ ID NO:200); GRMZM2G122850 (SEQ ID NO:201); GRMZM2G582028 (SEQ ID NO:202); GRMZM2G021276 (SEQ ID NO:203); GRMZM2G381376 (SEQ ID NO:204); GRMZM2G081127 (SEQ ID NO:205); GRMZM2G085111 (SEQ ID NO:206); GRMZM2G085038 (SEQ ID NO:207); GRMZM2G317468 (SEQ ID NO:208); GRMZM2G328030 (SEQ ID NO:209); GRMZM2G029450 (SEQ ID NO:210); and GRMZM2G077212 (SEQ ID NO:211).

Using a large fine mapping population of about 5,000 individuals, the maize Rf4 locus was mapped to a small region of approximately 12 kb, located on the top of chromosome 8. It was thereby demonstrated that the Rf4 gene is selected from the group consisting of a plant transposable element [GRMZM2G582028 (SEQ ID NO:202)] and a basic-helix-loop-helix (bHLH) transcription factor (GRMZM2G021276 (SEQ ID NO:203)). Of these two genes, the only likely candidate for Rf4 is the basic-helix-loop-helix (bHLH) transcription factor, GRMZM2G021276 (SEQ ID NO:203), is the Rf4 gene. Thus, in particular embodiments, the Rf4 gene is GRMZM2G021276 (SEQ ID NO:203), which is sometimes referred to herein as Rf4-bHLH. It will be understood that an Rf4 gene may also be a DNA sequence that encodes the same polypeptide as the maize Rf4-bHLH gene, for example, the coding sequence of SEQ ID NO:203.

The bHLH locus was cloned from the maize CMS line BE4207; maize line B104; and three maize restorer lines: XJH58, BE9515, and MLW03. A number of sequence variations between different inbreds were identified. Notably, the three restorer lines have identical Rf4-bHLH DNA sequences, whereas B73 and BE4207 (which do not contain a functional Rf4 restorer) are identical. The B104 sequence is more similar to the BE4207/B73 allele than to the restorer allele. At the protein level, BE4207, B73, and B104 all have the same sequence and are different from the gene product of the restorer allele by 4 amino-acid changes, including the substitution of a hydrophobic phenylalanine for a conserved hydrophilic tyrosine in the bHLH domain.

Consistent with Rf4 function in pollen fertility restoration, the restorer allele of Rf4-bHLH is specifically expressed in the developing tassels (with anthers and pollens) of plants that restore CMS-C. The maize CMS line BE4207 does not exert anthers nor develop functional pollens. As a result, very low or no rf4-bHLH expression was detected in leaves and male reproductive tissues from BE4207 plants. Because B73 (an inbred that neither contains CMS-C cytoplasm nor restores CMS-C) has significant expression of rf4-bHLH, it is unlikely that fertility restoration is due to a difference in expression level between the restorer allele (Rf4-bHLH) and the non-restorer allele (rf4-bHLH).

The male fertility restoration is believed to be due to amino acid sequence differences between the gene products of the restorer allele and the non-restorer allele. In particular, $Y_{186}$ of maize rf4-bHLH is located in the first helix (Carretero-Paulet et al. (2010) Plant Physiol. 153:1398-412; and Pires and Dolan (2010) Mol. Biol. Evol. 27:862-74) within the bHLH DNA binding domain, and this residue is absolutely conserved in B73 (non-CMS, non-restorer), BE4207 (CMS, non-restorer), and in *sorghum*, rice and *Brachypodium* orthologs. This hydrophilic residue is changed to a hydrophobic phenylalanine ($F_{187}$) in the three maize restorer lines. Such a non-conserved substitution could significantly alter the helix structure in the bHLH domain, and affect DNA binding and downstream gene transcription. In view of the foregoing, we predict that rf4 allele from B104 does not restore CMS-C fertility, since B104 bHLH has the identical protein sequence as B73 and BE4207 rf4-bHLH, including the conserved tyrosine at position 186.

In some embodiments, the Rf4-bHLH-based or tightly-linked high throughput molecular makers described herein may be used for identification of genotypes with an Rf4 restorer, introgression of Rf4 into new genotypes in corn and other plants for male conversion, and removal of Rf4 from CMS female plants. With the markers and Rf4 gene at hand, it is now possible to reliably transfer Rf4 into elite germplasms and to increase the scale of using the CMS-C/Rf4 system for hybrid seed production. Full implementation of this system may provide significant financial benefits for the agricultural industry and consumers of its products.

II. Terms

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the nonrecurrent parent.

Linked, tightly linked, and extremely tightly linked: As used herein, linkage between genes or markers refers to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are located within about 2.0 Mb of one another on the same maize chromosome. Thus, two "linked" genes or markers may be separated by about 2.1 Mb; 2.00 Mb; about 1.95 Mb; about 1.90 Mb; about 1.85 Mb; about 1.80 Mb; about 1.75 Mb; about 1.70 Mb; about 1.65 Mb; about 1.60 Mb; about 1.55 Mb; about 1.50 Mb; about 1.45 Mb; about 1.40 Mb; about 1.35 Mb; about 1.30 Mb; about 1.25 Mb; about 1.20 Mb; about 1.15 Mb; about 1.10 Mb; about 1.05 Mb; about 1.00 Mb; about 0.95 Mb; about 0.90 Mb; about 0.85 Mb; about 0.80 Mb; about 0.75 Mb; about 0.70 Mb; about 0.65 Mb; about 0.60 Mb; about 0.55 Mb; about 0.50 Mb; about 0.45 Mb; about 0.40 Mb; about 0.35 Mb; about 0.30 Mb; about 0.25 Mb; about 0.20 Mb; about 0.15 Mb; about 0.10 Mb; about 0.05 Mb; about 0.025 Mb; about 0.012 Mb; and about 0.01 Mb. Particular examples of markers that are "linked" to Rf4 include nucleotide sequences on the top of chromosome 8 of the maize genome, e.g., SEQ ID NOs:1-197; and the markers referred to herein as polymorphism ID nos. 1-106 (Table 3).

As used herein, the term "tightly linked" may refer to one or more genes or markers that are located within about 0.5 Mb of one another on the same maize chromosome. Thus, two "tightly linked" genes or markers may be separated by about 0.6 Mb; about 0.55 Mb; 0.5 Mb; about 0.45 Mb; about 0.4 Mb; about 0.35 Mb; about 0.3 Mb; about 0.25 Mb; about 0.2 Mb; about 0.15 Mb; about 0.12 Mb; about 0.1 Mb; and about 0.05 Mb. Particular examples of markers that are "tightly linked" to Rf4 include SEQ ID NOs:6-9; SEQ ID NO:105; SEQ ID NO:109; SEQ ID NO:111; SEQ ID NO:115; SEQ ID NOs:118-120; SEQ ID NO:123; SEQ ID NO:126; SEQ ID NO:134; SEQ ID NO:135; SEQ ID NO:137; SEQ ID NO:138; SEQ ID NO:144; SEQ ID NO:149; SEQ ID NO:151; SEQ ID NO:160; SEQ ID NO:163; SEQ ID NO:164; SEQ ID NO:167; SEQ ID NO:173; SEQ ID NO:177; SEQ ID NO:178; SEQ ID NO:183; SEQ ID NOs:189-191; and SEQ ID NO:197; and the markers referred to herein as polymorphism ID nos. 1-106 (Table 3).

As used herein, the term "extremely tightly linked" may refer to one or more genes or markers that are located within about 100 kb of one another on the same maize chromosome. Thus, two "extremely tightly linked" genes or markers may be separated by about 125 kb; about 120 kb; about 115 kb; about 110 kb; about 105 kb; 100 kb; about 95 kb; about 90 kb; about 85 kb; about 80 kb; about 75 kb; about 70 kb; about 65 kb; about 60 kb; about 55 kb; about 50 kb; about 45 kb; about 40 kb; about 35 kb; about 30 kb; about 25 kb; about 20 kb; about 15 kb; about 12 kb; about 10 kb; about 5 kb; and about 1 kb. Particular examples of markers that are "extremely tightly linked" to Rf4 include SEQ ID NO:105; SEQ ID NO:109; SEQ ID NO:111; SEQ ID NO:115; SEQ ID NOs:118-120; SEQ ID NO:123; SEQ ID NO:126; and SEQ ID NO:134; and the markers referred to herein as polymorphism ID nos. 1-106 (Table 3).

Linked, tightly linked, and extremely tightly genetic markers of Rf4 may be useful in marker-assisted breeding programs to identify restorer for maize C-type cytoplasmic male sterility gene types, and to breed this trait into maize varieties.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele, e.g., Rf4. A marker may be described as a variation at a given genomic locus. A genetic marker may be a short DNA sequence, such as a sequence surrounding a single base-pair change (single nucleotide polymorphism, or "SNP"), or a long one, for example, a minisatellite/simple sequence repeat ("SSR"). A "marker allele" refers to the version of the marker that is present in a particular plant.

The term marker as used herein may refer to a cloned segment of maize chromosomal DNA (for example, as defined by one of SEQ ID NOs:1-197 or polymorphism ID nos. 1-106 (Table 3)), and may also or alternatively refer to a DNA molecule that is complementary to a cloned segment of maize chromosomal DNA (for example, DNA complementary to one of SEQ ID NOs:1-197 or polymorphism ID nos. 1-106 (Table 3)).

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the maize genome. This is referred to herein as a "contiguous probe." The additional, contiguous nucleotide sequence is referred to as "upstream" or "downstream" of the original marker, depending on whether the contiguous nucleotide sequence from the maize chromosome is on the 5' or the 3' side of the original marker, as conventionally understood. The additional, contiguous nucleotide sequence may be located between the original marker and the 100 kb region on chromosome 8 of the maize genome that is located between map positions 564,922 and 601,460. Thus, the contiguous nucleotide sequence may be located between the original marker and the 12 kb region on chromosome 8 of the maize genome that is located between map positions 86247 and 98188. As is recognized by those of ordinary skill in the art, the process of obtaining additional, contiguous nucleotide sequence for inclusion in a marker may be repeated nearly indefinitely (limited only by the length of the chromosome), thereby identifying additional markers along the maize chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: Radiolabeling by nick translation; random priming; tailing with terminal deoxytransferase; or the like, where the nucleotides employed are labeled, for example, with radioactive $^{32}$P. Other labels which may be used include, for example and without limitation: Fluorophores; enzymes; enzyme substrates; enzyme cofactors; enzyme inhibitors; and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the maize genome so that the noncontiguous probe is genetically linked to the same gene (e.g., Rf4). For example, in some embodiments, a noncontiguous probe can be located within 500 kb; 450 kb; 400 kb; 350 kb; 300 kb; 250 kb; 200 kb; 150 kb; 125 kb; 120 kb; 100 kb; 0.9 kb; 0.8 kb; 0.7 kb; 0.6 kb; 0.5 kb; 0.4 kb; 0.3 kb; 0.2 kb; or 0.1 kb of the original marker on the maize genome.

A probe may be an exact copy of a marker to be detected. A probe may also be a nucleic acid molecule comprising, or consisting of, a nucleotide sequence which is substantially identical to a cloned segment of maize chromosomal DNA (for example, as defined by SEQ ID NOs:1-197 and polymorphism ID nos. 1-106 (Table 3)). As used herein, the term "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 µg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

With respect to all probes discussed, supra, the probe may comprise additional nucleic acid sequences, for example, promoters; transcription signals; and/or vector sequences. Any of the probes discussed, supra, may be used to define additionally markers that are tightly-linked to a gene involved in restoring fertility to C-type cytoplasmic sterile maize (e.g., Rf4). Markers thus identified may be equivalent to exemplary markers named in the present disclosure and, thus, are within the scope of the invention.

Marker-assisted breeding: As used herein, the term "marker-assisted breeding" may refer to an approach to breeding directly for one or more complex traits (e.g., CMS-C restorer of fertility). In current practice, plant breeders attempt to identify easily detectable traits, such as flower color, seed coat appearance, or isozyme variants, that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Operably linked: A first nucleotide sequence is operably linked with a second nucleic acid sequence when the first nucleic acid sequence is in a functional relationship with the second nucleic acid sequence. For example, a promoter is operably linked to a coding sequence if the promoter affects the transcription or expression of the coding sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

Promoter: As used herein, the term "promoter" refers to a region of DNA that may be upstream from the start of transcription, and that may be involved in recognition and binding of RNA polymerase and other proteins to initiate transcription. A promoter may be operably linked to a gene for expression in a cell, or a promoter may be operably linked to a nucleotide sequence encoding a signal sequence which may be operably linked to a gene for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions or the presence of light. Tissue-specific, tissue-preferred, cell type specific, and inducible promoters constitute the class of "non-constitutive" promoters. A "constitutive" promoter is a promoter which may be active under most environmental conditions.

Any inducible promoter can be used in some embodiments of the instant invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the 35S promoter from CaMV; promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similarity to said Xba1/NcoI fragment) (International PCT application WO 96/30530).

Any tissue-specific or tissue-preferred promoter may also be utilized in some embodiments the instant invention. Plants transformed with a gene operably linked to a tissue-specific promoter may produce the protein product of the transgene exclusively, or preferentially, in a specific tissue. Exemplary tissue-specific or tissue-preferred promoters include, but are not limited to: A root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Sequence identity: The term "sequence identity" or "identity," as used herein in the context of two nucleic acid or polypeptide sequences, may refer to the residues in the two sequences that are the same when aligned for maximum correspondence over a specified comparison window.

When percentage of sequence identity is used in reference to proteins, it is recognized that residue positions which are not identical often differ by conservative amino acid substitutions, where amino acid residues are substituted for other amino acid residues with similar chemical properties (e.g., charge, hydrophobicity, or steric effects), and therefore do not change the functional properties of the molecule.

Therefore, when sequences differ by conservative substitutions, the percent sequence identity may be adjusted upwards to correct for the conservative nature of the substitution at the site of the non-identical residue. Sequences that differ by such conservative substitutions are said to have "sequence similarity" or "similarity." Techniques for making this adjustment are well known to those of ordinary skill in the art. Typically, such techniques involve scoring a conservative substitution as a partial, rather than a full, mismatch, thereby increasing the percentage sequence identity. For example, where an identical amino acid is given a score between 0 and 1, and a non-conservative substitution is given a score of 0, a conservative substitution is given a score between 0 and 1. The scoring of conservative substitutions may be calculated, for example, as implemented in the program PC/GENE (Intelligenetics, Mountain View, Calif.).

As used herein, the term "percentage of sequence identity" may refer to the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Single-nucleotide polymorphism (SNP): As used herein, the term "single-nucleotide polymorphism" may refer to a DNA sequence variation occurring when a single nucleotide in the genome (or other shared sequence) differs between members of a species or paired chromosomes in an individual.

Within a population, SNPs can be assigned a minor allele frequency the lowest allele frequency at a locus that is observed in a particular population. This is simply the lesser of the two allele frequencies for single-nucleotide polymorphisms. There are variations between human populations, so an SNP allele that is common in one geographical or ethnic group may be much rarer in another.

Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

InDel: As used herein, the term "InDel" is used generally to describe an insertion or a deletion in a gene. Thus, an "InDel" simply refers to a particular mutation that may be either an insertion, a deletion, or a combination thereof.

Trait or phenotype: The terms "trait" and "phenotype" are used interchangeably herein. For the purposes of the present disclosure, a trait of particular interest is fertility restoration of C-type CMS.

III. Maize CMS-C Restorer Rf4 Gene and Molecular Markers Thereof

Molecular markers that are linked (e.g., tightly-linked) to the maize CMS-C restorer gene, Rf4, are provided. DNA segments containing sequences involved in restoration of fertility to CMS-C plants are identified. These segments are located between markers that are linked (e.g., tightly-linked) to the Rf4 gene. Thus, nucleic acid molecules comprising the Rf4 gene are also provided. The segments identified, and the markers thereof, are described herein, in part, by their position in a particular region on the top of maize chromosome 8.

The position of the segments identified, and the markers thereof, when expressed as recombination frequencies or map units, are provided herein as a matter of general information. The embodiments described herein were performed in maize population, BE4207×XJH58. However, the positions of particular segments and markers as map units are expressed with reference to the publically available B73 maize inbred genome sequence (B73 RefGen v1 or v2), which may be found on the world wide web at www2.genome.arizona.edu/genomes/maize, or ftp.maizesequence.org/current/assembly/. The genome sequences of maize varieties BE4207 and XJH58 are not yet available. It is expected that numbers given for particular segments and markers as map units may vary from cultivar to cultivar and are not part of the essential definition of the DNA segments and markers, which DNA segments and markers are otherwise described, for example, by nucleotide sequence.

The dominant allele of the Rf4 gene controls fertility restoration in the CMS-C/Rf4 system. In embodiments, the Rf4 gene is determined to be a gene selected from the group consisting of GRMZM2G122853 (SEQ ID NO:198); AC187051.4_FG005 (SEQ ID NO:199); GRMZM2G122851 (SEQ ID NO:200); GRMZM2G122850 (SEQ ID NO:201); GRMZM2G582028 (SEQ ID NO:202); GRMZM2G021276 (SEQ ID NO:203); GRMZM2G381376 (SEQ ID NO:204); GRMZM2G081127 (SEQ ID NO:205); GRMZM2G085111 (SEQ ID NO:206); GRMZM2G085038 (SEQ ID NO:207); GRMZM2G317468 (SEQ ID NO:208); GRMZM2G328030 (SEQ ID NO:209); GRMZM2G029450 (SEQ ID NO:210); and GRMZM2G077212 (SEQ ID NO:211). In particular embodiments, the Rf4 gene is Rf4-bHLH (SEQ ID NO:203). For example, an Rf4-bHLH gene is provided by SEQ ID NO:220.

In some embodiments, the invention also includes those nucleotide sequences which are substantially identical to Rf4-bHLH. For example, in some embodiments, a nucleic acid molecule is an Rf4 homologue that is at least about 85% identical to Rf4-bHLH. An Rf4 homologue may be 86%; 87%; 88%; 89%; 90%; 91%; 92%; 93%; 94%; 95%; 96%; 97%; 98%; 99% or 99.5% identical to Rf4-bHLH. Such an Rf4 homologue may be readily identified and isolated from any complete or partial genomes readily available to those of skill in the art for a variety of organisms.

Some embodiments also include functional variants of the Rf4 gene. Functional variants of Rf4 include, for example, the Rf4-bHLH sequence comprising one or more nucleotide substitutions, deletions, or insertions, wherein the functional variant restores male fertility to GMS-C corn, as may be measured by routine techniques well-known to those of ordinary skill in the art. For example, the capability of a particular variant of the Rf4 gene to restore male fertility to CMS-C corn may be determined by routine introduction of the mutation or fragment into plants homozygous for a sterile rf4 allele, followed by routine observation of the plant for male sterility. Functional variants of the Rf4 gene may be created by site-directed mutagenesis, induced mutation, or they may occur as allelic variants (polymorphisms, e.g., SNPs). In particular examples, a functional variant of Rf4 is the Rf4-bHLH sequence comprising one or more nucleotide substitutions, deletions, or insertions, such that the variant encodes an Rf4-bHLH polypeptide comprising a hydrophobic amino acid substitution (e.g., Phe) for $Y_{186}$ within the bHLH domain.

In some embodiments, therefore, functional variants of the Rf4 gene may be mutations of Rf4, or fragments smaller than entire sequence of Rf4, which retain the male sterility controlling properties of the Rf4 gene. Such mutations and fragments are therefore considered to be within the scope of the invention. In view of this disclosure, one of ordinary skill in the art can readily determine whether a mutation or fragment of the Rf4 sequence set forth herein retains the properties of the Rf4 gene.

In some embodiments, the invention also includes Rf4-bHLH polypeptides (e.g., SEQ ID NO:225) and polypeptides that are substantially identical to Rf4-bHLH. For example, in some embodiments, a polypeptide that is substantially identical to Rf4-bHLH may be at least about 25% identical to Rf4-bHLH and have a hydrophobic amino acid residue (e.g., Phe) at the position corresponding to $F_{187}$ of SEQ ID NO:225, as determined by a sequence alignment. In some embodiments, a polypeptide that is substantially identical to Rf4-bHLH may be 86%; 87%; 88%; 89%; 90%; 91%; 92%; 93%; 94%; 95%; 96%; 97%; 98%; 99% or 99.5% identical to Rf4-bHLH. Such polypeptides that are substantially identical to Rf4-bHLH may be readily identified and deduced from complete or partial genomes or cDNA libraries readily available to those of skill in the art for a variety of organisms.

IV. Methods of Using the Rf4 Gene

The Rf4 gene described herein may be used in any of the many ways known by one of skill in the art to manipulate a gene to cause a desired effect. For example and without limitation, the Rf4 gene may be used to: introduce a mutant Rf4 sequence into a plant to cause sterility; to introduce a mutation into the native Rf4 sequence; to introduce an antisense nucleic acid molecule targeting Rf4DNA or RNA into a plant to affect fertility; to use hairpin formations; or to link Rf4 sequence(s) with other nucleic acid sequences to control the expression of Rf4 gene product.

For example, in some embodiments, the Rf4 gene determined to be selected from the group consisting of GRMZM2G122853 (SEQ ID NO:198); AC187051.4FG005 (SEQ ID NO:199); GRMZM2G122851 (SEQ ID NO:200); GRMZM2G122850 (SEQ ID NO:201); GRMZM2G582028 (SEQ ID NO:202); GRMZM2G021276 (SEQ ID NO:203); GRMZM2G381376 (SEQ ID NO:204); GRMZM2G081127 (SEQ ID NO:205); GRMZM2G085111 (SEQ ID NO:206); GRMZM2G085038 (SEQ ID NO:207); GRMZM2G317468 (SEQ ID NO:208); GRMZM2G328030 (SEQ ID NO:209); GRMZM2G029450 (SEQ ID NO:210); and GRMZM2G077212 (SEQ ID NO:211) may be used to facilitate the utilization of the CMS-C/Rf4 male fertility system in conjunction with other genes or mutants impacting male fertility in maize. For example, in particular embodiments, the Rf4-bHLH gene may be used to facilitate the utilization of the CMS-C/Rf4 male fertility system in conjunction with other genes or mutants impacting male fertility in maize.

In some embodiments, the Rf4 gene may be introduced into a maize plant that is suitable for use in a male fertility system other than the CMS-C/Rf4 male fertility system. Alternatively, a gene or mutant gene other than Rf4 may be introduced into a maize plant that is suitable for use in the CMS-C/Rf4 male fertility system, such that the introduced gene or mutant gene may be used to provide additional or complementary fertility control. Specific examples of other male fertility genes and mutations in maize include: CMS-T/Rf1; CMS-T/Rf2; CMS-S/Rf3; ms1 (Singleton and Jones (1930) J. Hered. 21:266-8); ms2 and ms3 (Eyster (1931) J. Hered. 22:99-102); ms5, ms7, ms8, ms9, ms10, ms11, ms12, ms13, and ms14 (Beadle (1932) Genetics 17:413-31); ms17 (Emerson (1932) Science 75:566); ms20 (Eyster (1934) Bibliographia Genetica 11:187-392); ms23 and ms24 (West and Albertsen (1985) MNL 59:87); ms25 and ms26 (Loukides et al. (1995) Am. J. Bot. 82:1017-23); ms27 and ms38 (Albertsen et al. (1996) MNL 70:30-1); ms28 (Golubovskaya (1979) MNL 53:66-70); ms29 and ms31 (Trimnell et al. (1998) MNL 72:37-38); ms30 (Albertsen et al. (1999) MNL 73:48); ms32, ms36, and ms37 (Trimnell et al. (1999) MNL 73:48-50); ms33 and ms34 (Patterson (1995) MNL 69:126-8); ms43 (Golubovskaya (1979) Int. Rev. Cytol. 58:247-90); ms45 (Albertsen et al. (1993) Proc. Annu. Corn *Sorghum* Ind. Res. Conf. 48:224-33; and ms48, ms49, and ms50 (Trimnell et al. (2002) MNL 76:38-9).

When a nucleic acid sequence (e.g., Rf4) is "introduced" into an organism, such as a plant, the technique or methodology used for the introduction of a nucleic acid molecule comprising the particular sequence is not essential to the invention, and may occur by any technique or methodology known to those of skill in the art. For example, a nucleic acid molecule may be introduced by direct transformation methods, such as *Agrobacterium*-mediate transformation of plant tissue; microprojectile bombardment; electroporation; etc. Alternatively, a nucleic acid molecule may be introduced by crossing a plant having the particular nucleotide sequence with another plant, such that progeny have the nucleotide sequence incorporated into their genome. Such breeding techniques are well-known to one skilled in the art. Marker-assisted breeding techniques, as disclosed herein, may greatly facilitate the incorporation of Rf4 through such crosses.

In embodiments wherein the Rf4 gene is introduced to an organism, it may be desirable for the Rf4 gene to be introduced in such a manner that the Rf4 gene is operably linked to one or more regulatory sequences, for example, introduction via the use of a plasmid comprising the Rf4 gene operably linked to the desired regulatory sequences. Regulatory sequences useful in the expression of heterologous nucleic acid sequences are well-known in the art, and include, for example and without limitation: Promoters (e.g., constitutive promoters; tissue-specific promoters; and developmental stage-specific promoters); termination sequences; enhancer sequences; subcellular targeting sequences; stabilizing or leader sequences; and introns.

In some embodiments, the Rf4 gene may be introduced to an organism with one or more additional desirable nucleic acid sequences (for example, genes). Additional desirable nucleic acid sequences may include, for example: Genes encoding foreign proteins; agronomic genes; plant disease resistance genes; genes conferring resistance to a plant pest; genes conferring resistance to an herbicide; and genes that confer or contribute to a value-added trait (e.g., modified fatty acid metabolism; decreased phytate content; and modified carbohydrate composition). Examples of all the aforementioned nucleic acid sequences are known to those of skill in the art.

The Rf4 gene may also be introduced to an organism with one or more marker genes operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes for transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art. Examples of marker genes suitable for use in plant cells may include, for example, and without limitation: The neomycin phosphotransferase II (nptII) gene (Fraley et al. (1983) Proc. Natl. Acad. Sci. USA 80:4803); the hygromycin phosphotransferase gene (Vanden Elzen et al. (1985) Plant Mol. Biol. 5:299); gentamycin acetyl transferase, streptomycin phosphotransferase, aminoglycoside-3'-adenyl transferase, and the bleomycin resistance determinant (See, e.g., Hayford et al. (1988) Plant Physiol. 86:1216; Jones et al. (1987) Mol. Gen. Genet. 210:86); Svab et al. (1990) Plant Mol. Biol. 14:197; and Hille et al. (1986) Plant Mol. Biol. 7:171); selectable marker genes that confer resistance to herbicides, such as glyphosate, glufosinate or bromoxynil (See, e.g., Comai et al. (1985) Nature 317:741-744; Gordon-Kamm et al. (1990) Plant Cell 2:603-618; and Stalker et al. (1988) Science 242:419-423); mouse dihydrofolate reductase (Eichholtz et al. (1987) Somatic Cell Mol. Genet. 13:67); plant 5-enolpyruvylshikimate-3-phosphate synthase (Shah et al. (1986) Science 233:478); plant acetolactate synthase (Charest et al. (1990) Plant Cell Rep. 8:643).

Another class of marker genes suitable for plant transformation employs screening of presumptively transformed plant cells rather than direct genetic selection of transformed cells for resistance to a toxic substance, such as an antibiotic. These genes are particularly useful to quantify or visualize the spatial pattern of expression of a gene in specific tissues, and are frequently referred to as "reporter genes," because they can be fused to a gene or gene regulatory sequence for the investigation of gene expression. Commonly used genes for screening transformed cells include β-glucuronidase (GUS), β-galactosidase, luciferase and chloramphenicol acetyltransferase. See, e.g., Jefferson (1987) Plant Mol. Biol. Rep. 5:387; Teen et al. (1989) EMBO J. 8:343; Koncz et al. (1987) Proc. Natl. Acad. Sci. U.S.A. 84:131; and DeBlock et al. (1984) EMBO J. 3:1681.

Recently, in vivo methods for visualizing GUS activity that do not require destruction of plant tissue have been made available. Molecular Probes publication 2908, Imagene Green™, p. 1-4, 1993; and Naleway et al. (1991) J. Cell Biol. 115:151a. Further, genes encoding Fluorescent Proteins (e.g., GFP, EGFP, EBFP, ECFP, and YFP) have been utilized as markers for gene expression in prokaryotic and eukaryotic cells. See Chalfie et al. (1994) Science 263:802. Fluorescent proteins and mutations of fluorescent proteins may be used as screenable markers.

In some embodiments, the maize Rf4 gene and fragments or segments of the maize Rf4 gene disclosed herein may be used to identify homologous Rf4 sequences from organisms other than maize (e.g., by sequence comparison). Sequences from organisms other than maize that are homologous to the maize Rf4 gene may be identified and isolated according to well-known techniques, for example, based on their sequence homology to Rf4-bHLH. For example, all or part of the Rf4-bHLH coding sequence may be used as a probe which specifically hybridizes to other sequences present in a population of cloned genomic DNA fragments (i.e., a genomic library) from an organism according to routine techniques. Thus, in some embodiments, the invention includes those nucleotide sequences which specifically hybridize to a Rf4-bHLH sequence (e.g., SEQ ID NO:220).

Alternatively, sequences from organisms other than maize that are homologous to the maize Rf4 gene may be identified and isolated by sequence comparison. For example, the complete or partial sequenced genome of an organism may be searched according to routine techniques with a maize Rf4-bHLH sequence (e.g., SEQ ID NO:220) to identify genes within the genome of the organism that share a high degree of sequence identity with maize Rf4, and are therefore likely Rf4 homologues.

For example, all or part of a maize Rf4 sequence (e.g., SEQ ID NO:220) may be used as a "reference sequence." Generally, nucleic acid sequences (e.g., cloned or genomic DNA fragments of a genomic library) that are compared to the reference sequence comprise a "comparison window," which is a specific contiguous segment of the nucleic acid sequence. The comparison window may comprise additions or deletions (i.e., gaps) compared to the reference sequence (which does not comprise additions or deletions) for optimal alignment of the two sequences. The comparison window is typically at least 20 contiguous nucleotides in length, but may be 30, 40, 50, 100, or 200 nucleotides in length, or longer. To avoid a high similarity to the reference sequence due to inclusion of deletions in the polynucleotide sequence comparison window, a "gap penalty" may be introduced to be subtracted from the number of nucleotide matches.

Methods of aligning sequences for comparison are well-known in the art. The determination of percent sequence identity between any two sequences can be accomplished using available mathematical algorithms. Non-limiting examples of such mathematical algorithms are the algorithm of Myers and Miller (1988), CABIOS 4:11-7; the local alignment algorithm of Smith et al. (1981) Adv. Appl. Math. 2:482; the global alignment algorithm of Needleman and Wunsch (1970), J. Mol. Biol. 48:443-53; the search-for-local-alignment method of Pearson and Lipman (1988), Proc. Natl. Acad. Sci. USA 85:2444-8; the algorithm of Karlin and Altschul (1990), Proc. Natl. Acad. Sci. USA 87:2264, and Karlin and Altschul (1993) Proc. Natl. Acad. Sci. USA 90:5873-7.

One of ordinary skill in the art can implement these mathematical algorithms on a computer for comparison of sequences to determine sequence identity, or to search a database comprising a plurality of sequences (e.g., an organism genome database) according to shared sequence identity with a reference sequence. Such implementations include, but are not limited to, CLUSTAL in the PC/Gene program (Intelligenetics, Mountain View, Calif.); and the ALIGN program and GAP, BESTFIT, BLAST, FASTA, and TFASTA in the GCG Wisconsin Genetics Software Package, v. 10 (Accelrys Inc., San Diego, Calif.). Sequence alignments using these programs may be performed using their default parameters. Alternatively, it may be desirable to modify the default parameters in some searches (e.g., altering the value of a gap penalty). The selection of a particular computer implementation of mathematical algorithms for calculation of sequence identity, and the selection of parameter values for use in a selected algorithm, are within the discretion of one of skill in the art.

In some embodiments, the CMS-C/Rf4 system for hybrid seed production may be engineered into a maize variety lacking a functional Rf4 restorer gene or a plant species other than maize, for example, by introduction of the Rf4 gene into such maize variety or plant species.

Thus, in accordance with some embodiments, the Rf4 gene described herein may be used in a method for producing hybrid seed. A method for producing hybrid seed may comprise obtaining a nucleic acid molecule comprising a maize Rf4-bHLH sequence (e.g., SEQ ID NO:220), or a nucleotide sequence that specifically hybridizes to a maize Rf4-bHLH sequence. That nucleic acid molecule may then be introduced into a plant cell or plant tissue, wherein the plant from which the plant cell or plant tissue is obtained may be *Zea mays*, or a different plant species. Subsequently, a transformed whole plant may be generated from the plant cell or plant tissue into which the nucleic acid molecule has been introduced. A cytoplasmic male-sterile plant may then be pollinated by the transformed whole plant. A seed that generates a fertile plant may then be obtained from the cytoplasmic male-sterile plant that has been pollinated by the transformed whole plant.

In particular embodiments, functional variants or homologs of the maize Rf4-bHLH gene may be used in place of a maize Rf4-bHLH sequence (e.g., SEQ ID NO:220), or the nucleotide sequence that specifically hybridizes to the maize Rf4-bHLH sequence, in a method for producing hybrid seed. A transformed whole plant that is generated, for example, by the methods described above, may be capable of producing seeds. However, such seeds may or may not be able to grow into fertile plants. Accordingly, some embodiments of methods for producing hybrid seed involve plant tissue culture techniques. Such techniques are routine and widely known to those of ordinary skill in the art.

In embodiments where the CMS-C/Rf4 system for hybrid seed production is engineered into plant species other than maize, it may be necessary to also introduce nucleic acid molecules comprising one or more nucleic acid sequence(s) involved in the CMS-C male sterility system into the plant species. For example, the recessive rf4-bHLH allele may be introduced to replace an Rf4-bHLH ortholog in the plant species to generate a male sterile rf4/rf4 plant, into which the Rf4-bHLH gene may be introduced in order to engineer the CMS-C/Rf4 system for hybrid seed production into the species.

In some embodiments, the Rf4 gene described herein may be used in a method for producing hybrid seed comprising fertilizing a female plant having the trait of CMS-C type male sterility with pollen from a male plant comprising the Rf4 gene. In these and other embodiments, a maize Rf4-bHLH sequence (e.g., SEQ ID NO:220), a nucleotide sequence that specifically hybridizes to the maize Rf4-bHLH sequence, or functional variants or homologs of the maize Rf4-bHH sequence may be used.

In some embodiments, a method for producing hybrid seed comprises generating a first plant comprising Rf4 by, for example, backcrossing; mutagenesis; transformation; or homologous recombination. A second plant having the trait of CMS-C type male sterility may then be obtained, or generated by, for example, backcrossing; mutagenesis; or homologous recombination. The second plant may then be crossed with the first plant to obtain fertile hybrid seeds from the second plant. In embodiments, the first plant may be a male plant, and the second plant may be a female plant.

In particular examples of methods for producing hybrid seed, the plant may be a corn plant. In further examples, plants other than corn may be used. Embodiments of methods for producing hybrid seed according to the invention are applicable to any plant, such as sexually reproducing plants, including plants of agronomic value, for example and without limitation: maize; soybean; alfalfa; wheat; rapeseed; rice; *sorghum*; beet; *Brachypodium*; monocots; dicots; various vegetables including cucumber, tomato, peppers, etc.; various trees including apple, pear, peach, cherry, redwood, pine, oak, etc.; and various ornamental plants.

V. Methods of Using Rf4 Molecular Markers

Methods of using nucleic acid molecular markers that are linked to or that reside within the Rf4 gene to identify plants with a functional restorer gene for C-type CMS may result in a cost savings for plant developers, because such methods may eliminate the need to cross plants comprising a functional restorer gene with CMS plant lines and then phenotype the progenies of the cross.

Additional markers can be identified as equivalent to any of the exemplary markers named herein (e.g., SEQ ID NOs:1-197 and polymorphism ID nos. 1-106 (Table 3)), for example, by determining the frequency of recombination between the additional marker and an exemplary named marker. Such determinations my utilize an improved method of orthogonal contrasts based on the method of Mather (1931), *The Measurement of Linkage in Heredity*, Methuen & Co., London, followed by a test of maximum likelihood to determine a recombination frequency. Allard (1956) Hilgardia 24:235-78. If the value of the recombination frequency is less than or equal to 0.10 (i.e., 10%) in any maize cultivar, then the additional marker is considered equivalent to the particular reference marker for the purposes of use in the presently disclosed methods.

A means for restoring fertility to CMS-C corn may include a nucleic acid sequence from a plant, the detection of which nucleic acid provides at least a strong indication that the plant comprising the nucleic acid sequence comprises a functional restorer of CMS-C gene. In some examples, a means for restoring fertility to CMS-C corn is a marker that is linked to (e.g., linked; tightly linked; or extremely tightly linked) or that resides within the Rf4-bHLH gene.

A means for identifying corn plants carrying a gene for restoring fertility to GMS-C corn may be a molecule that presents a detectable signal when added to a sample obtained from a plant carrying a gene for restoring fertility to CMS-C corn. Specific hybridization of nucleic acids is a detectable signal, and a nucleic acid probe that specifically hybridizes to a CMS-C restorer gene, or a different genomic nucleic acid sequence that is an indicator of the presence of a functional CMS-C restorer gene, may therefore be a means for identifying corn plants carrying a gene for restoring fertility to CMS-C corn. In some examples, a means for identifying plants carrying a gene for restoring fertility to CMS-C corn is a probe that specifically hybridizes to a marker that is linked to (e.g., linked; tightly linked; or extremely tightly linked) or that resides within the maize Rf4-bHLH gene.

In some embodiments, markers flanking the Rf4 gene may be used to transfer segment(s) of donor parent DNA that unequivocally contain the Rf4 gene. In particular embodiments, the markers are selected from the group of markers comprising SEQ ID NOs:1-197 and polymorphism ID nos. 1-106 (Table 3), or from markers equivalent to the markers selected from the group of markers comprising SEQ ID NOs:1-197 and polymorphism ID nos. 1-106 (Table 3). In some embodiments, a method for using markers flanking the Rf4 gene to transfer segment(s) of donor parent DNA that unequivocally contain the Rf4 gene may comprise analyzing the genomic DNA of two parent plants with probes that are specifically hybridizable to markers linked (e.g., linked; tightly linked; or extremely tightly linked) to the Rf4 gene; sexually crossing the two parental plant genotypes to obtain a progeny population, and analyzing those progeny for the presence of the markers linked (e.g., linked; tightly linked; or extremely tightly linked) to the Rf4 gene; backcrossing the progeny that contain the markers linked (e.g., linked; tightly linked; or extremely tightly linked) to the Rf4 gene to the recipient genotype to produce a first backcross population, and then continuing with a backcrossing program until a final progeny is obtained that comprises any desired trait(s) exhibited by the parent genotype and the Rf4 gene. In particular embodiments, individual progeny obtained in each crossing and backcrossing step are selected by Rf4 marker analysis at each generation. In some embodiments, analysis of the genomic DNA of the two parent plants with probes that are specifically hybridizable to markers linked (e.g., linked; tightly linked; or extremely tightly linked) to the Rf4 gene reveals that one of the parent plants comprises fewer of the linked markers to which the probes specifically hybridize, or none of the linked markers to which the probes specifically hybridize.

In some embodiments, markers that are linked to (e.g., linked; tightly linked; or extremely tightly linked) or that reside within the maize Rf4-bHLH gene, or the maize Rf4-bHLH gene sequence itself, may be used to introduce the maize Rf4 gene into a maize plant by genetic transformation. In particular embodiments, the markers are selected from the group of markers comprising SEQ ID NOs:1-197 and polymorphism ID nos. 1-106 (Table 3), or from markers equivalent to the markers selected from the group of markers comprising SEQ ID NOs:1-197 and polymorphism ID nos. 1-106 (Table 3). In some embodiments, a method for introducing the maize Rf4 gene into a maize plant by genetic recombination may comprise analyzing the genomic DNA of a plant (e.g., a maize plant) with probes that are specifically hybridizable to markers linked (e.g., linked; tightly linked; or extremely tightly linked) to the Rf4 gene or the Rf4 gene itself to identify the Rf4 gene in the plant; isolating a segment of the genomic DNA of the plant comprising the Rf4 gene, for example, by extracting the genomic DNA and digesting the genomic DNA with one or more restriction endonuclease enzymes; optionally amplifying the isolated segment of DNA; introducing the isolated segment of DNA into a cell or tissue of a host maize plant; and analyzing the DNA of the host maize plant with probes that are specifically hybridizable to markers linked (e.g., linked; tightly linked; or extremely tightly linked) to the Rf4 gene or the Rf4 gene itself to identify the Rf4 gene in the host maize plant. In particular embodiments, the isolated segment of DNA may be introduced into the host maize plant such that it is stably integrated into the genome of the host maize plant.

In some embodiments, markers that are linked to (e.g., linked; tightly linked; or extremely tightly linked) or that reside within the maize Rf4-bHLH gene, or the maize Rf4-bHLH gene sequence itself, may be used to introduce the maize Rf4 gene into other organisms, for example, plants. In particular embodiments, the markers are selected from the group of markers comprising SEQ ID NOs:1-197 and polymorphism ID nos. 1-106 (Table 3), or from markers equivalent to the markers selected from the group of markers comprising SEQ ID NOs:1-197 and polymorphism ID nos. 1-106 (Table 3). In some embodiments, a method for introducing the maize Rf4 gene into an organism other than maize may comprise analyzing the genomic DNA of a plant (e.g., a maize plant) with probes that are specifically hybridizable to markers linked (e.g., linked; tightly linked; or extremely tightly linked) to the Rf4 gene or the Rf4 gene itself to identify the Rf4 gene in the plant; isolating a segment of the genomic DNA of the plant comprising the Rf4 gene, for example, by extracting the genomic DNA and digesting the genomic DNA with one or more restriction endonuclease enzymes; optionally amplifying the isolated segment of DNA; introducing the isolated segment of DNA into an organism other than maize; and analyzing the DNA of the organism other than maize with probes that are specifically hybridizable to markers linked (e.g., linked; tightly linked; or extremely tightly linked) to the Rf4 gene or the Rf4 gene itself to identify the Rf4 gene in the organism. In particular embodiments, the isolated segment of DNA may be introduced into the organism such that it is stably integrated into the genome of the organism.

In some embodiments, markers that are linked to (e.g., linked; tightly linked; or extremely tightly linked) or that reside within the Rf4 gene, or the Rf4 gene sequence itself, may be used to identify a plant with a functional restorer gene for CMS-C male sterility. In particular embodiments, the plant is a maize plant. In some embodiments, nucleic acid molecules (e.g., genomic DNA or mRNA) may be extracted from a plant. The extracted nucleic acid molecules may then be contacted with one or more probes that are specifically hybridizable to markers linked (e.g., linked; tightly linked; or extremely tightly linked) to the Rf4 gene or the Rf4 gene itself. Specific hybridization of the one or more probes to the extracted nucleic acid molecules is indicative of the presence of a functional restorer gene for CMS-C male sterility in the plant.

In some embodiments, markers that are linked to (e.g., linked; tightly linked; or extremely tightly linked) or that reside within the Rf4 gene, or the Rf4 gene sequence itself, may be used to produce hybrid seed. The production of hybrid seed according to such methods may result in a cost savings due to elimination of hand or mechanical detasseling, and may further increase seed yield. In particular embodiments, the method may comprise crossing of a male plant comprising nucleic acid molecular markers that are linked to (e.g., linked; tightly linked; or extremely tightly linked) or that reside within the Rf4 gene and a female plant having the phenotype of C-type CMS male sterility.

VI. Organisms Comprising the Rf4 Gene

Some embodiments of the present invention also provide an organism including a nucleic acid molecule comprising a Rf4-bHLH sequence (e.g., SEQ ID NO:220), a nucleic acid sequence that is specifically hybridizable to a Rf4-bHLH sequence, or a functional variant of a Rf4-bHLH sequence. A suitable organism can be any suitable plant, yeast, or bacterium. By way of non-limiting example, a plant comprising the aforementioned sequences may be a plant of agronomic value, for example and without limitation: maize; soybean; alfalfa; wheat; rapeseed; rice; *sorghum*; beet; *Brachypodium*; monocots; dicots; various vegetables including cucumber, tomato, peppers, etc.; various trees including apple, pear, peach, cherry, redwood, pine, oak, etc.; and various ornamental plants. In particular embodiments, the organism may be a sexually-reproducing plant. A seed-bearing plant that comprises a particular nucleic acid sequence may produce seeds that comprise the nucleic acid sequence.

Plant cells comprising a Rf4-bHLH sequence (e.g., SEQ ID NO:220), a nucleic acid sequence that is specifically hybridizable to a Rf4-bHLH sequence, or a functional variant of a Rf4-bHLH sequence, may be cultured and kept as plant tissue culture cells, or certain plant hormones known in the art can be added to the culture media, thereby causing the plant tissue culture cells to differentiate and form a new plant variety, which new plant variety may be fertile or sterile. Such plant culturing methods useful in these and other embodiments are routine and well-known in the art.

Some embodiments of the invention provide a virus (e.g., a bacteriophage, or plant virus) comprising a Rf4-bHLH sequence (e.g., SEQ ID NO:220), a nucleic acid sequence that is specifically hybridizable to a Rf4-bHLH sequence, or a functional variant of a Rf4-bHLH sequence.

The following examples are provided to illustrate certain particular features and/or embodiments. The examples should not be construed to limit the disclosure to the particular features or embodiments exemplified.

EXAMPLES

Example 1: Materials and Methods

Validation Population.

A male sterile line of CMS-C type, BE4207, and a male sterile restorer line responding to CMS-C type, XJH58, were used as parents to generate $F_1$ progeny. The $F_1$ progeny where then selfed to generate an $F_2$ population. The $F_2$ population, consisting of 500 individuals, was used for identification of the Rf4 gene and markers linked (e.g., linked; tightly linked; or extremely tightly linked) to the Rf4 gene.

Fine Mapping BE4207/XJH58 $F_3$ Population

A total of 5465 seeds selected from 15 heterozygous $F_2$ families from the validation $F_2$ population segregating for different fragments within the 4.2-Mb region on top of chromosome 8 were planted in a 2010 summer nursery in Arlington, Wis. Leaf samples were collected from 5104 germinated seedlings for genotyping.

Fertility Classification.

The 500 plants in this $F_2$ population were phenotypically classified according to pollen shed from the tassels. Plants that shed pollen were classified as fertile. Plants that did not shed polled were classified as sterile. The Rf4 restoration in this population was complete; no partial fertile plants were observed.

DNA Extraction and Quantification.

8 punches of leaf tissue were collected from each plant of the $F_2$ population, and DNA was extracted by using the Biocel™ 1800 (Agilent Inc., Santa Clara, Calif.). The DNA extraction process used was: (1) Add one ~⅛ inch diameter tungsten alloy bead to each tube; (2) add 300 μL of RLT Lysis Buffer (Qiagen Inc., Germantown, Md.) to each tube; (3) cap and grind for 6 minutes at 1500 strokes/minute in an SPEX 2000 Geno/Grinder® (OPS Diagnostics, LLC, Lebanon, N.J.); (4) spin down samples at 6000 rpm for 5 minutes; (5) uncap tubes; the following steps are carried out on the Biocel™ 1800: (6) Transfer 200 μL of supernatant to a 1.1 mL square well round bottom assay plate containing 10 μL MagAttract® Suspension G Beads (Qiagen Inc.); (7) incubate 2 minutes; (8) shake at 1200 rpm for 40 seconds; (9) incubate for 2 minutes; (10) place assay plate onto magnet shelf and allow beads to separate for 40 seconds; (11) remove supernatant; (12) first wash—add 190 μL RPW™ wash buffer premixed with RNase and Isopropanol, and shake at 1200 rpm for 40 seconds; (13) place assay plate onto magnet shelf and allow beads to separate for 20 seconds; (14) remove supernatant; (15) second wash—add 190 μL 100% ethanol wash buffer, and shake at 1200 rpm for 40 seconds; (16) place assay plate onto magnet shelf and allow beads to separate for 20 seconds; (17) third wash—add 190 μL 100% ethanol wash buffer; (18) shake at 1200 rpm for 40 seconds; (19) place assay plate onto magnet shelf and allow beads to separate for 20 seconds; (20) remove supernatant; (21) incubate plate for 5 minutes at room temperature; (22) add 100 μL, AE™ elution buffer (Qiagen Inc.); (23) shake for 2 minutes; (24) place assay plate onto magnet shelf and allow beads to separate for 30 seconds; and (25) transfer supernatant to a clean, labeled plate and seal.

DNA was stored at 4° C. DNA was quantified by using PicoGreen® (Invitrogen Inc., Carlsbad, Calif.), and the concentration was normalized to 5-6 ng/μL for use in the KASPar™ genotyping system (KBioscience Inc., Hoddesdon, UK).

KASPar™ SNP Genotyping System.

The competitive allele-specific PCR genotyping system (KASPar™) is a SNP detection system that uses a technique based on allele-specific oligo extension and fluorescence resonance energy transfer (FRET) for signal generation. Each SNP marker in a KASPar™ assay requires only two components: The assay mix (a mixture of three unlabelled primers: two allele specific oligo, and one common reverse locus specific oligo); and the reaction mix (the other components required for PCR, including the universal fluorescent reporting system and Taq polymerase).

KBioscience Laboratory Information Management System (KLIMS™) (KBioscience Inc.) was used for primer design, and oligonucleotides were synthesized by Integrated DNA Technology (Coralville, Iowa). KASPar™ reactions were performed according to the manufacturer's recommendation. PCR started with denaturing at 94° C. for 15 minutes, followed by 20 cycles of 10 seconds of denaturing at 94° C., 5 seconds of annealing at 57° C., then 10 seconds of extension at 72° C., which 20 cycles were followed by 22 cycles with 10 seconds of denaturing at 94° C., 20 seconds of annealing at 57° C., then 40 seconds of extension at 72° C. Fluorescent signals after the completion of KASPar™ reactions were read in a spectrofluorometer (Tecan GENios™, Mannedorf, Switzerland) with an excitation wavelength at 485 nm, and an emission wavelength at 535 nm for the FAM fluorophore; and an excitation wavelength at 525 nm, and an emission wavelength at 560 nm for the VIC fluorophore. The data were analyzed using Klustercaller™ software (KBiosciences Inc.) to determine the genotypes of each SNP marker in a population.

RNA Extraction and Real-Time PCR(RT-PCR)

Parents and $F_3$ plants segregating for the Rf4 region were grown in a greenhouse. Leaf tissues were collected from 5-week, 7-week, and 9-week old plants. Tassel tissues with developing anthers/pollens and shed pollens (in fertile plants) were also collected. Total RNA was extracted using an RNeasy™ Plant Mini Kit (Qiagen Inc.). cDNA was synthesized using QuantiTect™ Reverse Transcription Kit (Qiagen Inc.). For RT-PCR, Rf4 gene-specific primers, corn invertase control primers, and dual-labeled probes with FAM or VIC and Minor Groove Binding Non Fluorescence Quencher™ I (MGBNFQ) dyes were synthesized by Applied Biosystems (Foster City, Calif.). TaqMan™ genotyping master mix (Applied Biosystems) was used to set up 10 μl PCR reactions, and PCR was performed on a Light-Cycler™ 480 (Roche). The PCR program included: 10 minutes activation at 95° C., followed by 50 cycles of 95° C. for 10 seconds and 58° C. for 38 seconds. Fluorescence signals were recorded at the end of each cycle. Relative expression level was calculated using the Delta CT method using invertase as the control.

Example 2: Mapping of the Rf4 Gene

Fertility Segregation Analysis.

The ratio of fertility segregation in the $F_2$ population was 3:1. Table 1. The results demonstrated that fertility restoration in the CMS-C/Rf4 system is controlled by one dominant restorer gene, Rf4.

TABLE 1

Phenotype data from the validation population.

| Fertile | Sterile | No Tassel | Total |
|---|---|---|---|
| 373 | 126 | 1 | 500 |

Preliminary genetic mapping of Rf4 in the $F_2$ population using SNP markers.

Figure 2:
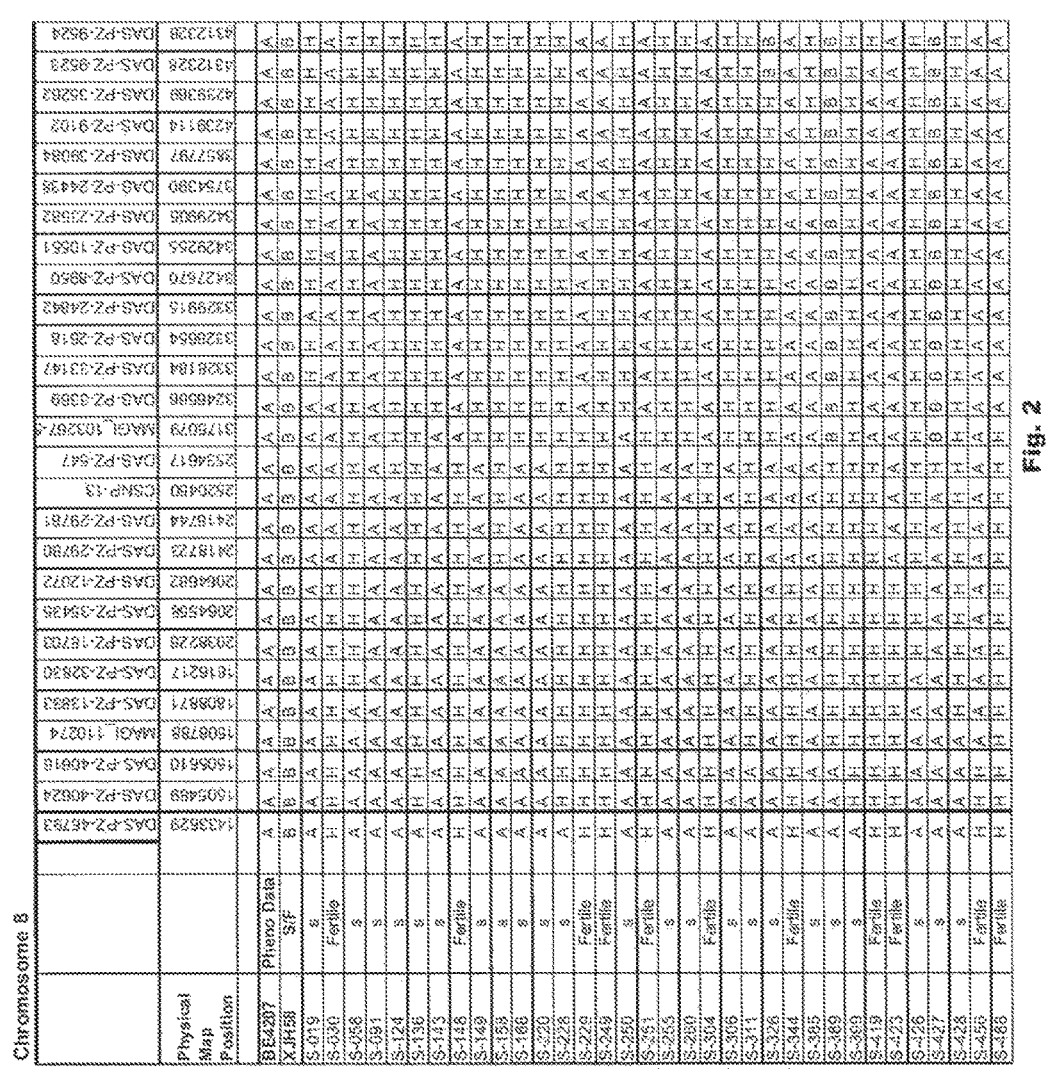

101 SNP markers located near the top of maize chromosome 8 were used in parental screening with 5 different Rf4 mapping populations, and were determined to be within the 5.0-Mb Rf4 region. A set of 12 markers were polymorphic in all five populations, whereas 27, including the 12 common polymorphic markers, showed polymorphism between parents of the BE4207×XJH58 $F_2$ population. The 12 common markers were initially used to genotype all 500 individuals in the $F_2$ population to identify recombinant lines within the 5.0 Mb region. The remaining 15 polymorphic markers were then used to genotype all 104 recombinant lines. Thirty-four randomly selected recombinants are shown in FIG. 2, with their phenotypic data and corresponding genotypic data for the 27 markers as examples. A more detailed analysis of the 42 most informative recombinant lines revealed that the Rf4 gene is located in an approximately 1.505 Mb region on the top of chromosome 8, defined by SNP marker DAS-PZ-40624 (SEQ ID NO:8). Within this region, there are approximately 30 genes (data not shown).

Figure 3:
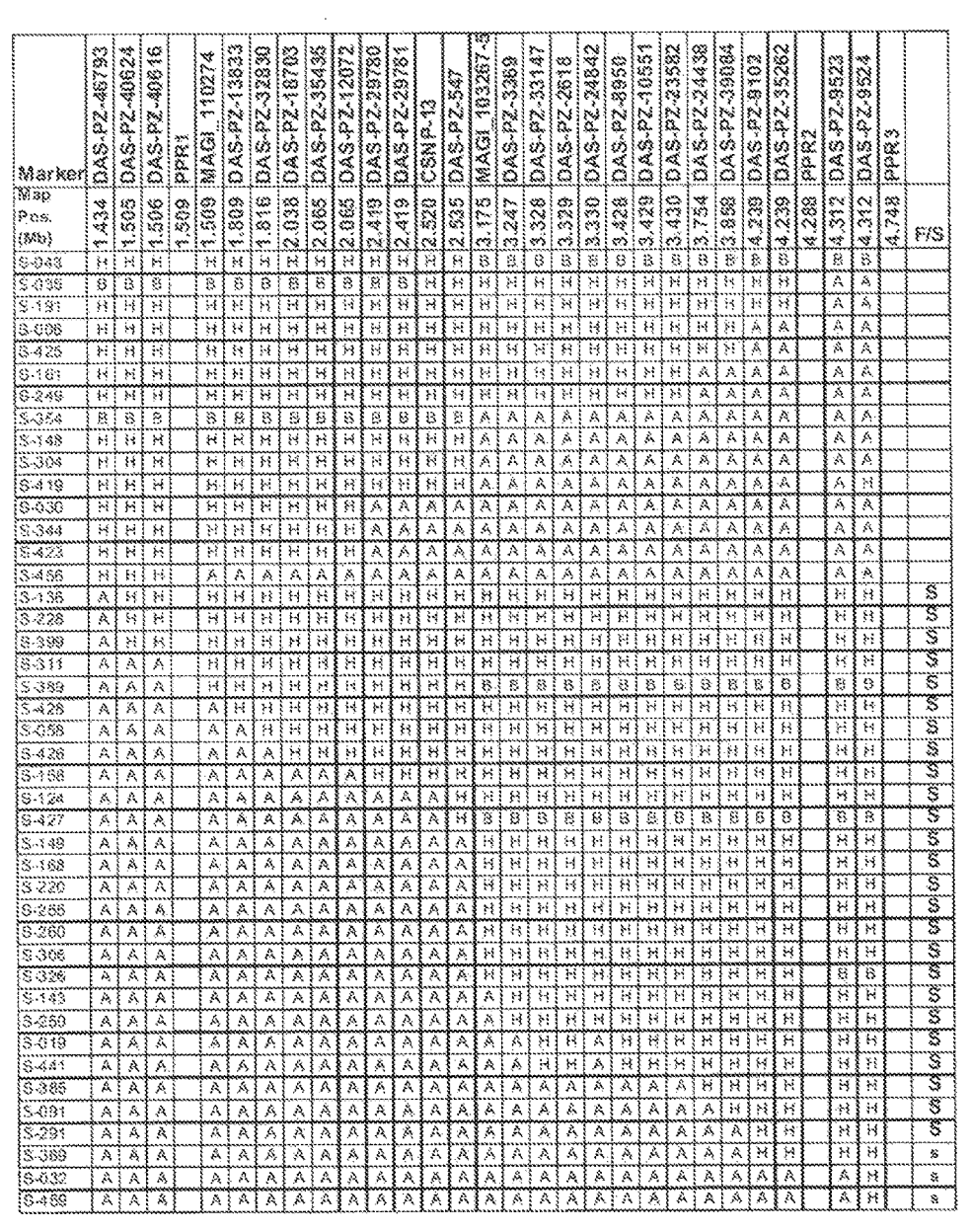

Interestingly and unexpectedly, in view of the fact that all previously-identified restorer genes, except for maize Rf2 and rice Rf17, encode pentatricopeptide repeat (PPR) proteins, there is no predicted PPR gene within the 1.505 Mb region containing Rf4, though there are three PPR genes located on 1.509, 4.288 and 4.748 Mb respectively. FIG. 3.

Genetic fine mapping of Rf4 with informative recombinants and additional SNP markers.

Figure 4:
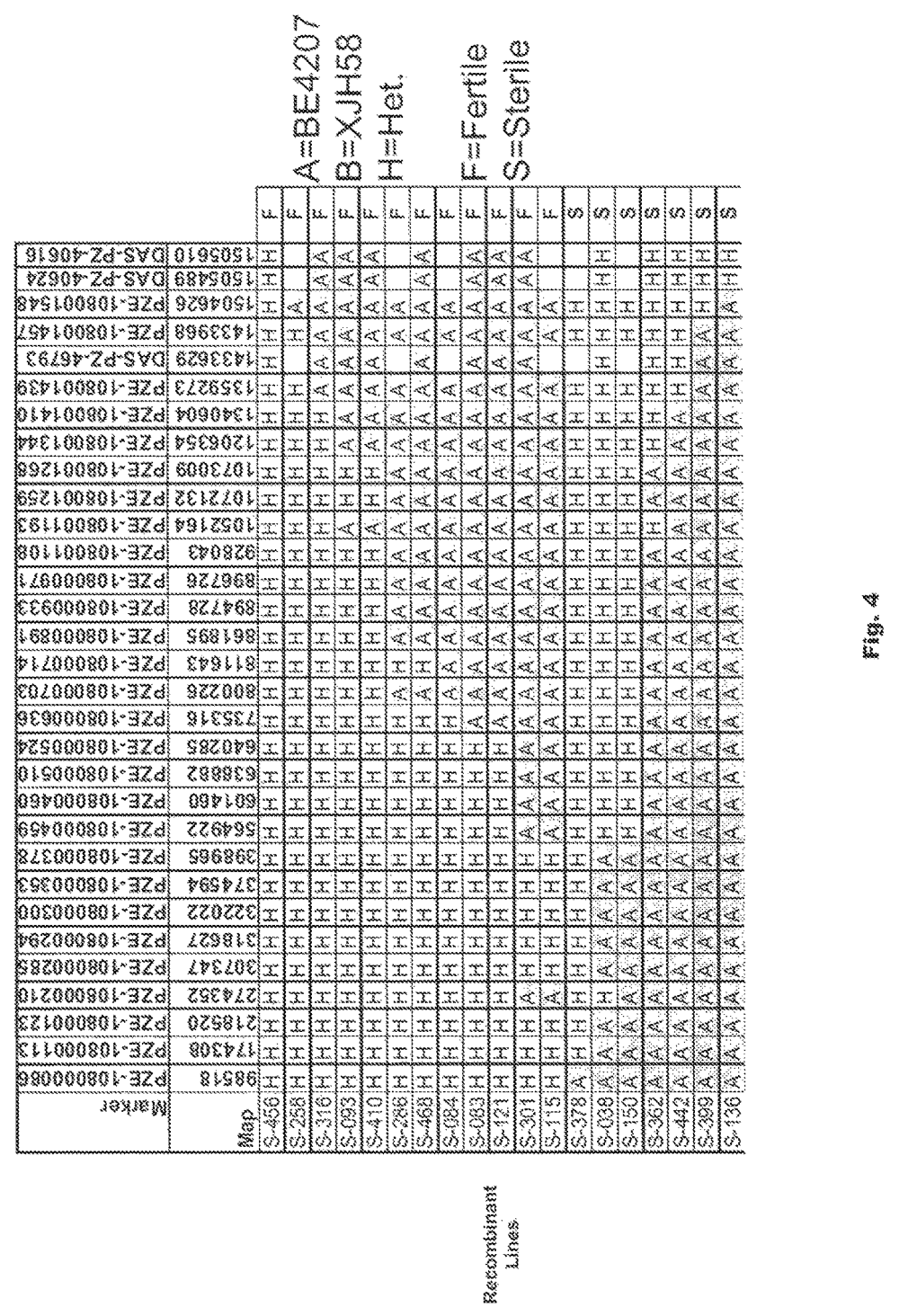

To further fine map the chromosome location of the restorer gene, Rf4, 96 SNP markers located from nucleotide position 12507 to 1504526 on chromosome 8 were selected for a parental polymorphism survey. 28 SNP markers were polymorphic between the two mapping parents. 93 recombinants, including some potential informative recombinants not included in the previous round of screening, were selected for genotyping with the 28 markers. Utilizing the same phenotype/genotype comparison described above, the Rf4 gene was positively mapped to a region of 0.56-Mb by using the 19 most informative recombinants, defined by plants S-301 and S-115 and SNP marker PZE-108000459 (SEQ ID NO:134) as the right border, as shown in FIG. 4. Based on the genotypic and phenotypic data from plant S-378 (sterile), the Rf4 gene may reside within a region of less than 100 kb, defined by SNP marker PZE-108000086 (SEQ ID NO:105). See FIG. 4. Therefore, Rf4 was mapped to a 0.56 Mb region that contains approximately 14 genes, and further mapped to a less than 100 kb region that contains six potential genes. See Table 2. The sequence of the Rf4 gene is selected from the group consisting of GRMZM2G122853 (SEQ ID NO:198); AC187051.4_FG005 (SEQ ID NO:199); GRMZM2G122851 (SEQ ID NO:200); GRMZM2G122850 (SEQ ID NO:201); GRMZM2G582028 (SEQ ID NO:202); GRMZM2G021276 (SEQ ID NO:203); GRMZM2G381376 (SEQ ID NO:204); GRMZM2G081127 (SEQ ID NO:205); GRMZM2G085111 (SEQ ID NO:206); GRMZM2G085038 (SEQ ID NO:207); GRMZM2G317468 (SEQ ID NO:208); GRMZM2G328030 (SEQ ID NO:209); GRMZM2G029450 (SEQ ID NO:210); and GRMZM2G077212 (SEQ ID NO:211).

TABLE 2

Predicted genes within the Rf4 region.

| Chr | Start | Stop | Gene_name | Description |
|---|---|---|---|---|
| 8 | 17505 | 19257 | GRMZM2G122853 | Peroxidase |
| 8 | 45481 | 50854 | AC187051.4_FG005 | Hypothetical Protein |
| 8 | 51763 | 53988 | GRMZM2G122851 | MULE transposase (TE) 129 AA |
| 8 | 67385 | 69586 | GRMZM2G122850 | Transposon protein, putative Prohibitin (TE) |
| 8 | 93160 | 93850 | GRMZM2G582028 | No significant hit, 68 AA |
| 8 | 95823 | 98367 | GRMZM2G021276 | HLH TF |
| 8 | 98418 | 98518 | PZE-108000086 | |
| 8 | 166253 | 166692 | GRMZM2G381376 | S-adenosylmethionine synthetase |
| 8 | 167824 | 174330 | GRMZM2G081127 | SPL1 TF (Squamosa promoter-binding-like) |
| 8 | 267226 | 273756 | GRMZM2G085111 | ABC transporter-like |
| 8 | 307170 | 319669 | GRMZM2G085038 | Pto kinase interactor 1 |
| 8 | 384128 | 387634 | GRMZM2G317468 | Transposon, En/Spm-like (TE) |
| 8 | 499230 | 502184 | GRMZM2G328030 | Lipase, class 3 (Pseudo gene?) |
| 8 | 505089 | 505924 | GRMZM2G029450 | GST (Pseudo Gene?) |
| 8 | 546182 | 548235 | GRMZM2G077212 | Isopenicillin N epimerase |
| 8 | 564822 | 564922 | PZE-108000459 | |

Those results are consistent with those reported in a poster entitled, "Restoration of c-type cytoplasmic male sterility in maize: Fine-mapping of Rf4," recently presented by Kohls et al. at the 2010 Maize Genetics Conference. Kohls et al. reportedly mapped an Rf4 gene to a 0.5 Mb region near the top of chromosome 8 using a limited number of markers. However, the genetic materials used by Kohls et al. were very different from those used in the presently described work. Importantly, Kohls et al. found significant percentage of only semi-fertile Rf4 individuals, while the fertility restoration in the present $F_2$ population was complete (no semi-fertile individuals were found). Additionally, better map resolution (<100 kb vs. 500 kb) was used to identify Rf4, and also to describe many more useful markers, including those that are extremely tightly linked to Rf4.

The results presented herein demonstrate the mapping of the Rf4 locus to a very small chromosomal fragment and identify the Rf4 gene. Unlike the majority of Rf genes cloned so far, Rf4 is almost certainly not a PPR gene. The linked molecular markers described herein (including tightly linked and extremely tightly linked markers) can be used to facilitate marker-assisted selection of restorer lines in the CMS-C/Rf4 system and to promote the development of hybrid corn using this system alone, or in conjunction with other systems.

Example 3: Fine Mapping of the Rf4 Gene

A large BE4207/XJH58 $F_3$ fine mapping population of 5,104 individuals derived from the recombinant lines described above was generated.

In the $F_2$ population, Rf4 was mapped to a region of less than 100 kb on top of chromosome 8. However, there are no existing molecular markers within this region except PZE-108000086, with a SNP at nucleotide position 98468. Two approaches were carried out to identify polymorphisms for additional markers within this interval. In the first approach, a NimbleGen™ (Roche Inc.) Sequence Capture experiment (Fu et al. (2010) Plant J. 62:898-909) was designed to capture all polymorphisms around the 6.0-Mb region on the top of chromosome 8 between the CMS line BE4207 and the restorer line XJH58, together with two additional restorer lines BE9515 and MLW03. Sequence capturing, sequencing of the captured targets, and SNP calling were performed by NimbleGen™ according to the manufacturer's recommended procedure. In tandem with the NimbleGen™ capture experiments, non-repetitive DNA sequences in the Rf4 region (the top 100 kb from chromosome 8) were retrieved from the B73 genome, and PCR primers were designed for amplification of genomic fragments from the two mapping parents, BE4207 and XJH58. PCR fragments were sequenced from both parents and polymorphisms (both SNPs and InDels) were identified.

Based on the results from both experiments, several thousand SNPs and InDels between the CMS line BE4207 and the restorer line XJH58 were identified within the 6-Mb captured region, including 77 SNPs and 29 InDels in the first 100 kb. Table 3. The PCR amplification experiment was targeted to the first 100 kb, with particular emphasis on the two expressed genes in this region, a plant peroxidase (GRMZM2G122853 (SEQ ID NO:198)) and a basic-helix-loop-helix (bHLH) transcription factor (GRMZM2G021276 (SEQ ID NO:203)). Sequencing of PCR products identified 35 SNPs and 24 InDels. Table 3. Notably, most of the changes identified in the PCR fragments were also found in the sequence capture project (50 out of 59, or 84.7%). Together, the two methods discovered 106 unique changes (Polymorphism IDs 1-106) between the two mapping parents, including 77 SNPs and 29 InDels in the 100 kb targeted Rf4 region. Table 3.

Based on their physical map location and the sequence context, 33 of the unique changes (24 SNPs and 9 InDels) were used to design primers for high throughput genotyping of the $F_3$ mapping populations using KASPar™ assays (Table 3), essentially as described in Example 1.

TABLE 3

Polymorphisms between CMS (BE4207) and restorer line (XJH58) and KASPar™ markers for Rf4 mapping. B73 nucleotide position is based on Maize B73 RefGen_v1, but v2 has the identical sequence within the 100 kb of chromosome 8.

| ID | B73 Chrom. 8 Position Start | Stop | NimbleGen™ Capture BE4207/XJH58 | PCR Sequencing BE4207/XJH58 | KASPar™ Marker |
|---|---|---|---|---|---|
| 1 | 8885 | 8885 | T/C | T/C | DAS-CMS1/2 |
| 2 | 11684 | 11684 | A/G | A/G | DAS-CMS3 |
| 3 | 11883 | 11883 | A/C | A/C | DAS-CMS4 |
| 4 | 12831 | 12831 | T/C | | |
| 5 | 13168 | 13168 | T/A | | |
| 6 | 13171 | 13171 | T/C | | |
| 7 | 13179 | 13179 | C/T | | |
| 8 | 13191 | 13191 | T/G | | |
| 9 | 14191 | 14191 | G/A | | |
| 10 | 15309 | 15309 | G/A | G/A | DAS-CMS5 |
| 11 | 15639 | 15639 | C/T | C/T | DAS-CMS6 |
| 12 | 15735 | 15735 | C/T | | |
| 13 | 15744 | 15744 | G/A | | |
| 14 | 15790 | 15790 | G/A | | |
| 15 | 17395 | 17395 | C/T | | |
| 16 | 18749 | 18749 | C/T | C/T | |
| 17 | 18796 | 18796 | C/T | C/T | |
| 18 | 18798 | 18799 | CT/GC | CT/GC | |
| 19 | 19119 | 19119 | T/A | T/A | |
| 20 | 22230 | 22230 | C/T | C/T | DAS-CMS7 |
| 21 | 22266 | 22266 | | T/C | DAS-CMS8 |
| 22 | 41082 | 41082 | G/C | | |
| 23 | 41335 | 41335 | G/C | | |
| 24 | 41944 | 41944 | C/T | | |
| 25 | 44285 | 44285 | G/C | G/C | DAS-CMS9 |
| 26 | 44387 | 44387 | C/T | C/T | DAS-CMS10 |
| 27 | 45202 | 45202 | | A/— | DAS-CMS11 |
| 28 | 46136 | 46136 | G/A | | |
| 29 | 46447 | 46447 | A/G | | |
| 30 | 46912 | 46912 | C/T | | |
| 31 | 46957 | 46957 | G/A | | |
| 32 | 46959 | 46959 | C/T | | |
| 33 | 46973 | 46973 | T/C | | |
| 34 | 46975 | 46975 | G/A | | |
| 35 | 46989 | 46989 | T/G | | |
| 36 | 47001 | 47001 | T/C | | |
| 37 | 47026 | 47026 | G/A | | |
| 38 | 65062 | 65063 | AT/— | | |
| 39 | 65438 | 65438 | —/GGT | —/GGT | DAS-CMS12 |
| 40 | 66993 | 66993 | | A/— | DAS-CMS13 |
| 41 | 79739 | 79739 | G/A | | |
| 42 | 82093 | 82093 | C/T | | |
| 43 | 85155 | 85155 | G/A | | |
| 44 | 85667 | 85667 | T/A | T/A | DAS-CMS14 |

TABLE 3-continued

Polymorphisms between CMS (BE4207) and restorer line (XJH58) and KASPar™ markers for Rf4 mapping. B73 nucleotide position is based on Maize B73 RefGen_v1, but v2 has the identical sequence within the 100 kb of chromosome 8.

| ID | B73 Chrom. 8 Position Start | Stop | NimbleGen™ Capture BE4207/XJH58 | PCR Sequencing BE4207/XJH58 | KASPar™ Marker |
|---|---|---|---|---|---|
| 45 | 85782 | 85784 | CGG/— | CGG/— | DAS-CMS15 |
| 46 | 86079 | 86079 |  | C/A | DAS-CMS16 |
| 47 | 86097 | 86097 |  | —/TC | DAS-CMS17 |
| 48 | 86113 | 86113 |  | G/T | DAS-CMS18 |
| 49 | 86247 | 86247 |  | —/T | DAS-CMS19 |
| 50 | 86653 | 86653 |  | T/— |  |
| 51 | 96248 | 96248 | C/T | C/T | DAS-CMS21 |
| 52 | 97087 | 97087 | C/A | C/A | DAS-CMS22 |
| 53 | 97177 | 97177 | —/GCC | —/GCC | DAS-CMS23 |
| 54 | 97337 | 97338 | AC/TT | AC/TT |  |
| 55 | 97341 | 97341 | C/G | C/G | DAS-CMS24 |
| 56 | 97371 | 97371 | A/G | A/G | DAS-CMS25 |
| 57 | 97382 | 97382 | —/GGCGTACTTGCGCGGAC (SEQ ID NO: 212) | —/GGCGTACTTGCGCGGAC (SEQ ID NO: 212) |  |
| 58 | 97405 | 97405 | —/GTC | —/GTC |  |
| 59 | 97411 | 97411 | T/C | T/C | DAS-CMS26 |
| 60 | 97421 | 97433 | GTTAAAAAATTAA (SEQ ID NO: 213)/— | GTTAAAAAATTAA (SEQ ID NO: 213)/— |  |
| 61 | 97452 | 97452 | —/GTT | —/GTT | DAS-CMS27 |
| 62 | 97673 | 97673 | C/T | C/T | DAS-CMS28 |
| 63 | 97827 | 97827 | T/C | T/C | DAS-CMS29 |
| 64 | 97962 | 97962 | C/T | C/T | DAS-CMS30 |
| 65 | 97964 | 97964 | —/ATGCATTACTT (SEQ ID NO: 214) | —/ATGCATTACTT (SEQ ID NO: 214) |  |
| 66 | 97973 | 97973 | —/GTGCTATACTACCTAACCTA (SEQ ID NO: 215) | —/GTGCTATACTACCTAACCTA (SEQ ID NO: 215) |  |
| 67 | 97989 | 97989 | T/C | T/C |  |
| 68 | 98188 | 98188 | C/A | C/A | DAS-CMS31 |
| 69 | 98323 | 98326 | ATAT/— | ATAT/— |  |
| 70 | 98335 | 98335 | —/A | —/A |  |
| 71 | 98350 | 98350 | T/C | T/C |  |
| 72 | 98359 | 98359 | T/C | T/C |  |
| 73 | 98367 | 98369 | AAT/— | AAT/— |  |
| 74 | 98393 | 98393 | G/T | G/T | DAS-CMS32 |
| 75 | 98403 | 98403 | C/T | C/T |  |
| 76 | 98426 | 98430 | CGGAT/— | CGGAT/— |  |
| 77 | 98468 | 98468 | C/TGGTTTCT | C/TGGTTTCT |  |
| 78 | 98489 | 98489 | T/G | T/G | DAS-CMS33 |
| 79 | 98533 | 98533 | A/C | A/C |  |
| 80 | 98540 | 98540 | G/A | G/A |  |
| 81 | 98552 | 98552 | G/T | G/T |  |
| 82 | 98557 | 98566 | CCCCTGAACC (SEQ ID NO: 216)/— | CCCCTGAACC (SEQ ID NO: 216)/— |  |
| 83 | 98660 | 98660 |  | —/T | DAS-CMS34 |
| 84 | 98679 | 98679 |  | —/A |  |
| 85 | 98735 | 98735 | G/A | G/A |  |
| 86 | 98811 | 98811 | A/C | A/C |  |
| 87 | 98857 | 98857 | —/ATAT |  |  |
| 88 | 98906 | 98906 | T/C |  |  |
| 89 | 98927 | 98927 | T/A |  |  |
| 90 | 98935 | 98935 | A/G |  |  |
| 91 | 99026 | 99026 | C/T |  |  |
| 92 | 99027 | 99027 | C/G |  |  |
| 93 | 99037 | 99037 | C/— |  |  |
| 94 | 99074 | 99074 | T/C |  |  |
| 95 | 99079 | 99079 | G/A |  |  |
| 96 | 99089 | 99089 | C/G |  |  |
| 97 | 99091 | 99091 | C/T |  |  |
| 98 | 99137 | 99137 | —/ATATT |  |  |
| 99 | 99298 | 99298 | G/A |  |  |
| 100 | 99418 | 99418 | A/C |  |  |
| 101 | 99443 | 99443 | C/T |  |  |
| 102 | 99447 | 99447 | T/A |  |  |
| 103 | 99491 | 99491 | A/G |  |  |

TABLE 3-continued

Polymorphisms between CMS (BE4207) and restorer line (XJH58) and KASPar™ markers for Rf4 mapping. B73 nucleotide position is based on Maize B73 RefGen_v1, but v2 has the identical sequence within the 100 kb of chromosome 8.

| ID | B73 Chrom. 8 Position | | NimbleGen™ Capture | PCR Sequencing | KASPar™ Marker |
|---|---|---|---|---|---|
| | Start | Stop | BE4207/XJH58 | BE4207/XJH58 | |
| 104 | 99622 | 99622 | —/CTAATGGT | | |
| 105 | 99925 | 99925 | T/A | | |
| 106 | 99962 | 99962 | A/G | | |

In Example 2, Rf4 was mapped to a region of less than 100 kb on the top of maize chromosome 8, defined by SNP marker PZA108000086. To map Rf4 to a much smaller interval, four flanking markers (DAS-CMS1 and DAS-CMS3 on the left, and PZE-108000378 and PZE-108000459 on the right) were selected to genotype all 5104 BE4207/XJH58 $F_3$ plants. FIG. 5. Plant S-378 was from $F_2$ and sterile. DNA from this plant was preserved for genotyping with new markers. A total of 307 recombinants within the larger 0.56-Mb Rf4 region were identified. These plants were selected for fertility scoring in the field, and all fertile plants were self-pollinated. Further, additional markers within the 0.56-Mb interval were used to genotype DNA from the 307 recombinants, and plant 5378 from the $F_2$ generation, to further define sites of recombination. Fine mapping was accomplished by comparing the phenotypic and genotypic data of the informative recombinants. Data from the 12 most informative recombinants show that Rf4 is delimited to the interval between DAS-CMS19 and DAS-CMS31, defined by plants 468-5048 and 468-4977. FIG. 5.

Using the maize B73 genome as a reference, DAS-CMS19 (−/T InDel; nucleotide position 86247) and DAS-CMS31 (C/A SNP; nucleotide position 98188) are approximately 12-kb apart, and are located in the same BAC clone; ZMMBBb0329M04 (accession no. AC187051). The sequence of the interval between DAS-CMS19 and DAS-CMS31 (in both B73 RefSeq v1 and v2) is provided in the Sequence Listing as SEQ ID NO:217. Since the most updated version of B73 RefGen (v2) still has two unresolved gaps (nucleotides 88058-88157 and 94849-94948) between the two markers, the exact length is not known. However, these gaps are more likely results of assembly difficulties due to repetitive sequences rather than actual physical gaps, since both markers have been located in the same BAC clone that has been sequenced.

Example 4: Characterization of the Maize Rf4 Gene

Rf4 Encodes a bHLH Transcription Factor

In the B73 genome, the 12 kb interval between DAS-CMS19 and DAS-CMS31 contains two predicted genes; GRMZM2G582028 (SEQ ID NO:202) (nucleotides 93160-93850) and GRMZM2G021276 (SEQ ID NO:203) (nucleotides 95823-98367). The first 9.4-kb fragment (nucleotides 86247-95642) of the 12-kb interval largely consists of repetitive sequences, including GRMZM2G582028. GRMZM2G582028 is annotated as a novel transposable element in B73 RefGen v2, and it is predicted to encode a small protein of 68-amino acids that does not have any significant hits in protein databases. Moreover, GRMZM2G582028 sequence itself is highly repetitive, and many identical or nearly identical copies are found in all 10 maize chromosomes. Therefore, GRMZM2G582028 is unlikely to be Rf4.

The remaining candidate for Rf4 is the only other predicted gene in this region, GRMZM2G021276. This gene encodes a basic-helix-loop-helix (bHLH) transcription factor of 365 amino acids, with a conserved bHLH domain located in approximately the middle portion of the protein. The promoter/5'UTR and the entire coding region, as well as an 82-bp 3' UTR, of this gene are located within the 12-kb interval, with the right-border marker (DAS-CMS31) residing in the 3' UTR region. BLAST results indicate that GRMZM2G021276 (hereafter referred to as Rf4-bHLH) is most likely a single-copy gene in the B73 genome. This gene and its gene product have not been characterized previously.

Rf4-bHLH Allelic Variations

The B73 genome sequence indicates that the Rf4-bHLH gene has 4 exons and three introns (FIG. 6), including a 635-bp intron1 located in the 5' UTR. Based on this information, PCR primers were designed to amplify a 3.2 kb Rf4-bHLH locus from the CMS line, BE4207, and three restorer lines (XJH58, BE9515 and MLW03), as well as from the non-CMS inbred, B104.

Sequencing results indicate that there are significant allelic variations between different inbreds. FIG. 7. The non-restorer allele rf4-bHLH from BE4207 (CMS; does not have a functional restore gene) is identical to that of B73, a well known inbred that also does not restore CMS-C. Interestingly, the three known restorer lines (XJH58, BE9515, and MLW03) have an identical Rf4-bHLH (restorer) allele that differs from the B73/BE4207 (CMS) allele. Restorer lines XJH58 and MLW03 share one common ancestor 2-3 generations ago. However, BE9515, an inbred that does not share any common ancestors with XJH58 or MLW03 also has the identical Rf4-bHLH sequence, suggesting that this particular allele is perhaps conserved among lines that restore CMS-C cytoplasm. Between the restorer allele (Rf4-bHLH) and the CMS/B73 non-restorer allele (rf4-bHLH), there are 20 SNPs and 16 InDels. FIG. 7. Notably, there is only one C/T SNP between the CMS/B73 allele and the restorer allele in the 1.1 kb 5'UTR/promoter region. When the predicted cDNAs from the 6 alleles are compared, there are only 6 SNPs and 2 InDels presented between the CMS/B73 allele and the restorer allele. FIG. 8.

B104 is an inbred line that does not have CMS-C cytoplasm. Experiments are in progress to determine whether B104 is a restorer of fertility to CMS-C. Out of the 44 sequence variations found in B104 allele, 28 of them have the same sequence as CMS/B73 allele, 8 are the same as the restorer allele, and 8 are unique to B104 (FIG. 7), indicating that the B104 allele is more similar to the CMS/B73 allele. Interestingly, all the cDNA variations in B104 have the same sequence as CMS/B73 allele, with the exception of a unique 12-bp (12 Cs) deletion found only in the B104 5' UTR. FIG. 8.

Alignments of predicted protein sequences of Rf4-bHLH are shown in FIG. 9. As expected, all three restorer lines have identical protein sequences, whereas B73, BE4207, and B104 share identical protein sequences. Between the two variants, there are only four amino-acid changes in the restorer lines: a His to Asn substitution ($H_{103}$ to $N_{103}$; Polymorphism ID 52; DAS-CMS22), an Ala insertion ($A_{130}$; Polymorphism ID 53; DAS-CMS23), a Pro to Leu substitution ($P_{266}$ to $L_{267}$; Polymorphism ID 62; DAS-CMS28), and a Tyr to Phe substitution ($Y_{186}$ to $F_{187}$; Polymorphism ID 54). Only the Tyr to Phe substitution occurs in the conserved bHLH domain. FIG. 9.

Rf4-bHLH is Specifically Expressed in the Developing Tassels/Pollens

The expression pattern of Rf4-bHLH was examined to provide further evidence that this transcription factor does play a role in CMS-C fertility restoration. Total RNA were extracted from the two mapping parents, BE4207 and XJH58, as well as $F_3$ individuals derived from an $F_2$ ear segregating for the first 0.56-Mb region of chromosome 8. Rf4-bHLH-specific and invertase control oligonucleotides (primers and probes) designed for RT-PCR are shown in Table 4.

TABLE 4

Oligonucleotides for RT-PCR

| Oligos | Sequences | SEQ ID NO: |
|---|---|---|
| bHLH-F | AGTACACCGCCCTCATGCA | 231 |
| bHLH-R | CCAGCTCCTGGATGTACTCGAT | 232 |
| bHLH-probe | 6FAM-ACAAAGACTGATAGGGCGA-MGBNFQ | 233 |
| INV59F | CGACGACTTGTCCGAGCAG | 234 |
| INV59R | TGCCGTCCGTGCCCT | 235 |
| INV-probe | VIC-CCGTGTACTTCTACCTGC-MGBNFQ | 236 |

Data from quantitative real-time PCR demonstrate that in restorer parent XJH58 plants, and $F_3$ plants homozygous or heterozygous for the restorer allele, Rf4-bHLH shows the strongest expression in tassels with developing anthers/pollens, weak expression in the shed pollens, and almost no expression in leaves from different developmental stages. These expression patterns are consistent with a role of Rf4-bHLH in pollen fertility restoration.

Figure 10:
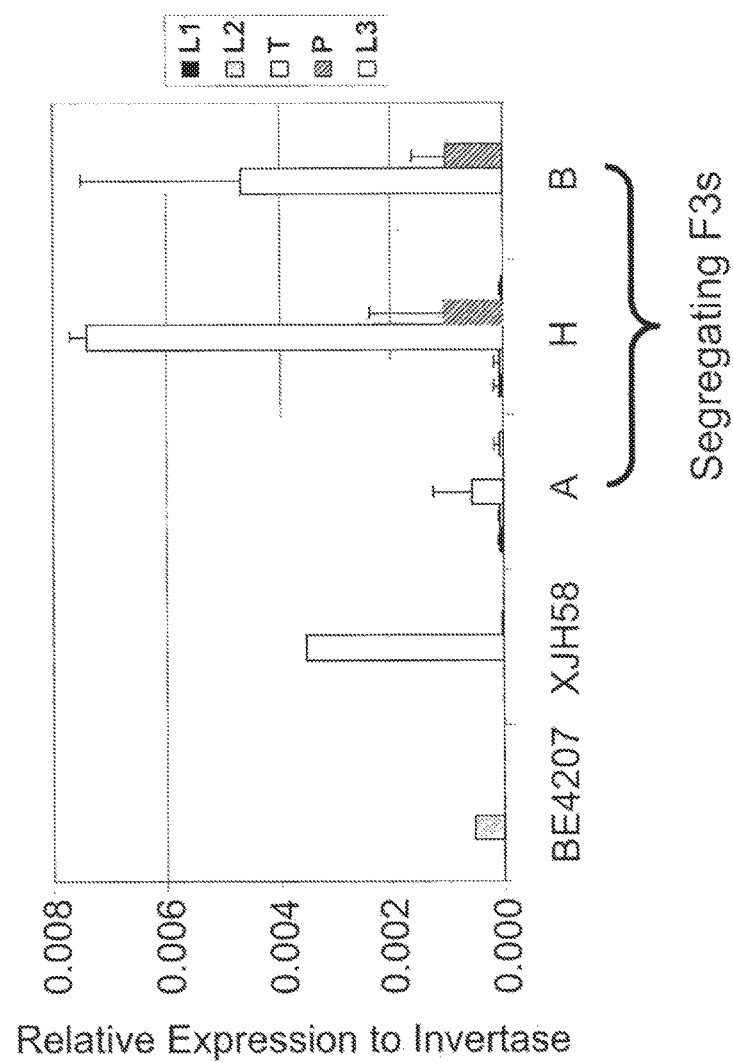
FIG. 10 includes data showing Rf4-HLH expression patterns. L1=5-week leaf, L2=7-week leaf, L3=9-week leaf, T=Tassels with developing anthers and pollens, P=Shed pollens. A=homozygous for BE4207, H=Heterozygous, B=Homozygous for XJH58. Data represent means of three plants of each genotype for the segregating F3 and 1 plant each for the parents. Error bars represent standard deviation FIG. 11 includes alignments of maize Rf4-bHLH (from restorer XJH58 and non-restorer BE4207) with their orthologs from other monocot species. The location of the conserved bHLH domain is underlined. The four amino acid changes between XJH58 Rf4-bHLH and BE4207 Rf4-bHLH are labeled.

Conversely, rf4-bHLH shows very low to no expression in leaves, as well as in developing tassels, in the CMS parent BE4207, and in $F_3$ plants homozygous for the non-restorer BE4207 allele. FIG. 10. However, the lack of rf4-bHLH expression in the developing tassels of plants homozygous for the non-restorer BE4207 allele is most likely conditioned by CMS itself (no exertion of anthers nor development of functional pollens), rather than allelic difference between XJH58 and BE4207. This is supported by the fact that rf4-bHLH (non-restorer allele) is apparently expressed at a significant level in B73, since there are 25 independent EST clones (for example: accessions BT043393, BT064392, etc.) specifically from this inbred in available EST databases. As mentioned previously, the B73 inbred does not restore CMS-C, and has the identical rf4-bHLH allele as the CMS inbred BE4207, which obviously does not have a functional Rf4 either.

Example 5: Characterization of the Rf4-bHLH Gene in Other Monocot Plants

Monocot Rf4-bHLH orthologs were retrieved from Sorghum (Sb03g011940), Brachypodium (BRADI2G11260), and rice (Os01g11870), which are all available from the National Center for Biotechnology Information (NCBI). These orthologs were compared to the maize sequences. As shown in FIG. 11, the Tyr ($Y_{186}$) residue within the bHLH domain is conserved among all species, with the notable exception of the Phe ($F_{187}$) substitution in the maize restorer allele. The other three changes are located in different variable regions and are generally not as conserved when compared across species. FIG. 11. These results suggest that $F_{187}$ in a restorer allele may play a crucial role in the fertility restoration of CMS-C cytoplasm.

The maize bHLH protein sequence is highly similar to the monocot orthologs from Sorghum bicolor (Sb03g011940; 84% identity), Oryza sativa (Os01g18870; 64%), and Brachypodium distachyon (BRADI2G11260, 63%), and to a lesser extent to bHLH domain proteins from dicot species (At2g31210 from Arabidopsis thaliana; 24%, for example). According to Pires and Dolan (2010), supra, the plant bHLH family of proteins can be classified into 26 subfamilies based on sequence homologies identified among 544 bHLH proteins from nine species of land plants (not including maize) and algae. If included in the analysis, Rf4-bHLH from maize would fall into subfamily II, which consists of the rice protein, OS01 g18870 (described above) and 10 other proteins. Similarly, Carretero-Paulet et al. (2010), supra, identified 32 bHLH subfamilies, and maize Rf4-bHLH be classified in their subfamily 9, which also consists of OS01 g18870 and 10 other proteins. The majority of members in Pires and Dolan's subfamily II, and Carretero-Paulet's subfamily 9, are the same sequences.

Rf4-bHLH is a transcription factor and its expected destination is the nucleus. In fact, several prediction programs, including PredictNLS™, identify two strong nuclear localization signals (NLSs) in Rf4-bHLH: 153-GRKRGRA-159 (SEQ ID NO:229) and 229-KKRRRR-234 (SEQ ID NO:230) (according to the XJH58 Rf4-bHLH amino acid position). FIG. 9.

All the Rf genes cloned thus far encoded proteins targeted to mitochondria (Liu et al. (2001), supra; Akagi et al. (2004), supra; Fujii and Toriyama (2009), supra), and presumably interact directly with CMS transcripts. However, the expected nuclear localization of Rf4-bHLH makes it unlikely that Rf4-bHLH is targeted to mitochondria and has a direct interaction with GMS-C transcripts. Rf4-bHLH likely functions further upstream to activate or increase expression of a nuclear gene that encodes a mitochondrial-targeted protein, which in turn leads to interference with CMS-C transcript expression to restore male fertility. This putative mitochondrial protein could be a member of the PPR protein family, or something similar to maize Rf2, rice RF17, or a novel protein. Chromatin immunoprecipitation, gene networking, or other molecular approaches may be used to identify the direct targets of Rf4-bHLH.

Example 6: Introduction of the Rf4-bHLH Gene into CMS Maize by Transformation

An Rf4-bHLH restorer gene (e.g., SEQ ID NO:220) is transformed into a maize CMS line. A transformed maize plant expresses the Rf4-bHLH polypeptide of SEQ ID NO:225, and the Rf4-bHLH is sufficient to restore male fertility in CMS-C cytoplasm.

What may be claimed is:

1. A maize plant comprising an Rf4 functional restorer gene for maize C-type cytoplasmic male sterility from restorer line XJH58,
wherein the plant comprises a marker nucleotide sequence selected from the group consisting of Marker ID Nos. 1-50:

| Marker ID No. | B73 Chrom. 8 Position | | Marker |
|---|---|---|---|
| | Start | Stop | |
| 1 | 8885 | 8885 | C |
| 2 | 11684 | 11684 | G |
| 3 | 11883 | 11883 | C |
| 4 | 12831 | 12831 | C |
| 5 | 13168 | 13168 | A |
| 6 | 13171 | 13171 | C |
| 7 | 13179 | 13179 | T |
| 8 | 13191 | 13191 | G |
| 9 | 14191 | 14191 | A |
| 10 | 15309 | 15309 | A |
| 11 | 15639 | 15639 | T |
| 12 | 15735 | 15735 | T |
| 13 | 15744 | 15744 | A |
| 14 | 15790 | 15790 | A |
| 15 | 17395 | 17395 | T |
| 16 | 18749 | 18749 | T |
| 17 | 18796 | 18796 | T |
| 18 | 18798 | 18799 | GC |
| 19 | 19119 | 19119 | A |
| 20 | 22230 | 22230 | T |
| 21 | 22266 | 22266 | C |
| 22 | 41082 | 41082 | C |
| 23 | 41335 | 41335 | C |
| 24 | 41944 | 41944 | T |
| 25 | 44285 | 44285 | C |
| 26 | 44387 | 44387 | T |
| 27 | 45202 | 45202 | — |
| 28 | 46136 | 46136 | A |
| 29 | 46447 | 46447 | G |
| 30 | 46912 | 46912 | T |
| 31 | 46957 | 46957 | A |
| 32 | 46959 | 46959 | T |
| 33 | 46973 | 46973 | C |
| 34 | 46975 | 46975 | A |
| 35 | 46989 | 46989 | G |
| 36 | 47001 | 47001 | C |
| 37 | 47026 | 47026 | A |
| 38 | 65062 | 65063 | — |
| 39 | 65438 | 65438 | GGT |
| 40 | 66993 | 66993 | A |
| 41 | 79739 | 79739 | A |
| 42 | 82093 | 82093 | T |
| 43 | 85155 | 85155 | A |
| 44 | 85667 | 85667 | A |
| 45 | 85782 | 85784 | — |
| 46 | 86079 | 86079 | A |
| 47 | 86097 | 86097 | TC |
| 48 | 86113 | 86113 | T |
| 49 | 86247 | 86247 | T |
| 50 | 86653 | 86653 | —, | and wherein the plant comprises a marker nucleotide sequence selected from the group consisting of SEQ ID NOs:6-9, SEQ ID NO:105, SEQ ID NO:109, SEQ ID NO:111, SEQ ID NO:115, SEQ ID NOs:118-120, SEQ ID NO:123, SEQ ID NO:126, SEQ ID NO:134, SEQ ID NO:135, SEQ ID NO:137, SEQ ID NO:138, SEQ ID NO:144, SEQ ID NO:149, SEQ ID NO:151, SEQ ID NO:160, SEQ ID NO:163, SEQ ID NO:164, SEQ ID NO:167, SEQ ID NO:173, SEQ ID NO:177, SEQ ID NO:178, SEQ ID NO:183, SEQ ID NOs:189-191, SEQ ID NO:197, and the markers referred to as Marker ID Nos. 51-106:

| Marker ID No. | B73 Chrom. 8 Position | | Marker |
|---|---|---|---|
| | Start | Stop | |
| 51 | 96248 | 96248 | T |
| 52 | 97087 | 97087 | A |
| 53 | 97177 | 97177 | GCC |
| 54 | 97337 | 97338 | TT |

NO:134, SEQ ID NO:135, SEQ ID NO:137, SEQ ID NO:138, SEQ ID NO:144, SEQ ID NO:149, SEQ ID NO:151, SEQ ID NO:160, SEQ ID NO:163, SEQ ID NO:164, SEQ ID NO:167, SEQ ID NO:173, SEQ ID NO:177, SEQ ID NO:178, SEQ ID NO:183, SEQ ID NOs:189-191, SEQ ID NO:197, and the markers referred to as Marker ID Nos. 1-106:

| Marker ID No. | B73 Chrom. 8 Position Start | Stop | Marker |
|---|---|---|---|
| 1 | 8885 | 8885 | C |
| 2 | 11684 | 11684 | G |
| 3 | 11883 | 11883 | C |
| 4 | 12831 | 12831 | C |
| 5 | 13168 | 13168 | A |
| 6 | 13171 | 13171 | C |
| 7 | 13179 | 13179 | T |
| 8 | 13191 | 13191 | G |
| 9 | 14191 | 14191 | A |
| 10 | 15309 | 15309 | A |
| 11 | 15639 | 15639 | T |
| 12 | 15735 | 15735 | T |
| 13 | 15744 | 15744 | A |
| 14 | 15790 | 15790 | A |
| 15 | 17395 | 17395 | T |
| 16 | 18749 | 18749 | T |
| 17 | 18796 | 18796 | T |
| 18 | 18798 | 18799 | GC |
| 19 | 19119 | 19119 | A |
| 20 | 22230 | 22230 | T |
| 21 | 22266 | 22266 | C |
| 22 | 41082 | 41082 | C |
| 23 | 41335 | 41335 | C |
| 24 | 41944 | 41944 | T |
| 25 | 44285 | 44285 | C |
| 26 | 44387 | 44387 | T |
| 27 | 45202 | 45202 | — |
| 28 | 46136 | 46136 | A |
| 29 | 46447 | 46447 | G |
| 30 | 46912 | 46912 | T |
| 31 | 46957 | 46957 | A |
| 32 | 46959 | 46959 | T |
| 33 | 46973 | 46973 | C |
| 34 | 46975 | 46975 | A |
| 35 | 46989 | 46989 | G |
| 36 | 47001 | 47001 | C |
| 37 | 47026 | 47026 | A |
| 38 | 65062 | 65063 | — |
| 39 | 65438 | 65438 | GGT |
| 40 | 66993 | 66993 | A |
| 41 | 79739 | 79739 | A |
| 42 | 82093 | 82093 | T |
| 43 | 85155 | 85155 | A |
| 44 | 85667 | 85667 | A |
| 45 | 85782 | 85784 | — |
| 46 | 86079 | 86079 | A |
| 47 | 86097 | 86097 | TC |
| 48 | 86113 | 86113 | T |
| 49 | 86247 | 86247 | T |
| 50 | 86653 | 86653 | — |
| 51 | 96248 | 96248 | T |
| 52 | 97087 | 97087 | A |
| 53 | 97177 | 97177 | GCC |
| 54 | 97337 | 97338 | TT |
| 55 | 97341 | 97341 | G |
| 56 | 97371 | 97371 | G |
| 57 | 97382 | 97382 | GGCGTACTTGCGCGCGGAC (SEQ ID NO: 212) |
| 58 | 97405 | 97405 | GTC |
| 59 | 97411 | 97411 | C |
| 60 | 97421 | 97433 | — |
| 61 | 97452 | 97452 | GTT |
| 62 | 97673 | 97673 | T |
| 63 | 97827 | 97827 | C |
| 64 | 97962 | 97962 | T |
| 65 | 97964 | 97964 | ATGCATTACTT (SEQ ID NO: 214) |

-continued

| Marker ID No. | B73 Chrom. 8 Position Start | Stop | Marker |
|---|---|---|---|
| 55 | 97341 | 97341 | G |
| 56 | 97371 | 97371 | G |
| 57 | 97382 | 97382 | GGCGTACTTGCGCGCGGAC (SEQ ID NO: 212) |
| 58 | 97405 | 97405 | GTC |
| 59 | 97411 | 97411 | C |
| 60 | 97421 | 97433 | — |
| 61 | 97452 | 97452 | GTT |
| 62 | 97673 | 97673 | T |
| 63 | 97827 | 97827 | C |
| 64 | 97962 | 97962 | T |
| 65 | 97964 | 97964 | ATGCATTACTT (SEQ ID NO: 214) |
| 66 | 97973 | 97973 | GTGCTATACTACCTAACCTA (SEQ ID NO: 215) |
| 67 | 97989 | 97989 | C |
| 68 | 98188 | 98188 | A |
| 69 | 98323 | 98326 | — |
| 70 | 98335 | 98335 | A |
| 71 | 98350 | 98350 | C |
| 72 | 98359 | 98359 | C |
| 73 | 98367 | 98369 | — |
| 74 | 98393 | 98393 | T |
| 75 | 98403 | 98403 | T |
| 76 | 98426 | 98430 | — |
| 77 | 98468 | 98468 | TGGTTTCT |
| 78 | 98489 | 98489 | G |
| 79 | 98533 | 98533 | C |
| 80 | 98540 | 98540 | A |
| 81 | 98552 | 98552 | T |
| 82 | 98557 | 98566 | CCCCTGAACC (SEQ ID NO: 216) |
| 83 | 98660 | 98660 | T |
| 84 | 98679 | 98679 | A |
| 85 | 98735 | 98735 | A |
| 86 | 98811 | 98811 | C |
| 87 | 98857 | 98857 | ATAT |
| 88 | 98906 | 98906 | C |
| 89 | 98927 | 98927 | A |
| 90 | 98935 | 98935 | G |
| 91 | 99026 | 99026 | T |
| 92 | 99027 | 99027 | G |
| 93 | 99037 | 99037 | — |
| 94 | 99074 | 99074 | C |
| 95 | 99079 | 99079 | A |
| 96 | 99089 | 99089 | G |
| 97 | 99091 | 99091 | T |
| 98 | 99137 | 99137 | ATATT |
| 99 | 99298 | 99298 | A |
| 100 | 99418 | 99418 | C |
| 101 | 99443 | 99443 | T |
| 102 | 99447 | 99447 | A |
| 103 | 99491 | 99491 | G |
| 104 | 99622 | 99622 | CTAATGGT |
| 105 | 99925 | 99925 | A |
| 106 | 99962 | 99962 | G. |

2. The maize plant of claim 1, wherein the plant comprises a marker nucleotide sequence selected from the group consisting of SEQ ID NO:8 and Marker ID Nos. 1-3, 10, 11, 20, 21, 25-27, 39, 40, 44-49, 51-53, 55, 56, 59, 61-64, 68, 74, 78, and 83.

3. The maize plant of claim 1, wherein the plant comprises a marker nucleotide sequence selected from the group consisting of SEQ ID NO:105; SEQ ID NO:109; SEQ ID NO:111; SEQ ID NO:115; SEQ ID NOs:118-120; SEQ ID NO:123; SEQ ID NO:126 and SEQ ID NO:134.

4. A hybrid maize plant that is an $F_1$ progeny plant having XJH58 and a second plant as parents, the progeny plant comprising a marker nucleotide sequence selected from the group consisting of SEQ ID NOs:6-9, SEQ ID NO:105, SEQ ID NO:109, SEQ ID NO:111, SEQ ID NO:115, SEQ ID NOs:118-120, SEQ ID NO:123, SEQ ID NO:126, SEQ ID -continued

| Marker ID No. | B73 Chrom. 8 Position Start | Stop | Marker |
|---|---|---|---|
| 66 | 97973 | 97973 | GTGCTATACTACCTAACCTA (SEQ ID NO: 215) |
| 67 | 97989 | 97989 | C |
| 68 | 98188 | 98188 | A |
| 69 | 98323 | 98326 | — |
| 70 | 98335 | 98335 | A |
| 71 | 98350 | 98350 | C |
| 72 | 98359 | 98359 | C |
| 73 | 98367 | 98369 | — |
| 74 | 98393 | 98393 | T |
| 75 | 98403 | 98403 | T |
| 76 | 98426 | 98430 | — |
| 77 | 98468 | 98468 | TGGTTTCT |
| 78 | 98489 | 98489 | G |
| 79 | 98533 | 98533 | C |
| 80 | 98540 | 98540 | A |
| 81 | 98552 | 98552 | T |
| 82 | 98557 | 98566 | CCCCTGAACC (SEQ ID NO: 216) |
| 83 | 98660 | 98660 | T |
| 84 | 98679 | 98679 | A |
| 85 | 98735 | 98735 | A |
| 86 | 98811 | 98811 | C |
| 87 | 98857 | 98857 | ATAT |
| 88 | 98906 | 98906 | C |
| 89 | 98927 | 98927 | A |
| 90 | 98935 | 98935 | G |
| 91 | 99026 | 99026 | T |
| 92 | 99027 | 99027 | G |
| 93 | 99037 | 99037 | — |
| 94 | 99074 | 99074 | C |
| 95 | 99079 | 99079 | A |
| 96 | 99089 | 99089 | G |
| 97 | 99091 | 99091 | T |
| 98 | 99137 | 99137 | ATATT |
| 99 | 99298 | 99298 | A |
| 100 | 99418 | 99418 | C |
| 101 | 99443 | 99443 | T |
| 102 | 99447 | 99447 | A |
| 103 | 99491 | 99491 | G |
| 104 | 99622 | 99622 | CTAATGGT |
| 105 | 99925 | 99925 | A |
| 106 | 99962 | 99962 | G. |

5. The $F_1$ hybrid maize plant of claim 4, wherein the nucleotide sequence is selected from the group consisting of SEQ ID NO:8 and Marker ID Nos. 1-3, 10, 11, 20, 21, 25-27, 39, 40, 44-49, 51-53, 55, 56, 59, 61-64, 68, 74, 78, and 83.

6. The $F_1$ hybrid maize plant of claim 4, wherein the nucleotide sequence is selected from the group consisting of SEQ ID NO:105; SEQ ID NO:109; SEQ ID NO:111; SEQ ID NO:115; SEQ ID NOs:118-120; SEQ ID NO:123; SEQ ID NO:126 and SEQ ID NO:134.

7. The $F_1$ hybrid maize plant of claim 4, comprising some but not all of the nucleotide sequences selected from the group consisting of SEQ ID NOs:6-9; SEQ ID NO:105; SEQ ID NO:109; SEQ ID NO:111; SEQ ID NO:115; SEQ ID NOs:118-120; SEQ ID NO:123; SEQ ID NO:126; SEQ ID NO:134; SEQ ID NO:135; SEQ ID NO:137; SEQ ID NO:138; SEQ ID NO:144; SEQ ID NO:149; SEQ ID NO:151; SEQ ID NO:160; SEQ ID NO:163; SEQ ID NO:164; SEQ ID NO:167; SEQ ID NO:173; SEQ ID NO:177; SEQ ID NO:178; SEQ ID NO:183; SEQ ID NOs:189-191; SEQ ID NO:197; and the markers referred to as polymorphism ID nos. 1-106 in Table 3.

8. The maize plant of claim 1, wherein the maize plant is an inbred maize plant.

9. The inbred maize plant of claim 8, wherein the plant comprises a marker nucleotide sequence selected from the group consisting of SEQ ID NO:8 and Marker ID Nos. 1-3, 10, 11, 20, 21, 25-27, 39, 40, 44-49, 51-53, 55, 56, 59, 61-64, 68, 74, 78, and 83.

10. The inbred maize plant of claim 8, wherein the plant comprises a marker nucleotide sequence selected from the group consisting of SEQ ID NO:105; SEQ ID NO:109; SEQ ID NO:111; SEQ ID NO:115; SEQ ID NOs:118-120; SEQ ID NO:123; SEQ ID NO:126 and SEQ ID NO:134.

11. A population consisting of at least 126 maize plants of claim 1, wherein the population does not comprise a semi-fertile maize plant.

12. A maize plant comprising an Rf4 functional restorer gene for maize C-type cytoplasmic male sterility from restorer line XJH58,
wherein the plant comprises a genetic marker selected from the group consisting of Marker ID Nos. 1-50:

| Marker ID No. | B73 Chrom. 8 Position Start | Stop | Marker |
|---|---|---|---|
| 1 | 8885 | 8885 | C |
| 2 | 11684 | 11684 | G |
| 3 | 11883 | 11883 | C |
| 4 | 12831 | 12831 | C |
| 5 | 13168 | 13168 | A |
| 6 | 13171 | 13171 | C |
| 7 | 13179 | 13179 | T |
| 8 | 13191 | 13191 | G |
| 9 | 14191 | 14191 | A |
| 10 | 15309 | 15309 | A |
| 11 | 15639 | 15639 | T |
| 12 | 15735 | 15735 | T |
| 13 | 15744 | 15744 | A |
| 14 | 15790 | 15790 | A |
| 15 | 17395 | 17395 | T |
| 16 | 18749 | 18749 | T |
| 17 | 18796 | 18796 | T |
| 18 | 18798 | 18799 | GC |
| 19 | 19119 | 19119 | A |
| 20 | 22230 | 22230 | T |
| 21 | 22266 | 22266 | C |
| 22 | 41082 | 41082 | C |
| 23 | 41335 | 41335 | C |
| 24 | 41944 | 41944 | T |
| 25 | 44285 | 44285 | C |
| 26 | 44387 | 44387 | T |
| 27 | 45202 | 45202 | — |
| 28 | 46136 | 46136 | A |
| 29 | 46447 | 46447 | G |
| 30 | 46912 | 46912 | T |
| 31 | 46957 | 46957 | A |
| 32 | 46959 | 46959 | T |
| 33 | 46973 | 46973 | C |
| 34 | 46975 | 46975 | A |
| 35 | 46989 | 46989 | G |
| 36 | 47001 | 47001 | C |
| 37 | 47026 | 47026 | A |
| 38 | 65062 | 65063 | — |
| 39 | 65438 | 65438 | GGT |
| 40 | 66993 | 66993 | A |
| 41 | 79739 | 79739 | A |
| 42 | 82093 | 82093 | T |
| 43 | 85155 | 85155 | A |
| 44 | 85667 | 85667 | A |
| 45 | 85782 | 85784 | — |
| 46 | 86079 | 86079 | A |
| 47 | 86097 | 86097 | TC |
| 48 | 86113 | 86113 | T |
| 49 | 86247 | 86247 | T |
| 50 | 86653 | 86653 | —, | and
wherein the plant comprises a genetic marker selected from the group consisting of the markers referred to as Marker ID Nos. 51-106:

| Marker ID No. | B73 Chrom. 8 Position Start | Stop | Marker |
|---|---|---|---|
| 51 | 96248 | 96248 | T |
| 52 | 97087 | 97087 | A |
| 53 | 97177 | 97177 | GCC |
| 54 | 97337 | 97338 | TT |
| 55 | 97341 | 97341 | G |
| 56 | 97371 | 97371 | G |
| 57 | 97382 | 97382 | GGCGTACTTGCGCGCGGAC (SEQ ID NO: 212) |
| 58 | 97405 | 97405 | GTC |
| 59 | 97411 | 97411 | C |
| 60 | 97421 | 97433 | — |
| 61 | 97452 | 97452 | GTT |
| 62 | 97673 | 97673 | T |
| 63 | 97827 | 97827 | C |
| 64 | 97962 | 97962 | T |
| 65 | 97964 | 97964 | ATGCATTACTT (SEQ ID NO: 214) |
| 66 | 97973 | 97973 | GTGCTATACTACCTAACCTA (SEQ ID NO: 215) |
| 67 | 97989 | 97989 | C |
| 68 | 98188 | 98188 | A |
| 69 | 98323 | 98326 | — |
| 70 | 98335 | 98335 | A |
| 71 | 98350 | 98350 | C |
| 72 | 98359 | 98359 | C |
| 73 | 98367 | 98369 | — |
| 74 | 98393 | 98393 | T |
| 75 | 98403 | 98403 | T |
| 76 | 98426 | 98430 | — |
| 77 | 98468 | 98468 | TGGTTTCT |
| 78 | 98489 | 98489 | G |
| 79 | 98533 | 98533 | C |
| 80 | 98540 | 98540 | A |
| 81 | 98552 | 98552 | T |
| 82 | 98557 | 98566 | CCCCTGAACC (SEQ ID NO: 216) |
| 83 | 98660 | 98660 | T |
| 84 | 98679 | 98679 | A |
| 85 | 98735 | 98735 | A |
| 86 | 98811 | 98811 | C |
| 87 | 98857 | 98857 | ATAT |
| 88 | 98906 | 98906 | C |
| 89 | 98927 | 98927 | A |
| 90 | 98935 | 98935 | G |
| 91 | 99026 | 99026 | T |
| 92 | 99027 | 99027 | G |
| 93 | 99037 | 99037 | — |
| 94 | 99074 | 99074 | C |
| 95 | 99079 | 99079 | A |
| 96 | 99089 | 99089 | G |
| 97 | 99091 | 99091 | T |
| 98 | 99137 | 99137 | ATATT |
| 99 | 99298 | 99298 | A |
| 100 | 99418 | 99418 | C |
| 101 | 99443 | 99443 | T |
| 102 | 99447 | 99447 | A |
| 103 | 99491 | 99491 | G |
| 104 | 99622 | 99622 | CTAATGGT |
| 105 | 99925 | 99925 | A |
| 106 | 99962 | 99962 | G. |

13. The maize plant of claim 12, wherein the plant comprises a genetic marker selected from the group consisting of Marker ID Nos. 73-106.

14. The maize plant of claim 13, wherein the maize plant is an inbred maize plant.

15. The maize plant of claim 13, wherein the maize plant is a hybrid maize plant that is a progeny plant having XJH58 and a second plant as parents.

16. A population consisting of at least 126 maize plants of claim 13, wherein the population does not comprise a semi-fertile maize plant.

17. The maize plant of claim 12, wherein the plant comprises in its genome a polynucleotide at least 95% identical to SEQ ID NO:217.

18. The maize plant of claim 17, wherein the plant comprises in its genome a polynucleotide at least 99% identical to SEQ ID NO:217.

19. The maize plant of claim 18, wherein the plant comprises in its genome the polynucleotide of SEQ ID NO:217.

\* \* \* \* \*

SEQUENCE LISTING

<160> NUMBER OF SEQ ID NOS: 236

<210> SEQ ID NO 1
<211> LENGTH: 201
<212> TYPE: DNA
<213> ORGANISM: Zea mays

<400> SEQUENCE: 1

```
acctccagag ccccaacgag tacatccgcg gcgtcactct gcggttcctc tgcaggctct      60
ccgagcccga ggtgctcgag ccgctcgtgc cgtccgtgct ygcgaacctg gagcacaggc     120
accaattcat ccggagacac gctgtctccg cggtttccgc gatctaccgc ctcccgcatg     180
gtgaccagct catccccgac g                                               201
```

<210> SEQ ID NO 2
<211> LENGTH: 201
<212> TYPE: DNA
<213> ORGANISM: Zea mays

<400> SEQUENCE: 2

```
gcgtcgcgag cgtgcgtaca tgaagatgtc gtctgttgcc tgctgctgct gctgcggcgg      60
cgcgggccgg ccctcctccg tccgctcgtc tgaactcccg ycgtctccg cgcgcaccac      120 gccagcgccg tggtcgtcgt cagctgagcc gaagctccag agcgcccagc cgccgctctg     180
gtcgtccaac agctcgccgc c                                               201
```

<210> SEQ ID NO 3
<211> LENGTH: 201
<212> TYPE: DNA
<213> ORGANISM: Zea mays

<400> SEQUENCE: 3

```
cccgaactcg aacgtctctt tctctcctca aatcagataa ccgaacttgc tgtttgacgc      60
taacatccag ctgcgccttg atctcctcca gatgagcgcc rccatggcgt ggtatccatt     120
accgcagagc ggaggcacag gcacgccgtc gggcggcggc gagctgttgg acgaccagag     180
cggcggctgg gcgctctgga g                                               201
```

<210> SEQ ID NO 4
<211> LENGTH: 201
<212> TYPE: DNA
<213> ORGANISM: Zea mays

<400> SEQUENCE: 4

```
cagcggtgct ggccatcaag gccctgcaca gcaggtgcct gataccgcgg ccgcccttcc      60
tcgccgcggc gcgcgactcg ctgctgtccg tttgtgctgc rgcgccacgc agcggcagcg     120
gcggcggaga gagcgacctc gcgcgcggcg cgccgccgtc gctgcgcacc ttctccagcg     180
ccgccgcgaa cgggtcgaag c                                               201
```

<210> SEQ ID NO 5
<211> LENGTH: 201
<212> TYPE: DNA
<213> ORGANISM: Zea mays

<400> SEQUENCE: 5

```
tcgccgcggc gcgcgactcg ctgctgtccg tttgtgctgc agcgccacgc agcggcagcg      60
gcggcggaga gagcgacctc gcgcgcggcg cgccgccgtc sctgcgcacc ttctccagcg     120
ccgccgcgaa cgggtcgaag cccctgtgct tcctgcatcc ggcctgcagc gccgcggccg     180
```
acggcgtggg cgacgtcgcg g                                                    201

<210> SEQ ID NO 6
<211> LENGTH: 201
<212> TYPE: DNA
<213> ORGANISM: Zea mays

<400> SEQUENCE: 6
gaaggagcct gccggcgacc gacctgtaga agccctcgga ggcgccggcg gggacgaggc           60
agtaggcgtt ggtgagcctc gcgaagacgc ccacctcgct wgagttctcg aacttgacgc          120
ctgcattata tcatttgttg gaccattatt gttggcgttt tgctatggct atcaatcaat          180
ccgcgcgctg tttgtaacca a                                                    201

<210> SEQ ID NO 7
<211> LENGTH: 201
<212> TYPE: DNA
<213> ORGANISM: Zea mays

<400> SEQUENCE: 7
cactgaggtc tgagagggg taccgtacct ggaacacgac gtcctcgagc tcccggagca            60
ccagcgcttg gaagaggaag ccccccttcat ccgcgacgga ygacctgctc cttttcgtcg         120
cagcaaagct cgccccatcc tggcaccaac ggaacgaaca cccagggctc ggctcatcag          180
agcagtgccg tgcgtgatcg a                                                    201

<210> SEQ ID NO 8
<211> LENGTH: 201
<212> TYPE: DNA
<213> ORGANISM: Zea mays

<400> SEQUENCE: 8
agcaaagctc gccccatcct ggcaccaacg gaacgaacac ccagggctcg gctcatcaga           60
gcagtgccgt gcgtgatcga gtcgagagca gcaccacacg ycacttgcgc aaaccagtac         120
ctggtcctca ggcgtgagcg tgagatccgg cgccgcgctc tgcagctgca ggtcgtggct         180
gaagagaggg aagccgcagg t                                                    201

<210> SEQ ID NO 9
<211> LENGTH: 201
<212> TYPE: DNA
<213> ORGANISM: Zea mays

<400> SEQUENCE: 9
cccgttcact ctctcctcct cccctccgct ccctcccagt cccagatccc gattcgccgc           60
cgcctccggc agatccagcc agcagctccc gccgcagaac ygccgcgggc gccatggaga         120
agccatgctc tctcctggtc cacttcgaca agggctcggc atcgatggcg aacgagatca         180
aggcggatct ggagggcagc g                                                    201

<210> SEQ ID NO 10
<211> LENGTH: 121
<212> TYPE: DNA
<213> ORGANISM: Zea mays

<400> SEQUENCE: 10
ttgcattctg ctaaagaata cggcgggata ataatgtgtc ctagtcttgt aatgaactac           60
wagtgtcttt gcatttggac tggttcgctt gtgagtcata gagattgctg aactcgtgag         120
t                                                                          121

<210> SEQ ID NO 11
<211> LENGTH: 201
<212> TYPE: DNA
<213> ORGANISM: Zea mays

<400> SEQUENCE: 11
cgcatcacac ctccgatcag ctcccccttt gccagcatgt ggatccgacc cggacagcca      60
aacccatacg acgtgcacca ccgcggccgt tctcaccaag ycgccatcga cttgctgacg     120
acgacgacgt tcgtcaggcg gtgcgcgctc agaccaccat ggccagcgtc ggcgacgacg     180
cgccgctgct cggcggcggc g                                               201

<210> SEQ ID NO 12
<211> LENGTH: 201
<212> TYPE: DNA
<213> ORGANISM: Zea mays

<400> SEQUENCE: 12
ggcggcagcg agagagctc gagggcgtgg agcagacggg gagaccagga aggaaacggt       60
cggggagagg aggagcgcca tgggtgggtg tggcattctt kgccttgctg cggctgcgcc     120
tgcgagaggt agggataata ataaccggat aagccttgga gagcagagaa tgctttccgt     180
ccgatcggca cttaacggtc a                                               201

<210> SEQ ID NO 13
<211> LENGTH: 201
<212> TYPE: DNA
<213> ORGANISM: Zea mays

<400> SEQUENCE: 13
accaatgatc gtttacccgg catttgcaca tctgcagagc tgcatttcgt tgcttgttct      60
ttcttgattt tgttgatctt gtgtagccag agcaatctat mcatcctttc ctgatctcct    120
ggagtgagtg cagggcaggc aggcaggcag gcgatgcgac gaagaataag tatctgctga    180
ctgttgcaat agcgctactt g                                              201

<210> SEQ ID NO 14
<211> LENGTH: 201
<212> TYPE: DNA
<213> ORGANISM: Zea mays

<400> SEQUENCE: 14
ctttcttgat ttgttgatc tgtgtagcc agagcaatct atccatcctt tcctgatctc       60
ctggagtgag tgcagggcag gcaggcaggc aggcgatgcg rcgaagaata agtatctgct    120
gactgttgca atagcgctac ttgtagtagt cacactgatg gaggctccag gaatgttact    180
agtagcagcc ttccaggttg c                                              201

<210> SEQ ID NO 15
<211> LENGTH: 201
<212> TYPE: DNA
<213> ORGANISM: Zea mays

<400> SEQUENCE: 15
tctccttcac cgacagcctc gtcggccgcg acggcaagct ctaccacggc gccgccacct      60
tctgggcttt ctaccgtttt aactacacgg ggacccgcga rcagcgggag gcggcgttcg    120
atgacgaaga cctctcccgg ttccgggtca cggcgctgga cttcgtgcac gccttcttct    180

```
cggcgctcgt gttcctcgcc g                                              201

<210> SEQ ID NO 16
<211> LENGTH: 201
<212> TYPE: DNA
<213> ORGANISM: Zea mays

<400> SEQUENCE: 16
ctgtcgtttg ttgtcccata ctcccatctg ttctccgcga ggcgcaacga aggcacaaaa    60
cccttacctc catcaaaccc tagcgctcgt gtccccgttt wgctcccgtc gccgctacca   120
tgggctcagg taatccgatc cctccgactc gtgggctaaa ttctctatta tttgtggctt   180
gttctcttgc ggagaatttt t                                              201

<210> SEQ ID NO 17
<211> LENGTH: 121
<212> TYPE: DNA
<213> ORGANISM: Zea mays

<400> SEQUENCE: 17
aaattgttct tgcttcccga tttccagtcc tctgtcgttt gttgtcccat actcccatct    60
sttctccgcg aggcgcaacg aaggcacaaa accccttacct ccatcaaacc ctagcgctcg  120
t                                                                    121

<210> SEQ ID NO 18
<211> LENGTH: 201
<212> TYPE: DNA
<213> ORGANISM: Zea mays

<400> SEQUENCE: 18
tgcagcccgg ctgcaacaaa ttttttttcca gtattccagg caatgcggag cccgccgaag   60
ccgaagagaa cggcagccgg ttgccgccat ccttgcagtg sctcaacagc ctgttctcgc   120
catcggcgca gtcctccggt agcggcagcg gcagttcgca tcattgggag aattgaacaa   180
taatgcaata taagaatgga t                                              201

<210> SEQ ID NO 19
<211> LENGTH: 201
<212> TYPE: DNA
<213> ORGANISM: Zea mays

<400> SEQUENCE: 19
tgccgctgcc gctaccggag gactgcgccg atggcgagaa caggctgttg agccactgca    60
aggatggcgg caaccggctg ccgttctctt cggcttcggc kggctccgca ttgcctggaa   120
tactggaaaa aaatttgttg cagccgggct gcaaaccagg ccgtttgcag cccggctgca   180
acaaattttt ttccggaata c                                              201

<210> SEQ ID NO 20
<211> LENGTH: 201
<212> TYPE: DNA
<213> ORGANISM: Zea mays

<400> SEQUENCE: 20
tcctgagtcc tgaccctcct ccgtgcgctg cgcaggcatg aggctcctcc tcgtcggcgc    60
cctactccta tgtgccaccg cggcggtgga gtccaagccg mccctcgaca ccctgggcat   120 accccgcaa ggttcaaccg gatctgtcca cgcctgctct gctatttctt tccatctttc   180
```

```
cctgtttcct tcggtcgatg c                                              201

<210> SEQ ID NO 21
<211> LENGTH: 133
<212> TYPE: DNA
<213> ORGANISM: Zea mays

<400> SEQUENCE: 21
gtggggtcta tcctcatttt tgtgaggggc tgyaaacggc ctggtttgca gcccggctgc     60
aacaaatttt tttccagtat tccaggcaat gcggagcccg ccgaagccga agagaacggc    120
agccggttgc cgc                                                       133

<210> SEQ ID NO 22
<211> LENGTH: 153
<212> TYPE: DNA
<213> ORGANISM: Zea mays

<400> SEQUENCE: 22
gttgagccac tgcaaggatg gcggcaaccg gctgccgttc tcttcggctt cggcgggctc     60
cgcattgcct ggaatactgg aaaaaaattt gttgcagccg rgctgcaaac caggccgttt    120
gcagcccctc acaaaaatga ggatagaccc cac                                 153

<210> SEQ ID NO 23
<211> LENGTH: 201
<212> TYPE: DNA
<213> ORGANISM: Zea mays

<400> SEQUENCE: 23
ccggttgccg ccatccttgc agtggctcaa cagcctgttc tcgccatcgg cgcagtcctc     60
cggtagcggc agcggcagtt cgcatcattg ggagaattga rcaataatgc aatataagaa    120
tggatgattg ttgctgcttg agcccattgg tgccaatgta cataggaaga gcaggagcat    180
gccggcatga aaaatttgga g                                              201

<210> SEQ ID NO 24
<211> LENGTH: 201
<212> TYPE: DNA
<213> ORGANISM: Zea mays

<400> SEQUENCE: 24
ccgatcttgc tacccaccgc tccctgcctt tttatgatca cctcccgttc aatcggaggc     60
gggcctctct cccccgatcg gattccgctc gaatctagag rgtttcctcg gatcaaatcc    120
cgctcgtggg gacgggtggt ttcgtgtata gtttgagttg ttaggcacca tgcaggcgtc    180
tttccgtccc gcgacgatca g                                              201

<210> SEQ ID NO 25
<211> LENGTH: 201
<212> TYPE: DNA
<213> ORGANISM: Zea mays

<400> SEQUENCE: 25
ttcgagctgc gagatggccg ggtaagcacc gatagaaagc aacctcacgc aagctgctcc     60
tgatccgcct aatgagggca gagggcttac aattgcgcca ygttgcattt catgaatcgg    120
cttgtataat tcctgttgtc tggtttggtt tcctggcgtg cagctggcgg agctgcggcg    180
gccgccctcc gcggacgggt g                                              201
```

<210> SEQ ID NO 26
<211> LENGTH: 201
<212> TYPE: DNA
<213> ORGANISM: Zea mays

<400> SEQUENCE: 26

| gctccccagg | gacggccatg | cggccatcgc | cgctgtccct | ggccggctcc | ctgttcatgg | 60 |
| tgtccgagca | cggggggctg | gtggagtacc | acttcagccc | rcaggacggg | tgggagtggg | 120 |
| tagagcacgg | gacgccccac | cggggcgtga | ccctcgtcgg | cgcccctggc | ccgtgcttcg | 180 |
| acggctccca | gctgttcgtg | g | | | | 201 |

<210> SEQ ID NO 27
<211> LENGTH: 201
<212> TYPE: DNA
<213> ORGANISM: Zea mays

<400> SEQUENCE: 27

| ggccatcgcc | gctgtccctg | gccggctccc | tgttcatggt | gtccgagcac | ggggggctgg | 60 |
| tggagtacca | cttcagccca | caggacgggt | gggagtgggt | rgagcacggg | acgccccacc | 120 |
| ggggcgtgac | cctcgtcggc | gcccctggcc | cgtgcttcga | cggctcccag | ctgttcgtgg | 180 |
| tcggctccga | cgggcacgtg | t | | | | 201 |

<210> SEQ ID NO 28
<211> LENGTH: 201
<212> TYPE: DNA
<213> ORGANISM: Zea mays

<400> SEQUENCE: 28

| tcccccccact | cgcgtttacg | tacacgcatt | cgcgaccctg | tttccgattg | gaattgattg | 60 |
| ggtcaattct | gtactggaat | ttgaaaccca | ttatgatcga | ygttgcgtta | cataggagtt | 120 |
| ttggcacctg | gccagtcgca | atgctgggcg | tggggaagag | caagacactt | gtggaagggc | 180 |
| cggtttgtga | caacagccag | g | | | | 201 |

<210> SEQ ID NO 29
<211> LENGTH: 201
<212> TYPE: DNA
<213> ORGANISM: Zea mays

<400> SEQUENCE: 29

| tggccagtcg | caatgctggg | cgtggggaag | agcaagacac | ttgtggaagg | gccggtttgt | 60 |
| gacaacagcc | aggtagtggg | atggcacacg | aacgagagga | scaagaggca | acgaaggttt | 120 |
| catgtcaata | cttcgggctt | tgctttcaat | agcagtatgc | tctgggacgc | cgacaagagg | 180 |
| gctcgtcagg | cgtggaatta | c | | | | 201 |

<210> SEQ ID NO 30
<211> LENGTH: 201
<212> TYPE: DNA
<213> ORGANISM: Zea mays

<400> SEQUENCE: 30

| actactagag | cccttcccccg | atccttttg | tttagtagtt | tatttgttga | tcatagtact | 60 |
| agtaaatagt | agtacacgga | caaagccatt | tgattaatgt | ktccgtggat | ctttgcctac | 120 |
| cctgcacgca | caaagcacca | acagttgcat | ttccgatgac | tcccggactt | ccacacgtac | 180 |
| gcgcgaggct | caccggccgt | g | | | | 201 |

<210> SEQ ID NO 31
<211> LENGTH: 201
<212> TYPE: DNA
<213> ORGANISM: Zea mays

<400> SEQUENCE: 31
gcatcaggac gccgccgagg aggtgtacca cgtggacgat gtcgacgagg gcagcggtga      60
cggccgtggc cacggcggcg ccggccaggg gaagctgtgc rccaggggcc actggcgccc     120
cgccgaggac gccaagctca aggagctcgt cgctcagttt gggccccaga actggaacct     180
catcgccgag aggctggacg g                                                201

<210> SEQ ID NO 32
<211> LENGTH: 201
<212> TYPE: DNA
<213> ORGANISM: Zea mays

<400> SEQUENCE: 32
agcaagtata ctgtacttcc gttgttgcta tacgatgccg gctggaccgg aagctacatg      60
atataagcaa tgttgtgctg atcattcacc ctccaagcta yaaataaaca atgcaatgat     120
catcactatc ggttcatcac tgtggcttga ctaggtcacc aactttattg tcaacaattt     180
ttttatttaa aatcattttt a                                                201

<210> SEQ ID NO 33
<211> LENGTH: 201
<212> TYPE: DNA
<213> ORGANISM: Zea mays

<400> SEQUENCE: 33
ccgttgttgc tatacgatgc cggctggacc ggaagctaca tgatataagc aatgttgtgc      60
tgatcattca ccctccaagc tacaaataaa caatgcaatg rtcatcacta cggttcatc     120 actgtggctt gactaggtca ccaactttat tgtcaacaat ttttttatttt aaaatcatttt    180 ttatgataaa atatttgatc t                                                201

<210> SEQ ID NO 34
<211> LENGTH: 201
<212> TYPE: DNA
<213> ORGANISM: Zea mays

<400> SEQUENCE: 34
aagcgcaggg ttggttaaaa cagatttgtt ggacattagc agttctggtg aggtttgact      60
accggagttg ttgggcgtcc gtcgtattaa ccctgacgtg ycgtgcgtg cgtgtgttga     120 gctaattaaa cgcagatcgg cgccggggtc aggcctgcac tgctgcatcc ttcccagcag     180
cggctggtga aatggttgtg c                                                201

<210> SEQ ID NO 35
<211> LENGTH: 201
<212> TYPE: DNA
<213> ORGANISM: Zea mays

<400> SEQUENCE: 35
aacagatttg ttggacatta gcagttctgg tgaggtttga ctaccggagt tgttgggcgt      60
ccgtcgtatt aaccctgacg tgtgcgtgcg tgcgtgtgtt sagctaatta acgcagatc     120 ggcgccgggg tcaggcctgc actgctgcat ccttcccagc agcggctggt gaaatggttg     180
tgcgcaccgc cgagtctggg g                                                201

<210> SEQ ID NO 36
<211> LENGTH: 201
<212> TYPE: DNA
<213> ORGANISM: Zea mays

<400> SEQUENCE: 36

```
ctgttcttga atcggccgca gatggtgttc tcttcgtagc cctggtccgg cccggtacag      60
tccagtagcg gctctgtaaa ggagtgatga agctgcgtgc wgtgcagagg tggcagcagc     120
gtgatgtgct gctgctgctt gtcgctttgc ttgcgcgagt cctagcaaca aggggggggc     180
gttgcaacag cagtttcgtt g                                               201
```

<210> SEQ ID NO 37
<211> LENGTH: 201
<212> TYPE: DNA
<213> ORGANISM: Zea mays

<400> SEQUENCE: 37

```
ttcacatcac cccgatccac cagcagcagg aaccactttc ggttgacaga tggttgaagc      60
gagtagctag gtgtgacggc ccaagcaaaa agtctcgttg mgttaagttg ctgcgtgcag     120
ctactactct cctcacacga atgtacgtac gtacacatgc atgcatgtag tatatatgta     180
tgtacacttg tgatatagat a                                               201
```

<210> SEQ ID NO 38
<211> LENGTH: 201
<212> TYPE: DNA
<213> ORGANISM: Zea mays

<400> SEQUENCE: 38

```
caaggagcag gacagggttg cgttgcgttg cgtcggtctc aacgcttttc gcttcgggtc      60
ccgccgccgg acgtctcttt cggagatcat cctatctgtc scatctacgc gtgtcgtcct     120
gaccgaaagg gcaagcaaca cggtggccaa ggggcctcac tcaccgaccg ccgagcgccg     180
agaaaacaac gggacacggc a                                               201
```

<210> SEQ ID NO 39
<211> LENGTH: 201
<212> TYPE: DNA
<213> ORGANISM: Zea mays

<400> SEQUENCE: 39

```
acgacgacga ccggcatcat gagctcacgg tcgtatccat cttggaggcg tcttcgatgc      60
ccttgaaggc cacacggagc ttcctcaacg aggacacttt yttcccgttg ttctctgcca     120
tgcccgtggc atggacagtg gtgtatggga cctctttgag aagctcaaac atggggatgc     180
tcaggtttgg ccgtgtcatc t                                               201
```

<210> SEQ ID NO 40
<211> LENGTH: 201
<212> TYPE: DNA
<213> ORGANISM: Zea mays

<400> SEQUENCE: 40

```
agcttcctca acgaggacac tttttccccg ttgttctctg ccatgcccgt ggcatggaca      60
gtggtgtatg ggacctcttt gagaagctca aacatgggga ygctcaggtt tggccgtgtc     120
atctgctcca gcacctccgg tgactgcatg tacaggttgt taccttcgtg cgtcacgctg     180
```

```
gctttcgaca tccgcaactt g                                              201

<210> SEQ ID NO 41
<211> LENGTH: 201
<212> TYPE: DNA
<213> ORGANISM: Zea mays

<400> SEQUENCE: 41
acgccaagat caggagcggc gagatccggg tgctccccgc cgccgtcaag agcgtccgcg     60
ggaacgtcgt cgagttcggg gacggcagcc gccacccttt ygacgccatc gtcttcgcca    120
ccggctaccg gagcactgtc aggcggtggc tcaaggtacg ccgccgcgcg ccgcacgctt    180
taactaacta ccgcatcatc t                                              201

<210> SEQ ID NO 42
<211> LENGTH: 201
<212> TYPE: DNA
<213> ORGANISM: Zea mays

<400> SEQUENCE: 42
ctacccgtcc gattgccatc cctagtcctg tcacaaaaaa atgctgcctt tgctgttact     60
agtcctgctt aaattaggcc gacccgacca taactgcggt ytgcgcggct tgctggtaaa    120
tgcgagcgga ttagttggac gagcgaccgt gaaggcccca gccggcggcc gtacctgtac    180
tacgtcctcg gtcctctccc t                                              201

<210> SEQ ID NO 43
<211> LENGTH: 121
<212> TYPE: DNA
<213> ORGANISM: Zea mays

<400> SEQUENCE: 43
aagtggcttt tgtctgatgg gcggcggtgc atcgtctgtt tcattcatca gatcgcacat     60
rtacatttta ctacagtgca gtgcaggtga ctgtcctgtg gcaacgggta cggttatgag    120
t                                                                    121

<210> SEQ ID NO 44
<211> LENGTH: 201
<212> TYPE: DNA
<213> ORGANISM: Zea mays

<400> SEQUENCE: 44
catcctgcat acccccaccgt agtggcagcg agccagcgac ctcgagtagc agcagaggct     60
ccgcaggggc gaaaaggtgt gaagcttcct tcggagatcc magtagcaga agcaacgcag    120
gcatcggctt gcgacaggag aggacggaga tgacgcagaa gcagaccctg ttcaaggggc    180
agagcaagaa gaagactatc c                                              201

<210> SEQ ID NO 45
<211> LENGTH: 201
<212> TYPE: DNA
<213> ORGANISM: Zea mays

<400> SEQUENCE: 45
attgagttcc gcctcccgct tccgctccag cccctcgtcc agtagcttcc gcttctacgg     60
cacggcaata gattaagcgg aaatcaataa ttgcagtgtc racccaccgc gcgcggccat    120
agaaacggga tggggaagaa gcggacgtgc ccgcagtacc ttcagagcag tgtacttctc    180
gtggaacttg tagtcgagct g                                              201
```

<210> SEQ ID NO 46
<211> LENGTH: 121
<212> TYPE: DNA
<213> ORGANISM: Zea mays

<400> SEQUENCE: 46
tgacgtggat ggttttgttg ggttgggttc ccagtctggt gctgtagcgg tgtagcagga        60
wcgcgtgggt agccttgagc ctggcgattc tgtaattgtc ctttgagttc tgaaatgtta       120
a                                                                       121

<210> SEQ ID NO 47
<211> LENGTH: 121
<212> TYPE: DNA
<213> ORGANISM: Zea mays

<400> SEQUENCE: 47
taagagattc atttttacat gactttttgt tttttcattt ttacactctg gatatggacg        60
rgactagttg aatttaggaa gatcgtatga tctcgaaaat gttcagtaac tgcatcaaca       120
c                                                                       121

<210> SEQ ID NO 48
<211> LENGTH: 201
<212> TYPE: DNA
<213> ORGANISM: Zea mays

<400> SEQUENCE: 48
ttttcgcaaa taatggtcgc cggaatcttg acctgtgccg aactgccgat gccgtcgcag        60
cgatggcagg acagatacac catcaatgct aatgctcgaa mcaacaggac acatgcgcat       120
ggctgcctgc cggtgagccg acggtccagc ttgtgttcag atctccccca agggaccggc       180
gctacctagt taagagcaag t                                                 201

<210> SEQ ID NO 49
<211> LENGTH: 201
<212> TYPE: DNA
<213> ORGANISM: Zea mays

<400> SEQUENCE: 49
gcacaggaat tcaaacgaat cacggagcac ccggagggag accgatcgag aagcaacgga        60
aggccaggga gaggccgctg acctcgcgcc tgttgtgctc rtcgacggcg aagcggccga       120
gcccgtcgga ctcggcgctg ttggccgcgg ctgggttctc cttcacgccg ccgaggacgt       180
ggccggccat ggctgctcct c                                                 201

<210> SEQ ID NO 50
<211> LENGTH: 201
<212> TYPE: DNA
<213> ORGANISM: Zea mays

<400> SEQUENCE: 50
agcacatacc ctcttactac tcttgaggat ttgcttcctc catccaaaag aaataattgc        60
acatgtcaaa caatccgcac taaggcattt ctacaaacac rctactgcac aggccaccca       120
ggctccagcc cttgtactcg ctatgcagac gcatcaacag tggtagcaat gtctccatct       180
cataagcggg agcacgaacc t                                                 201

<210> SEQ ID NO 51

<211> LENGTH: 201
<212> TYPE: DNA
<213> ORGANISM: Zea mays

<400> SEQUENCE: 51

```
tgggacgtga agccgcagga aactacgggg cgtccttctc gggtagtggt cccgctggac      60
cacggacggg acggcggccg tcgtcgtcgc gtaatccgcc ygtattatat gcccgtgtgt     120
cggaaggaaa catggcctgt tcttcttccc agcgcagacc taatcatgct gccattgccc     180
cgggtggcgc atagcttcaa a                                              201
```

<210> SEQ ID NO 52
<211> LENGTH: 201
<212> TYPE: DNA
<213> ORGANISM: Zea mays

<400> SEQUENCE: 52

```
ggcctcgacg gcctcgagcg tgaggtggtg cagcgtgccg ccaccacct gctccttggc       60
ctccaccacg cgcacgaact ccagcagcgc gttctgaagc maggcgcaca gatgtgcatc     120
gacagaaccg tccccccccag atcagcacag gaattcaaac gaatcacgga gcacccggag   180
ggagaccgat cgagaagcaa c                                              201
```

<210> SEQ ID NO 53
<211> LENGTH: 201
<212> TYPE: DNA
<213> ORGANISM: Zea mays

<400> SEQUENCE: 53

```
gcgtggccag ctgctccagc gtcacccccgc gcctgtacca ggggaacgcc accagcgtcg     60
acccgctgct ggactccgcc tacgcccgcg cgctcatgtc stcgtgcccc aacccgtcgc    120
ctgcgtccgc caccgtgggc ctggacggcg gctcgccggc caggttcgac agcgggttct    180
acgcccgggt gcgccagggc c                                              201
```

<210> SEQ ID NO 54
<211> LENGTH: 201
<212> TYPE: DNA
<213> ORGANISM: Zea mays

<400> SEQUENCE: 54

```
cggggcgtcg ctgtggcagg tggagacggg gcggcgggac ggcggggcgc cgtcgctggc     60
gtccgacgcg ttgggggcgc tgccgtcgcc cttcgcgggg ytcggcggcc tgctggcggg   120
cttcgccagt cgcgggctca acctgacgga cctggtggcg ctgtcggggg cgcacaccat   180
cggcgtggcc agctgctcca g                                              201
```

<210> SEQ ID NO 55
<211> LENGTH: 201
<212> TYPE: DNA
<213> ORGANISM: Zea mays

<400> SEQUENCE: 55

```
ggcggcggga cggcggggcg ccgtcgctgg cgtccgacgc gttgggggcg ctgccgtcgc     60
ccttcgcggg gttcggcggc ctgctggcgg gcttcgccag kcgcgggctc aacctgacgg    120
acctggtggc gctgtcgggg gcgcacacca tcggcgtggc cagctgctcc agcgtcaccc   180
cgcgcctgta ccagggggaac g                                             201
```

<210> SEQ ID NO 56
<211> LENGTH: 201
<212> TYPE: DNA
<213> ORGANISM: Zea mays

<400> SEQUENCE: 56

```
ctagctagat ggacataaat aaaaatctac tcactactag ctccgaggcc gtatttattt      60
gaatagcctc agtctattta ttaccatgcg ctaattttac ygcaattatc tgcagtaggg     120
gatcatggta aattgtcaga gtttggaggc gttcgcggta actttgctca gagcggtcgc     180
tgccttggac ccagactggc g                                               201
```

<210> SEQ ID NO 57
<211> LENGTH: 201
<212> TYPE: DNA
<213> ORGANISM: Zea mays

<400> SEQUENCE: 57

```
tttgttggga aatctaggga tcaatagagt accgcaggtc cgcagcaaca acgactcaac      60
gagtgggcag ttcaccgtgc tggcggcaca atacctcccg ycgtcggggc actctgccgc     120
caaatcgcga acccgtgcca ttagcgaaca cgtattaagc atggctgcga tcaaacagta     180
aaagttgata tagattagag t                                               201
```

<210> SEQ ID NO 58
<211> LENGTH: 201
<212> TYPE: DNA
<213> ORGANISM: Zea mays

<400> SEQUENCE: 58

```
gagtaccgca ggtccgcagc aacaacgact caacgagtgg gcagttcacc gtgctggcgg      60
cacaatacct cccgccgtcg gggcactctg ccgccaaatc rcgaacccgt gccattagcg     120
aacacgtatt aagcatggct gcgatcaaac agtaaaagtt gatatagatt agagtcaaac     180
gaacactagt atgtctttct t                                               201
```

<210> SEQ ID NO 59
<211> LENGTH: 201
<212> TYPE: DNA
<213> ORGANISM: Zea mays

<400> SEQUENCE: 59

```
tgggcagttc accgtgctgg cggcacaata cctcccgccg tcgggcact ctgccgccaa       60
atcgcgaacc cgtgccatta gcgaacacgt attaagcatg rctgcgatca aacagtaaaa     120
gttgatatag attagagtca aacgaacact agtatgtctt tctttagcaa agctttctt      180
tagaatgtaa aggagtgttt g                                               201
```

<210> SEQ ID NO 60
<211> LENGTH: 201
<212> TYPE: DNA
<213> ORGANISM: Zea mays

<400> SEQUENCE: 60

```
cgtggtcgtc gccgtcgccg ggggcgactt ggcagggtca gcgtgcgagc aggtccattg      60
gtagtcgccg atcttgacgc tgaacctaac ctgcgtgtcg stcttctcct cgagaaggat    120
ccagtaccgc gccgagagca cgggcctcgc cgccgccgcc gcgctccggg cgcggcgacc    180
tgccgcgcgc aagcgcaacc c                                               201
```

<210> SEQ ID NO 61
<211> LENGTH: 201
<212> TYPE: DNA
<213> ORGANISM: Zea mays

<400> SEQUENCE: 61
acggagtcaa ccggacggcc gccggttctt cccaggtgga tcacgtccgg cgccgtcgtc    60
ggcatgcagg gtggcacaga cgccgtccgc agagtttggg rccagctcaa ggactacgac   120
gtccctgtct ctgcgttctg ctacaggtc tgaggaggaa ctgacagttc ttcgtgtctg    180
acgacgcacc ctgaaccggc c                                              201

<210> SEQ ID NO 62
<211> LENGTH: 201
<212> TYPE: DNA
<213> ORGANISM: Zea mays

<400> SEQUENCE: 62
atatgtccca cccgtccgac ggcgagctca cctacatgcg cgcgcatttc gaccgcctcg    60
tcggttccaa ggactccgag acgtactaca tgcacaaccc mgagggcggc accgccgggc   120
cggagctcac aatcttcttc attaggactt agaatcaaat taaaccaaca acctcatctc   180
tggtatgtgt tctttcctgc c                                              201

<210> SEQ ID NO 63
<211> LENGTH: 201
<212> TYPE: DNA
<213> ORGANISM: Zea mays

<400> SEQUENCE: 63
tctccgtccc gacaaggaac tgctggtacg tgagcgcctg cacgcgctcg tccgccgggt    60
agtgcaggaa caggtggcgc gccacgggga gccccgtccg mgcggcctcc ccgacgaggc   120
gcgcgcggta gaactcccag gccttgtaca tcttggcgca gcgcgcgaag tgcgccagcg   180
tgcggccgct ggagtagaac t                                              201

<210> SEQ ID NO 64
<211> LENGTH: 201
<212> TYPE: DNA
<213> ORGANISM: Zea mays

<400> SEQUENCE: 64
tctggctaca ggtctgagga ggaactgaca gttcttcgtg tctgacgacg caccctgaac    60
cggccctgaa ctgcttgctt gctgcacgtt ggctgggtct ytggctgcag gattgggttg   120
gccagaggaa gacggcgatc gggtctcagc tctggtggaa ctgggagctc gatgatgccc   180
actacaatgg gtggaacgat c                                              201

<210> SEQ ID NO 65
<211> LENGTH: 201
<212> TYPE: DNA
<213> ORGANISM: Zea mays

<400> SEQUENCE: 65
ctctccgccg cggcacggcg gcggctggct ctccactcgt cggcgatctc gcggttgacg    60
cgcgcccaca gctccgggta ccggttgtgc gcggcgacgg rgtcctcgcc cgagtgcagc   120
cgcgcgtcca gcgcaggcc ctcgccgaag tcggccatcc agccgctgac gccgcggtcc   180
accatccccc gcaggacggt g                                              201

<210> SEQ ID NO 66
<211> LENGTH: 201
<212> TYPE: DNA
<213> ORGANISM: Zea mays

<400> SEQUENCE: 66
ctcgtccatg gccggccgca gctccgcgct gtccgacacg caccgcgccg ccacggcgag    60
gacgcggtcc gcgcacgccg tgggcggcgc ggccaccctg scgtccagca cctcccgcgc   120
gcgcccggcg ccgatcagcg gcgcggccca ggacacgatg gacgacgggc acgagtccac   180
gtccatcacc ctgcgcccgc t                                             201

<210> SEQ ID NO 67
<211> LENGTH: 201
<212> TYPE: DNA
<213> ORGANISM: Zea mays

<400> SEQUENCE: 67
gcgcgatgca tgccacgggg actctgtacg gccaccgccg ggcgcgcatc accatcgcgc    60
tgcacgagag ccccggtagc ccgccgtgcg tgctgctgga ygtcggcgtg cccacggcca   120
agttcatcca ggacgtgagc gcggcgggga tggtgcgcgt cacgctcgag tgcgagaagc   180
agcaccatac ggtggacgtg g                                             201

<210> SEQ ID NO 68
<211> LENGTH: 201
<212> TYPE: DNA
<213> ORGANISM: Zea mays

<400> SEQUENCE: 68
actctgtacg gccaccgccg ggcgcgcatc accatcgcgc tgcacgagag ccccggtagc    60
ccgccgtgcg tgctgctgga tgtcggcgtg cccacggcca rgttcatcca ggacgtgagc   120
gcggcgggga tggtgcgcgt cacgctcgag tgcgagaagc agcaccatac ggtggacgtg   180
ggggcgcgga ggctgctcga t                                             201

<210> SEQ ID NO 69
<211> LENGTH: 201
<212> TYPE: DNA
<213> ORGANISM: Zea mays

<400> SEQUENCE: 69
gccagcgtgg gttcattttt gctacctgag ctacccgtgc ccagattatt gtccagctcc    60
agccgcctaa caaccacgta cgtacgcgtc tcttgcacga sgtgaacaac gatcaaatta   120
aacagccgta gattagtcag tcagtcagtc tcctaactgc gcgctgtgac agtaacagta   180
gcaagcaaca gtaaacatcc g                                             201

<210> SEQ ID NO 70
<211> LENGTH: 201
<212> TYPE: DNA
<213> ORGANISM: Zea mays

<400> SEQUENCE: 70
acgcgtctct tgcacgaggt gaacaacgat caaattaaac agccgtagat tagtcagtca    60
gtcagtctcc taactgcgcg ctgtgacagt aacagtagca mgcaacagta acatccgtc   120 caaaggtttt accaatcaac tacctgaaaa cgagatccaa ttcgctctcg aatcgagcca   180

```
acgcgtcctc ttctgctttc g                                              201

<210> SEQ ID NO 71
<211> LENGTH: 201
<212> TYPE: DNA
<213> ORGANISM: Zea mays

<400> SEQUENCE: 71
tctctccctc caggaacagc ggcctgctca acatgctcag cctcatgaag cgcaaggcac     60
ttgagatcgc cggtggtgac tcaacgtcaa gtcagcaatc wgtccaagag gttaccagac    120
cgcgtctagt gaacgggaaa gagcctgaat ttgcagcttt cgaggtgcaa gaaaaggaaa    180
aggaaaggcc acaggatgca g                                              201

<210> SEQ ID NO 72
<211> LENGTH: 201
<212> TYPE: DNA
<213> ORGANISM: Zea mays

<400> SEQUENCE: 72
cacacctcca caagggccat gctggcgtgg ctgggaccaa tggggagaca catttcaatg     60
tgagggtggt gtccaaggag tttgagggga agagcttgct yaagaggcac agggctgtct    120
atgatctcct gcaggaggag ctcaagaccg ggttgcacgc cctgtcaatc gatgcaaaga    180
ctccatctga gtttaggta c                                               201

<210> SEQ ID NO 73
<211> LENGTH: 201
<212> TYPE: DNA
<213> ORGANISM: Zea mays

<400> SEQUENCE: 73
agtccgtccc ggacgcgcgc acccggtaca agcagctcct tgcctatgcc gcgcgcctgc     60
cgcccatgga cccggcgctc aagaccgacg ccaaccgcgt scggggttgc gtctcacagg    120
tctgggtcca cgccgagccc gacgagggcg acgccggccg ccgcagcgtc aggttccacg    180
ccgactccga cgcgcagctc a                                              201

<210> SEQ ID NO 74
<211> LENGTH: 201
<212> TYPE: DNA
<213> ORGANISM: Zea mays

<400> SEQUENCE: 74
agggcaatca aatcaaatca acaaagagat gagttgcaaa ttatagatg taaaagatca      60 taaacgaagg aaccttaaca gataatttga tcccacctat ktacagacag aataaatgct    120
atagtattac agaagataat aggaacaatt ggatctatac cattaaaaga tccaaacttt    180
agatatatac catggacccc a                                              201

<210> SEQ ID NO 75
<211> LENGTH: 201
<212> TYPE: DNA
<213> ORGANISM: Zea mays

<400> SEQUENCE: 75
gcaagcaagc aaattttggg tcctagcttg aaggactgcc atcttttttt ttggttggtg     60
agctacacat caaatgttaa tccccgtttt ccgtactctt rtattgtgct tattattatt    120
ctcttgggaa atttggatcc ataccattaa aagatcacca ctttggatcc ataccattac    180
```
tatctcactt acatgtgggt c                                            201

<210> SEQ ID NO 76
<211> LENGTH: 201
<212> TYPE: DNA
<213> ORGANISM: Zea mays

<400> SEQUENCE: 76
cgacggatcg aacggccgag cccacgcccc cttgaagtag atggcgttgg cgaggacgag    60
cgccgtggac gagtcgacgg agccgggagg caggacgtcg ycgatgagcc ctttcgttgc   120
tcctttcacg aagtcgttga cttgctgcct tgccgcctcg gagttcttca agaagtcgac   180
ggactccgcg accgccgcgt a                                            201

<210> SEQ ID NO 77
<211> LENGTH: 201
<212> TYPE: DNA
<213> ORGANISM: Zea mays

<400> SEQUENCE: 77
ccgtccggca acgtgtcgtc cgaaaagcag cacttgacgt cctgcgcaac agcagcagcc    60
ccgcaaccaa gtcatccacc acccgatcaa tccgccgacg rccgacgtgc ggtgcaagac   120
caaccaacta gtgtgtgttc caggaaggtg ccgagttccg aatagctcac gatgggtacg   180
gaagggtaga gccggagggt c                                            201

<210> SEQ ID NO 78
<211> LENGTH: 201
<212> TYPE: DNA
<213> ORGANISM: Zea mays

<400> SEQUENCE: 78 cccccctacag gccgcatgca aggagaggga gctgcgtagg ggcagccgtt gcagttagtc    60
tcacaacgag ggtccgcacc agcgccagca ccgacaccac racggtgacg agccatcgcc   120
agactccgga cagtgggggt tcagcatctc ctccatccta gtcttcgtcg cgggctcgag   180
gttgtacgag aataaggtgc c                                            201

<210> SEQ ID NO 79
<211> LENGTH: 201
<212> TYPE: DNA
<213> ORGANISM: Zea mays

<400> SEQUENCE: 79
ggagctgcgt aggggcagcc gttgcagtta gtctcacaac gagggtccgc accagcgcca    60
gcaccgacac cacaacggtg acgagccatc gccagactcc rgacagtggg ggttcagcat   120
ctcctccatc ctagtcttcg tcgcgggctc gaggttgtac gagaataagg tgccctgctt   180
ttcctcaccc gtgggcggcg g                                            201

<210> SEQ ID NO 80
<211> LENGTH: 201
<212> TYPE: DNA
<213> ORGANISM: Zea mays

<400> SEQUENCE: 80
caccgacacc acaacggtga cgagccatcg ccagactccg acagtgggg gttcagcatc    60 tcctccatcc tagtcttcgt cgcgggctcg aggttgtacg rgaataaggt gccctgcttt   120
tcctcacccg tgggcggcgg cacgatgtga gcgaacgcgg ccggtcggag gtcagcgcgg       180
cgagcgtgaa cggggtcgtt c                                                201

<210> SEQ ID NO 81
<211> LENGTH: 201
<212> TYPE: DNA
<213> ORGANISM: Zea mays

<400> SEQUENCE: 81
gggcaggatg cggttcctgt ggggcgcgga cgccgaggag ttcaggccgg agaggtggct       60
ggacgacgcc ggcgtcttcg tccccgagag ccccttcaag ytcacggctt ccaggtgaa       120 atctcacgtt cgaccctgtt ctgtgctgtt gctgtccact cgttttctca gtttacttga      180
tgagctcttg tttgactgtt g                                                201

<210> SEQ ID NO 82
<211> LENGTH: 201
<212> TYPE: DNA
<213> ORGANISM: Zea mays

<400> SEQUENCE: 82
tcccggcgac gacacgacct tatcatagag atcattgagg gttagggtct caccgtcggg      60
gaggagtaga agcatgtaga acgcgtcctg ctgcgcgccg ycgtcgttct tgtagggcag      120
cttgagcgcc ttgaatccgg ggaacacggc aaccgctgc cgctggtcct cgaaaccgct       180
cgtagtcatg aacggcacgc g                                                201

<210> SEQ ID NO 83
<211> LENGTH: 201
<212> TYPE: DNA
<213> ORGANISM: Zea mays

<400> SEQUENCE: 83
gttgcgggtt tgcccggatg gatcaggtca tcaggttgag acacgaagaa gcgaagtttg      60
agccgctgtt ccatttccca tactggcggc agacgcgccg magagcctga cgtgcgagcc      120
tgtgccacac tgccccacgg cccccacgcc cggaagtggc tcgatgccaa gaggttttta     180
cgcggcgcgc ggcgggtcat c                                                201

<210> SEQ ID NO 84
<211> LENGTH: 201
<212> TYPE: DNA
<213> ORGANISM: Zea mays

<400> SEQUENCE: 84
atggaacaga atgctttaat tcaacctttc aaagaaggga agcataaatt attgaccgac      60
ctgctgaact gagctaaaca acaaattgga tcaaaacaaa watacggacg ggcacgaatc      120
tctcacgtgt tcccggaaca aaggacaaag attaggtctc cacagtcggc gtgaagacac      180
aacgaaagct aacgtggtcc t                                                201

<210> SEQ ID NO 85
<211> LENGTH: 201
<212> TYPE: DNA
<213> ORGANISM: Zea mays

<400> SEQUENCE: 85
atgcctggtc cctggcaggg gagatgcgat gcgaggagct ggtgccagag cgggcttttc      60
cttctccgag cccgagggcg tatcacgtac gggagtggga sacggaggag cggggaagaa     120

```
ggcgacggga aggaaggcag gcgggtgtgg gaatgtggga agggaactgg gaagtgcgga    180
atcgaagccg agacagggag g                                             201

<210> SEQ ID NO 86
<211> LENGTH: 201
<212> TYPE: DNA
<213> ORGANISM: Zea mays

<400> SEQUENCE: 86
ggaggaaggc ggtctcggag atgttgaact cggcggcgac ggactgcatc caccgctcgt    60
cggcggcctt ggcggcgtcc tcgaggaggc acaccgcggc kgggttgccc ttgaacggct   120
ccgccgtgaa ggcgtccacc tgcgacgacc acggcgacga tgtcaggtat ccagagagga   180
ggaagaatcg ctcccgctcc t                                             201

<210> SEQ ID NO 87
<211> LENGTH: 201
<212> TYPE: DNA
<213> ORGANISM: Zea mays

<400> SEQUENCE: 87
cgcggctggg ttgcccttga acggctccgc cgtgaaggcg tccacctgcg acgaccacgg    60
cgacgatgtc aggtatccag agaggaggaa gaatcgctcc mgctcctcca agggagtaca   120
gagcagtatc tgaccactgc gtactggatg ccgtccttgc ccattcctgc gacgaagaaa   180
cagctccggg ctcctgggct a                                             201

<210> SEQ ID NO 88
<211> LENGTH: 120
<212> TYPE: DNA
<213> ORGANISM: Zea mays

<400> SEQUENCE: 88
cccggacwtt gatcaatgaa tgtttttgaag caagaactra ctgagtgtta aaggagctta    60
katcaattta aggagagcgg ttgtgtcaag gctactctta ggtccacagt tgggtgtttg   120

<210> SEQ ID NO 89
<211> LENGTH: 201
<212> TYPE: DNA
<213> ORGANISM: Zea mays

<400> SEQUENCE: 89
gccgcgtccg gagctccggc gggttcacgt tcccggagct cagcctcagc gccggcatct    60
tggacgagcc accgcgcgtg tcgttggagg tgttccgccc satcgacgag gactcggtga   120
tgcccgcgga ccctccgctc gccgccgccg ccgtgccccg tgtcgggcta ccccccgcgcg   180 ctccgccggc ggcgctggtg g                                             201

<210> SEQ ID NO 90
<211> LENGTH: 201
<212> TYPE: DNA
<213> ORGANISM: Zea mays

<400> SEQUENCE: 90
gtgagcggcg agatgttgcc catactgacc atggactgcg caaagtggcg gaagaagaga    60
ccggcgtcgg cggcatacgc cttgacgagg acgccgtct sggcgctctt ggtcaacaga   120
acctcgtcgg agctgagaag gcccctgccg gccaggaggt tcttgtagta aagttgtcg   180
```

```
aacttggctg gggcgacgac g                                              201

<210> SEQ ID NO 91
<211> LENGTH: 201
<212> TYPE: DNA
<213> ORGANISM: Zea mays

<400> SEQUENCE: 91
aatatctacg tccaaacgtg atatataagt cgggtccatt aacatcgagt ccggagttga    60
tatgttcgaa atatggacag cccaatagga aagtggcctg satttctgaa tcgacgggcc   120
aggacgatgg atttaaagcg gtccgttttt ccagcccagt agatctcgca gtcatgtatc   180
ggacggctgc ggcctcaatt g                                              201

<210> SEQ ID NO 92
<211> LENGTH: 201
<212> TYPE: DNA
<213> ORGANISM: Zea mays

<400> SEQUENCE: 92
ggtccgtttt tccagcccag tagatctcgc agtcatgtat cggacggctg cggcctcaat    60
tgctgatcgg atcgcggccg ctggaaatct gcgtgactgc rtctatactg cgcaggcacg   120
agcgtttgtg ttgcggcgag gttttcgtgc ggccgctgcg gtgacaagca ggtcctccct   180
caagctcgcg gcggatcagc g                                              201

<210> SEQ ID NO 93
<211> LENGTH: 201
<212> TYPE: DNA
<213> ORGANISM: Zea mays

<400> SEQUENCE: 93
cacgagcgtt tgtgttgcgg cgaggttttc gtgcggccgc tgcggtgaca agcaggtcct    60
ccctcaagct cgcggcggat cagcgaccga tcgacccgtc wtcctcggtt cctcatccat   120
cccgggcatc cggattccgg tgagcggagg aaggcgccat gaaagctgcg gaggacgcca   180
cgcgctgccc tcagatcccc c                                              201

<210> SEQ ID NO 94
<211> LENGTH: 201
<212> TYPE: DNA
<213> ORGANISM: Zea mays

<400> SEQUENCE: 94
agggtgaatg gcgtcgcgct ctcatctact agggcattat ctcagggcag tatactttcc    60
gaactagcaa cgggcacgtg gcctggcact gtagcggccc racatgagaa cggtccagtc   120
cgaatggaag tgtgtttggg ccggcccgac atgtcacatt tggaattaag gataaattca   180
aatgtatctt aaatacgtgt t                                              201

<210> SEQ ID NO 95
<211> LENGTH: 201
<212> TYPE: DNA
<213> ORGANISM: Zea mays

<400> SEQUENCE: 95
ctcatctact agggcattat ctcagggcag tatactttcc gaactagcaa cgggcacgtg    60
gcctggcact gtagcggccc aacatgagaa cggtccagtc ygaatggaag tgtgtttggg   120
ccggcccgac atgtcacatt tggaattaag gataaattca aatgtatctt aaatacgtgt   180
```
tagaatcaaa tctcacacat a                                                    201

<210> SEQ ID NO 96
<211> LENGTH: 64
<212> TYPE: DNA
<213> ORGANISM: Zea mays

<400> SEQUENCE: 96
agtagaacaa tggtaaaaga cgacgaaggt gtactcatcg yccgtgtttt tagattatct          60
gcag                                                                       64

<210> SEQ ID NO 97
<211> LENGTH: 121
<212> TYPE: DNA
<213> ORGANISM: Zea mays
<220> FEATURE:
<221> NAME/KEY: misc_feature
<222> LOCATION: (27)..(30)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 97
gacaagaagc tcytcaccgy tgtaagnnnn cgggtacaac agttcctcta cataactccg          60
yctgccttgn agaaactacc ctattattta actatgcaag acycrtccca tcctactcta         120
t                                                                         121

<210> SEQ ID NO 98
<211> LENGTH: 121
<212> TYPE: DNA
<213> ORGANISM: Zea mays

<400> SEQUENCE: 98
agctgagagc aacatgaacg atctggtgtc tgagtaccag cagtaccagg atgccactgc          60
mgatgaggag gagtacgagg acgaggagga ggtccatgac gagtaaggtg atcttggacc        120
c                                                                         121

<210> SEQ ID NO 99
<211> LENGTH: 77
<212> TYPE: DNA
<213> ORGANISM: Zea mays

<400> SEQUENCE: 99
ttaacatcgt ctctctatgg acagatgcag tagaaagwgt gtatctgaag aaaatccggc          60
acatgcggtt ggtgcgt                                                         77

<210> SEQ ID NO 100
<211> LENGTH: 75
<212> TYPE: DNA
<213> ORGANISM: Zea mays

<400> SEQUENCE: 100
ctgcagagca gctgccattg tcccgtgaag aactrgggcc gggcctggag ttgcagttca          60
atcgtgttgt tactc                                                           75

<210> SEQ ID NO 101
<211> LENGTH: 70
<212> TYPE: DNA

<213> ORGANISM: Zea mays

<400> SEQUENCE: 101
aacaagtgaa aactaagctt cctggagcac ccaagtttct tttrtgtgtt ctagcggaaa    60
gaaagaattc    70

<210> SEQ ID NO 102
<211> LENGTH: 101
<212> TYPE: DNA
<213> ORGANISM: Zea mays

<400> SEQUENCE: 102
gttagctgtc cagcttaacc ttccgaatat ttttagatgt aaaggaaatg wgaattgatt    60
gctgcaataa atctaaccag cttaacacag cacattaatt g    101

<210> SEQ ID NO 103
<211> LENGTH: 101
<212> TYPE: DNA
<213> ORGANISM: Zea mays

<400> SEQUENCE: 103
atgcatacgg ttccacatgg accagtacgc gcgtcatgag gagtaaccac rtggatggac    60
cccggtttgg ctgttttaaa taaattagtt aaaaatgttt t    101

<210> SEQ ID NO 104
<211> LENGTH: 101
<212> TYPE: DNA
<213> ORGANISM: Zea mays

<400> SEQUENCE: 104
gggcgtcgtt gaggtgagaa gagatggaaa aaaggcgtga tccaacctcc ragggcaccg    60
gtctaacagc ccgcttgcat tgcattgcat tgcccggtta a    101

<210> SEQ ID NO 105
<211> LENGTH: 101
<212> TYPE: DNA
<213> ORGANISM: Zea mays

<400> SEQUENCE: 105
gataggatcg gatgagtagg ttcacttgct tgagttcacc ggtataattc yggatacatc    60
tggttaggtc atcctttggt cagctgcccg caagcttaac t    101

<210> SEQ ID NO 106
<211> LENGTH: 101
<212> TYPE: DNA
<213> ORGANISM: Zea mays

<400> SEQUENCE: 106
atggagacca aggaaagcat cgcagtccta ttagacagaa acctatttgt ycggggatgg    60
aatgcaagct gctgggcctg ctggacacac tgtctgcagc t    101

<210> SEQ ID NO 107
<211> LENGTH: 101
<212> TYPE: DNA
<213> ORGANISM: Zea mays

<400> SEQUENCE: 107
tgatcaaatg aaactaaatc caatccatgc tccaacatcc gaatctcaga rcatacatct    60
ttgtccgtga caacaaaggg aacagaaagg ctgctttgat c    101

<210> SEQ ID NO 108
<211> LENGTH: 101
<212> TYPE: DNA
<213> ORGANISM: Zea mays

<400> SEQUENCE: 108
agtcgaggct cctgttcttg ttcccaccgg acattctcgc cgcaccggct kggtcaccga    60
tctctttcca caggaaaccg gcttccattt cctcggcctt c                        101

<210> SEQ ID NO 109
<211> LENGTH: 101
<212> TYPE: DNA
<213> ORGANISM: Zea mays

<400> SEQUENCE: 109
tcctggggag gcagagccct ccccaccggc atattcacac tcgaaccacc rccgcctctt    60
tttcatctcc cctgtctctt gtctggcgct cggacagcga c                        101

<210> SEQ ID NO 110
<211> LENGTH: 101
<212> TYPE: DNA
<213> ORGANISM: Zea mays

<400> SEQUENCE: 110
tccaaggaga accaatcagc catggtctca taaacgctgc agggtctagc yaggaaaggt    60
taagagacaa catctccaaa ttttaactga atccatctgt c                        101

<210> SEQ ID NO 111
<211> LENGTH: 101
<212> TYPE: DNA
<213> ORGANISM: Zea mays

<400> SEQUENCE: 111
taaataaggt gttttggtgg aggggtttaa agaatgatgt gacacaatat rtgcagcaat    60
gtgttgtctg ccaaaaggct aagactgaga gagtgcatcc a                        101

<210> SEQ ID NO 112
<211> LENGTH: 101
<212> TYPE: DNA
<213> ORGANISM: Zea mays

<400> SEQUENCE: 112
tgggctgtct atcgagcttt attgaaggac tcctgtatcc atgtgctaaa sagaggagca    60
gctgctagat catgctgagc tgataaccaa gagtccactg g                        101

<210> SEQ ID NO 113
<211> LENGTH: 101
<212> TYPE: DNA
<213> ORGANISM: Zea mays

<400> SEQUENCE: 113
aagatctggc ggtcacaacc tagccgcgcc gtcgacgagg ttcgttctgc yttgagcttt    60
gttactaggt tttcgcctgt gattccataa ttcgaggaag a                        101

<210> SEQ ID NO 114
<211> LENGTH: 101
<212> TYPE: DNA
<213> ORGANISM: Zea mays

<400> SEQUENCE: 114
tgtctggccg cgttacgcaa gaggtggaac ttacggacga aggaagcgac rgcggaggcc    60
atggcgaggt agacgaagtc gagcgagacc atggcaccc g                         101

<210> SEQ ID NO 115
<211> LENGTH: 101
<212> TYPE: DNA
<213> ORGANISM: Zea mays

<400> SEQUENCE: 115
ccctgccggc tgcagcaggc acacggtacc cttgtggatg gcactgctgc ratatggcgc    60
gcacgcaaca gctgaggctc ggcacgcgtg cttgcattgg c                        101

<210> SEQ ID NO 116
<211> LENGTH: 101
<212> TYPE: DNA
<213> ORGANISM: Zea mays

<400> SEQUENCE: 116
ggccaaagtg gaccgtatat gtacgtgtac tatatcttct cgaactcagc ytgtttccat    60
cttggctctt gcccgccgct gaaaggagga attccaaact t                        101

<210> SEQ ID NO 117
<211> LENGTH: 101
<212> TYPE: DNA
<213> ORGANISM: Zea mays

<400> SEQUENCE: 117
tctcttgaca gcagcgagat gttcctggcg tggcgcctcc atgaaccggc wgaggtaccc    60
caccaagtac gccagatccg gcctggagtt gcataggtac c                        101

<210> SEQ ID NO 118
<211> LENGTH: 101
<212> TYPE: DNA
<213> ORGANISM: Zea mays

<400> SEQUENCE: 118
gaattttctt gtcccgtgcc ggccgccgtg tctaccctgc gccaccgccc yttccaacgc    60
ctgccgtgaa gacaaaaggt gagctttta tccctcttc c                          101

<210> SEQ ID NO 119
<211> LENGTH: 101
<212> TYPE: DNA
<213> ORGANISM: Zea mays

<400> SEQUENCE: 119
acgtacgaga tttgctaatg cccgaagtaa tgcaacgaag cagctttgac racgaaggaa    60
gaggacaggc gagcgcgggc gtacgcggcg cacacatccg g                        101

<210> SEQ ID NO 120
<211> LENGTH: 101
<212> TYPE: DNA
<213> ORGANISM: Zea mays

<400> SEQUENCE: 120
tttttcctgt tccctttgtt gttcaaatag tttgcagctg ttgctgcact stgtgtgcaa    60
tatgaagctg actttcgacc caacatgagc atcgtggtga a                        101

<210> SEQ ID NO 121
<211> LENGTH: 101
<212> TYPE: DNA
<213> ORGANISM: Zea mays

<400> SEQUENCE: 121
aatcgatgaa gggccggcag cggggaattg aagttctgcc ggcagcgggg rattgaagtt    60
ctggtacgtg gtaaaaaaaa acaaagtagt tgtcatggtg t    101

<210> SEQ ID NO 122
<211> LENGTH: 101
<212> TYPE: DNA
<213> ORGANISM: Zea mays

<400> SEQUENCE: 122
atctgtggac gtagatgatg agcggccgga ttatacggcg acgacgcaaa kacagtgaat    60
gcatcatgca tggttggtga gactcaaaaa gactcgcaag a    101

<210> SEQ ID NO 123
<211> LENGTH: 101
<212> TYPE: DNA
<213> ORGANISM: Zea mays

<400> SEQUENCE: 123
tccaatgcca tgcaagaggc ccagcgcacc actggactgg tccggtgccc rccacgtcag    60
atagccattg gagctagtcg ttgctgactg ttgtgtctct t    101

<210> SEQ ID NO 124
<211> LENGTH: 101
<212> TYPE: DNA
<213> ORGANISM: Zea mays

<400> SEQUENCE: 124
actcgaagct gatgacttcc ccggatcact cgatagctac tgatttgaca ycgcgcatgg    60
agatgtcaag gcggggtgac acatcaataa tgggagagcc g    101

<210> SEQ ID NO 125
<211> LENGTH: 101
<212> TYPE: DNA
<213> ORGANISM: Zea mays

<400> SEQUENCE: 125
gtcatcttgc atctaagacg tcggaccggt ttggtgtgca tcggaccggc yatgcagaga    60
ggatgtaaaa tggacacttc gaaggatggg ttctcggacc g    101

<210> SEQ ID NO 126
<211> LENGTH: 101
<212> TYPE: DNA
<213> ORGANISM: Zea mays

<400> SEQUENCE: 126
gaaaaggatg gccggcccta cgacgcaagt tgctgctgct agctgcaccc rtacgtgagc    60
caatgtagta gctttcccat cccctgcatc gatctgctca t    101

<210> SEQ ID NO 127
<211> LENGTH: 101
<212> TYPE: DNA
<213> ORGANISM: Zea mays

<400> SEQUENCE: 127

```
attcaaagtg ggcatgtgcc ggtccggtcg aataattgtg tcatgcctcg rccgccttct      60
cggcccttag taccggcttg tctcgatacg attatatttt t                          101
```

<210> SEQ ID NO 128
<211> LENGTH: 101
<212> TYPE: DNA
<213> ORGANISM: Zea mays
<400> SEQUENCE: 128

```
aattgaacca ccatccatcc gagacagcac gcagcaacgc atacgctact rgtcaacgga      60
ggacctcacc gtgatgagga aagatccaca tctcaacaag c                          101
```

<210> SEQ ID NO 129
<211> LENGTH: 101
<212> TYPE: DNA
<213> ORGANISM: Zea mays
<400> SEQUENCE: 129

```
agacgaagaa tccggcattc agatctaagc ctgcgcaaca tgaagcaaac kgatttgtcg      60
ctaaatcgaa acaaagtagc tcaccgaggg cgcgcgaggt a                          101
```

<210> SEQ ID NO 130
<211> LENGTH: 101
<212> TYPE: DNA
<213> ORGANISM: Zea mays
<400> SEQUENCE: 130

```
tgctgcgcac cctcgtcacc cccatgtcgt gctcgccgtc atccgtaaga rtgtccggtg      60
tccgggccac gtcgcgaggt aataatgtcc ggtgttccca g                          101
```

<210> SEQ ID NO 131
<211> LENGTH: 101
<212> TYPE: DNA
<213> ORGANISM: Zea mays
<400> SEQUENCE: 131

```
agattttttcc cggccggtga agcctcgttc gcaacgtaga gcatgcactc scgtcttgcg     60
cactatcatc agctcgagct ccagcctcca gctgctaaaa c                          101
```

<210> SEQ ID NO 132
<211> LENGTH: 101
<212> TYPE: DNA
<213> ORGANISM: Zea mays
<400> SEQUENCE: 132

```
gcttttggat aaggaaatac tagtggaagt ccagggcatc catgagaggt mgagaaataa      60
gagtacattg ttttacttac ataagccatg gtgtcttttta t                         101
```

<210> SEQ ID NO 133
<211> LENGTH: 101
<212> TYPE: DNA
<213> ORGANISM: Zea mays
<400> SEQUENCE: 133

```
ggtgccgtcg tggtgcgcga actcggcgcg aatatcggct tccgtgatag ktgcgctggt      60 gcgttttttcc ggcggcgcag cgttcctgcc cttggccgcg t                         101
```

<210> SEQ ID NO 134
<211> LENGTH: 101

```
<212> TYPE: DNA
<213> ORGANISM: Zea mays

<400> SEQUENCE: 134
tcttctcagc accttgtgga gatgtcttct cagtgccttc gcaagcatcg rtcacgtaaa    60
gtgcagctcg tgttttttg ctgcttggga tctcacgcaa g                        101

<210> SEQ ID NO 135
<211> LENGTH: 101
<212> TYPE: DNA
<213> ORGANISM: Zea mays

<400> SEQUENCE: 135
cccagtccca ctccgtccac tcgagctctc caccagcttt cccttctct mcggtccggg    60 aatcggaagc tcagggcaga aggtaagcta ccagaccatg t                       101

<210> SEQ ID NO 136
<211> LENGTH: 101
<212> TYPE: DNA
<213> ORGANISM: Zea mays

<400> SEQUENCE: 136
ttctctctct acctatcggt tcttcttaga tgatcgccgg aatctcaacg ycggtcgtca    60
catattcata ttcatattcg aattaaaaca tggtagatag t                       101

<210> SEQ ID NO 137
<211> LENGTH: 101
<212> TYPE: DNA
<213> ORGANISM: Zea mays

<400> SEQUENCE: 137
accattggtg cctcagatcg cgcacgcaca gacacccttg tcttgtgggc yggcaactcc    60
gcccgctcgc cgccgccgtt ctctctcgcc ggcggtgctg t                       101

<210> SEQ ID NO 138
<211> LENGTH: 101
<212> TYPE: DNA
<213> ORGANISM: Zea mays

<400> SEQUENCE: 138
gacctggaga agctgctggt acatcgcgcc atagttccgt gtgagctcgt ycatcatgcc    60
acgcagccgc ctgttatcct ccaccacccg cctgagctct g                       101

<210> SEQ ID NO 139
<211> LENGTH: 101
<212> TYPE: DNA
<213> ORGANISM: Zea mays

<400> SEQUENCE: 139
agtgtatgta tgtatattta atttgatatg tggttagcat gctcaataga matgtaaaac    60
ataagttcgt gacaaaccta atgtgaatgc aaatgcatat g                       101

<210> SEQ ID NO 140
<211> LENGTH: 101
<212> TYPE: DNA
<213> ORGANISM: Zea mays

<400> SEQUENCE: 140
ttcgcccttg atcatatggt gtgtaacttt catctgcatt aggtagactt yggtgttgtg    60
```
gttgtacgaa gtcgtcacta agcagcggag gatgtgctcg a                                 101

<210> SEQ ID NO 141
<211> LENGTH: 101
<212> TYPE: DNA
<213> ORGANISM: Zea mays

<400> SEQUENCE: 141
gtttgaaagt gttgcgactg gcgactccaa agagtccaag ctaattaggc yaccacacca            60
catcgacgac gacgatgatc ggtgggtcgt cagtatggat c                                101

<210> SEQ ID NO 142
<211> LENGTH: 101
<212> TYPE: DNA
<213> ORGANISM: Zea mays

<400> SEQUENCE: 142
tggtgtgaac attcaaatca ccttgtctga actcccccca aattggtcgt yttcccgtcc            60
cggccactat aggtccatag ttgtgttcac ccccccccccc t                               101

<210> SEQ ID NO 143
<211> LENGTH: 101
<212> TYPE: DNA
<213> ORGANISM: Zea mays

<400> SEQUENCE: 143
gtgtcgatgg ggagaggtaa gagctccttt tttgcatctc tgttcggctg yaagaagcag            60
gtctccgccg gcgggaggca ggaggaatcg gcggcggcga g                                101

<210> SEQ ID NO 144
<211> LENGTH: 101
<212> TYPE: DNA
<213> ORGANISM: Zea mays

<400> SEQUENCE: 144
tttgtcgctg cttcaactat tatccaactg tctctattct agttcttgcg ygcacaaaca            60
ctaggagagt gtaggcctct gcaacgagcg ttgtccaaga g                                101

<210> SEQ ID NO 145
<211> LENGTH: 101
<212> TYPE: DNA
<213> ORGANISM: Zea mays

<400> SEQUENCE: 145 cgcccctttcg ccatgattta tactcgcgtg acgcccacac aacgcccatg wttagaagtc           60
gcccggccgc ccgcgcgctg ccagatcca tcagctctta t                                 101

<210> SEQ ID NO 146
<211> LENGTH: 101
<212> TYPE: DNA
<213> ORGANISM: Zea mays

<400> SEQUENCE: 146
tcccacaccc agattgttcc tttcaatttg cttgcttgcg tatttctccc kctccgatga            60
tcgatgattg cattactgat tgttttatgc ataataataa t                                101

<210> SEQ ID NO 147
<211> LENGTH: 101
<212> TYPE: DNA
<213> ORGANISM: Zea mays

<400> SEQUENCE: 147
acgaacggga aaattcctgt cctaacccgg tcagtattcc cactttttc ygaccatttt    60 cgaattcccg gaaaaatatg aaaataggat gagaccaacc a                       101

<210> SEQ ID NO 148
<211> LENGTH: 101
<212> TYPE: DNA
<213> ORGANISM: Zea mays

<400> SEQUENCE: 148
cggtcttcat aggtgagaac atgtgcaggc ttctcgtgag gaactcgttg rtggtactcc   60
atagcatcag caactaatca tacaatacaa tattatgaca t                       101

<210> SEQ ID NO 149
<211> LENGTH: 101
<212> TYPE: DNA
<213> ORGANISM: Zea mays

<400> SEQUENCE: 149
ttcaccaaca gtgtccggcg tcggcgtgcc gaggctgtca aggcgcttct saggaatggt   60
ttgatcgggg gccagtcttg ggtggtcctg ctgcctcatg c                       101

<210> SEQ ID NO 150
<211> LENGTH: 101
<212> TYPE: DNA
<213> ORGANISM: Zea mays

<400> SEQUENCE: 150
gccccgccgg agaggatgac gcggcggtgc tcgcactgca gcaacaacgg ycacaactcg   60
cgtacctgcc ccgtccgctc cgccggcggc ggcagcggcg g                       101

<210> SEQ ID NO 151
<211> LENGTH: 101
<212> TYPE: DNA
<213> ORGANISM: Zea mays

<400> SEQUENCE: 151
ggccgacact aatcaaatca gctaaatatc ttttcccacc tgattaagtt rtatgggcat   60
gtgctgctgt gcatcacaat accttgatag atcacgtccc a                       101

<210> SEQ ID NO 152
<211> LENGTH: 101
<212> TYPE: DNA
<213> ORGANISM: Zea mays

<400> SEQUENCE: 152
ttccactaac tctttggcct ccaagtgttt cccacgtgga ggaagcagcc rgaacccatg   60
aaatcctaaa accaactcct ttgaatggta aggggtggt t                        101

<210> SEQ ID NO 153
<211> LENGTH: 101
<212> TYPE: DNA
<213> ORGANISM: Zea mays

<400> SEQUENCE: 153
tcagatgtgt tgtgccagta cccacgattt cagaggaaga agccggtgcc sggatcgcca   60
atgcaaagca aaatatgaca gcatcgagat cacgattcgg c                       101

<210> SEQ ID NO 154
<211> LENGTH: 101
<212> TYPE: DNA
<213> ORGANISM: Zea mays

<400> SEQUENCE: 154
acagtcccgc ttcaatcctg cccaccagct ccgaggttct ttctcgcccc raaaccgtcg    60
ctccccggcc gcgctgaaat catcgtgccc gggctctcct c                        101

<210> SEQ ID NO 155
<211> LENGTH: 101
<212> TYPE: DNA
<213> ORGANISM: Zea mays

<400> SEQUENCE: 155
gtcccgacgc tcctccacta gagcagaatt aaaacctcta tatatatgta sagcgagcac    60
gcctgtgcga acatgccgct ccagcacaca cagcacccat t                        101

<210> SEQ ID NO 156
<211> LENGTH: 101
<212> TYPE: DNA
<213> ORGANISM: Zea mays

<400> SEQUENCE: 156
gcgctagctg gctagtcctt ggtgataacg tatatcgcgt agatgatccc sgggagatag    60
gcgaggaagg tgagcaggag gcagagccag aattcgacct g                        101

<210> SEQ ID NO 157
<211> LENGTH: 101
<212> TYPE: DNA
<213> ORGANISM: Zea mays

<400> SEQUENCE: 157
ccggtggtcg ttggggttgg cttttgtacc tgtgcagaaa acagctcagg saggcgagga    60
ctcctagcgg aaaacatgac ggccgatgac gcgatgcgac a                        101

<210> SEQ ID NO 158
<211> LENGTH: 101
<212> TYPE: DNA
<213> ORGANISM: Zea mays

<400> SEQUENCE: 158
gtcacctcca tgaaacttcg gcaggaatcg cccggcaccc gccgatctgc mtcatcgatc    60
ctcaaatcag cagctgttct ttttcagtca tattgcgagc t                        101

<210> SEQ ID NO 159
<211> LENGTH: 101
<212> TYPE: DNA
<213> ORGANISM: Zea mays

<400> SEQUENCE: 159
aaaggagcta gtaaagccaa tcaattatgg atttgatatt gggtgagcga saggaggcgg    60
cagccagcag gcagggctcc cttatcctcc gtgatcttcc a                        101

<210> SEQ ID NO 160
<211> LENGTH: 101
<212> TYPE: DNA
<213> ORGANISM: Zea mays

<400> SEQUENCE: 160

```
tcctgcaaca tagttccctc ctaggaacag cccatcgtag ccacctcggt ycagggcagc    60
ttttgcggct tccagaagat caagatgtcc taccaggaac t                       101

<210> SEQ ID NO 161
<211> LENGTH: 101
<212> TYPE: DNA
<213> ORGANISM: Zea mays

<400> SEQUENCE: 161
gtccccaaaa accaagtcat ccttcagtcc gctgtccacc tgcgcgcgcg yataaaatcc    60
attcagcatc tcaattccat ggctccgcat gagtctgaga a                       101

<210> SEQ ID NO 162
<211> LENGTH: 101
<212> TYPE: DNA
<213> ORGANISM: Zea mays

<400> SEQUENCE: 162
acgttacagg tgggctggga atcgcattcc cgtgcgtgat tggttccgtt ratatccaat    60
ccctctcaaa gtctacacaa gacctgcttc gcctgacggg c                       101

<210> SEQ ID NO 163
<211> LENGTH: 101
<212> TYPE: DNA
<213> ORGANISM: Zea mays

<400> SEQUENCE: 163
tgagagagtt gatggagaaa cagaaactgg tggcatcgca gtagcggaaa wggtgctgcc    60
acttgactca ttctggttaa tccagagtaa attgttgcta c                       101

<210> SEQ ID NO 164
<211> LENGTH: 101
<212> TYPE: DNA
<213> ORGANISM: Zea mays

<400> SEQUENCE: 164
attacggagg aactatatgg gctcctacag tggcgtgtga cagggtggag yttgacggag    60
aacagcagca tctagtggct actgatatca agatttggtg g                       101

<210> SEQ ID NO 165
<211> LENGTH: 101
<212> TYPE: DNA
<213> ORGANISM: Zea mays

<400> SEQUENCE: 165
atatgctttc tttttctagg ttgaagaaga tgtacgtact ttaagactat ytcaagtgca    60
gcatttcaga taaaaattta gtcccgtctt ttcattcttg c                       101

<210> SEQ ID NO 166
<211> LENGTH: 101
<212> TYPE: DNA
<213> ORGANISM: Zea mays

<400> SEQUENCE: 166
gcctgcaggg tcttcctctt ctgttggcgc caggactcgt cgtcctttcc ygtcccagca    60
ccattgccgg agcagaccga tgaggtggcg gtggcgcccg c                       101

<210> SEQ ID NO 167
```

```
<211> LENGTH: 101
<212> TYPE: DNA
<213> ORGANISM: Zea mays

<400> SEQUENCE: 167
gcttgccaca gtctcttcct tgtactcttc ttcctctcct agctaggagt kgagttgggc      60
atacagtggc aattattttt cgttgcgcag ttggctgatc c                         101

<210> SEQ ID NO 168
<211> LENGTH: 101
<212> TYPE: DNA
<213> ORGANISM: Zea mays

<400> SEQUENCE: 168
ctcgcaacgg ccgacgatgg atgacgacga tagcactcgc cgaggacact sccaagagcc      60
tgcctccact ggcgctgcca ctgccactga taaagaaagg t                         101

<210> SEQ ID NO 169
<211> LENGTH: 101
<212> TYPE: DNA
<213> ORGANISM: Zea mays

<400> SEQUENCE: 169
ctcgcgatcc gtcgaagaat ccggccagga cgaagcggta tcgcctgacg scgaccggcg      60
gctacgtttc gcgctcctgg aggccgcggg agggccatcg a                         101

<210> SEQ ID NO 170
<211> LENGTH: 101
<212> TYPE: DNA
<213> ORGANISM: Zea mays

<400> SEQUENCE: 170
gaccactcgc cggccagtac ggaagcaggg acgccgacat ggagaagctt racgaggcgc      60
tgggcgtgcg tcgcgagcag acaggagagc gccaaggagc a                         101

<210> SEQ ID NO 171
<211> LENGTH: 101
<212> TYPE: DNA
<213> ORGANISM: Zea mays

<400> SEQUENCE: 171
cgctcaggga ggtacgccga cgaggagaac caaggacgca gaacgacgcc rtgggaggag      60
ccgctcggcg agctggagga gtaccgcacg cagggaattt g                         101

<210> SEQ ID NO 172
<211> LENGTH: 101
<212> TYPE: DNA
<213> ORGANISM: Zea mays

<400> SEQUENCE: 172
tcttcaagtg cggcttggtg ttcttcacgt gagcgatgca cccaaatgtg yggaagaagc      60
tcactactgg ctgctcgcca tgccaggcct cgtatggcgt c                         101

<210> SEQ ID NO 173
<211> LENGTH: 101
<212> TYPE: DNA
<213> ORGANISM: Zea mays

<400> SEQUENCE: 173
tcgaccgagc aatataatcg ttgccgcggg atatttattg agaaaccaac raatgcagac      60
```
acgctgcctg gtcgtcgtct acttgggtgc gaagtttgcc t    101

<210> SEQ ID NO 174
<211> LENGTH: 101
<212> TYPE: DNA
<213> ORGANISM: Zea mays

<400> SEQUENCE: 174
gcttcgagga tcctgttgga gcctgcgtcg gagaggacgg gtatgattac rgcagggaga    60
cttcgtggaa cacgcctgcc ggtactgtgg gatccataat c    101

<210> SEQ ID NO 175
<211> LENGTH: 101
<212> TYPE: DNA
<213> ORGANISM: Zea mays

<400> SEQUENCE: 175
ttataatctg gtcgtcgcgc agaagcttgc tagctagctg cctcctgtct ytgtctttgt    60
ctgcatcgat cctctatgcg ccgaaaaagc gtgatgtcga a    101

<210> SEQ ID NO 176
<211> LENGTH: 101
<212> TYPE: DNA
<213> ORGANISM: Zea mays

<400> SEQUENCE: 176
tatgccctgt cagttgcttc cctccaccaa caaaacccgg caaccaaaca mtataccgtc    60 gttttttgctc cgcaagtctt ctctgcgcag cttggctctc t    101

<210> SEQ ID NO 177
<211> LENGTH: 101
<212> TYPE: DNA
<213> ORGANISM: Zea mays

<400> SEQUENCE: 177
ttttgtcaac gagtgctccg gccgatcggc ttgtccgtac gcacgcgagt ygcgtcggtc    60
cggccgagcc gatgaggtcg ctcctcgctc gccccgcgtc a    101

<210> SEQ ID NO 178
<211> LENGTH: 101
<212> TYPE: DNA
<213> ORGANISM: Zea mays

<400> SEQUENCE: 178
ttgggcagcg ggtggggtgt gcaaggcgac ccaactgctt tacaggtgtt stcattcatg    60
tgttgaatct acagaaaaaa aagaaagaaa gcgaaacatc t    101

<210> SEQ ID NO 179
<211> LENGTH: 101
<212> TYPE: DNA
<213> ORGANISM: Zea mays

<400> SEQUENCE: 179
agttttgcag acagagccca atggatgtat cattattgac tatgattaac rgtggaaata    60
gaagtgacaa attgcataaa gagagctgca ttgtgctaat g    101

<210> SEQ ID NO 180
<211> LENGTH: 101
<212> TYPE: DNA

<213> ORGANISM: Zea mays

<400> SEQUENCE: 180

| gacaatgagt gaccttagag cttgcaacca aggtgctatg aaaatgcagt rccactattt | 60 |
| catttgcagc agagccaggt ccgattttca attttgtgga a | 101 |

<210> SEQ ID NO 181
<211> LENGTH: 101
<212> TYPE: DNA
<213> ORGANISM: Zea mays

<400> SEQUENCE: 181

| aaggagcgga gggcggaggg gttctgcgtg ggcggtgatt gaaccgcaga wtggggcggc | 60 |
| tgctgctcag cctgtggaga atgaggagag ttgaggggag a | 101 |

<210> SEQ ID NO 182
<211> LENGTH: 101
<212> TYPE: DNA
<213> ORGANISM: Zea mays

<400> SEQUENCE: 182

| ctcaccggta agggtcggta ccaactgatt ctccagtgca tggatcagta ytggccggtc | 60 |
| gaaccgaccg acatcggagc taaaccgatc ggtactgatt g | 101 |

<210> SEQ ID NO 183
<211> LENGTH: 101
<212> TYPE: DNA
<213> ORGANISM: Zea mays

<400> SEQUENCE: 183

| taggcgccta tgacgacgac gaggtatggg cccccgtggc agtcaagatg rtcgcagcca | 60 |
| tccgcggcgc agagaacagc tgcggtgcgg cagaagtaag g | 101 |

<210> SEQ ID NO 184
<211> LENGTH: 101
<212> TYPE: DNA
<213> ORGANISM: Zea mays

<400> SEQUENCE: 184

| aggattggtc acttaacaac acgattgaac tgcaactcca ggcccggccc yagttcttca | 60 |
| cgggacaatg gcagctgccc tgcagagcag atatcgcgct c | 101 |

<210> SEQ ID NO 185
<211> LENGTH: 101
<212> TYPE: DNA
<213> ORGANISM: Zea mays

<400> SEQUENCE: 185

| catttagacc tgcttctgtg taagtagatg tagatctgct tcagtgtcag matgagaatg | 60 |
| tttatttcat gagttgctgg gaccttaagc ataagtttac a | 101 |

<210> SEQ ID NO 186
<211> LENGTH: 101
<212> TYPE: DNA
<213> ORGANISM: Zea mays

<400> SEQUENCE: 186

| attggacagc gctggatttt gaccgggcca tagttccatg acttaggtgg yttatgttta | 60 |
| cttttcctcc ccaataatct tgggtcgagc gatgttataa a | 101 |

<210> SEQ ID NO 187
<211> LENGTH: 101
<212> TYPE: DNA
<213> ORGANISM: Zea mays

<400> SEQUENCE: 187
gttcagcgcc gcacaaagtg tgctgataac aatggattta catcatctac ygaatctttg     60
cagcctcctt cggcgtatct catcaactgt gagttctcca g                        101

<210> SEQ ID NO 188
<211> LENGTH: 101
<212> TYPE: DNA
<213> ORGANISM: Zea mays

<400> SEQUENCE: 188
ccaaccgcgt attggtcgta gtacgcagta taatcaccaa gcaagagtag scctttggac     60
aagagcagcg cgatgccctg tgacagccca agcaatgcag c                        101

<210> SEQ ID NO 189
<211> LENGTH: 101
<212> TYPE: DNA
<213> ORGANISM: Zea mays

<400> SEQUENCE: 189
cctgcaaagg gagtggtagg aggtgcacgc caaagcatgg ccggtggcgc kcgcccgtg      60 cttggcttct cttccctgtc ctagggcgac ctcgagcacg g                        101

<210> SEQ ID NO 190
<211> LENGTH: 101
<212> TYPE: DNA
<213> ORGANISM: Zea mays

<400> SEQUENCE: 190
tttacggaga ataacaagct ccggcacgaa tttaaacaga tccgggcaca rcatggaaaa     60
agtgcaaata aaaagaggc tcgtagaaaa aaaaatcatt t                         101

<210> SEQ ID NO 191
<211> LENGTH: 101
<212> TYPE: DNA
<213> ORGANISM: Zea mays

<400> SEQUENCE: 191
tcgctcctcc tcaacggaga gaccctccct cagctcttca taaccatcgt mcgctacgtg     60
ctcccctccg aggaccacac cgtgcagaag cttctcctcc t                        101

<210> SEQ ID NO 192
<211> LENGTH: 101
<212> TYPE: DNA
<213> ORGANISM: Zea mays

<400> SEQUENCE: 192
gcgccgcgcg cgaggtcgct ctctccgccg ccgctgccgc tgcgtggcgc ygcagcacaa     60
acggacagca gcgagtcgcg cgccgcggcg aggaagggcg g                        101

<210> SEQ ID NO 193
<211> LENGTH: 101
<212> TYPE: DNA
<213> ORGANISM: Zea mays

<400> SEQUENCE: 193

```
ctgccgctgc gtggcgctgc agcacaaacg gacagcagcg agtcgcgcgc ygcggcgagg    60
aagggcggcc gcggtatcag gcacctgctg tgcagggcct t                      101
```

<210> SEQ ID NO 194
<211> LENGTH: 101
<212> TYPE: DNA
<213> ORGANISM: Zea mays

<400> SEQUENCE: 194

```
gctaaaaatt tcagaactgc cgatcctggc cgtcgatcat ggatccgagc rccatcccgg    60
caccactttc cattaataaa atttcgaccg ttggagacag c                      101
```

<210> SEQ ID NO 195
<211> LENGTH: 101
<212> TYPE: DNA
<213> ORGANISM: Zea mays

<400> SEQUENCE: 195

```
aacgtcggca acaagaagcc acttgttcct caggcagcag caagaggcct kcgacccctt    60
gccgacgtta cgaatcttat gatcaaagac cgtgctgctc c                      101
```

<210> SEQ ID NO 196
<211> LENGTH: 101
<212> TYPE: DNA
<213> ORGANISM: Zea mays

<400> SEQUENCE: 196

```
agcaggggag gggagagatg cgtgttcgtc ttccttccca cccatccctg yttctagctc    60
ctcctccttc cccagcgggt ggccgcagca atttgcaagc a                      101
```

<210> SEQ ID NO 197
<211> LENGTH: 101
<212> TYPE: DNA
<213> ORGANISM: Zea mays

<400> SEQUENCE: 197

```
cctctcccctt cgtttcctgc tctctgctcg caccgaatcc ctcgtctcct rgctccatct    60
cagcatttcg gatccccgaa gaacaaacaa actgccgcca a                       101
```

<210> SEQ ID NO 198
<211> LENGTH: 1753
<212> TYPE: DNA
<213> ORGANISM: Zea mays

<400> SEQUENCE: 198

```
cggtagtggt gtgggcttgt gggaggctgt agttatggta gtgccgtggt ctatattatt    60
ggcttaatag atagtataga tttagtatat atcgtagcaa ttagctgttt tatccgacca   120
ctcatatgtt gtacacgaca atgacatttg ccaatagaag tagcacttca cttgttgttg   180
cacatatcag gaacaaagtt ttattgcagt ttgacagata tgcatgagaa atacacaaaa   240
agatgagtgt agcacaaacg aatgataatc aaagaatgg atgaaacaaa aaagcgcaac   300
cttatggctt tctgatctcc gatggttgat atatatgtgt tgtgctggca cgacctcttt   360
cttcgatttc cacggcatct ggcaggctta gtataagcgg tggttaacga cgctgcactt   420
cttcctgatc tctcccttgc ttcctttcgg catgggcagc ttgctgagct tgagcagcga   480
gtccgagaag tcctcgtccc atagcgtggc gttctcggcg tactccacga cgtggccgaa   540
```

```
cgcctccttg tgcgtgagca gcgtccagtc ggagtggaag gtgacgatct tggccaggtt      600
gttgtggtag aaggagttgt ccaggaagtc ggggatcttg cgcacccggc tggtgaaccc      660
cggcatgaac ctcgccacca cgtcgtagtc ctcgtcgcgg acgttgttgt ccacgggcgg      720
gttggacccc tgggagcact tgtagttgag caggtcgcgg tacgccgggg tgatctgctg      780
cgatggctcg gagaggcggc cggtgaagga cgagcagtgg ccctggccga tggagtgcgc      840
cccggtgagg atgacgagct cctccaccgt gaagttcttc ctggcgaagt tgtcgatgag      900
ctgctgcacg tcttggttgg agtccgggag ctccgcctgg gcctcctcgg ccttggagac      960
gaagccgtcc aggcggccgg cggggacggc gaagtggacg tggccgttgc tgaggacgct     1020
ggccgcgtcg cgggccgcgt agatgaggat gtccgagcag agacgacgc cggggcacct      1080 cttctcgaca gcggccttga tctcctccag gaggtcgaag gcggcgaggc cgatgttcac     1140
cggcgcctcc ttctccggat gagggttgtc gtaggaagcg tccaggagga cagaaccatc     1200
gcatccctgc attgcatgga tgtccagttc aatcaatcaa tcaactaata tacggccaag     1260
tagtatgtac atgaatgcgc atgctgctgc tcttattacc ctgacgaagc agtcatggaa     1320
gagaaggcgg acgagagcgg cgccggtgcg cggctggcc ttgagcgcct tgatcacgtg      1380
ccacttcacc acgttctcca cgcccttgca tttcttgctg tagtacccga cctccagctc     1440
gctggcctgc gacgtcggca cggtggcgag gagcaccgcc gcctggacag ccagaagcgc     1500
gcagaggact gccaccgaga gcttcatttt tggtctcctg gagcctggtc cgcgcggccg     1560
ggcgcctagc tgatgaagca agagacagat gctgctggct caggaacagg cactttgatg     1620
gtgtgcttag gagatgggcc tgcaggggta tatattgccg ggtttggcca gtagtttaac     1680
tgttaatgat tgaggttgcc gccgataatg agatgggaga gaatagggag ggaacgtggt     1740
cgccttgcgg cgt                                                        1753

<210> SEQ ID NO 199
<211> LENGTH: 5374
<212> TYPE: DNA
<213> ORGANISM: Zea mays

<400> SEQUENCE: 199
atggtctgga tgacttgtcg gatcaatgtg tgttaaatga tttcagaata tatatatagt       60
atatgtattt atatatatat agtatatgta tttagagccc tgagttctgt ttaactattg      120
gaagctacga ccacaccact gaccacgtgt gcagaccgca ccgaacactt tttgtctttt      180
tgtacctaac ttcttacgtc aaattataat acgtgttatg ctaatttgtg tatcagttta      240
tacacttatg gtatgcgcat gttccgggca tccgggccca cgagaagatt gtgttcccgc      300
aatctgggca gtcgtactag tccccacaca aatattggta ttacgatgat ttatgttttcc     360 gtttacgaaa cagtaatgga cgtgtcggtc tatggacctt tgcgtagatt tcttcccgca      420
gattacgtgt ctcgggccca ggattccatc cacttctcac ggtagttatt ccgctcacct      480 caccccgaaac gcacgaggcg atcgaaccct agcattatcg cccgctgtca ccttgttctt     540
ctccaccgca gagaccgagt cggcttcgct ccaccgtggc ggccgaaccc taggggatct      600
cgccgccgtc gacttcatcg tatccaacgc agagaccgag ctgctgtcgc cttcagcttc      660
tccaccgcag agaccgagac ccagccgccg tcgcattggt cttctccact gcagagagac      720
cggaaatcgg ctggtcctca ttcccctcca cacaccggtc agtcctccac tgccatctcc      780
ttcattttct ccgccgcatt ctcgttgtcg ccgtcatctt ctccaccgca gggagacttc      840
```

```
gtccttttcg cccaactcca tttgaaggaa gcgctaaata attacattgg aggagctgtt    900
atcagtaagt cctgaatccc taacattcta tttgatttta tcgttgttct acattttagt    960
tcagcaactt tcattgcaat tacacatagt tgcatccggt tattcagact gaccatcatt   1020
tagttattga tctgcatatc atatttacac aaattgtatc gtaaatcagt gtcaccttat   1080
aataactcaa ttgtttcata tatcgaaaaa caaatcagcg taaattcatt gttaatttag   1140
cgtaagtcat ttagggctag tacgcaagaa agaacccaga tgtcatattt ggtaacctaa   1200
tggtcatttg tggtttgtac gttgtcgtgg cttactacat taatttgttg ttgcatatgt   1260
gcagattttt tttggtccaa aaggttgtat ttatacgttt tatatgtata tgtgttgttt   1320
gttttggcag gaaaatcata catgaagaac gtagaccgac ctccgcctaa tccaaagcgc   1380
attataattc agtctactca agagtgcttt agtgtcgaca taccccgtgt tccggcgaac   1440
actgtcagtc acaaaccaat gcatgccggt gatgaggacg atgaatttat gcttgtattg   1500
aagaagcgta accttgctag tagtcctcca agaatgatga agaaggtcgt tacaaagcgg   1560
atgaaagcag tggatcccct ccgacaggtt agaattgatg ttcaatgcca atataccatt   1620
ttctgcgtga aattatgttg tactgagttg tcaattaaaa actgagctgt gattatgcag   1680
atgtaaatgt tttacattat tcattgttac atttttacag tagaggctta atgttagatg   1740
caatccccaa gatgttatag taagcatcca gatcttaaat gccagacaac gtcaagctat   1800
tgcacggaag gggttctcca gtatacttga tatgagagtt gatgtgcttg gcagtagatc   1860
acatttatct tggctgatgg agaagcttga tcataatgat atgacaattc gagctggacc   1920
agggaaggag ctaaaaatta caaaggaaac ggtgcacctt atattagggt taccaaatgc   1980
tggtggagga aagccattag gcattgacga ggctgttgct gcaaataatt taagggttga   2040
acttggttta tccaaagaag aattcggtgt tgcagctcta caagatcgtt taaggaaagg   2100
atttgacaat gatctaagca tcagatcctt tttctgatac tgttcaatag gttgttgttc   2160
cctactgcta gttggggaat aactaaccat gaggttcttt taactgaaga atgggccgt    2220 ttccatgaga tggactggtg ccagctcata tttaatgatt tataccaagc ggccaagaag   2280
tggcatacta ggagcaatac caatgtgtct acaacaattt acggatgctc catcgtcatt   2340
cttgtaagca tatcaccttt ttttttgttt gttttatgta gacaaatttt ggtatgcaaa   2400
tatcatctgc attagattat gatttgttat gtgtcacaac gattcatgtt atgcttttgt   2460
agctgtacta tctggatcat cttcatgact cagctgcacc tcagaataag cgtggaactc   2520
cgcacataaa atattttgat aggaatatta ttcaagcatt gacaagagct gacaagggca   2580
agatacgcca aggacaagaa ccatttgggc attgttcggt aattttttta tgcgcatcta   2640 ttatatttt tatctatta ttttggctta tatatggtac atggatagag gtagtgtcgt    2700
tttaatgtcc aaatgaaact ccatttata tgtgtgtatc agtttgtact ccatcttaca    2760
cgtctttttt tagttccgaa gcagcacaga gacctgctac acagctgtac cacatgttca   2820
accacaattt aaggcaagct tttatctata acttttttgt cttaaaattt caacataatg   2880
ttcagttata ctatatacat ttatttaata atattcattt tacaacacca taacaacgga   2940
acaaacactt tgatgtaccg cgtcctgac ccatgtggcc agcacaccat tcacatcgaa    3000
ctcccgctca tcagggattt gatatcaagc aagctgaacc agcttccatc ccgccaccgc   3060
ctaggattca tagagaagct atcacattat gatacggtgg ttgtcaaggc ttgttcagtg   3120
atcaaacaga ctcttcagca gattgttgag aaaacaatac aatctatctt atgttttttag   3180 cgagttaatt gatgaggtcc tctgtgctga gtcagaggac aatgaagatg gttataatgt   3240
```

-continued

```
gcagcaacca actaaaaaat cagatgatat tcttcaccat tcggcaggtt agtcagtttt    3300
atggtcttta cgttaatcta aacaattata caaacatttc caatatcatt atgataccat    3360
tattaaatcg atgtattttt ttgcttaaat gttacgtaaa gaaggatgta cgagtccggc    3420
cactcaaact gtaccggata tgtctactcc agcatcccag catgagacgc agttgacaga    3480
cacacaggta catgaattac tattaataca acaacatatt cgtgtactat tacaaagttg    3540
ccctgatgaa gttgacattg atccactggt tcatacaatt ataacgaaac agaccaaaac    3600
acctacaacc ccagtggtaa tgttttttta ttacttgtat tttccttgaa ggtttgtatt    3660
catcgttttc tttaaataac atataaccat tatatttttt tcagggtcaa catggtgacg    3720
ctggcaagaa catgccgacc aacacaaacg tcactcctca agcaacacca gaatgctcat    3780
tcaacatacc acatacagaa tcttgctcgc cgatatttga tgcgacgccg caaataaata    3840
tatgattaca ccccctcgtt gttttttctat ataattatta gtagtttact aaacatctaa    3900
tccatttata ccataattgt tagtctcccg gcagtgtcca cccggcggca caaacaaatc    3960
tccccgacag tggcccatgt tttgatcaga ctccatctga acatgtcagc tcagtaatat    4020
acattttaat tataattgcc aaaactatgc agagattgaa atctatattt catatacctt    4080
ttttaggttt ctgttgtaac cgatccagat ataaacactt ctcaggttga ctaggtttca    4140
cttaattcga atatgcaatg tgtgttagct ttacgtgact acttgtgtgg tacgcaatct    4200
gacaccagca ggtataaagt ccagacaaaa ttaaaatttg tttatatcct ggtagttgca    4260
cgcgacctca ctaattgtta tcaaaatttc cacaggaaca taatagatta tggtgaatat    4320
tgttcgatat gttctgatat atatgaatct tccgccgatg ggaagtgcct cgacaatgtg    4380
ttcatgcagt ctttcattca atgtgttgat gatgatgcca aaaatcagca gctttccatg    4440
agttccaaca gattaattct cgacgttaat gttggggtaa attatcataa catacctata    4500
ccatagtcat atacacaatg gtatcccaag tatattgact ccattcattt tgtttattgc    4560
agtcactact gaactttgag gaacaggaac gacacagccg aaacccacaa ccttttgatg    4620
aatctgtact gcacacactt ctcgacaata cattgcctga gacaaacgaa ttggataaat    4680
gcaaagcggt aacaatcgta ttacatttta caaacataat ttatgttaaa tggtacatat    4740
cacatcgtca tgcataacca tttacatttc tgttgatctt tatgcttttt tacatggtca    4800
gatcatgatt cccatggtaa gcaggggggca ctagacatta tatgttgtca atacagtcaa    4860
acggtgcatt cacattttag attccaatcc ctatgggcca acacttggtg gtactacttg    4920
gaaggattac cattttgccc aaatggactt aggtggcagg aagttaccat gggctaaggt    4980
tattatgagt aggttaaaca aagccctaca acatgtacgg cccaggtcat gctttcccaa    5040
atttggcaac ttcgcaattg acttgtcccc aaactgtcct actatggcag caggatccaa    5100
tgattgtggg ttttatgtta tgggatacat tctcttttat gattgcgtcg aaggatctct    5160
ccggtcagac atagaagcaa tacgtacaaa tttatcagtt cattttatag ttggctcaaa    5220
gcaacatatg gtacacatgt atatctaaca caatttttatt ggcttgcagg gcaacactag    5280
ggaggtacgg tctcttgcgc tgcattacat cacattccat cgcaagaaca aagccatatc    5340
gctgcttgaa gacatccaaa gattcaatgt ctaa                                5374
```

<210> SEQ ID NO 200
<211> LENGTH: 2226
<212> TYPE: DNA
<213> ORGANISM: Zea mays

<400> SEQUENCE: 200

```
tcatttcgca cccaatttaa gaacttgttg ctcactactt ttgatcgttc ttcccttagg      60
cttggcctta tctggtcttg ctaagtttac accttccata tgaaactcca gtttctacaa     120
atcaaagata ttaagtcagt tttcattttc acatactaat catatattat agcaatgtta     180
ttacctttct agcttccaca tccgtagcac tactatcaac cagacacata ccagtgttat     240
gttccaatgt taatatcggc atattacatt gatcatcgtt agtattgcat tcatttttat     300
tagaccccat tacaatttcc tatgaaataa cacaaaacca gtgaagacac aaatgttata     360
gagcagcata aataatacat tataaaagtt tgttgcatac ctcgttccca tcatctaaat     420
tgcgtaaatt atttctaact aagtcttctg tttcatacgc ttcgacctat atcatttaaa     480
ttacatacat ggatcattat cgacatttaa taattgtgta ttcataataa cacgatgtgc     540
gtacctgaat gtcatcgcca gcactggtgc cacaactctc actagtacat atatcaagct     600
ccacaagcat caataaccct aacaattcgt tcatcatctc tagggcttta tcattcccac     660
ctttagatag actcgcatgg tgtactacct tcattgcctt tttaagcaac atcttctgtc     720
tatatgatct agtttctcca tcttttcctt tcaaattcct atcgtctctt gaaaaagcca     780
catcttgtcg cgcggagtat gtgtatcgtt gcaaatatat ctcactcagg atcctttcaa     840
tttggagatg catgaatgcg cgtacaagat gaacacaaaa taggcctata attgattaac     900
catacaatat gtcatatatt agttgcaaag agtgttatat tcgtaataat taatcatttc     960
atatagaaat atccgtttaa tataacacac ctgtatgctc ccaatgcttg cactcacatg    1020
aatacttccc ggcatccaca tcagcccttta ttttgaattg gtgttgtccc caaacaattt    1080
tatttgatat tgtagtatgt ttcaccaccc aatcatttac atcaccctct gtatcacggt    1140
ctattcggta tgcagttgca tattttacgg tctcctagaa ccttgtcatt acagctctag    1200
ctagtgtatg tcctcgcaac tcttatttca aacatataca atgtagttgt atccttttga    1260
ccctgcaaat tacacaatac agtattaata ccggtttgtt tttaatagca taaaacatat    1320
gttttttatt tttgtcactt accatgcatc ctagtgcctc tttggcctct ttcatcttcc    1380
tactatgcag gagtttcatc atttgctttg caaattgatg aagcggtgtg tttgcatcca    1440
cgtgggcact cttcaccagc ttgttcatgc tctcgcttcg ttgtgtagag accataagac    1500
cacaatagtc tcctttgaaa aatgcaggta cccaatcttt acgtatttca tacaatctga    1560
caagggtgtt gttctcgtgt agctagaaat cattgagcat catttgccag gcagcctcga    1620
acttcatttc attcaatgga tgatgtatta tagattggaa ccttgttttg caatccattt    1680
cttcaaatct tgcatacaat tcattcaagt ggggcatata cctgttttgc acatgccaca    1740
aacacaatcg atgtattatg tttgggaata ctctgcctag tgcgattggc atcgcagggt    1800
cttgatctga aatcgataaa tttacataac attgtgcaag tcagtatgat atcatatagt    1860
acgtgtttaa tcaatacgag ccatttatta taacatacct gtcaacatca ctcgtggtcc    1920
gtcacatccc atgcatgttt tgaacgtatt gaagacccac tcgaatgtat caactgtctc    1980
gtctcctagt aaagcaaacc caaatattgt gcattgtagg tggtggtttg aaccaacaaa    2040
catgcctaat ggcttatcat acatattagt cttatgtgta gtatcaaagg taactgcatc    2100
accaaaatca atgtactcgg cttgctggct agcatgggac caaaatatgc ttaaaatctt    2160
cccttctttg tccagttgaa agtcagaaaa aaattgtgga ttatctttct tgcataatga    2220
aaaaaa                                                                2226
```

```
<210> SEQ ID NO 201
<211> LENGTH: 2202
<212> TYPE: DNA
<213> ORGANISM: Zea mays

<400> SEQUENCE: 201
atgtcaatcg tccgatccca cccgcatacg ttgctccccg cctcgaggct cgccggaacg      60
gacgcctgga tgccgcggcc gcaatccagc gccgcgcaag gaggctgcgc ccacactaaa     120
atggagcata gggaggctcc gcccccccgc aacccgagg atgcgcggag gcggagggaa     180
atgggggaat tcgtgttgag gtctatgcat cgacatcttc ttcaaggtat acgtaccatc     240
gccatcccaa tccctacccc cagattgagc cagtacccca caacaacact gttgaacatt     300
ttcggcggcc catgcaattt tcggtggccc acctttagcc gccaaaaatt atctgctatt     360
tttggcggcc tgacacagcc gccggaaata aggctatttt cggcggcctc tgacacagcc     420
gccgaaaata gccttacttt cggcggctgt gtcaaagggc caccgaaagt aacgctattt     480
tcggcggctg tgctagggg gccgccgaaa atagtctttt taaaaccgac gtcccttctt      540
cttctctgtt ttcctctctc ctctcccaaa tcagcccacg cgcgcctttg tccgccgccc     600
gcacgcctgc gcgccgcccg cacgcccacc tgcgcgccgc cgcgccgcgc cacctgctgc     660
ccaagccgct gctcgccccg gccaccgccg cccgcgctgc cactcgcccg ccgcgccgcg     720
ctactcggcc gtcttgctgc ccgtcacttc gagccgccac tccgccgtcg tcgtcaagtc     780
gccgcatcga gaggtatttt tgcatagtt tatttcttat tttcggcggt tgttatttag      840
ttgccgccga aattagtata tatttgtaaa tgtttgtttg atttgtgtgt ttgattagtg     900
ttattgttta atttgatttc attaatatat tagtggtata tgtggtttag gtattggcat     960
attagatcta gcaatgcttt gtgaccgacc aacccaagtg ttcaatgaca acggtaagcc    1020
gccacgtgcc ttgtttttgtc ttacctctaa agacaagatc gaggtaatga aactggaata    1080
aactcatatt tgcaggaggt tcaaactgga gttgtcttga gcccaatcga tgtttataga    1140
agagggcata gagcgaaaaa cactgaaatc tccgatgagc tgtgtagtca gcggctgtt     1200 gagtgtatgg ttagttgttg ttaggattaa tgttttcttg tcatatagct ataaattaca    1260
tgtgtgctga accttcgtat tttattgcag gagacatatg ggcaggagat ggttaggaag    1320
tatggagaag actacgattg gcgaggagcg cctaccatcg acgctgaagt tgtgcattct    1380
attggaggaa aggcgcatga acggtattaa cttgtgaatt ttttcaataa tattggaact    1440
atgaccgaat agctaatttt attgttttca agatattcta tgtttaccgg tgtgatcgat    1500
tcgacggagt tgcgttctag ttgcggctct tcgtcgctgg cgggcagtgg tagtagcagc    1560
cgtagtcggc gctctgtatc tagcatggag gacgctatga gggagcagca agaaaagttt    1620
cgtgaagaga tgcggcaaca acaaatgaca ttcctccaac agcaatcaga gtacatggct    1680
gcttacaacg cacaggcgca acaagcaacg aacgtgagtg tcttatttat tctcaacacg    1740
ctcgatattg gttctataac taatatatta tatttgcaac agtcttggtt tccacagcag    1800
gcacagcagt aaccatttgt tttcccttag tttcagtcgc cgatgcctca gtgggaatta    1860
catgctccgc cacctccacc tccacctcag gtgcttcaat ttagttaaga cttgtcgttt    1920
gtatcaacct aatttcaaat ctttactaaa cttgattttg tagggatcca aggtcatggg    1980
ccacaacacg ccaccaccgg tcatatcagc accaggagga gcttatgtag gggagggagc    2040
tactccaaga gaggttagta tgagaaacaa tttgttgaa tagtggtcaa acatgtaacc     2100
aatgcagtta ttaatgtctt ctttttctt tacaatgcaa acccgttaca cgacttcatc    2160
```

```
aacgagtttt tcgcttctgg aggtagtgga cacaactcca ac                        2202

<210> SEQ ID NO 202
<211> LENGTH: 691
<212> TYPE: DNA
<213> ORGANISM: Zea mays

<400> SEQUENCE: 202
gacggccgtt gattcggccg aagggggaga ggtatgtaac tttatgttct tcattcttgt       60
tcatattatg tgttcaaaat cataatataa actaatactt tttatttatc acttggacag      120
gtcttggacg gttttggatt atgctggggg tcatcgtcgc cccccaaca acatcctcgg       180 cctgctgtgc agggaacact tccctggact tgtggagtac gccggagtga cgggcccagc      240
cttcaccttc gaccactacg ccgtcgcccc cgatgcagta gacccgggacg gcagggaatt     300 caataacaag gcggagcggg tgaagcaaga gctgtgggta agtcttagta taatataaaa      360
tatgtcgcat tcgttgcaaa ttcttgaaat aatgtatgga tacatcgttt ttgtatgcag      420
gatttcttca gatgcgatgc tggatacgag gctagggcgg atgtggtggc caccacgtgc      480
tgtaagaagc tcgtcgtgga catgcactat gaggcccgca tccaggccat catcacctac      540
cacggctccg tccttgggga aaggtgacc aaacctcaag cccgaacaat gtcgttgacc       600
agggagcagt acctgcaggt aaagtcatgc atgtttggta ccagtactcc atgcatgaat      660 tttatttat cttctgatat gcactttatg t                                       691

<210> SEQ ID NO 203
<211> LENGTH: 2554
<212> TYPE: DNA
<213> ORGANISM: Zea mays

<400> SEQUENCE: 203
ttgtcagtgt gtgcggtgta tggcaggttt tggttcggc aagtggggcc ctccggggag        60
gaatctcagt aacaaaccgc tcttctgaaa aggtcagcca tccccggtcc ggtccggtga      120
tgtcgtcgct gtcgctctgc tagcttgctg ccgatccccc ccccccccc cccccttctt       180 ctctctaccc ctccctccac ctcataaata cttagtttaa taaccttgca ctgccgcagt      240
agcccttaac tgctgctatc tatctctttt ctgaaggaaa aaaaggtttt gatactcctc      300
tacctagcta gtcctgcatg ccgctaatgt gcgtcttgcc tgtttatttg ttcttaataa      360
gggctgccta tctattatat tttgcacctg ttttgctgtg ttcttggtaa ctagcttaat      420
tccttcgcct acaatcgtca atccccccc atcatcagtc agatgaactt ttgatcgaat      480
tgaagttgtt cttctaattc ggccccagca gcgcccatgc atctggtttt atttgctttc      540
tgttgggtat aaatatgcaag acctttgtt gctagggcaa ggctgcaacc acatgcgtgt     600
actgaactca tgatgtaact catcctttt gtttgctcac agaatcacta ctctactgca      660
cttccttttc atccgatccg caatctttt tttcttttac atgctttagt tttctctctt      720
tcttgattac aaacatgatt actggaactt tcttaggctg ccttcccctt ccttggatct     780
gctttagttt tcttttttgg gctaccgcgc gcggcttatt tgagtttatc acttgctgca    840
tatacataat atatatatac atgcatgcga tggcgttcat gttactcaac tacagatctg     900
tttctgttcg tgtgtttcag ttcagcgcgc agttaagcat agcaggacga ccacgacgat     960
gtatcacccg cagtgcgagc tcctgacgat ggcgcacgaa acgccggacc tggacgccgg    1020
ccagccgcac ctaaccgtct ccggcgtcgc cagcatcccg gcagagctga gcttccacct    1080
gctgcactcg ctcgacgccg cggcggcggt caatcccgtc acggcgccgc gcagtccac    1140
```

```
catcgactac ttcctcggcg gcgccgatcc ccaccagcag gccatgcagt acgagccgct    1200
gccgcccgcc gcgggcggcc accaccagta caccatggac atgttccgcg actactgcga    1260
cggccactac cccaccgccg agccgtacat ccgcgggaca atgactggag ccctcgtgtt    1320
cggggccacc gacgacgacg actcggccgc tgcctacatg cccgggggggc actttgagac    1380 ctccccgccg ccgccacgcg ccaccggccg cggcaggaag cggggcaggg cgctgggcgg    1440
cggcttccat gctgtgctgg ccaacggcgt cgagaagaag gagaagcagc gccggctgcg    1500
gctcaccgag aagtacaccg ccctcatgca cctcataccc aacgttacaa aggtcgtacc    1560
aaatcctcct cttatgttcg tccatcgttt caaattaagt taaaaaatta attcacggtt    1620
cttgttgttt attttttgcg cactgcagac tgatagggcg acggtgatct cggacgcgat    1680
cgagtacatc caggagctgg ggaggacggt ggaggagctg acgctgctgg tggagaagaa    1740
gcggcgccgg agggagctgc aggggacgt cgtggacgcg cgccggctg cggtggttgc    1800 tgccgccggt gaggcggaga gctcggaggg cgaggtggct cctccgccgc cggccgtgcc    1860
gcggcagccg atccggagca cgtacatcca gcggcggagc aaggacacgt ccgtggacgt    1920
gcggatcgtg gaggaggacg tgaacatcaa gctcaccaag cgccggcgcg acgggtgcct    1980
cgcagccgcg tcgcgcgcgc tggatgacct ccgccttgac ctcgtccacc tctccggcgg    2040
caagatcggt gactgtcaaa tctacatgtt caacaccaag gtacatacga atacgatacg    2100
tagccattga tcgatctgta attctgtagc ctgacgattc cgaggtttct ggtgctaaaa    2160
aatgcatctt ttttctcag atgacaatgc tttctgtctt tgttcaccgc agattcacaa    2220
ggggtcttca gtgtttgcga gtgcagtggc cggtaggctg atggaagtgg tggacgagta    2280
ctaggctacc atgcacttga atttctagct agctctacgt accgcgctgc tatgaatcta    2340
gctatagcgt ttcttggatg aaagactagt tagttgttac cttctatctt tgcttcaatt    2400
aaatccgctt gctcgttaca gactgagttt gtttctaaat gtcaaggttg ttttggtcaa    2460
attgaataaa ttggcacact ggcctgtgag gttattatat atatttatgt gtttattact    2520
ggtctattaa tttgtcttat tattaatgta ttgc                                2554

<210> SEQ ID NO 204
<211> LENGTH: 440
<212> TYPE: DNA
<213> ORGANISM: Zea mays

<400> SEQUENCE: 204
gttgcgcatg ttactgtgtt atgcaggtcc atgaagatgg ctgtacttga cacgttcctt      60
ttcacatccg agtctgtcaa tgaaggctac cctgtgacca gaaatctgat gcagtgcctg     120
atgcatgcct ccctgaagat cctgacagca aggttgcttg tgagacctgc accaagacta     180
acaacatggt catgatcctt ggtgagatca ctaccaaaga caacgttgac catgagaaga     240
ttgtcacgga tacctgccgt gggattggct ttgtgtccaa tgatgtaggg ctggatgcag     300
acaactgcaa ggtgcttgtc aacattgaac agcagtcacc tgacattgca caaggtgctc     360
atggtcactt cgccaagcgt cctggggagt tttttttataa ggaaggcttt attaattttta     420 agaacattac atcgaggtga                                                    440

<210> SEQ ID NO 205
<211> LENGTH: 6507
<212> TYPE: DNA
<213> ORGANISM: Zea mays
```

```
<400> SEQUENCE: 205
tttagaagta aaaggttttc ttcctctcaa ccaaaacaag taaaagcttt acttcagtca      60
ggatgcaaat gcaatggagt tacaagctag gcaagttcac aggttttact ataaacagaa     120
ataagttaga catttagtat aagaaacatg tacattacaa gaaactagct tcgctcggcg     180
caaacatctt catcatacac tgatacaatc gggctggctc ttctgcagtc tatcaattgg     240
ggccccaacg tatattgtcc cagaggaaag gcttcataca accaacttgt ggcaggctct     300
tcatgatcaa tcccacacag acgcagacgg cagcaatgga gaccaaggaa agcatcgcag     360
tcctattaga cagaaaccta tttgtccggg gatggaatgc aagctgctgg gcctgctgga     420
cacactgtct gcagctcaat gtttggttga tgcttagttg tttttctca acaccaaatg     480
tgatttgatc ggcaggcttc attcggctac catgctttcc gacagtatca attgtgctgg     540
ggatggtaac cgagacatga gctctggtca cccttctgtc aattttgtcc tgtaccattt     600
gaatatagga tatgttgcct ctctttgcag catattcctc aggagtgaag ccagtggcgt     660
cacgagcatt cttccacgct tgattccca actgagacat ttaggcagaa agaagccaga     720
cagcaaatgt ttcagtgctt gcacaaattc tcaaaagtaa agaaaatgt ttttaaggta     780
aatgaatttt tatcatacta cacctcatgc ggaactctga tgtgatatta tacccctac     840
acgatctatt caacaatcaa tgtaatacac aaaccaatgt tttgatggaa gtcctttctt     900
tttcttgata tgtacataat gcatttcaga tgaaaatatt tcaggtgcag acttaggttc     960
taacaataaa tggtggtctt agttttatt ttaactgttt tacactaaga atcggaaatc    1020
tgctactttg aaatttgaat gtagatgtgc ttttttttag ttaaagcagg ctacaacagg    1080
taagaacatg gcaatttaga gtagttacct gctgaggatc atcagttaaa gcatctaaaa    1140
caccaatagc atcactgatt gtggctgcaa tatgaagagg tgtgatattt gacagttcag    1200
tcatcgcagg agtgaacaag aactgaactg gagcaccatc tccaccgccc actggagcaa    1260
tatttgttgt ggtgtatctt aatagaaatt caactaaagg ctttgagcgt ttttgaccg    1320
cagtatgcaa tagattttct cccaaggcaa attcaattgg tgacaataca tcaatatcac    1380
cctggaacat ggtgttcaga agcttcctta gaacagcaca ccattcctga tcaactgcaa    1440
aggatagcag ccatctaaat cttgcaacag ggaagcggtc aggacaatat tgtcgctgct    1500
cagacgtagc tcgcacatgg ctcctttgaa gaagccatcc gatttcatgc aaaaaatgta    1560
atgctcgact gcgataaatc atcagatcat ctattctttt ggaggtttga tcaaatgaaa    1620
ctaaatccaa tccatgctcc aacatccgaa tctcagaaca tacatctttg tccgtgacaa    1680
caaagggaac agaaaggctg ctttgatcat agtcttcaat ctgaaaacgg agtcaagtct    1740
gtaatataca caaaaaatga ggatataaaa aatatacaaa cattgtacct ctatgaatcc    1800
tcttccactt gtacaaggaa aggaacaaga gaaggtcagg cattgagggc cttgctgcat    1860
agttgaatct tcaagtagca tttgtgtctc ttcttgaatt aaatattttt catcaaacac    1920
acaaagtaat ctataacaaa atcagaatgt gtcagttaaa agaactaaag aagtaagttt    1980
agaggagaca tttaaatgtg aaaaagata catactttgt ggttggctga actatattga    2040
aacctttcac agagaatttt actgacgaag aacaatcaac tgcaattgga gttacacaca    2100
gtctctgatg cttgtcacca attaccggtt gccagggaga tgcaaacata agactaccta    2160
acaaaaataa ggaaagaaat acaaatgaag ctgatcctcg aatatatgaa taactactcc    2220
aaataagatg aacggaccat tgcaactcag tgttaggcag tcctgtaccc tagcatacaa    2280
ccatcctgtt ctccagaatc catcattgga taagctaata agatttttcta tccatgaagc    2340
```

```
tgggtcatca ttaaactata atagaaaaga aaataacag taagcactt  gcttctgcat    2400 catatactat aaagaaaaca tatacagatc taaattcact gttaatgtag tgcaatacta   2460
cctcatccca catccaatta gggaggtgaa ggtaaatagt tagaataaca caaccaggtc   2520
taatataact ttccatatca gttggataat gcgacaacca gtttaggatc tgtaaattca   2580
aaccatttaa taaagaatt  agcattagcg tattaaaata tccacattga caaagttaat   2640
agaaaaatat gattccagtt tgtaacatga taactgacct gttcccgtag atctacagga   2700
aaatcttttg gctcttttcc aaagagtttg aacacaattt tatctgttcg gctctgcaaa   2760
tgttgtgcat aagagatatt aagtcggaat caaacatcag aaatacatct gggagaatct   2820
atctacaaat tctagagtaa cttccacaaa attacactaa gattggaaaa cctgagtaac   2880
tacacttcac atccacattc caggtctatc tcccactttg gatgattatt ctttccctaa   2940
gtggtggagc gaggtggttc gtttgacgcc aaagggaagg cgtaggggc  tgaactctct   3000 gatcatcctt gctgcctggg aaatttggaa gcaccgaaat aactgtgttt ttggtttcat   3060
atgttctagg cactccacat tccacgtcta tctcccgctc tggatgatta ttctttccct   3120
aagtggtgga gcaaggtggt tcgtttgacg ccaaagggaa ggcatagggg gctgaactct   3180
ctgatcattc ttgctgcctg ggaaatttgg aagcactgtg tgttttcgat aatggaagac   3240
cgtgtatatt tgatcttcta aggaagattg tagaagaatg caaaatgtgg tgcatggcta   3300
gagcttcaaa gctacaggag ttcctggttg ggtcgctaga tggtttagtt tgagttttct   3360
tgagggtgtt cttttgttg  gtcgtggttg aggactctcg tctgagttgt gggttttgtt   3420
gtgttccttt tgtaatcggt ctggccttgc cagacctctt gtttttctc  tccttaaatg   3480 aaatgacacg caaatctcct gtgttgttcg agaaaaaaaa aactacactt caaactactt   3540
tcacaaagct acacttttaa aaaccatttc cataatatta tacttctatt gtcaaatagt   3600
atcattagac tacacatttg tggttaattt gtatcgaaaa acaacagttt ttaagagcta   3660
aaatgtgtag ttttgtgata ttgaatggca ataattgtgt attttctgtg atttgtctgg   3720
acaatagaaa tgcaattcca tgaagttgct tctcaaaata tagctgagac agttttttag   3780
attggtttgg aaaaagtgta ttttgcgat  agtttgtcca agattggtgt agtttatgaa   3840
atttactaaa catttacctc ggcttcttca atgcatgaat cgttcaaatc aaagtcctgt   3900
actcgtcttt tcaccgcagg ctcttctgag aacacaagtt attcaaatca ttttatttat   3960 accttttgata tttgacatgc taaatagaat caagtaaacg ataaagtgct ttacctgcta   4020
atgattctct cctgacagga attgaccgta tggtttgctc atgcattata gagccatttg   4080
cagcattatt accatcattt gatgatattg aagttgcatt ctttagaaca tcttgatatg   4140
catgtgtgct agcaatagca gcaaggttct tcaaaaggtt aaccaaagaa ttaggatggt   4200
tgatttgctc agaagagcta ccagctgtca tccacacaag cgcacagtta gaattgctgt   4260
ctggattgca tgtcgtttga aatatttgta ttttaaattg gtaatcaaat tttgtataga   4320
acttacactc gagcccggaa agttgtttta acagaaggaa taaggtgcta cttagagact   4380
gatcttcatt catggaattc ccgttcacag caggttgcgg ttgaactttc cttctccttc   4440
cattatgttg tgccagacgt gatcggcagc tcttcttacc atcatcaaat tcgtgaagaa   4500
ggtgaaacct aaaatggcat acaaattatt tactttcttc agctgatgag caaatgaaag   4560
gaaacataaa aaatgctcgg tgtattaaaa tatgaatttc aagttttatg ctaaactcaa   4620
tatcatgata ggctgctaaa gttaagatgt atgtagaaga aagagcaatg tttggttttt   4680
```

| | |
|---|---|
| tttcttctgc tatgttgtac gatgcaaaat gttggcctac aaaaatatga catgtccaac | 4740 |
| agataactat tgcggaaata tgtatgcgat aatgaattttg tggtcgaaca agaagagatt | 4800 |
| gagcctataa ctatgatgtc ataggctagg ggtagcacca attaaagaaa aacttgtcca | 4860 |
| acaccggttg agatggttca gacacgtaga acgaagacct ctaaaggcac tagtgcctag | 4920 |
| tgggatccta aggggatagc aatgggaaca gagacaagag aagaccaaag ttgacataaa | 4980 |
| aagaaacagt aaaaagact tgaaggatg gaatatataa agtttgcttt agtcttaaat | 5040 |
| aagagtgcat gaaaacaac tatccaagtg gttgaacctt agacttgtgc tttcggttgg | 5100 |
| gtttcaactc tgagtctctg acctacacca acttatttat gaacggatcc tatcatggag | 5160 |
| caaaaaaaac taatgtgttc agcatttctc aaggttaacg atcagtaatt cgtttgtgtt | 5220 |
| gtgtgcctgt gacaccaagg taatgagcct ttttatctct tttatttccc cctttgggtt | 5280 |
| ttgtaccgga gaagtgtttc ttttctttc tccaatacag gtagggcaca ggactcttgc | 5340 |
| tggagaaaaa aaattcagca gctgtaatct cacaacgaaa ttggtgacca acctgctgca | 5400 |
| ctgctgacag aaccgatgct ctacattatt gatgcagacc actgttgtcc tggtatgcgc | 5460 |
| ttcacacacc ttgtgcctct tatggtagtc cctggcacca ctaagatcag cttggcagcc | 5520 |
| gtcaacctgg caagaaggag tggtgctcga attggcacct tcctgggtc tcgtctcctc | 5580 |
| agtgttccgc cctctctgaa cacacaccac gtgactgttg tctccatctg ctaccgcaga | 5640 |
| attgctgcac ccaccgctgc cgtcctcctc tggtgagagc cgccgcctct tgtcaacgac | 5700 |
| gacgccgaaa tcgatctccc cctgacctcg gctcagctcc ctgctgatgg actcggatgg | 5760 |
| cgcggcggcc gctggtgtgg ccaggaacag gttggcgtcc cacctccagt cgttcaaatc | 5820 |
| ccagtcgagg ctcctgttct tgttcccacc ggacattctc gccgcaccgg cttggtcacc | 5880 |
| gatctctttc cacaggaaac cggcttccat ttcctcggcc ttctctttcg agggaaattg | 5940 |
| accctgctgt tggcacgtat gacgagcatc caaagatcgc tggattcaat tacatccccg | 6000 |
| actacagccg aaacaaacac agggaattag atacgaacac caacgaac acaaagggac | 6060 |
| tgccaaccct gggttgggac ttgggacaaa atcctgaaac tactgaagag tacaagaacc | 6120 |
| aagaagtacc ttcgttcggc cccggcggct agaacgatac cgtggttggc aagcaacgcc | 6180 |
| cttgaacatg aaaggcgaga atgattgaa gaaatggaga tggaacagta gctcatggag | 6240 |
| agagccgagt caagtattgg gtaccgtggg ttaggaccgg ttgggggatgg ggctactact | 6300 |
| tttcctctca cggatcctgg aggctggagc ggcggaacag aggcggaagc cggaagggct | 6360 |
| cgcggtggaa cggggggcga agtatcctgg ggaggcagag ccctcccac cggcatattc | 6420 |
| acactcgaac caccaccgcc tctttttcat ctcccctgtc tcttgtctgg cgctcggaca | 6480 |
| gcgacgccac gaccaagggc cggttgg | 6507 |

<210> SEQ ID NO 206
<211> LENGTH: 6531
<212> TYPE: DNA
<213> ORGANISM: Zea mays

<400> SEQUENCE: 206

| | |
|---|---|
| ggttatcatt aaacgtttgg gagctgccct ttctttcctg agcagggtta tcattacttg | 60 |
| catataagct ataaggggg gaaacgacag caagaacatc atgagttata gcataaccat | 120 |
| catctatttg gtttctatgt tcgaagctac atatacatat taagattat agattataaa | 180 |
| aagttatctt aaggaccagc tccttgcatt tacatctggt ccttgctatt tgtaacattt | 240 |
| ctccgcttag gtataagcaa ttatgtatgc catcaaatag aggaacagag actagcacct | 300 |

```
ggattgctac acaggttgtg ccagctcgct ctgttcatat atgtcttagc agacgtatgc    360
aggatcccat accatcacct gctatgaaga ggctgccgag tgaagggcga cgagggacgc    420
ataggcgcca tccttgatgt tgatcaaggc atcgtgcttt cccttctcga tgataacccc    480
attcctcacg accgcaatca aatctgcatt ttgtattgtt gacagacggt gagcgacgat    540
cactgttgtc cggttcacca tcaccctgtc cagtgcgtcc tggacgatcc gctcggactc    600
agcatccagc gcactagtcg cttcgtccag aagcaggatc ctagggtcct tcacaattgc    660
acgggcgatc gccactcgct gcttctgccc tcctgacaac tgggctccac gctctccaac    720
cactgtgtca tatccctgca tttttcaggt agacacttcc ctcagcaacg gttttggtg     780 cttgattgat tgcatagaaa agccacatat aatattcctt gacatcagat gaaagaaact    840
aacctgcagc gccgaactga taaacttgtg agcatttgcc aattctgcag cagatatgat    900
ctcagattct gttgcttgtc catctttttcc ataggcaatg tttgccctta ttgtgtcatt    960
aaacaaagct ggttcttgac taaccaggcc catttgttgc cttaaccacc taagctggaa   1020
cttctgtatg tccacgccat ctagtagtat atggcctaca tctgggtcat agaacctctg   1080
gagcaatgaa attgccgttg atttgccact accactctct ccaacgagtg caacagtctg   1140
caaacaaata ctagagttgt tatgctcgtg ataataaaca ctgttgctca atacaggaat   1200
tatacattcc ctaaaaaaca ggatttatga attagaaatc acttgccttt ccagcatgaa   1260
ttgtcaagca aggtcccgg aatatctgaa catctggcct ggtaggatac ttgaagctaa    1320
catgctggaa tacgatgttt ccttgtagtg cctcaacagt taccctgca tcctcacttg     1380 ggtctatcct tgattttcga tctacaattg caaatataga agatgcagct gattttgctt   1440
tggaagaatc tgatgtaagg gtacttgatt gcgacactcc aattgccgcc attgcaagag   1500
ctaggaaaac ctgcgtatag aaggacaaat ttttagagct tttcattgga aagattcatg   1560
atactcactc caaatcatct ttaaaaaagg aaaacacaaa ccatgttgat ttgacttcac   1620
atttatgtag tcctttcttc cttaatatga aagccagata aggttaaatt tatcagtact   1680
accatagagt acttaccctg aaaactttag gaaaggttgt cttcctgtcc tcaacaagcc   1740
gagcaccagc ataaaagcta gctgcatata ccccaaaatag caagaaaaag gaaactccaa   1800
aaccgattcc acttataatc cctgtcctga ttcctgttct tagaggacct tcacatttct   1860
tcttgtacaa atccatgacc ttctcttcag ctgagaatga ggccactgtt cttatgctgc   1920
ctactgcatc attagccacc tggcttgcct cttcatacat catctgcatt cacaaataac   1980
tggatgaagt ctgatgcgat agacaataaa tttaaggaaa ggcagttcag tacaagagaa   2040
cagacctttg cgtctgcact gaaaccgtga ataaacttca tctggatcca tccatttagg   2100
ccaatgagtg gtattaaagc taagatgatg agggatagct cccagtttga cacaaatgca   2160
ataaccaaac cagcaactag tgtcgaagag ttttgtacaa ccaattgaag cgcatccccc   2220
acaaggcctc taacttttgc tgcatcagct gacaacttg cacctattgc tccacttgag    2280
ttttctgggt gatcaaacca ctcgacctcc atatttacca ccttctcaaa tgtcatcagt   2340
cggatccttc taatcaacct gcaccctgct atggagaaaa ggtacgaact gacagggagt   2400
gacaagaagt acactgcacc aaacaccaag aacatgaag cccagaactg tgaatccctc    2460
cttaggagat gtggaggctc atagaacgct tttatcacat ttgacaggag tatcgcaaag   2520
atcgggaaga taactccact gatgactgag gcaatggagc ctagtataag gaccgggatc   2580
tctgccttgt tgagagatgc aagccggctg agaggcactt cctgtggcat ctcatcacac   2640
```

```
agtttgttag atgaaccatc ctgaatgtca atcccatgag gcataccgaa tgggactgag   2700
aatgaatggt ggctactgtt atcacgggac gacctcctgc tagctgactt gtttattgat   2760
atttgtttgc ctggacgagc attggcatca accttcccat tgttctgctg gtttgcttcc   2820
tgtagcctta tcagttggct ataagctcct tctggatctc ttagaagctc actgtgtgga   2880
cctggtccaa aatgttaaat ggttaagcaa agatgcattg agcgatcaaa gactggcaaa   2940
tgatgttttt tgctattgat gtttcacaat gtaccttttt caaccagtgt tccctgatga   3000
ataacagcaa tggtatcagc atttcgaaca gtgctcagac ggtgtgcgac tatgactgtc   3060
gtcctgtttg tcatgaccct gtcgagagct tcctgcacaa tcctttcaga ctcggcatcc   3120
agagcacttg tagcttcatc caatagtagg attcttggat ctttcagaat agcccttgca   3180
atcgcaattc tttgcttctg cccaccagaa agctgtgtcc catgctcacc aacgaagta   3240 tcaaacccct gtgaaatatc agaaaagaa gagatctcaa tgcatgctgc ataattatcc   3300
aagccaatgg aaattgtatt tttcttatat atttgaataa gggcacaacg tctcctgttt   3360 cttttctaaaa aaaagagca aaaacaaaaa tctgaaccac tgagagaggt aaaccttgct   3420
gattgaacag cattctgacc tgaggcattt tatctatgaa tttggcagca ttggcaagct   3480
cagcagcagc tctgatttcc tgatccgtcg cgttgtcttt gccataagct atgttctcct   3540
ttatgctggc agcaaaaagg accggctcct ggctgacaag gccgatttta cttctgatcc   3600
acctcaactg gaactccttg agattcacac catctatcag aacatcgcca agctgagggt   3660
cataaaaccg ttcgatcagg ctgatgaccg tggatttacc gctcccgctc tggcctacca   3720
acgcgatcgt cgtgccacta ggtatggcga gggagaaacc cttgaatatc tgttcgttgg   3780
gccttgtcgg gtaggagaaa tagacatccc tgaactcgat gtcccctcga acgtcctcca   3840
gcttcctccc cgtggtgctg tacgcgtcga tttctggcgt tctgttgatc gtctcgaaca   3900
ttttgtgtgc ggcagcctgc ccacctgcaa acgccttcat gcttggagac gcctgaccta   3960
gagccctggt gaaatacgat aagagatgcc aggtatcagg taaagcatca aacgttaact   4020
gaaaaaaagc agtcaagata ttggagacag agtcacagac agagagtttg aggggcaagg   4080
gtgaggacag gcaaaagagc aaaatacatc ctcaatagct aaaaacaaat atattgtcaa   4140
cacaacagca ggcaaaagaa caaagtattt tgggttctgt tcagcagaga gataggagtt   4200
gttagttagg agcagtccaa tatactactc ctataacagt atagcttgag aaagaaggga   4260
cgggtccatg agtggcttcc taatagtgaa cgggtggaaa agtctgctaa gcaattttgc   4320
ggcggttttg ttttctgaaa ggccacctaa cgcgtccaaa tcatcataaa caggaagctt   4380
tatctgcctg caaccaccct ttgcagtaac aacttgtaag tacgcatgat ggacccgagt   4440
ggttgcatcc aaaaccgtta cctcgatcat gcgccagcta ccaaatatag tggtttcgga   4500
tattcccagg atcaccaaac aagaaaatga ctgaactaca gaacctactg ttgttactgt   4560
taagaagggg agccttgaac ttacagaaa ccagtgagga ctgcaaagat gacgttcatg   4620
accttggctc ccgtgtaccc cttctccagg atgagcttag cgccatacca aatccctagc   4680
gagtagccgc agaagaggag caccatgacc gtgcccattc caagcccagt ggcgaggccc   4740
tctcggacgc cggacttgta cgcgttcttc aaggacatgt tgtacttgtc caccgcccgt   4800
ttctcgccgg tgaaagacgc gacctgcagc agcaggagga ggtttcgtca gtcagtcatg   4860
gtcacacatg tgtgtactgt ttcgtttgtg tgctctcacc gttctgatgg aaccgatggt   4920
ctgctccacc accaccgacg attccgcgta ggccgcctgg cccagggacg ccatcttggt   4980
gacgacgttg gacatgaccg cgcccgccag gacgagcggc gggatggtcg ccatcatgac   5040
```

```
cagggtgagc agccagccct gcgcgaaggc gacgatgaag ccgccgaaga aggtcaccag    5100
cagctggacg aacttgccga ccttctcgcc catggcgtcc tggatgagca ccgtgtcgcc    5160
ggacatcctg cccacgacct cgccggtgct ggtgtacttg tcgaagaagg cgatctcctg    5220
cctgaggatc gtcttgaggt acaggttccg tatccgcgcc gcctgacgct cgccggtgat    5280
catccagcag gtgacctctg gtcggacggc gaacagttga gtgctcagtg ctcagtgtct    5340
ggccgcgtta cgcaagaggt ggaacttacg gacgaaggaa gcgacggcgg aggccatggc    5400
gaggtagacg aagtcgagcg agaccatgga caccggctg acgacgtcgt ggacgctgag    5460
cgcgccacca aaggcgtcga tgaggttgcc gaagagcacg tcatgaagg caaggcggc    5520 gccgttggcc acggccccga gcgcgcccag cagcatgagc gccacgtcgg cggagtccgc    5580
gaacgcgaac agcctgtgga acggcacccg cgtcgccgca gcgccggggg gctccccgc    5640 cccgcgcccc ttggcgccat tgcccgggct ccagccgag gggccggacg cggacgccgt    5700
gcctgccgcc ggctgcaggg catccgcctc ggcgggtctc caggactccg gcatggctgc    5760
cgccggcgct cacgaatccc cctcccccg cgcgagatcg ggcagtgctg gtcggcgcag    5820
aacgcgcggt gtgcctcggc tccgctcgcc cttgccttcg tatggttgtt gcctacctcc    5880
tagctcctgc ataccaccag cagcgcctca ctcgccacct gccacggccc aataattgta    5940
cacacattca gcagcggatc catctcagtg cctcacagct agaaagaagc tcgcagtagt    6000
agaaatccgg ggagcagagc agcacaagag caacagcaaa tctgaatcta taccgccgac    6060
gaggaattcc accagcgcaa gaagaccgat ttgggagata aggagggca ggtgggggat    6120 ggaggtaaga gtttggaaat ggatgcgagc ttggcgaaga agtggtgtgg ctggcctgga    6180
gaagggaaaa ccgagcaggg aaagagttgg cagctttcgc acttgcccgc cggatgcgga    6240
cgcagaggcc agcagtccag cacccgcacc gcaccgcacc accggggaaa gagagagaga    6300
gagaaaatgc aagcttgaga cggggaaaga gagagagagg agaacggcgc ctggtagtga    6360
ttaaaatcta gtaggagaca gcagtacggt ggtttcggta tccatggcgg gcgagcaagc    6420
atataaaaat gtgagaggct accagtacca ctaccatacc acgcgctact caccatggcg    6480
gcagtgtcac agggtgggat aaagcatccg tgctccgtct cccactcgcc g            6531
```

<210> SEQ ID NO 207
<211> LENGTH: 12500
<212> TYPE: DNA
<213> ORGANISM: Zea mays

<400> SEQUENCE: 207

```
atctcctagg aaagagaaac aacgaagact cgaaacgagt acaccaacct ttctttctct     60
cctctcgctt ctgcggcgaa ttttcttgtc ccgtgcgcc gccgtgtct acctgcgcc    120 accgcccctt ccaacgcctg ccgtgaagac aaaaggtgag cttttttatcc cctcttccag    180 tttcagtact tcccccaaagt tcttcgaagg cgtttatcgg gtgccgggga acgcctcacc    240
gtccgcatga agccccagcg tgctgcggtc cgtcacaacc gccgttgcga ccttttgtgc    300
gccgtggttt ccccacggcg gcagcaagtg gagagggaga gcctgtggct gcgtcgattg    360
cgacggatgt gagtactgta cgggcctagg ggaaggttg tgtatgatta gtgcttattt    420
ccaaaggttt ggacctgagt caaaagtgct gtttcaattg cttgtgatct gggatgtgat    480
tgctggtagg tacctctcgt caagtgcaaa gaaggtctac cttaattctc agtctctatc    540
tccgattcat ctgtcggagc tagttctttg atcataagaa tacatcgaaa gtgaagcttg    600
```

```
ttttagttgt ccttacctaa caacgacgac aacaacaaag ccttttccca aataaattgg      660
ggaaggctcg aattaaaaac ccaaccgggc ggtatgtgat aactgttttc cacattccaa      720
gtcttctttt aatgtctctt cccatgtcaa aaacttcggt cttctctct ctattcccat      780
tgctatcgtg ccttaggatc ccattacaca ttggtgctta tgaaggtctc cgttggacat      840
gtccgaacta tatcaaccaa tgttgaacaa gttttttctt caatttatgt catacctagc     900
ctattacgta tatcatcatt tcggactcaa cccttttgtat ggccataaat cccacgcaac     960
acacattttc gtaacactta ttctggctaa acgtgtcctt gcccacaatt tttatatcta     1020
ttctttgttt aaagtagcta aggaagtatt tttttttgtta atcaatcagt tctttgtttt     1080
tgtttccttc tgtttgttct gttatatact catattttac agcttcttcc tgtcttgtaa     1140
acgtggtagg cattgcgatc cgaaacaaac ccaaaggtca tcgttgtatt actgtgctag     1200
taaaggccct ctaaggccct tctttttcct ttttaatata acgatacgca gttctcctgc     1260
gctttcgaga aaaaaatgag tgatcgatac acaatttcta ctaggtccag tggaggatta     1320
ggccatgagc gagcgattat atatataatg ttttttctaat aatgatggta cacacggcgc     1380
aaccttcata gaatgccagg ggtgcgggat ggggttcga acccccgctg gctcgaccag     1440
gccataggcc tatctgcatt gaacctacat tttggtgcgg aaacctttt tgcttgtaat      1500
tagtatgagc attttttgt ttaaagaaaa tcctaagaaa aagcagggta tgatttagct      1560
aactaatact gaatgcttgg ttggtatggc ttatagtggc tcttgcttgt ttaattagtg     1620
ttttctatgt aactttgtaa taggtatatt gttcttttg tgcatcctta aatatctagt      1680
gggttctaga tgtctgattt agtaggcgcc gttcgatctc atggttttga tgtttttta     1740
gtcgtcgagt aggtaccgtt tcatggagtc taatcaatgt ccacccaaaa tctttggcaa     1800
ttacttagcg atagtctaat caatgtccgc ccaaaatctt cgacaattac tttagtgata     1860
taaaatcaaa gtgttccttt gcatgcaacc taggtccccg acgtgaattg tttctgctga     1920
tgtactgcat gcatgcatac atgcataact aatacgtggc aagaacgcgg ccatgcgagc     1980
aactttcggc gcgttatttta ccttccacct ccctcctaga gttccttggt atctgtaaaa     2040
cgcctctgtg tgccttagaa aagattatgg agggagtatt ccatagcgag atttatgctt     2100
tggatcatga caagaggtga tgagcgtcat ctagtgcctt gttttgcatt aagcttcatt     2160
actcagaagt tagaacatat ggtattggat taatgttaat tgctatatat ttaattctaa     2220
ccatggtaag tttgcactta aggcattgca aaattcttca atgatctagg atttattaca     2280
cctaaaaata atgacatgtt ggactttcta accatgacta gtttggaatc tttgattttg     2340
tcattacttt tataaaaatt gcagagagtc gttttctagt tcttttctat attttaatgc     2400
gagtgatctt tgctagtttt ttggttctag tgcctgcttg acatcgaagt gatttcttag     2460
gtcttctccc ttctgttgct agtgcttcct gatatctagc aacatcaaca acgacgtctt     2520
ttagccccaa gcaagttggg gtagactaga gttaaaaacc caacagaacc cttcccttcc     2580
tgtgcacttc ctattcaatg ctaaatcttt agatataccc tatcctttca agtctctttt     2640
tactgtctttt tcccatgtca acgttggtct tcctcttcat ctcttctcat tgttatcgtg     2700
tcttaggatc ccactacgca cttaagcctc tggaggtctt ggttggacat ctccaaacca     2760
tctcaaccga tattggacaa acaattgatg ctacctgttg gtcactcgtt ctcaattgct     2820
atacacaata aaaaacaagg caacacaata ttaaaagaga caatcaacct tcgtcttcaa     2880
gcataattcc ttcgggataa ctccttcgaa gacgaagatt aaaactttac tgagtgaatc     2940
gtgatttatt attacaagta agtgaacata taaaatatac ttaagtttaa acatgacaac     3000
```

```
ttgtttata  tatcaataac  atgtttcttc  tccttcatac  ataaagttta  cgaacatacc  3060
gtcggctcta  ggaaatgttt  tagagcgaaa  gtgaagtgag  gagaaggtta  cactcaacaa  3120
ttgcttggcc  ctccaaaaag  gtacttcatg  cagtgcactg  ttcatctatt  tatagggaat  3180
catacaactt  cgtacaatat  tacatttatg  ccctcaaaga  ttacacatag  ggtttataaa  3240
taatacaagg  acgacattgt  cttttgcctt  cagcgtttag  gatgacacct  tctccttgca  3300
tcatcttctt  gtgttgttat  gacgaagcta  ccttcgttac  ccttccaccg  ttccgtatcg  3360
aagctattct  agtttcgaag  ctcctgtaat  acttggcaat  atgctgatag  caaatgatta  3420
gccgtgtttt  tgaggacctt  cggaagatga  aggcccccaa  cactaccttt  agcctatcac  3480
gcatatcatc  attctggaat  ctggactcga  tcacttcttg  tatggccaca  aatctaacgc  3540
aacatacgta  tttctgcaac  acttatctgc  tgatggaagt  aatcttagac  aaagtggaat  3600
cagattttac  agattcttga  tagttgatat  taaaccgtta  aacatttatc  agctgcaggt  3660
ccatgaaact  ttcttctcgt  gttatttgga  aattctttgt  tgatattgtg  ggaaaccctg  3720
accctaacaa  ggggttgggt  gatgtatgtc  atgtacgggc  gctcatacgc  caggcagcgt  3780
cgcgcccgtg  acaggcgctg  cgcccaggag  cacgcagatc  gccaggagcg  cgatctagga  3840
gggcgcgtag  atcgccagga  tctgggagat  ccgcaggagc  atatggaaag  tagtggctag  3900
gaaggaaaat  cggaaaatgg  aaagtagaag  gaaagtagga  attgattagt  attactatgt  3960
ttaagcttgc  ctaaaataaa  ggagcgattg  gctctaggac  agcaggccaa  tggccttata  4020
tgcggcacaa  ggagagagga  ataaaaccag  aaaagaagtt  atctcttctc  cacctctctc  4080
taccaactaa  gcctacggct  gtgggggata  accacgccgg  agaagacgac  gaaccgcggc  4140
tacgaccttc  gtagccgagg  gcccctgct  ctagacgccc  aggcccttga  caacctggta  4200
tcacgagtca  ggcgatcttc  gtcctctcga  tcccacacct  ctgatcagtc  cccgtcgtc  4260
acccaaccac  cacccagccc  tccaccctca  ccgccgtcgg  cctcctccat  tatgagcacc  4320
aaaaccatcg  acgatctggc  tgcgatgacc  gagaagctca  cgggcacgat  ctctgtcctc  4380
caaaatgacg  tcgagtcgtt  gaagaaggac  aaggcgcctt  cctcctcgcc  atccggcagc  4440
ggcggccacg  acggccagca  ccacatcgat  cgaccgccga  ggttccaaaa  gatcgacttc  4500
ccgcgttttg  acggcaagtc  ggaccccatg  ctcttcgtca  accgctgcga  gtcctacttt  4560
catcagcaac  ggatcatgga  ggagaaggtt  tggatggctt  cttaccacct  cgagggcgtg  4620
gcccagtcgt  ggtacctcca  gctatagacg  gatgagggga  cccgcgctg  gcaccgcttc  4680
aaggacatcc  ttcagttgcg  cttcggacct  cccctacact  cggcaccgcc  gttcgaactc  4740
gctgagtgta  ggcggacggg  caccgtggag  gagtaccaga  accgcttcca  ggagctacta  4800
ccacgcgccg  gaccactgga  ggaacgccaa  cacgtgcaac  tcttcacggg  cgggctgctg  4860
ccgccgctca  gccatgcgat  gcgcatccac  aaccccccagt  cgctcgcggc  agctatgagc  4920
ctcgcacggc  aagtggagct  gatggaactc  gacagggccc  cagcgccagc  ccagaccagg  4980
ccagtcgcgc  gcggcatcct  gcctcctcct  ccgccgcgac  cggcgcctat  ggcgcttccg  5040
gcgccccacg  ttcctttgac  gctccctgcg  ccaccggcgg  gcgcgactcc  gggccgtggc  5100
gagggcagaa  ggctcagcac  tgaggagatg  gccaaacgcc  gtcgcctcgg  attatgtttc  5160
aattgcaatg  acaagtattc  tagggtcac  aacaggttct  gcaagcgcat  cttcttcgtc  5220
gaaggcgtcg  agatcatgga  cgaagacggc  accgaccacc  ccgacggccc  cgacgctgag  5280
gcactgtgct  tctcgttgca  ggccatctcg  ggctgctccg  tggccgacac  catgcaggtg  5340
```

```
gccgtcatgc tagggggccac cccgctcgtc gccctcctcg actcgggcag cacacacaat   5400
ttcatatccg aggcagcggc gcggcgttcc ggccttcccc agcaacagcg cctgcgccta   5460
tcgaccatgg tggccaacgg caagcgcatc acttgcgtgg gcgtcatccg caacgcgccc   5520
ctcaccgtca gcggcgacgc attcccggcc gatctcttcg tcatgccgtt ggccgggtac   5580
gacgtcgtcc tcggcactcg ctggctaggc gctctggggc ccatcgtgtg ggatctcgcg   5640
tgacggcgca tgtcgttcca gcaccaggac cgtacagtct gctggaccgg cgtgcccacg   5700
tcctcggctc cggtgctggg cgccaccacc gcggccgagc ctcttctgga caccttcgcg   5760
accgtcttcg cagagccggc cgatctgccc ccgtcgcgcg cccatgacca ccacatcatt   5820
ctcaagcagg gcgcgcagtc ggtggaggtc cggccctacc ggtacccggc ggcacacaaa   5880
gacgagctgg aaggccagtg cgccgccatg atcgcgcagg ggatcgtccg tcgcagcgat   5940
tcaccgtttt cgtcgtcggt cctcctcgtg aaggagcccg acggatcgtg gcggttctgc   6000
gtcgactacc gcgcgctaaa cgcggtcacc atcaaggacg ccttcccgat cccggtggtc   6060
gacgagctgc tggacgagct tcatggtgcc cagttcttct ccaagctgga cctgcgttcc   6120
gggtaccatc aggtgcgcat gacgcccgga ggacatgcac aaaacgacat ttcatacaca   6180
cgacggcctg tacgagttcc tggtgatggc gttcgggctt tgcaacgcac cggcgacatt   6240
ccaggcgctc atgaacgatg tactccgtcc cttctagcgt cggtttgtcc ttgttttctt   6300
tgatgatatc ttgatatata gcaagaattg ggaggagcac ctgcaccacc tcaggatggt   6360
cctcgaggaa ctgcaacgcc accaactctt cgtcaagcgc tccaaatgcg ccttcggagc   6420
cccgtccgtc gcctacctcg gtcatgtgat ctcggcggtg ggcgtggcca tggacccggc   6480
gaaggtgcag gccatcttcg actggccggt gccgcgctcg gctcgggcgg tgcgcgggtt   6540
tcttggcctg gcgggctact accgcaagtt tgtgcccaac tacgacacgg tcgccgcacc   6600
gctcacagcc ctcctcacga aagacggctt cgcctaggat gacaaggcag cggcggcttt   6660
cggcgccctc aaggccgccg tcacctcagc accggtcctc tccatgccgg acttcacaaa   6720
gaccttcgtg gttgagtgtg atgcgtcgtc acacggtttt ggcgccgtgc tcacccaaga   6780
gggacacccg gtggcattct tcagccgccc catcgctcct cgtcaccggg cgttggcagc   6840
ctacgagcgc gagctcatcg acttagtcta ggcggtccgg cactggcggc cgtatctctg   6900
ggggcggtgc ttcgtcgtca agacggacca ctatagcctc aaatacctcc tcgaccagcg   6960
cctatccacg atcacgcaac accattgggt cgggaagttg ttgggctttg ctttcactgt   7020
ggagtacagg tcaggtgcca tgaacgtcgt tgcggatgct ctttcccgcc gcgacacgaa   7080
ggagagcgtg ctgctggcgc tctccgcgcc ccgcttcgac ttcatcgcgc gccttcgtca   7140
ggcccaggcc atggacccgg ctctagcagc catccatgaa ggagtcggcg tcggcacccg   7200
cgatgcaccg tgggtggtgg ctgacggcat ggtcacctac gacgggcgcc tgtacattcc   7260
cccggcgtcg cccctgctgc aggagatcgt ggccgccgtg catgacgatg gcatgagggg   7320
agtccaccac acccttcacc gcctgcgccg ggacttccac ttccccaaca tgagacgcct   7380
ggtgcaggat ttcgtgcggg tgtgtacgac gtgccagcgg ttcaagtcgg aacatctaca   7440
tccagctggc ttgctgcagc cgctgccggt gccctcggcg gtctgggcgg acattgcgac   7500
ggaattcgtc gaagcgctac cccaggtgca cggcaagacg gtcatcctct tcgtcgtcga   7560
ccgcttcagc aaatactgcc atttcatccc cctagcgcac ccgtacacgg cggagtctgt   7620
ggcacaggct ttcttcaccg acatcgtccg cctccacggg ataccgcagt ccatcgtctc   7680
cgatcgcgac ccgttgttca cctcgtcgtt ctggagcgag ctgatgcgcc tcatgggcac   7740
```

```
caagctcctc atgtcgtcgg cgttccaccc gcagacggat ggccagacgg aggcggccaa   7800
ccatgtcatc gtcatgtacc tgcgctgcct cacgggggat cgtcctcgac attggcttcg   7860
ccggctcccc tgggcggagt acgtctacaa cacggcctac cagtcgtccc tccgcgacac   7920
ctcgttccgg gtggtctacg gtcgtgatcc gccctccatc cgctcctacg agcccgacga   7980
cacaagggtg gcggcggtgg cacaagaaat ggaagcgcgg gaagcctttc tggctgacgt   8040
tcgcttccgt ctcgagcagg ctcaggcgat ccaaaagctg cagtacgata agcaccaccg   8100
ggaggtcaca tatgaggttg gggactgggc cttccttcgc cttcgccaac gtgtggcagc   8160
gtccctgccg cgaaccatca ctgggaagct caagcctcgc tacgtgggac cctaccgcgt   8220
caccgagctc atcaatgacg tggctgttcg tctagaattg ccgtcaggcg cgcgcatgca   8280
cgacgtgttt catgtcggcg tgctccggaa gtacgtgggc tcgccaccca ccacaccgcc   8340
ggctctgccg cctctgctca atggtgcggt agtgcctgag cccgcaagaa tcgcggggc   8400 tcgcttgtcg cgtggcgtgc ggcaagtcct cgttcactgg agcggcgaac cagcttcatc   8460
agccacctgg gaggagttcg acgacttccg cgcccaattc ccagccttcc agctcgagga   8520
caagctggcc ttcgacgagg gagagatgtc atgtacgggc gctcgtacgc caggcagcgt   8580
cgcgcccgtg acaggcgccg ccctcaggag cgcgcagatc gccaggagcg cgatctagga   8640
gggcgcacag gtcgccagga tctgggatat ccacaggagc atatggaaag tagtggctag   8700
gaaggaaaat aggaaaatgg aaagtagaag gaaggaaagt aggaattgat tagtgattga   8760
ttagtattac tatgtttaag cttgcctaaa ataaaggagc gattggctcc aggacagcag   8820
gccaatggcc ttatatgcgg cacagggaga ggaataaaac cagaaaagaa gttatctctt   8880
ctccacctct ctctaccaac taagcctacg gctgtggagg ataaccacgc cggagaagac   8940
gacgaaccgc ggctacgacc ttcgtagccg agggcccccg tgctccagac gcccaggccc   9000
ttgacaatgt attaatagac tgagttagtt gggtctggcc cattacatag gggtgagaag   9060
gtaaatacat ggggtaaacc ccaaacccta aagggaact ctaacagata ttacttattc   9120
aaaatacatt actaattaca ttttgttgca atctttgttt attattttgg tattcaattt   9180
tttgagttat ggtcatgttt aggaagttga atatgtctgt acccggttac catgtctacc   9240
atagggaaac aatcatttgt aatttgaaca aatcctggta gtaggcagtg ctttgtttgt   9300
ttacacatta tctttctcca ttcagttact tgcagttttt agcctattt tttggctttt   9360 ttttagttttt tcctgcataa tgcttataag ataaagtgt tttatttctc aggtcttggt   9420
taagtttgaa gatgtcgtgc ttggcatgct gtggcggcga agatactcaa agaacacctg   9480
ataatggagg tccatacct ggtggctacc caccaagtaa tgttcctcta aattatacta   9540
cctctgttct cgaatatttc tcatccgcta gtttattttt gaactaaacc gcgacaaata   9600 aaaagaacg gagggagtat atgtaactta gcattttcta atactattat cgatattcat   9660
atatcagtct cataatccaa actattagta gctgacttta aaattgacct aaattatgtc   9720
aaccttcagg ggatgatgct tatcgcacag ctgatccaac tccgaggggt gctcaacctt   9780
tgaaaatgca gccaatcact gtccccacta ttcctgtaga agaaattagg gaggtcacag   9840
tggcttttgg tgatgaagct ttgattggtg agggtctttt tggcagagta tattttggtg   9900
tactaaaaaa tggtaggagt gcagcgataa aaaagttaga ttcaagcaag cagccagagc   9960
aagagttttt ggcacaggtg tgcattgatt ttgacaatga attgtgcatc tttgctagtc  10020
tttcttctat aaaatatgtc tctacacctg caggtatcca tggtgtcaag gcttaagcat  10080
```

```
ggcaatgtcg tagagttgct tggttactgt gttgatggaa acacccgcat ccttgcatat   10140
gaatttgcta ctatgggttc tcttcacgat atgcttcatg gtattactct gtttacttct   10200
aaaatctagt gttctaataa cattgaaata ttttattctc tttagcttct ttctagatag   10260
ctgatgagtt tgaatttgaa ctccacagga cgcaaaggtg tgaaaggagc tcagcctggt   10320
ccagtcctgt cctggacaca acgagtgaag attgctgttg gagcagcaaa aggccttgag   10380
tatcttcatg agaaagcgca gcctcatatt atacacaggg acatcaagtc cagtaatgtt   10440
cttctatttg atgacgacgt atctaaaata gctgattttg atttgtcaaa ccaagctccg   10500
gatatggcag ctcgacttca ttcgaccaga gttcttggaa catttggcta tcatgcacct   10560
gagtatgtgc agttttcctt tcagtttcac tgacgcctgt atcctttgtt tgcttatatt   10620
tgaaaacttt ggtgtaggta tgcaatgact ggacaactta gctctaagag tgacgtttac   10680
agttttggag ttgttcttct ggagctcctg actggaagaa agcctgtgga tcatacatta   10740
ccaagaggac agcaaagtct tgtgacatgg gtaaacattt atattagcta ttatatgtta   10800
tagttctgtt agaggttatc ttgtatttgt gcaatactcc ctccggtgtc ctattaattg   10860
tcgttttgga caaggttcga gtcaaactta taaaattctg acaacaatta actattttgt   10920
tatttagttt tgaaacctaa tatttaaatg caccgatgtg tcttaaaaag tagttttata   10980
aaagtataaa tgtattaagg tagtgtttgg ttccagagcc tagttgaatg aacgactct    11040
gttctagatt atgaggattt ctgtgtttgg tagttagaac agagccgctc tattttttgt   11100
ttggttctac agtgaagtag aatggagcgg ctccatcctg tgtttggtta caaagtgtag   11160
cagatcccta tggtattgaa ttatataaca agttaagaaa acttactgat gctatttat    11220
tatattaatt gtatatacaa acttacatat gctatacgaa ttaattaagc ttctacatca   11280
taactttata tacgaacatg catatactat atatatgaat accttaaagt ggctgcatac   11340
aagtcactcc acgaagtacg tacgagattt gctaatgccc gaagtaatgc aacgaagcag   11400
ctttgacgac gaaggaagag gacaggcgag cgcgggcgta cgcggcgcac acatccggtt   11460
gttttctggg agcgcacaca tgcatgatat tgagggaata ttcctatact agaacgactc   11520
cgttctattt ggatccaaac caaacatcca cattactgga acggagcggt tctatcctac   11580
caaactctag aaccaaacac tacctaaaag cttatttgta ttttaacaaa aaaacattgg   11640
tcaaaactat attttggaga ccgtgtcgtt gtcctaaaca acaattaaca ggacaccgga   11700
gggagtatat tgcattcttt taaaaaatac tcatgtaggc tttgtgctgt ttgacgaatc   11760
aagataatgc ctattttaat gcctgcaggc aactccacgg ctttgtgaag ataaagttag   11820
gcaatgcgtt gattcaagac ttggagtaga atatcctcct aaatccgttg caaaggtatg   11880
ataagttatt taggctctag ttgttgcgat ctttagattt tttcttagtg atatgttcct   11940
tcctcaaagg ccaccaaaag gagatacatg cttcatataa aatcatagac attaacattg   12000
ttagagcatc tccaacattg tcttaaactg gtgcctcaaa tctaaatata gagctccacg   12060
cagaaaaaac tattccaaca atgccttatt ttataaaatc ttggtaaaaa aattatagag   12120
caccctctca agtgcctcaa atatactaca ccgtagtgag ctgccctata atctagattt   12180
ggagatttac tgttagagca gaatatttta ttggtgccct aaattatata aaatatactc   12240
attttttaaat tatagggcat tttataggtc acgttgttgg agatgctctt atacttacat   12300
tatgcaaacc tgatattaaa ttatcagtaa cttataccat ttcatttatt gttgcttgtc   12360
gtcagttgat gttaaatgtt aatactccct gtgttccaaa atgtaagaca tagtaaaact   12420
atgtatctag acaacatata tttagatgca aatacaataa agccttttag tttcaagcaa   12480
```
cttgggtagg ctagagttga                                                  12500

<210> SEQ ID NO 208
<211> LENGTH: 3507
<212> TYPE: DNA
<213> ORGANISM: Zea mays

<400> SEQUENCE: 208

| | | | | | |
|---|---|---|---|---|---|
| ttagtcgtat | tcaaaatcag | gatcaaattg | ttttcttcga | ttagatgtta | tcttctttga | 60 |
| cttccgtttc | cgttttttgg | gacttactac | atcttcagga | tctcccacta | atgattctgg | 120 |
| caaaacctca | gtatctatat | taaaattggc | cggaagttca | tcttcttggt | aaatttcttc | 180 |
| aacttccgcc | tcaaaccatt | cacccttgtt | gtgtaactgt | tcacgaggat | taactttgta | 240 |
| cactacccat | gtggcttcca | gctttataga | tggatatgtt | atgtagtaca | cctggtcaac | 300 |
| ttggtgagca | agaacaaatt | tgctacatgc | acttgttttg | agctcatgtt | tgacttctac | 360 |
| catgccaaat | tggttttcta | cagtcccttg | attgggatca | aaccaatcac | atttgaaaaa | 420 |
| caccaccttta | agattttgc | tcccagcgaa | gtcgtactcg | agtatgtcat | taataactcc | 480 |
| ataataattc | atctctcttc | cacgatcatc | gactgccctg | catacaactc | cagtattttt | 540 |
| tgtcgccgca | aatggacgag | tacattcaaa | tttggtcgaa | cgaaaacgaa | acccttaat | 600 |
| gtcgtaacga | ccgtagcttc | tgacttttac | gattgcgtaa | gacatctgaa | gcaagtcctc | 660 |
| gtctaaattt | ggaattttgt | cacactgcca | atcagatggt | gaaattagat | ttctaaaaaa | 720 |
| atatataaag | tagaacaaga | gtgttaggtt | atttacataa | gctcgcaacc | aattaatgaa | 780 |
| attgggcttc | ccatgtcttc | ctcgaagtgc | gttttcatac | tgcctcgagg | acaatttctc | 840 |
| attaagttgc | gattggaatt | ctctgttaca | acaagtaaac | aaatgaggtg | cggaacacga | 900 |
| ttactatata | gatacacaaa | tgacaaatta | aatttcatct | tacttgaaat | atgggggtcat | 960 |
| ctcatccata | ttttcataca | tatagagcaa | agcgtccaac | ttttcttcgc | actcaggatg | 1020 |
| atattccgtg | gatgctccaa | cagtcttgcc | ctcaatctca | aaaatttgga | gattgctgcg | 1080 |
| agtccgtact | ttggcatcat | gatacctcaa | tgtaggggca | ttgatattgt | gctcgtctgc | 1140 |
| aaagtataca | ctcgtgaagg | ttgctacctc | tttatatttg | aattcttcag | ctatacaccc | 1200 |
| ttcaactctt | cctttgttac | caaccattga | actaagcttc | tttaaagccc | tttcaatatg | 1260 |
| gtacatccac | ctgtattgca | caggtccacc | aaccttagct | tcatatggaa | ggtggacaag | 1320 |
| tagatgttgc | attggattga | agaatcctgg | ggggaatatt | ttttccaact | tgcatataag | 1380 |
| gacaggaatt | tctgtctcca | acttctccat | cacctctttc | tttatttctt | tagcacaaag | 1440 |
| ttgcctataa | aagtagctta | actcagctaa | cgccttccag | atactgactt | tcaagtaccc | 1500 |
| acggaacatt | ataggggagga | gcctttccat | cattatatga | taatcatggc | ttttcaatcc | 1560 |
| agttattttc | tttgtcttca | agttcacagc | tctcctaaac | ccagccgcat | aaccatctgg | 1620 |
| gaatttcaat | tttttcaacc | attccattac | ttcattttttc | tgtttaggtt | ttagacaaaa | 1680 |
| ttgagcacgt | ggcttttttc | catttttcgtc | gagttcctgg | gttggtcggt | tacaaagttt | 1740 |
| tgctaagtcc | ttcctggcct | ttatattgtc | ttttgttttg | tcgcctagat | tcatgcaagt | 1800 |
| acttagaatg | ctttcaccaa | cattacgttc | ctgatgcatg | acgtcaatgt | tatgcatcag | 1860 |
| aatcaatgcc | ttaacataag | ggagttccca | taaaccacat | ttatgtgtcc | agttatgctc | 1920 |
| ggttccaaaa | cctatgtatc | catcaccact | ttcattctct | ttcaaattat | taagcatagc | 1980 |
| ctcaatctct | attccgctca | gacgtctggg | cggtcccttt | gtcacgatag | tgcccttctt | 2040 |

```
aaaggtgtta acctcgaacc tatacgggtg tttttggggc aagaagcatc tgtggcagtc    2100
aaagtaacag atcttccctc caaactctag gcggaaacaa tctgtatcct tgccacatat    2160
tgggcatgtc agagttccat ggcaactcca tccagcaaat aaactgtatg ccatgaaatc    2220
atgaatggac cacaaatacg caactcgaag tgtgaatctc tcattttgt agcaatcgta    2280 tgcttcaact cctttccata acttttgag atcatcaatc aagggttgca tcatcacatt    2340
caacccttta ccaggatggt ctggaccagg aataattagg gaaagaaaca tgtaatcata    2400
tttcatgcac agatgaggtg gaaggttgta tggaataaca aatacaggcc aacaagaata    2460
tgatgccgcg tttgtattga aaggtgtgaa tccatctgtc gccaacccaa ttcgaatgtt    2520
tctcgcttca ctagcaaatt ctggatcaaa gtcatctaga gccttccacg catcactgtc    2580
agacgggtgc gtcatcacat gagtgtcctc ccgttcacgt tctttatgcc atctcatgtg    2640
cctagctgtg ttcctcgaaa gaaacaaacg cttaacacga ggtgcaagag gcatgtaacg    2700
aagttgcttt tgggctaccg ttgatgtgac catttcacca tcatcatttt aacctctac    2760 atatctcgac ttgccacact ttagacactt actatcattc tcatgatcct tccagaacag    2820
catacaatta tctggacata catcaatttt ctgatagtcc ataccctagac cagagagcag    2880 tttcctgcac tgatacacgt cttcggcat cttgtgattt ggtggaaaca cttcgctgat    2940
taagttcaag agctcgttat aacaattgtt cgagaacacg aacttggact tgatagccat    3000
aagtcgagtc acgaaagcga ggactgaaac tgttgtgtgt tcgtgcaaag gctcttctgc    3060
agccttaagg aggtcgaaga acttttttaac ctctggagga ggcggctcct catgatttgg    3120
tggaaactca aaatcaggat cctcccttaa atcttcaagc atctcgtcca ttctatcgca    3180
ctccacgtcg tcagtgttgt tggcttccgg cgaattttca cggggaaagt cctcgccgtg    3240
atacacccag acttcatagt caggcatgta gccatattg caaaggtgtc ccgacagagt    3300
tctcttgtct tgacatctac aaatccgaca catactacat ggacaacgca catccgtgcc    3360
ggttcttgat atagcaaaag cacgatcaat aaaatcctct gtctttctta tccaatccac    3420
cgagggatca ttcatacgcc aaccttcata catccatcga cggtcctcac ccaccatatt    3480
tgatgctaaa atagtaaaac acatcat                                        3507

<210> SEQ ID NO 209
<211> LENGTH: 2955
<212> TYPE: DNA
<213> ORGANISM: Zea mays

<400> SEQUENCE: 209
tcagtaagaa acctctgaac caagatcgtc tactaacgca gcagaaaatg ttggaaccag     60
atcagctccg ttgatgactg tagtgataaa atgcactcct gactctgcca gtttccatgt    120
catacatgca gctgcagaac aaaacatttt ctaagaaaat atatactcct taatatttct    180
acatagttaa atggaattta agcttatcaa agattctagt atgatagaaa cattgaactt    240
aggttgcaaa acgtataaca gttccaatca taatatcagc taaggactta actactgtgt    300 actaacatttt ggattttatg aatagagttc cagaaccaat cacaagttca caagcagtat    360
gtactatcta ctataccaac ctgccccctgt gagtataaaa acataagaca agcaagtata    420
tatggtaatg aaaagagaga gaaaatgcca tgcacacatc gttttcatgg tttgattgag    480
aaattaaggt tctaaaagag aaaaaaaagc atagcataga aacctggagc aaatgccaga    540
caagtagtag aggcaaactc cttctgttcc ctcagaacgt atgtcaacag agcagctgta    600
ccacctccca gtgaatgtcc aacaacctaa atagatttgc taattgccat gaacacccat    660
```

```
caattgcaac actttgaaag aaacatgtaa acatagttat gatgcatcat aagtcataaa    720
aaggttatgc tgtagcaatg ctcatactct agcatcaaag agaaagaaaa tggctatgaa    780
ataactcaaa cctttatttt gaagtctggg tacatctgca atgcttgtgc cagacaaggc    840
cctgagagct ttgcaatcca cctagcagcg gcaaccatcc caatgggtct ccgcagcggc    900
aaccatccca atgggtctcc gagctgtagc aatgctcgta cttctccgca cgaccgctgg    960
ttcgtcccgt gggtctccgc gcgcggggc ggggctgatt gggccgctgc ggagcgggat    1020
tctccgtccg cgtcccctac acgttgaggt tccatggcaa gaccaatgaa catctagtat   1080
tcgaatggta atggcctaag acaccaattt atcatattaa cctcagatgc ataacgtcaa   1140
ggatgtgagt tcatacagta catttctagc tcaaagaatt attctctaca ttacttttat   1200
ggaaagacat aagttaggtt aggttagtta tctagtcagt tcgtattagg aaaatctaga   1260
ggtcagtttc ctagttccct aagttagcta gatgacctct cttataaacg cagccgagtc   1320
tttgttaggg gatcaaccaa gaacaaatca aagttctcaa aagaccagca tggtcaaagc   1380
ctgctgccac agaaacaacc cctggttgat gagggaacct atcgctatta tcaatcataa   1440
caatattgaa tgtctaatag caataggaaa ctttatctat cttatatatc agtttcctat   1500
ttgcataagt tctgctgaca cctgtgatgg ttgtagtttt ttaccccctta cttttaggtg   1560 caacaatcag tgctaaaaga catatagcat accttgccac actgagcaaa aaaagattcg   1620
acttcctcca gttttacatt gtaaggaagc ggtgatgcag caactgtcct agagtccact   1680
tgctctataa cctcatctgg cttcaacaac tccttagacc taccaacttt cttccctgtg   1740
gcaaagacaa tactgaacct taatacagga tataagcacc aagttactga tgtatacaac   1800
attccaacta aagtgagtat ttttttcatt tgaaccgtgc agaaaatgtc catattagta   1860
tgcgaccagg tgattcagtg atagttataa tgtaaggtcg aacattcatc agaattcagg   1920
aaagggccat tgttctgaca ttgctgaaaa tggaaatgga acattgccat attctgctga   1980
atgaaattaa gcttctacac catcttaatt caaaaatcaa ttttaactaa atactactac   2040 acgattttg cataacacgt atggacgaaa agatagagat aacgagctta ccatcctctg    2100
atacgcggag cgctgtggaa tggcgcaaga tgtcggcaac gcaagtacgg tctcctctgg   2160
cactgtttct ggtttcgcat ccccttcgag acctaggtgt gacctcatcc acgagaagga   2220
acatatgaga gccaagctca ccactaacca atcagccccg cacccaaaaa ggagatagcc   2280
atgaattagc accatgaatt agcacctgga aaaatctcag agaaaatttt aaaaacatca   2340
aaatcaccat gaatgaaatg ctcaccagtg ttttcgcgg tggagatgaa ctggatgctt    2400
cgcctcgcga tgacgtagtt gccatgttgc tgctacgcga tccaaacgaa acccagccag   2460
ggatgaggaa ccgagactgc aatagaaatc aagcgtgatg gcgctaaaga aggtgaagaa   2520
gcaccagcct tctccatata cagacattcc cttccataca caagctacaa actctacagt   2580
cctgaaaaaa aaaacggtgc ccagccaccc aggagaaaat cacaaactca tgatcagata   2640
tacaggaaag gacagtcatg atctaaagct aaatccttgc aaagaaacat gatggattcc   2700
atgtacatac ctcttcgtat gtgtcgccac taactatact tgttcagcc ccatctgaaa    2760 catttttgc attagggtct tgtactcctg gcttcttgac tactcatcaa tctctctggc    2820
tcgcatcaca ggcaaagggt gtgaaagctc tctggtttgt gcgttcctgc aacatgtaaa   2880
gagattgaga aagaaatgtc atacaacaca aacacatatg catttccaca acaataatat   2940
cgtgaatcat ggttc                                                    2955
```

<210> SEQ ID NO 210
<211> LENGTH: 836
<212> TYPE: DNA
<213> ORGANISM: Zea mays

<400> SEQUENCE: 210

| | | | | | |
|---|---|---|---|---|---|
| gtccagcccg | gggttcctgg | cgatgccgtt | gaactcggcg | ttgagcatcc | ggatgatctc | 60 |
| ggagctctcg | ttgttcacca | ccgtcttcag | ctgcttgtcc | cacagcacct | gaaacgcaat | 120 |
| ggaacactgg | aatcagctcg | gctgttgggc | tactctgcac | ttctgcgtgc | tggaaaggag | 180 |
| gaggggggga | atcagattcg | ctgtttgttt | ggtggatttg | gagtgacggg | attggaggct | 240 |
| cacggggatg | gttggcttcc | cggcgtagtt | ggagctggca | atctcgtaga | gctccctcac | 300 |
| gctccaggcg | ccgttgagag | ggttgggctc | ggcgccgggc | tcctcgtcgg | cgacggcggg | 360 |
| gaacacccag | cccagatgct | cgtcgctctc | cttggtccgc | tcgaagatgg | gcttcatgac | 420 |
| ctacggttcc | gatgcagcgc | atcacgggga | actggaatca | atccactgcc | gagcgaaccc | 480 |
| ccgatccggc | ttgccggctc | gcgatggtga | gggcgaggct | agggttaccg | acgtaccgtg | 540 |
| acgccgatgg | cgtggtcgag | gcccttgagc | ttgaggaagg | cgaggcaccg | ggatgcccag | 600 |
| gggcacgcgt | acgagacgta | gaggtggtac | cgccctgcca | cggtggggaa | ccgcccgtcc | 660 |
| ctagaaacgg | agctccggaa | ggtggatggc | gaccggtcga | agtcgcccgt | gtaggtgacc | 720 |
| tcgtccagcg | ccgaccgcgc | aatcatctga | cgcgcgcgca | tgagtccatg | aacatagcaa | 780 |
| gcgtcaatca | agagtccatg | acggcagcat | ctcggtgtcg | tgggagggga | tacgag | 836 |

<210> SEQ ID NO 211
<211> LENGTH: 2054
<212> TYPE: DNA
<213> ORGANISM: Zea mays

<400> SEQUENCE: 211

| | | | | | |
|---|---|---|---|---|---|
| acaagagtta | aaacgatcta | atgtcgtgtt | tgaagagtcc | aataataaga | ttcataaatg | 60 |
| tccatagatc | aaccgaaact | actaaactgt | aattattacc | caaatgcata | acttaattag | 120 |
| ttattgctca | gattaggcct | ttctatacca | tatatatgaa | cagaagctga | aacattgtag | 180 |
| gcgtcggtgc | aatttttcatc | ttcatatagt | aggccaacga | cgtagataaa | cacaccaaca | 240 |
| acacatatat | aaatgtaaat | ggacatgcgg | tacagtaaaa | acgtgtttca | ttacagacta | 300 |
| gagtctacaa | gaacgagtag | tcagcagata | acatgctaca | gcagttcata | ctttcatcaa | 360 |
| gaaattgaag | tgagtgaaca | aaggtaaaga | cattgtaatt | aagcgtaata | acagtttcag | 420 |
| ttagaaataa | ccttctcaga | aggtctcagc | ttggtgcagg | agaaaccatc | aagaacaagc | 480 |
| ttgcctacgg | catctctcaa | gacctcatac | tcctccgtga | cattgtaaac | ctgatgtgag | 540 |
| attctcacgt | accctgtcac | ttgatcgccc | ttggccatct | cttgtccttc | ctcaacactt | 600 |
| cttgagttgt | tgaatattgg | cacctcgacc | ttgaattcgt | tcctcagcat | gtccctcact | 660 |
| ctcatcgcat | catcatcgct | ctcaatgcca | aggcaacctg | gcagcccgac | catagccatg | 720 |
| cttccgcaca | tttccggcgg | cgagccaaga | aacgtccccc | aagcctcggc | gagcatcgtg | 780 |
| cccatctcga | tcaccttctc | atggttccgt | ttgcttatcg | tctcgatgcc | gccctcgaac | 840 |
| cgtctcatga | agtcaacggc | atcaggcaca | acgagctggg | cactgtaatc | ccgcaccccg | 900 |
| atccaggcgc | tctccatggg | cagcccgttg | ccgtactcgc | tagacacgac | ggggtggtgg | 960 |
| agctgcgagg | ctacggggtc | atccttgcgg | atgtgcagga | aggccacggc | ggaagggcag | 1020 |
| aagaaccact | tgtggaggtt | gctggtgtag | aagtcggcgc | cgatgtcgcg | cacgtcgatg | 1080 |

```
ggcacctggc cgatggcgtg cgccccgtcg acgaagacct tgtccacgcc ctcctcgcgg    1140
cagatggcga cgagctcctt cacggggagg aggacgctgg gcatcgaggt gatgtggtcg    1200
atgacggcga ggcggactct gcggccccca gcctgggcga gcgcgagcgc ggcacggaac    1260
tcggcgacga cggcgaccgc cgaggcgacg gggaacggga cggcacctc gacgacggtg     1320 gcccccgcgc ggaccacgta cgcgtggatg gacttcttga cggagctgta ggtgtagtgg    1380
agcatgagca ccacgtcgcc gcgtgcgaag gcgccctccg cgaagctcca ggccacgtgc    1440
tgcatgatga tggccgcggc cgtggtagcg ttgtcgacga gggagacctc ggaggcgtca    1500
cccgccccga cggcggacgc cacggcggca cgcgagcggg cgagcccgg ctggagagag     1560 tcgaagtaga acgcgtcggg ctgagagaga aaaagccgtt gccaccgcgc cctcgccgcg    1620
aggaccgacg ccgggcagca gccgaaggtg ccgttgttga cgcgggctac ggtgccgtcg    1680
tggtgcgcga actcggcgcg aatatcggct tccgtgatag ttgcgctggt gcgttttttcc    1740 ggcggcgcag cgttcctgcc cttggccgcg tcgtcgtgcg gagccgaggc catcggaatt    1800
tggggatgga gagggccggg tgcgggcctg aggctgagat agcgatgagg gggagagtaa    1860
tggttgactt gcaggagcca ggtgcccctg cccccttgat gtaaagaact ggtcaacggg    1920
ctaaggcatc tctcccgaag acttttagg gagcgttact gctccaattc aataaatttc     1980
tgctctaatt tgcaactctg tctggagcaa tcttcacgtt catgtggagt tagagctgag    2040
agaggcgttt ggct                                                      2054

<210> SEQ ID NO 212
<211> LENGTH: 19
<212> TYPE: DNA
<213> ORGANISM: Zea mays

<400> SEQUENCE: 212
ggcgtacttg cgcgcggac                                                 19

<210> SEQ ID NO 213
<211> LENGTH: 13
<212> TYPE: DNA
<213> ORGANISM: Zea mays

<400> SEQUENCE: 213
gttaaaaaat taa                                                       13

<210> SEQ ID NO 214
<211> LENGTH: 11
<212> TYPE: DNA
<213> ORGANISM: Zea mays

<400> SEQUENCE: 214
atgcattact t                                                         11

<210> SEQ ID NO 215
<211> LENGTH: 20
<212> TYPE: DNA
<213> ORGANISM: Zea mays

<400> SEQUENCE: 215
gtgctatact acctaaccta                                                20

<210> SEQ ID NO 216
<211> LENGTH: 10
<212> TYPE: DNA
```

```
<213> ORGANISM: Zea mays

<400> SEQUENCE: 216
cccctgaacc                                                                10

<210> SEQ ID NO 217
<211> LENGTH: 11942
<212> TYPE: DNA
<213> ORGANISM: Zea mays
<220> FEATURE:
<221> NAME/KEY: misc_feature
<222> LOCATION: (1812)..(1911)
<223> OTHER INFORMATION: n is a, c, g, or t
<220> FEATURE:
<221> NAME/KEY: misc_feature
<222> LOCATION: (8603)..(8702)
<223> OTHER INFORMATION: n is a, c, g, or t

<400> SEQUENCE: 217
tttttttatt agattgtgga tacaagataa attattagct atggctttcg ttatgtacaa      60
taatatggaa accaacagct ttatatttag cttcaattgt actaaatccg ttctcgaata     120
tctgtcgccc ggttgatagt tcattttga actaaaccgt gacgaatata ataaaaaaga     180
agactagcta gctagtagta tttacacgca tcgtcgtaat gaaacttaat ttataatcag     240
catatgatgg ctgcttaacg ctgatgagcc tactctttgc atatttcact cgcatgcact     300
tagaaataga gagacatgca tgcatgccag gtgtggttgg ttgtgcactc attcaaagga     360
gctaataatg gccatgttca aacgatctgt ataacgtttt ttttttgtg ttacgtatgc     420 atgcaagatc gatcttgtca gctgagaggc gcatgcgtac tgttactaat aataagatta     480
attatagaga gatcgattgc attatattgt tgcaaaacaa caagagatat gcatggtttt     540
acatgatgtg aactgtttat ttatttatgt aaagcaagga aatatctcaa ttattattgc     600
acaagtaaac tcttcacact actgtgcctg tggtaaataa atagtaattt tctcgtaaca     660
aacgagctac gtacgtctgt ctcgctagtt ggctacctac gtacgtttgg cacctcaaca     720
cacgttgcac tcaaattaac gaagaccata ctaacacctg cacctaaaca tcaacgaacc     780
aactcgtagg ggctgggcta attaaaatac atacaataca caagtccaag cttttttttat     840 gacgcctgtt ttttttcta gtaggatgta tttacactag ccggtgtatt aagtaaaccg     900
tcagtggaaa tatcatatac actggcggtt cacttaacta aaccgtcagg gtaaaacaaa     960
tatgtacact agcagttgta ttaggtgaac cgccaatgga aatatatata cactggcgga    1020
ctacttttgc gccaaaggtg tacactgatg ttccatggcc gagcgcaatg agtacatcaa    1080
caataggtac gagcaactgc atgatcccgt caaatatact cagtcgcaat gagtacatca    1140
acaataggcg tatttgtttg gttgcctgta tatctgaagt ataagttgca cgagtggatg    1200
caaaacaaat tattttaaga ctctttggct gcatccactc atacgccaaa aatactcgtt    1260
tctggtcagc ctggatcggg agagcgtggg tgcactcgtc catctaacca atcagccggt    1320
atatgatctg catctagcta tctaatctct cacatgtctc ccttgcacta ccggaatcca    1380
aggctttgcc gagtgttgca atctttgccg agtgcttttt gtcgggcact cggcaaagaa    1440
ggctttgccg agtgccgcac tcggtaaagc tagactctcg gcaaagaggc tctttaccga    1500
gtgctggaca ctcggcacag gacgacactc ggcaaagact agtttgccga gtgtcaaaca    1560
ctcggcaaag agggctctcg gcaagggcc gtcaacggcc gtcctaaagt tgacggccgt    1620
cagtcttgtc cgagagccag cggctggcac tcggcaaaga ggattctttg ccagtgtca    1680 cacagctggc actcggcaaa gcttcctttg ccgagtgcca gctgcgtggc actcggcaaa    1740
```

-continued

```
gaataggggg gagtctttgc cgagtgtcac caacgggaca ctcggcaaaa acgaatcaag    1800
ctgatcatcg cnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nttcggcaaa    1920
ggaggcctct tccgcctagg gccgtcaacg acgtcctaaa gttgacgccg tcagtttttt    1980
ccgagagcat ccgctgcact cgcaaaggag gattttttcc agtgtcacac cgtgactcgg    2040
caaagcttcc ctttccatcc agctgcctgg cactccgtca agaatagggg atagagtctt    2100
tgcgagtgtc accaacggac actcggcaaa gaatgtttcc agtgccagcg atctggcact    2160
cggcaaagct tattttaaaa ttaaaaaaaa aaactttgcg agtgcccaga tcacgggcac    2220
tcggcaaagc gccctatta caacggccga atgcttcttc tcctcactct ctctctcact    2280
tactcactca aacgccgtca ccccgcgcc ctcaccgtcg ccgccgtgcc gtatcttcgt    2340
gccggccgcg cccgcccgcc gtgccccatc gcccgccgcc gcggccgcc cgtgcgccat    2400
cgccgccgcg ggtcccgccg ccgcgcccgt gcacgcgccg cctccgcgcc ctcgccgccg    2460
cgctcccgtg ccgccgcccg cccgcgtcgc cctcacgctc gccgaagccg cgtccgccgt    2520
gcccgcgctc gccgtgtcgt tgcccgcgct cgccgtgccg tgccctcgt cgtgtcgcgc    2580
cctcgcccgt cgtcgtgccc ctcgcctaac ccctcgccct tgcccgtgcc ccgccgcgg    2640
ccccgcccac cgccccgcc cgtgcccccg ccgcactcct cgtccgtcgt daccccgccg    2700
tttccccgcc gtgccctcgc ccgccaggcg cctcgcccgc gacccgacgc ctcgcccgcg    2760
acccgtcgtc tcgcccgcgc cccgtcgcct cgcccgtgcc aaaacctcta aggtgattac    2820
ttgatttatg ttatacgtgt atgatttata tgaaatgatt agttttaata ttaagttagt    2880
tatatacgtg catgattagg ttaatatgta gtattgtgga ttgccggcca tcgtgccgtt    2940
gaattatgcg tggatgtcag ccatcgtgct gatagtttta tttgcaggat tttgaaacct    3000
ccccgtgcag gggaggtgct gccgaaattt tctgttgcta ggcttctgtt agaggatgga    3060
ggaccgtgag tggatgtaca tgggccgtag aggaaggaac gatgtcacca ctgaatggat    3120
tagaaagacc gatgatttcg tggaacgggc atatggcgaa gctgctaaag gggcgaagct    3180
agtcccatgc ccgtgcggca aatgtgacaa tcggaaaaga aaaccaaaga aggtcatggt    3240
agaacatatt tggaagaatg gatttacgcc gggctatact cggtggatat ttcatggtga    3300
agcgcatcgt acgagagagg aggtgttgag acaacgtgtc gaggattatg acgcggatgc    3360
gggggtagca gatatgttga acgactatca ggaggcacaa tacacgggag gatgtatgga    3420
tgacgagcca gagccgactg caaaggcgtt ctacgacatg ttcgacgcgg cacagaaacc    3480
ccttcacggc cagacaaagg tttctcaact ggatgccatt gggcgtgtaa tggcattcaa    3540
gtcgcagtac agcatgagta gagacgcatt cgatggcttg ttgacggtta ttgggagtct    3600
gcttccggat gatcacgtta tgccaaagag catgtacgag gcacaaaaac tacttcgtgc    3660
actcaagatg acgtatgagc agattcatgc ttgtccgaag ggctgcgtgc tatttaggaa    3720
agaatacgca gaggcaaagt actgtcccaa gtgtaattcg tctaggttta tggaggtaga    3780
ctctagtgat ggacagaaga ggcagctcga catcccttg acaatcctac gacaccttcc    3840
gttcatacc aggatccagc gtctttacat gacagaggaa tccgcgaaaac agatgacatg    3900
gcacaaaaat ggaaaacgat acaatcctga caagatggtg cacgcatcag atgatgaagc    3960
atggaaacac tttgatgaca ttcaccgtga gaaagccgaa gaggctcgta atgtacgtgt    4020
tgcgttggcc acagatgggt tcaatcccta tggaatgagc gctgccccgt acacatgttg    4080
```

```
gcccgtgttt gttatcccaa tcaatctccc ccctggtgtg tgctttcaaa ggcagaatat      4140
attcgtgtcg ttgataattc caggacaccc gggcaacaaa atgggcgtgt atatggagcc      4200
tttgatcgat gaattggtac gtgcctggga ggaaggggta tggacgtatg accgagctac      4260
gaagacaaac ttcagaatgc atgtttggta ccagtactcc atgcatgact taccggcgta      4320
tgggctactc tgtgcctggt gtgttcacgg taagttccca tgcccagttt gcaaggaagc      4380
tcttaggttc atttggttga aaaagggtgg caaatattcg tccttcgata aacatcgaca      4440
atttcttcct gctgaccatc cattccgcct agacatcaag aactttacga aggtgtcgt      4500 agtgacagac cgcccacctg caacgatgac tggtgccgaa attcgtcaac aaatagatgg      4560
gctcgtggcc aatacagaag gtggttttgt gggatatggt gagcagcata tgtggacaca      4620
taagtctggt ttgactcggc tcccctatta tgacgacctg ctccttccac acaacattga      4680
cgtgatgcac actgaaaaaa atgttgccga ggcactgtgg gcaacaatta tggacattcc      4740
tgataagtca aaggataatg tgaaggcaag agtggatctg gcagcgttat gtgatagacc      4800
aaaactagag atgaagccgc caagtggcgg aaagacatgg agaaggccta aggccgactt      4860
cgtcctaaga agggaccaga ggaatgaagt actttagtgg atcaaaattt tgatgttccc      4920
tgatgggtat gcagctaacc tgagtagggg ggtgaactta tctactatgc gagtcttagg      4980
gatgaagagt catgacttcc acatatggat tgaacggatt cttcctgcga tggttcgagg      5040
ctatgtccct gagcatgtct ggctaacgct ttcagagttg agctatttct tccgtcagct      5100
ttgtgcaaaa gagttatctc ggaccgtggt tgcagacttg gaaagattgg cccccgtgtt      5160
actgtgtaag cttgagaaga tatttccacc cggcttcttc aatccaatgc agcatttgat      5220
tcttcatctc ccctatgagg cacgaatggg gggccccgtg cagggacgtt ggtgctatcc      5280
aatcgagaga tgtctaaaga ctattcgaaa gaaatgtaga aataaatgca aaatcgaggc      5340
ttccattgca gaggcataca ttctagagga ggtctcaaac ttcacaacaa cttattatgg      5400
tgacaaactg ccgagcgtgc ataatccacc ccctcgttac aatgatggcg acaatgaatc      5460
gaaccttagc atatttcgag gccaactcga aagcgcaagt ggctcgacca cgaagaccct      5520
gacacatgaa gagtggcgac atatcatgct atacgtattg accaaccttg aagaggtgac      5580
gccatacatg gaacaatttc ttcatgaatt ctggcgtcga tcaagggacc ccactccaca      5640
ggaatatgac gctcttctta gaaagggtgc gagaaatggg ttgcccgatt tcatttcctg      5700
gttcaaacgt aaggtacgtg cttagtttgt aaaagagata cgcctttgaa ctcaatttag      5760
cgtcttttaa cttgcgaata cttgcagggc caaagagatc cgtctatgag tgccgagttg      5820
agacaagtag ccaacggctt tgcttatagg gtcaagaaat attctgggta tgacgtcaat      5880
ggataccgtt ttcgcacaac acactacgac caaagtcggc ccaatcggaa acaacgtgt      5940 tctggagtct ttacgccggg gcttgacaat gtcgattatt ttggacgaat tgaagaaata      6000
tatgagctca atttttatgg ttccaaacct cttactccag tgatattcaa atgtcattgg      6060
tttgaccctc aagtgacgag acggacacat tctaatcttg gatagtcga aattcgacaa      6120 gattccacct tagcaggaga cgatgtctat atcgtggccc aacaggccac acaagtgtat      6180
tatctcccat atgcgtgtca acgaaagaa catcttaagg gttgggatgt tgtgtataag      6240
gtatcgccgc atgggaggtt acctgttcct aacgatgaag attacaactt agacccggac      6300
acatatgatg gagagttctt ccaagaagat gggctagaag ggcgatttga gatagactta      6360
acagaagcta tcggaatgaa cgtagatatt gaaatggttg ttgatgagga ggatgatgag      6420
gtgcaaaatg ataatgactt agtaatcctt gaaggcaatg atgaggttgc gtcttccgat      6480
```

```
ggtgttgaga ttgaaatgct tgatagtgat gatgagagtt ttgatccggc taaccccgac      6540
acatatgaag attattttta atcgatgtaa tgctatatga cttttttattt cgcacctgtt      6600 tttaaataca tcttttttata tgtgcttatt tgtttactct taattgcagg ttgttggaca      6660
aatatggtgg gcggtttcct gaggaggagg aggggggagga ggagtaggac ggcggacgat      6720
gcagagcagg cagcgcagca gcacgaggca gagcaggcag cgcagcagca ggcggcgcct      6780
caggacgacg acgaccagca gcaggacgac gacgaccagc agcaggacgc ctcaggttca      6840
ggcggctcta gttcgaggag catctacctg cgaggccccg cgagtctccc gccgcgtccc      6900
atacttcggg acagacggcc gttgattcgg ccggaagggg agaggtatgt aactttatgt      6960
tcttcattct tgttcatatt atgtgttcaa aatcataata taaactaata cttttttattt     7020 atcacttgga caggtcttgg acggttttgg attatgctgg gggtcatcgt cgcccccca       7080 acaacatcct cggcctgctg tgcagggaac acttccctgg acttgtggag tacgccggag      7140
tgacgggccc agccttcacc ttcgaccact acgccgtcgc ccccgatgca gtagaccggg      7200
acggcaggga attcaataac aaggcggagc gggtgaagca agagctgtgg gtaagtctta      7260
gtataatata aaatatgtcg cattcgttgc aaattcttga aataatgtat ggatacatcg      7320
tttttgtatg caggatttct tcagatgcga tgctggatac gaggctaggg cggatgtggt      7380
ggccaccacg tgctgtaaga agctcgtcgt ggacatgcac tatgaggccc gcatccaggc      7440
catcatcacc taccacggct ccgtccttgg ggagaaggtg accaaacctc aagcccgaac      7500
aatgtcgttg accagggagc agtacctgca ggtaaagtca tgcatgtttg gtaccagtac      7560
tccatgcatg aattttattt tatcttctga tatgcacttt atgtgtttac tttgcaggtg      7620
attccacatt ggtgcgccgc acatcctctc tgctgggagc agatggtgga taggtggtgt      7680
tcggctgagt gggacgaggc gcacacagct agccgggaac ggcgtttgca gatgcaaggc      7740
ccctcgcacc accaaggcag ccggagcctg ggccaatatg ccgaagcatg ggtacgccac      7800
cttttttatt tagatatata gcactaagtt agatattatt tctaactatc tcgttggttt      7860
tcgttgcagt cggcgtcaca tggtggcagg ccttgttcca ccttctcggc ctatgctatg      7920
gcccataagg gtaaggcgac gtccgacgtc acctacaacc cggatgacgg gcccgaggcc      7980
tacaccaacc ccgccgtcta cagccgcctc catgactaca ccgccatggc gcaggaggtc      8040
catggcccag actatgatcc gagcaccgag cctatcgacc ccgatgtgct catgagggtc      8100
ggaggaggca agagacatgg gcggtactgg attgccgaca gggcaatcaa ctcgtcctcc      8160
actcccactc tgtctcaggt gagagcaagg agcatgggct cgagcccagc cattcgacct      8220
cggcacgaca gctcacatca tcgcatacag caactcgagg ttagtacttc tataactcgt      8280 ccttcccttta gttatatatc tagtctttga gttactataa cgttggcttg taatattaca      8340
gacccaacta gaagagatgg aggcgaggat aatggcggag cgggcggcgg ctgatcagag      8400
gatggcggag atgttccagt acatgcagag ccttggcgcc gcacagggca tcgctccgcc      8460
acctccattg ttccccccag ttgaccctac tctcttccac actcctgtga gtatcaaaat      8520
tgtagtttga tgtttgtaat gcatctggta taacacatgc tatctcttct ctgtacgaat      8580
caagctgatt catcagtata ggnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnatctgtgg gttgaacatc aaaataaaaa atcaaatgac caatacagca tagtatgcta      8760
cgtgctccag ggatggggat caacttcggt gatgcgaggg ggaactgggt tctataagaa      8820
```

```
gtggtcgaga tatgaagcat ctgatcgagg tctcatcacc atgagaactg tgttgactca    8880
tgccattatc aacgctattc aacttgagta ttagtagatg ctgcaggccc ttgcgtaccg    8940
gttggagtaa atatgacctt agtctgatta tgcacctcca gagacaagat aagcaagcaa    9000
atcccgcacc ctaacccgac catcagactc aaccaatgga agacacccct cctcgacaac    9060
atctgccccg agtgtcccaa atggcactcg gcaaagaagg cggctttgcc gagtgctgcc    9120
aggaggacac tcggcaaaga tatcttcgtt gccgagtgtc aacggtgaca ctcggcaaag    9180
ccgccgtctc cgtcaaccgg cgccgtaacg gtcgcttttc tttgccgagt gctccctgac    9240
actcggcaaa gatcttcgcc gagtgccgga gaaaaagtac tcggcaaaga agtcttttgcc   9300
gatgcactgt ttgccgagcc ttcttttgccg agtgttacac tcggcaaagc ctttgccgag   9360
tgtttttagg gcttcgccga gtgcttccgg cactcggcga agctattgat tccggtagtg    9420
ttggtagcta ggcaagctaa tggggtacat atggaaggag gaaaccaagt cgatcgtcgt    9480
cgtagcatgt cggtgtgggt actacactac acacacatat acatgggcaa cgcaaggcca    9540
cctttctgaa tcctgcatga gcgtgtacca ctagaattgt cagtgtgtgc ggtgtatggc    9600
aggttttttgg ttcggcaagt ggggccctcc ggggaggaat ctcagtaaca aaccgctctt    9660
ctgaaaaggt cagccatccc cggtccggtc cggtgatgtc gtcgctgtcg ctctgctagc    9720
ttgctgccga tccccccccc ccccccccc cttcttctct ctaccctcc ctccacctca      9780
taaatactta gtttaataac cttgcactgc cgcagtagcc cttaactgct gctatctatc    9840
tcttttctga aggaaaaaaa aggtttgata ctcctctacc tagctagtcc tgcatgccgc    9900
taatgtgcgt cttgcctgtt tatttgttct taataagggc tgcctatcta ttatattttg    9960
cacctgtttt gctgtgttct tggtaactag cttaattcct tcgcctacaa tcgtcaaatc   10020
ccccccatca tcagtcagat gaacttttga tcgaattgaa gttgttcttc taattcggcc   10080
ccagcagcgc ccatgcatct ggttttattt gctttctgtt gggtataata tgcaagacct   10140
tttgttgcta gggcaaggct gcaaccacat gcgtgtactg aactcatgat gtaactcatc   10200
cttttttgttt gctcacagaa tcactactct actgcacttc cttttcatcc gatccgcaat   10260
cttttttttc tttacatgc tttagttttc tctctttctt gattacaaac atgattactg     10320
gaactttctt aggctgcctt cccccttcctt ggatctgctt tagttttctt ttttgggcta   10380
ccgcgcgcgg cttatttgag tttatcactt gctgcatata cataatatat atatacatgc   10440
atgcgatggc gttcatgtta ctcaactaca gatctgtttc tgttcgtgtg tttcagttca   10500
gcgcgcagtt aagcatagca ggacgaccac gacgatgtat cacccgcagt gcgagctcct   10560
gacgatggcg cacgaaacgc cggacctgga cgccggccag ccgcacctaa ccgtctccgg   10620
cgtcgccagc atcccggcag agctgagctt ccacctgctg cactcgctcg acgccgcggc   10680
ggcggtcaat cccgtcacgg cgccgccgca gtccaccatc gactacttcc tcggcggcgc   10740
cgatccccac cagcaggcca tgcagtacga gccgctgccg cccgccgcgg gcggccacca   10800
ccagtacacc atggacatgt tccgcgacta ctgcgacggc cactacccca ccgccgagcc   10860
gtacatccgc gggacaatga ctggagccct cgtgttcggg gccaccgacg acgacgactc   10920
ggccgctgcc tacatgcccg gggggcactt tgagacctcc ccgccgccgc cacgcgcgcac  10980
cggccgcggc aggaagcggg gcagggcgct gggcggcggc ttccatgctg tgctggccaa   11040
cggcgtcgag aagaaggaga agcagcgccg gctgcggctc accgagaagt acaccgccct   11100
catgcacctc atacccaacg ttacaaaggt cgtaccaaat cctcctctta tgttcgtcca   11160
tcgtttcaaa ttaagttaaa aaattaattc acggttcttg ttgtttatttt tttgcgcact   11220
```

-continued

```
gcagactgat agggcgacgg tgatctcgga cgcgatcgag tacatccagg agctggggag    11280
gacggtggag gagctgacgc tgctggtgga gaagaagcgg cgccggaggg agctgcaggg    11340
ggacgtcgtg gacgcggcgc cggctgcggt ggttgctgcc gccggtgagg cggagagctc    11400
ggagggcgag gtggctcctc cgccgccggc cgtgccgcgg cagccgatcc ggagcacgta    11460
catccagcgg cggagcaagg acacgtccgt ggacgtgcgg atcgtggagg aggacgtgaa    11520
catcaagctc accaagcgcc ggcgcgacgg gtgcctcgca gccgcgtcgc gcgcgctgga    11580
tgacctccgc cttgacctcg tccacctctc cggcggcaag atcggtgact gtcaaatcta    11640
catgttcaac accaaggtac atacgaatac gatacgtagc cattgatcga tctgtaattc    11700
tgtagcctga cgattccgag gtttctggtg ctaaaaaatg catctttttt tctcagatga    11760
caatgctttc tgtctttgtt caccgcagat tcacaagggg tcttcagtgt ttgcgagtgc    11820
agtggccggt aggctgatgg aagtggtgga cgagtactag gctaccatgc acttgaattt    11880
ctagctagct ctacgtaccg cgctgctatg aatctagcta tagcgtttct tggatgaaag    11940
ac                                                                  11942
```

<210> SEQ ID NO 218
<211> LENGTH: 3197
<212> TYPE: DNA
<213> ORGANISM: Zea mays

<400> SEQUENCE: 218

```
ggcaagctaa tggggtacat atggaaggag gaaaccaagt cgatcgtcgt cgtagcatgt      60
cggtgtgggt actacactac acacacatat acatgggcaa cgcaaggcca cctttctgaa     120
tcctgcatga gcgtgtacca ctagaattgt cagtgtgtgc ggtgtatggc aggttttttgg    180 ttcggcaagt ggggccctcc ggggaggaat ctcagtaaca aaccgctctt ctgaaaaggt     240
cagccatccc cggtccggtc cggtgatgtc gtcgctgtcg ctctgctagc ttgctgccga     300
tccccccccc ccccccccc cttcttctct ctaccccctcc ctccacctca taaatactta     360
gtttaataac cttgcactgc cgcagtagcc cttaactgct gctatctatc tcttttctga     420
aggaaaaaaa aggtttgata ctcctctacc tagctagtcc tgcatgccgc taatgtgcgt     480
cttgcctgtt tatttgttct taataagggc tgcctatcta ttatattttg cacctgtttt     540
gctgtgttct tggtaactag cttaattcct tcgcctacaa tcgtcaaatc cccccatca     600 tcagtcagat gaactttga tcgaattgaa gttgttcttc taattcggcc ccagcagcgc     660
ccatgcatct ggttttattt gctttctgtt gggtataata tgcaagacct tttgttgcta     720
gggcaaggct gcaaccacat gcgtgtactg aactcatgat gtaactcatc cttttttgttt    780 gctcacagaa tcactactct actgcacttc cttttcatcc gatccgcaat cttttttttc     840
ttttacatgc tttagttttc tctctttctt gattacaaac atgattactg gaactttctt     900
aggctgcctt ccccttcctt ggatctgctt tagttttctt ttttgggcta ccgcgcgcgg     960
cttatttgag tttatcactt gctgcatata cataatatat atatacatgc atgcgatggc    1020
gttcatgtta ctcaactaca gatctgtttc tgttcgtgtg tttcagttca gcgcgcagtt    1080
aagcatagca ggacgaccac gacgatgtat cacccgcagt gcgagctcct gacgatggcg    1140
cacgaaacgc cggacctgga cgccggccag ccgcacctaa ccgtctccgg cgtcgccagc    1200
atcccggcag agctgagctt ccacctgctg cactcgctcg acgccgcggc ggcggtcaat    1260
cccgtcacgg cgccgccgca gtccaccatc gactacttcc tcggcggcgc cgatccccac    1320
```

```
cagcaggcca tgcagtacga gccgctgccg cccgccgcgg gcggccacca ccagtacacc    1380
atggacatgt tccgcgacta ctgcgacggc cactacccca ccgccgagcc gtacatccgc    1440
gggacaatga ctggagccct cgtgttcggg gccaccgacg acgacgactc ggccgctgcc    1500
tacatgcccg gggggcactt tgagacctcc ccgccgccgc cacgcgccac cggccgcggc    1560
aggaagcggg gcagggcgct gggcggcggc ttccatgctg tgctggccaa cggcgtcgag    1620
aagaaggaga agcagcgccg gctgcggctc accgagaagt acaccgccct catgcacctc    1680
atacccaacg ttacaaaggt cgtaccaaat cctcctctta tgttcgtcca tcgtttcaaa    1740
ttaagttaaa aaattaattc acggttcttg ttgtttattt tttgcgcact gcagactgat    1800
agggcgacgg tgatctcgga cgcgatcgag tacatccagg agctggggag gacggtggag    1860
gagctgacgc tgctggtgga gaagaagcgg cgccggaggg agctgcaggg ggacgtcgtg    1920
gacgcggcgc cggctgcggt ggttgctgcc gccggtgagg cggagagctc ggagggcgag    1980
gtggctcctc cgccgccggc cgtgccgcgg cagccgatcc ggagcacgta catccagcgg    2040
cggagcaagg acacgtccgt ggacgtgcgg atcgtggagg aggacgtgaa catcaagctc    2100
accaagcgcc ggcgcgacgg gtgcctcgca gccgcgtcgc gcgcgctgga tgacctccgc    2160
cttgacctcg tccacctctc cggcggcaag atcggtgact gtcaaatcta catgttcaac    2220
accaaggtac atacgaatac gatacgtagc cattgatcga tctgtaattc tgtagcctga    2280
cgattccgag gtttctggtg ctaaaaaatg catcttttt tctcagatga caatgctttc    2340
tgtctttgtt caccgcagat tcacaagggg tcttcagtgt ttgcgagtgc agtggccggt    2400
aggctgatga agtggtggta cgagtactag gctaccatgc acttgaattt ctagctagct    2460
ctacgtaccg cgctgctatg aatctagcta tagcgtttct tggatgaaag actagttagt    2520
tgttaccttc tatctttgct tcaattaaat ccgcttgctc gttacagact gagtttgttt    2580
ctaaatgtca aggttgtttt ggtcaaattg aataaattgg cacactggcc tgtgaggtta    2640
ttatatatat ttatgtgttt attactggtc tattaatttg tcttattatt aatgtattgc    2700
ctgtcaagga ataaatggta tgatgaccat atttatgcat agataggatc ggatgagtag    2760
gttcacttgc ttgagttcac cggtataatt ccggatacat ctggttaggt catcctttgg    2820
tcagctgccc gcaagcttaa ctccgtgcga tatacaatat acagatttta ttatggtttt    2880
cccctgaacc ttcgtgacta actatgttat cattttttata gctttatagt ctacaaactg    2940
ttttatactc agcttgataa gtacattctg gtttggacga tggttttttt ttcttgcaaa    3000
atgaatttgt cttcagcctt tacgactaca tacagtttag tttgtattaa ttgataccgg    3060
aagatcagat tcggaccaca tataaacaag gaatatatag cacgtactcg ctgaacctta    3120
aatatagtca ggaaaataga gggttaacta aaccgatcca gaaaccaatt acattgatat    3180
tgactctatt cttcgtt                                                   3197
```

<210> SEQ ID NO 219
<211> LENGTH: 3173
<212> TYPE: DNA
<213> ORGANISM: Zea mays

<400> SEQUENCE: 219

```
ggcaagctaa tggggtacat atggaaggag gaaaccaagt cgatcgtcgt cgtagcatgt      60
cggtgtgggt actacactac acacacatat acatgggcaa cgcaaggcca cctttctgaa    120
tcctgcatga gcgtgtacca ctagaattgt cagtgtgtgc ggtgtatggc aggttttttgg   180 ttcggcaagt ggggccctcc ggggaggaat ctcagtaaca aaccgctctt ctgaaaaggt    240
```

```
cagccatccc cggtccggtc cggtgatgtc gtcgctgtcg ctctgctagc ttgctgccga   300
tccccccccc ttcttctctc taccccctccc tccacctcat aaatacttag tttaataacc   360
ttgcactgcc gcagtagccc ttaactgctg ctatctatct cttttctgaa ggaaaaaaaa   420
ggtttgatac tcctctacct agctagtcct gcatgccgct aatgtgcgtc ttgcctgttt   480
atttgttctt aataagggct gcctatctat tatattttgc acctgttttg ctgtgttctt   540
ggtaactagc ttaattcctt tgcctacaat cgtcaaatcc cccccatcat cagtcagatg   600 aactttgat cgaattgaag ttgttcttct aattcggccc cagcagcgcc catgcatctg    660
gttttatttg ctttctgttg ggtataatat gcaagacctt tgttgctag ggcaaggctg    720 caaccacatg cgtgtactga actcatgatg taactcatcc tttttgtttg ctcacagaat   780
cactactcta ctgcacttcc ttttcatccg atccgcaatc ttttttttct tttacatgct   840
ttagttttct ctctttcttg attacaaaca tgattactgg aactttctta ggctgccttc   900
cccttccttg gatctgcttt agttttcttt tttgggctac cgcgcgcggc ttatttgagt   960
ttatcacttg ctgcatatac ataatatata tatacatgca tgcgatggcg ttcatgttac  1020
tcaactacag atctgtttct gttcgtgtgt ttcagttcag cgcgcagtta agcatagcag  1080
gacgaccacg acgatgtatc acccgcagtg cgagctcctg acgatggcgc acgaaacgcc  1140
ggacctggac gccggccagc cgcacctaac cgtctccggc gtcgccagca tcccggcaga  1200
gctgagcttc cacctgctgc actcgctcga cgccgcggcg gcggtcaatc ccgtcacggc  1260
gccgccgcag tccaccatcg actacttcct cggcggcgcc gatccccacc agcaggccat  1320
gcagtacgag ccgctgccgc cgccgcgggc cggccaccac cagtacacca tggacatgtt  1380
ccgcgactac tgcgacggcc actaccccac cgccgagccg tacatccgcg gacaatgac   1440 tggagccctc gtgttcgggg ccaccgacga cgacgactcg gccgctgcct acatgcccgg  1500
ggggcacttt gagacctccc cgccgccgcc acgcgccacc ggccgcggca ggaagcgggg  1560
cagggcgctg ggcggcggct tccatgctgt gctggccaac ggcgtcgaga agaaggagaa  1620
gcagcgccgg ctgcggctca ccgagaagta caccgccctc atgcacctca tacccaacgt  1680
tacaaaggtc gtaccaaatc ctcctcttat gttcgtccat cgtttgaaat taagttaaaa  1740
aattaattca cggttcttgt tgtttatttt ttgcgcactg cagactgata gggcgacggt  1800
gatctcggac gcgatcgagt acatccagga gctggggagg acggtggagg agctgacgct  1860
gctggtggag aagaagcggc gccggaggga gctgcagggg gacgtcgtgg acgcggcgcc  1920
ggctgcggtg gttgctgccg ccggtgaggc ggagagctcg gagggcgagg tggctcctcc  1980
gccgccggcc gtgccgcggc agccgatccg gagcacgtac atccagcggc ggagcaagga  2040
cacgtccgtg gacgtgcgga tcgtggagga ggacgtgaac atcaagctca ccaagcgccg  2100
gcgcgacggg tgcctcgcag ccgcgtcgcg cgcgctggat gacctccgcc ttgacctcgt  2160
ccacctctcc ggcggcaaga tcggtgactg tcaaatctac atgttcaaca ccaaggtaca  2220
tacgaatacg atacgtagcc attgatcgat ctgtaattct gtagcctgac gattccgagg  2280
tttctggtgc taaaaaatgc atcttttttt ctcagatgac aatgcttttct gtctttgttc  2340 accgcagatt cacaagggt cttcagtgtt tgcgagtgca gtggccggta ggctgatgga   2400
agtggtggac gagtactagg ctaccatgca cttgaatttc tagctagctc tacgtaccgc  2460
gctgctatga atctagctat agcgttcttt ggatgaaaga ctagttagtt gttaccttct  2520
atctttgctt caattaaatc cgcttgctcg ttacagactg agtttgtttc taaatgtcaa  2580
```

```
ggttgttttg gtcaaattga ataaattggc acactggcct gtgaggttat tatatatatt    2640
tatgtgttta ttactggtct attaatttgt cctattatta atgtattgcc tgtcaaggaa    2700
taaatgatat gatgaccata tttatgcata gataggatga gtaggttcac ttgcttgagt    2760
tcaccggtat aattctggat acatctggtt aggtcatcct ttggtcagct gcccgcaacg    2820
tgcgatatac aatatacata ttttattatg tttttttcgt gactaactat gttatcattt    2880
ttatagcttt atagtctaca aactgtttta tactcagctt gataagtaca ttctggtttg    2940
gacgattttt ttttcttgca aaaatgaatt tgtcttcagc ctttacgact acatacagtt    3000
tagttcttag agtatctcat ctgtattaat tgataccgga agagattcgg gccacatata    3060
aacaaggaat atatagcacg tactcgctga accttaaata tagtcaggaa catagagggt    3120
taactaaacc gatccagaaa ccaattacat tgatattgac tctattcttc gtt           3173

<210> SEQ ID NO 220
<211> LENGTH: 3235
<212> TYPE: DNA
<213> ORGANISM: Zea mays

<400> SEQUENCE: 220
ggcaagctaa tggggtacat atggaaggag gaaaccaagt cgatcgtcgt cgtagcatgt      60
cggtgtgggt actacactac acacacatat acatgggcaa cgcaaggcca cctttctgaa     120
tcctgcatga gcgtgtacca ctagaattgt cagtgtgtgc ggtgtatggc aggttttggg     180
ttcggcaagt ggggcccctcc ggggaggaat ctcagtaaca aaccgctctt ctgaaaaggt    240
cagccatccc cggtccggtc cggtgatgtc gtcgctgtcg ctctgctagc ttgctgccga    300
tccccccccc cccccccccc cttcttctct ctaccccctcc ctccacctca taaatactta    360
gtttaataac cttgcactgc cgcagtagcc cttaactgct gctatctatc tcttttctga    420
aggaaaaaaa aggtttgata ctcctctacc tagctagtcc tgcatgccgc taatgtgcgt    480
cttgcctgtt tatttgttct taataagggc tgcctatcta ttatattttg cacctgtttt    540
gctgtgttct tggtaactag cttaattcct ttgcctacaa tcgtcaaatc ccccccatca    600
tcagtcagat gaacttttga tcgaattgaa gttgttcttc taattcggcc ccagcagcgc    660
ccatgcatct ggttttattt gctttctgtt gggtataata tgcaagacct tttgttgcta    720
gggcaaggct gcaaccacat gcgtgtactg aactcatgat gtaactcatc cttttgtttt    780
gctcacagaa tcactactct actgcacttc cttttcatcc gatccgcaat cttttttttc    840
ttttacatgc tttagttttc tctctttctt gattacaaac atgattactg gaactttctt    900
aggctgcctt cccccttcctt ggatctgctt tagttttctt ttttgggcta ccgcgcgcgg    960
cttatttgag tttatcactt gctgcatata cataatatat atatacatgc atgcgatggc    1020
gttcatgtta ctcaactaca gatctgtttc tgttcgtgtg tttcagttca gcgcgcagtt    1080
aagcatagca ggacgaccac gacgatgtat caccccgcagt gcgagctcct gacgatggcg    1140
cacgaaacgc cggacctgga cgccggccag ccgcacctaa ccgtctccgg cgtcgccagc    1200
atcccggcag agctgagctt ccacctgctg cactcgctcg acgccgcggc ggcggtcaat    1260
cccgtcacgg cgccgccgca gtccaccatc gactacttcc tcggcggcgc cgatccccac    1320
cagcaggcca tgcagtacga gccgctgccg cccgccgcgg gcggccacca ccagtacacc    1380
atggacatgt tccgcgacta ctgcgacggc aactacccca ccgccgagcc gtacatccgc    1440
gggacaatga ctggagccct cgtgttcggg gccaccgacg acgacgactc ggccgctgcc    1500
gcctacatgc ccgggggggca ctttgagacc tccccgccgc cgccacgcgc caccggccgc    1560
```

| | |
|---|---:|
| ggcaggaagc ggggcagggc gctgggcggc ggcttccatg ctgtgctggc aacggcgtc | 1620 |
| gagaagaagg agaagcagcg ccggctgcgg ctcaccgaga agtttacggc cctcatgcac | 1680 |
| ctcatacccca acgttacgaa ggtcgtacgg cgtacttgcg cgcggaccaa atcctcctct | 1740 |
| tatgttcgtc gtccatcgtc tcaaattaat tcacggttct tgttgttgtt tattttttgc | 1800 |
| gcactgcaga ctgatagggc gacggtgatc tcggacgcga tcgagtacat ccaggagctg | 1860 |
| gggaggacgg tggaggagct gacgctgctg gtggagaaga agcggcgccg agggagctg | 1920 |
| caggggacg tcgtggacgc ggcgccggct gcggtggttg ctgccgccgg tgaggcggag | 1980 |
| agctcggagg gcgaggtggc tcctccgccg ctggccgtgc cgcggcagcc gatccggagc | 2040 |
| acgtacatcc agcggcggag caaggacacg tccgtggacg tgcggatcgt ggaggaggac | 2100 |
| gtgaacatca agctccaccaa gcgccggcgc gacgggtgcc tcgcagccgc gtcgcgcgcg | 2160 |
| ctggacgacc tccgccttga cctcgtccac ctctccggcg gcaagatcgg tgactgtcaa | 2220 |
| atctacatgt tcaacaccaa ggtacatacg aatacgatac gtagccattg atcgatctgt | 2280 |
| aattctgtag cctgacgatt tcatgcatta cttttccgag gtttctgtgc tatactacct | 2340 |
| aacctaggtg ctaaaaaatg cacctttttt tctcagatga caatgctttc tgtcttttgtt | 2400 |
| caccgcagat tcacaagggg tcttcagtgt ttgcgagtgc agtggccggt aggctgatgg | 2460 |
| aagtggtgga cgagtactag gctaccatgc acttgaattt ctagctagct ctacgtaccg | 2520 |
| cgctgctatg aatctagcta tagcgtttct tggatgaaag aatagttagt tgttaccttc | 2580 |
| tatctttgct tcaattaaat ccgcttgctc gttacagact gagtttgttt ctaaatgtca | 2640 |
| aggttgtttt ggtcaaattg aataaattgg cacactggcc tgtgaggtta ttatatttat | 2700 |
| gtgtattatt actggtctat caatttgtcc tattattgta ttgcctgtca aggaataaat | 2760 |
| tgtatgatga tcatatttat gcatagatag gatgagtagg ttcacttgct tgagttcacc | 2820 |
| ggtataattc tggtttctgg atacatctgg ttaggtcagc cttttggtcag ctgcccgcaa | 2880 |
| gcttaactcc gtgcgatata cactatacaa attttattat gttttttttcg tgactaacta | 2940 |
| tgttatcatt tttatagctt tatagtctac aaactgtttt atactcagct tgataagtac | 3000 |
| attctggttt ggacgatggt tttttttttc ttgcaaaaat gaatttgtct tcagcccttta | 3060 |
| cgactacata cagtttagtt tgtattaatt gataccagaa gatcagattc ggaccacata | 3120 |
| taaacaagga atatatagca cgtactcgct gaaccttaaa tatagtcagg aacatagagg | 3180 |
| gttaactaaa ccgatccaga aaccaattac attgatattg actctattct tcgtt | 3235 |

<210> SEQ ID NO 221
<211> LENGTH: 1495
<212> TYPE: DNA
<213> ORGANISM: Zea mays

<400> SEQUENCE: 221

| | |
|---|---:|
| ctctgctagc ttgctgccga tccccccccc cccccccccc cttcttctct ctacccctcc | 60 |
| ctccacctca taaatactta gtttaataac cttgcactgc cgcagtagcc cttaactgct | 120 |
| gctatctatc tcttttctga aggaaaaaaa agttcagcgc gcagttaagc atagcaggac | 180 |
| gaccacgacg atgtatcacc cgcagtgcga gctcctgacg atggcgcacg aaacgccgga | 240 |
| cctggacgcc ggccagccgc acctaaccgt ctccggcgtc gccagcatcc cggcagagct | 300 |
| gagcttccac ctgctgcact cgctcgacgc gcgggcggcg gtcaatcccg tcacggcgcc | 360 |
| gccgcagtcc accatcgact acttcctcgg cggcgccgat ccccaccagc aggccatgca | 420 |

| | |
|---|---|
| gtacgagccg ctgccgcccg ccgcgggcgg ccaccaccag tacaccatgg acatgttccg | 480 |
| cgactactgc gacggccact accccaccgc cgagccgtac atccgcggga caatgactgg | 540 |
| agccctcgtg ttcggggcca ccgacgacga cgactcggcc gctgcctaca tgcccggggg | 600 |
| gcactttgag acctcccgc cgccgccacg cgccaccggc cgcggcagga agcggggcag | 660 |
| ggcgctgggc ggcggcttcc atgctgtgct ggccaacggc gtcgagaaga aggagaagca | 720 |
| gcgccggctg cggctcaccg agaagtacac cgccctcatg cacctcatac caacgttac | 780 |
| aaagactgat agggcgacgg tgatctcgga cgcgatcgag tacatccagg agctggggag | 840 |
| gacggtggag gagctgacgc tgctggtgga aagaagcgg cgccgagggg agctgcaggg | 900 |
| ggacgtcgtg gacgcggcgc cggctgcggt ggttgctgcc gccggtgagg cggagagctc | 960 |
| ggagggcgag gtggctcctc cgccgccggc cgtgccgcgg cagccgatcc ggagcacgta | 1020 |
| catccagcgg cggagcaagg acacgtccgt ggacgtgcgg atcgtggagg aggacgtgaa | 1080 |
| catcaagctc accaagcgcc ggcgcgacgg gtgcctcgca ccgcgtcgc gcgcgctgga | 1140 |
| tgacctccgc cttgacctcg tccacctctc cggcggcaag atcggtgact gtcaaatcta | 1200 |
| catgttcaac accaagattc acaagggggtc ttcagtgttt gcgagtgcag tggccggtag | 1260 |
| gctgatggaa gtggtggacg agtactaggc taccatgcac ttgaatttct agctagctct | 1320 |
| acgtaccgcg ctgctatgaa tctagctata gcgtttcttg gatgaaagac tagttagttg | 1380 |
| ttaccttcta tctttgcttc aattaaatcc gcttgctcgt tacagactga gtttgtttct | 1440 |
| aaatgtcaag gttgttttgg tcaaattgaa taaattggca cactggcctg tgagg | 1495 |

<210> SEQ ID NO 222
<211> LENGTH: 1484
<212> TYPE: DNA
<213> ORGANISM: Zea mays

<400> SEQUENCE: 222

| | |
|---|---|
| ctctgctagc ttgctgccga tccccccccc ttcttctctc taccctccc tccacctcat | 60 |
| aaatacttag tttaataacc ttgcactgcc gcagtagccc ttaactgctg ctatctatct | 120 |
| cttttctgaa ggaaaaaaaa gttcagcgcg cagttaagca tagcaggacg accacgacga | 180 |
| tgtatcaccc gcagtgcgag ctcctgacga tggcgcacga aacgccggac ctggacgccg | 240 |
| gccagccgca cctaaccgtc tccggcgtcg ccagcatccc ggcagagctg agcttccacc | 300 |
| tgctgcactc gctcgacgcc gcggcggcgg tcaatcccgt cacggcgccg ccgcagtcca | 360 |
| ccatcgacta cttcctcggc ggcgccgatc cccaccagca ggccatgcag tacgagccgc | 420 |
| tgccgcccgc cgcgggcggc caccaccagt acaccatgga catgttccgc gactactgcg | 480 |
| acggccacta ccccaccgcc gagccgtaca tccgcgggac aatgactgga gccctcgtgt | 540 |
| tcggggccac cgacgacgac gactcggccg ctgcctacat gcccgggggg cactttgaga | 600 |
| cctcccgcc gccgccacgc gccaccggcc gcggcaggaa gcggggcagg cgctgggcg | 660 |
| gcggcttcca tgctgtgctg gccaacggcg tcgagaagaa ggagaagcag cgccggctgc | 720 |
| ggctcaccga gaagtacacc gccctcatgc acctcatacc caacgttaca aagactgata | 780 |
| gggcgacggt gatctcggac gcgatcgagt acatccagga gctggggagg acggtggagg | 840 |
| agctgacgct gctggtggag aagaagcggc gccgagggga gctgcagggg gacgtcgtgg | 900 |
| acgcggcgcc ggctgcggtg gttgctgccg ccggtgaggc ggagagctcg gagggcgagg | 960 |
| tggctcctcc gccgccggcc gtgccgcggc agccgatccg gagcacgtac atccagcggc | 1020 |
| ggagcaagga cacgtccgtg gacgtgcgga tcgtggagga ggacgtgaac atcaagctca | 1080 |

```
ccaagcgccg gcgcgacggg tgcctcgcag ccgcgtcgcg cgcgctggat gacctccgcc    1140
ttgacctcgt ccacctctcc ggcggcaaga tcggtgactg tcaaatctac atgttcaaca    1200
ccaagattca caagggtct tcagtgtttg cgagtgcagt ggccggtagg ctgatggaag     1260
tggtggacga gtactaggct accatgcact tgaatttcta gctagctcta cgtaccgcgc    1320
tgctatgaat ctagctatag cgtttcttgg atgaaagact agttagttgt taccttctat    1380 cttttgcttca attaaatccg cttgctcgtt acagactgag tttgtttcta aatgtcaagg   1440 ttgtttggt  caaattgaat aaattggcac actggcctgt gagg                    1484

<210> SEQ ID NO 223
<211> LENGTH: 1498
<212> TYPE: DNA
<213> ORGANISM: Zea mays

<400> SEQUENCE: 223
ctctgctagc ttgctgccga tccccccccc ccccccccc cttcttctct ctacccctcc      60
ctccacctca taaatactta gtttaataac cttgcactgc cgcagtagcc cttaactgct    120
gctatctatc tcttttctga aggaaaaaaa agttcagcgc gcagttaagc atagcaggac    180
gaccacgacg atgtatcacc cgcagtgcga gctcctgacg atggcgcacg aaacgccgga    240
cctggacgcc ggccagccgc acctaaccgt ctccggcgtc gccagcatcc ggcagagct     300 gagcttccac ctgctgcact cgctcgacgc cgcggcggcg gtcaatcccg tcacggcgcc    360
gccgcagtcc accatcgact acttcctcgg cggcgccgat ccccaccagc aggccatgca    420
gtacgagccg ctgccgcccg ccgcgggcgg ccaccaccag tacaccatgg acatgttccg    480
cgactactgc gacggcaact acccaccgc cgagccgtac atccgcggga caatgactgg     540
agccctcgtg ttcggggcca ccgacgacga cgactcggcc gctgccgcct acatgcccgg    600
ggggcacttt gagacctccc cgccgccgcc acgcgccacc ggccgcggca ggaagcgggg    660
cagggcgctg ggcggcggct tccatgctgt gctggccaac ggcgtcgaga agaaggagaa    720
gcagcgccgg ctgcggctca ccgagaagtt tacggccctc atgcacctca tacccaacgt    780
tacgaagact gatagggcga cggtgatctc ggacgcgatc gagtacatcc aggagctggg    840
gaggacggtg gaggagctga cgctgctggt ggagaagaag cggcgccgga gggagctgca    900 ggggacgtc gtggacgcgg cgccggctgc ggtggttgct gccgcggtg aggcggagag      960 ctcggagggc gaggtggctc ctccgccgct ggccgtgccg cggcagccga tccggagcac    1020
gtacatccag cggcggagca aggacacgtc cgtggacgtg cggatcgtgg aggaggacgt    1080
gaacatcaag ctcaccaagc gccggcgcga cgggtgcctc gcagccgcgt cgcgcgcgct    1140
ggacgacctc gccttgacc tcgtccacct ctccggcggc aagatcggtg actgtcaaat     1200
ctacatgttc aacaccaaga ttcacaaggg gtcttcagtg tttgcgagtg cagtggccgg    1260
taggctgatg gaagtggtgg acgagtacta ggctaccatg cacttgaatt tctagctagc    1320
tctacgtacc gcgctgctat gaatctagct atagcgtttc ttggatgaaa gaatagttag    1380
ttgttacctt ctatctttgc ttcaattaaa tccgcttgct cgttacagac tgagtttgtt    1440
tctaaatgtc aaggttgttt tggtcaaatt gaataaattg gcacactggc ctgtgagg     1498

<210> SEQ ID NO 224
<211> LENGTH: 365
<212> TYPE: PRT
<213> ORGANISM: Zea mays
```

<400> SEQUENCE: 224

```
Met Tyr His Pro Gln Cys Glu Leu Leu Thr Met Ala His Glu Thr Pro
1               5                   10                  15

Asp Leu Asp Ala Gly Gln Pro His Leu Thr Val Ser Gly Val Ala Ser
            20                  25                  30

Ile Pro Ala Glu Leu Ser Phe His Leu Leu His Ser Leu Asp Ala Ala
        35                  40                  45

Ala Ala Val Asn Pro Val Thr Ala Pro Pro Gln Ser Thr Ile Asp Tyr
    50                  55                  60

Phe Leu Gly Gly Ala Asp Pro His Gln Gln Ala Met Gln Tyr Glu Pro
65                  70                  75                  80

Leu Pro Pro Ala Ala Gly Gly His His Gln Tyr Thr Met Asp Met Phe
                85                  90                  95

Arg Asp Tyr Cys Asp Gly His Tyr Pro Thr Ala Glu Pro Tyr Ile Arg
            100                 105                 110

Gly Thr Met Thr Gly Ala Leu Val Phe Gly Ala Thr Asp Asp Asp Asp
        115                 120                 125

Ser Ala Ala Ala Tyr Met Pro Gly Gly His Phe Glu Thr Ser Pro Pro
    130                 135                 140

Pro Pro Arg Ala Thr Gly Arg Gly Arg Lys Arg Gly Arg Ala Leu Gly
145                 150                 155                 160

Gly Gly Phe His Ala Val Leu Ala Asn Gly Val Glu Lys Lys Glu Lys
                165                 170                 175

Gln Arg Arg Leu Arg Leu Thr Glu Lys Tyr Thr Ala Leu Met His Leu
            180                 185                 190

Ile Pro Asn Val Thr Lys Thr Asp Arg Ala Thr Val Ile Ser Asp Ala
        195                 200                 205

Ile Glu Tyr Ile Gln Glu Leu Gly Arg Thr Val Glu Glu Leu Thr Leu
    210                 215                 220

Leu Val Glu Lys Lys Arg Arg Arg Glu Leu Gln Gly Asp Val Val
225                 230                 235                 240

Asp Ala Ala Pro Ala Ala Val Val Ala Ala Gly Glu Ala Glu Ser
                245                 250                 255

Ser Glu Gly Glu Val Ala Pro Pro Pro Ala Val Pro Arg Gln Pro
            260                 265                 270

Ile Arg Ser Thr Tyr Ile Gln Arg Arg Ser Lys Asp Thr Ser Val Asp
        275                 280                 285

Val Arg Ile Val Glu Glu Asp Val Asn Ile Lys Leu Thr Lys Arg Arg
    290                 295                 300

Arg Asp Gly Cys Leu Ala Ala Ser Arg Ala Leu Asp Asp Leu Arg
305                 310                 315                 320

Leu Asp Leu Val His Leu Ser Gly Gly Lys Ile Gly Asp Cys Gln Ile
                325                 330                 335

Tyr Met Phe Asn Thr Lys Ile His Lys Gly Ser Ser Val Phe Ala Ser
            340                 345                 350

Ala Val Ala Gly Arg Leu Met Glu Val Val Asp Glu Tyr
        355                 360                 365
```

<210> SEQ ID NO 225
<211> LENGTH: 366
<212> TYPE: PRT
<213> ORGANISM: Zea mays

<400> SEQUENCE: 225

Met Tyr His Pro Gln Cys Glu Leu Leu Thr Met Ala His Glu Thr Pro
1               5                   10                  15

Asp Leu Asp Ala Gly Gln Pro His Leu Thr Val Ser Gly Val Ala Ser
            20                  25                  30

Ile Pro Ala Glu Leu Ser Phe His Leu Leu His Ser Leu Asp Ala Ala
            35                  40                  45

Ala Ala Val Asn Pro Val Thr Ala Pro Pro Gln Ser Thr Ile Asp Tyr
    50                  55                  60

Phe Leu Gly Gly Ala Asp Pro His Gln Gln Ala Met Gln Tyr Glu Pro
65                  70                  75                  80

Leu Pro Pro Ala Ala Gly Gly His His Gln Tyr Thr Met Asp Met Phe
                85                  90                  95

Arg Asp Tyr Cys Asp Gly Asn Tyr Pro Thr Ala Glu Pro Tyr Ile Arg
                100                 105                 110

Gly Thr Met Thr Gly Ala Leu Val Phe Gly Ala Thr Asp Asp Asp Asp
                115                 120                 125

Ser Ala Ala Ala Ala Tyr Met Pro Gly Gly His Phe Glu Thr Ser Pro
    130                 135                 140

Pro Pro Pro Arg Ala Thr Gly Arg Gly Arg Lys Arg Gly Arg Ala Leu
145                 150                 155                 160

Gly Gly Gly Phe His Ala Val Leu Ala Asn Gly Val Glu Lys Lys Glu
                165                 170                 175

Lys Gln Arg Arg Leu Arg Leu Thr Glu Lys Phe Thr Ala Leu Met His
                180                 185                 190

Leu Ile Pro Asn Val Thr Lys Thr Asp Arg Ala Thr Val Ile Ser Asp
                195                 200                 205

Ala Ile Glu Tyr Ile Gln Glu Leu Gly Arg Thr Val Glu Glu Leu Thr
    210                 215                 220

Leu Leu Val Glu Lys Lys Arg Arg Arg Arg Glu Leu Gln Gly Asp Val
225                 230                 235                 240

Val Asp Ala Ala Pro Ala Ala Val Ala Ala Gly Glu Ala Glu
                245                 250                 255

Ser Ser Glu Gly Glu Val Ala Pro Pro Leu Ala Val Pro Arg Gln
                260                 265                 270

Pro Ile Arg Ser Thr Tyr Ile Gln Arg Arg Ser Lys Asp Thr Ser Val
    275                 280                 285

Asp Val Arg Ile Val Glu Glu Asp Val Asn Ile Lys Leu Thr Lys Arg
    290                 295                 300

Arg Arg Asp Gly Cys Leu Ala Ala Ala Ser Arg Ala Leu Asp Asp Leu
305                 310                 315                 320

Arg Leu Asp Leu Val His Leu Ser Gly Gly Lys Ile Gly Asp Cys Gln
                325                 330                 335

Ile Tyr Met Phe Asn Thr Lys Ile His Lys Gly Ser Ser Val Phe Ala
                340                 345                 350

Ser Ala Val Ala Gly Arg Leu Met Glu Val Val Asp Glu Tyr
    355                 360                 365

<210> SEQ ID NO 226
<211> LENGTH: 366
<212> TYPE: PRT
<213> ORGANISM: Brachypodium distachyon

<400> SEQUENCE: 226

Met Tyr His Pro Gln Cys Glu Leu Leu Met Pro His Glu Ser Leu Asp
1               5                   10                  15

Met Asp Ala Val Val Gly Gln Ser His Leu Ala Ala Ser Gly Val Ser
                20                  25                  30

Ala Ile Pro Ala Glu Leu Asn Phe His Leu Leu His His Ser Phe Val
            35                  40                  45

Asp Thr Ala Ala Ser Pro Gln Pro Pro Thr Val Asp Tyr Phe Phe Pro
        50                  55                  60

Gly Thr Asp Pro Pro Ala Ala Val Gln Phe Glu Gln Leu Ala Ala
65                  70                  75                  80

Thr Asn His His Ala Met Ser Met Leu Arg Asp Tyr Tyr Gly Gln Gln
                    85                  90                  95

Tyr Pro Ala Glu Thr Tyr Leu Arg Gly Pro Arg Thr Thr Thr Gly
            100                 105                 110

Ser Ser Ser Leu Val Phe Gly Val Ala His Asp Asp Glu Ser Ala Ala
        115                 120                 125

Tyr Asn Met Val Gly Pro Phe Val Glu Ser Pro Thr Thr Arg Ala
130                 135                 140

Ala Gly Gly Gly Arg Lys Arg Asn Arg Gly Ser Arg Ala Ala Gly Gly
145                 150                 155                 160

Pro Ala His Gly Gly Val Glu Lys Lys Glu Lys Gln Arg Arg Leu Arg
                165                 170                 175

Leu Thr Glu Lys Tyr Thr Ala Leu Met Leu Leu Ile Pro Asn Arg Thr
            180                 185                 190

Lys Glu Asp Arg Ala Thr Val Ile Ser Asp Ala Ile Glu Tyr Ile Gln
        195                 200                 205

Glu Leu Gly Arg Thr Val Glu Glu Leu Thr Leu Leu Val Gly Lys Lys
    210                 215                 220

Arg Arg Arg Asn Gly Ala Gly Glu His His Leu His Gln Gly Asp Val
225                 230                 235                 240

Val Asp Ala Ala Pro Ala Val Gly Ala Ala Gly Glu Leu Val Leu Ala
                245                 250                 255

Ala Glu Ser Ser Glu Gly Glu Val Gln Ala Pro Leu Ala Ala Leu Gln
            260                 265                 270

Pro Ile Arg Ser Thr Tyr Ile Gln Arg Lys Ser Lys Glu Thr Phe Val
        275                 280                 285

Asp Val Arg Ile Val Glu Asp Glu Val Asn Ile Lys Leu Thr Lys Arg
    290                 295                 300

Arg Arg Asp Gly Cys Leu Ala Ala Ser Arg Ala Leu Asp Asp Leu
305                 310                 315                 320

Arg Leu Asp Leu Val His Leu Ser Gly Gly Lys Ile Gly Asp Cys His
                325                 330                 335

Ile Tyr Met Phe Asn Thr Lys Ile His Gln Gly Ser Pro Val Phe Ala
            340                 345                 350

Ser Ala Val Ala Ser Lys Leu Ile Glu Val Val Asp Glu Tyr
        355                 360                 365

<210> SEQ ID NO 227
<211> LENGTH: 379
<212> TYPE: PRT
<213> ORGANISM: Sorghum bicolor

<400> SEQUENCE: 227

Met Tyr His Pro Gln Cys Glu Leu Leu Met Ala His Glu Ala Gln Asp
1               5                   10                  15

Leu Asp Ala Ala Gly Gln Pro His His Leu Ala Val Ser Gly Val Ala

```
            20                  25                  30
Gly Ser Ile Pro Ala Glu Leu Ser Phe His Leu Leu His Ser Leu Asp
        35                  40                  45

Ala Thr Ala Ala Val Asn Asn Ser Val Thr Pro Gln Ser Thr Ile Asp
 50                  55                  60

Tyr Phe Leu Gly Val Gly Ala Asp Pro His Gln Pro Ala Ala Leu
 65                  70                  75                  80

Gln Tyr Glu Pro Leu Pro Pro Gly Gly His His Gln His Thr Met
                 85                  90                  95

Asn Met Leu Arg Asp Tyr Cys Ser Asn Gly Gly Gly His Tyr
                100                 105                 110

Pro Thr Ala Glu Pro Tyr Leu Arg Gly Thr Arg Thr Gly Ala Leu Val
                115                 120                 125

Phe Gly Ala Thr Asp Asp Glu Ser Ala Ala Tyr Met Pro Gly
            130                 135                 140

Gly Pro Phe Val Glu Thr Ser Pro Pro Arg Ala Thr Gly Gly Arg
145                 150                 155                 160

Lys Arg Gly Arg Ala Leu Gly Gly Phe His Ala Gly Leu Ala Asn
                165                 170                 175

Gly Val Glu Lys Lys Glu Lys Gln Arg Arg Gln Arg Leu Thr Glu Lys
                180                 185                 190

Tyr Thr Ala Leu Met His Leu Ile Pro Asn Val Thr Lys Pro Asp Arg
                195                 200                 205

Ala Thr Val Ile Ser Asp Ala Ile Glu Tyr Ile Gln Glu Leu Gly Arg
                210                 215                 220

Thr Val Glu Glu Leu Thr Leu Leu Val Glu Lys Lys Arg Arg Arg Arg
225                 230                 235                 240

Glu Leu Gln Gly Asp Val Val Asp Ala Ala Pro Thr Ala Val Val Val
                245                 250                 255

Ala Ala Ala Ala Thr Gly Gly Glu Ala Glu Ser Ser Glu Gly Glu Val
                260                 265                 270

Ala Pro Pro Pro Pro Pro Ala Ala Val Gln Arg Gln Pro Ile Arg
                275                 280                 285

Ser Thr Tyr Ile Gln Arg Arg Ser Lys Asp Thr Ser Val Asp Val Arg
                290                 295                 300

Ile Val Glu Glu Asp Val Asn Ile Lys Leu Thr Lys Arg Arg Arg Asp
305                 310                 315                 320

Gly Cys Leu Ala Ala Ser Arg Ala Leu Asp Asp Leu Arg Leu Asp
                325                 330                 335

Leu Val His Leu Ser Gly Gly Lys Ile Gly Asp Cys His Ile Tyr Met
                340                 345                 350

Phe Asn Thr Lys Ile His Lys Gly Ser Ser Val Phe Ala Ser Ala Val
                355                 360                 365

Ala Ser Arg Leu Met Glu Val Val Asp Glu Tyr
                370                 375

<210> SEQ ID NO 228
<211> LENGTH: 379
<212> TYPE: PRT
<213> ORGANISM: Oryza sativa

<400> SEQUENCE: 228

Met Tyr His Pro Gln Cys Glu Leu Leu Met Pro Leu Glu Ser Leu Glu
1               5                   10                  15
```

```
Met Asp Val Gly Gln Ser His Leu Ala Ala Val Ala Ala Ala Met
         20                  25                  30

Pro Gly Glu Leu Asn Phe His Leu Leu His Ser Leu Asp Ala Ala
         35                  40                  45

Ala Ala Ala Ser Ser Thr Ala Ala Ser Ala Ser Ser Gln Pro Thr Val
         50                  55                  60

Asp Tyr Phe Phe Gly Gly Ala Asp Gln Gln Pro Pro Pro Ala Ala
65                   70                  75                  80

Met Gln Tyr Asp Gln Leu Ala Ala Pro His His Gln Thr Val Ala
                     85                  90                  95

Met Leu Arg Asp Tyr Tyr Gly Gly His Tyr Pro Pro Ala Ala Ala
                    100                 105                 110

Ala Ala Ala Thr Glu Ala Tyr Phe Arg Gly Gly Pro Arg Thr Ala Gly
             115                 120                 125

Ser Ser Ser Leu Val Phe Gly Pro Ala Asp Asp Glu Ser Ala Phe Met
         130                 135                 140

Val Gly Pro Phe Glu Ser Ser Pro Thr Pro Arg Ser Gly Gly Gly Arg
145                 150                 155                 160

Lys Arg Ser Arg Ala Thr Ala Gly Phe His Gly Gly Gly Pro Ala Asn
                 165                 170                 175

Gly Val Glu Lys Lys Glu Lys Gln Arg Arg Leu Arg Leu Thr Glu Lys
            180                 185                 190

Tyr Asn Ala Leu Met Leu Leu Ile Pro Asn Arg Thr Lys Glu Asp Arg
         195                 200                 205

Ala Thr Val Ile Ser Asp Ala Ile Glu Tyr Ile Gln Glu Leu Gly Arg
     210                 215                 220

Thr Val Glu Glu Leu Thr Leu Leu Val Glu Lys Lys Arg Arg Arg Arg
225                 230                 235                 240

Glu Met Gln Gly Asp Val Asp Ala Ala Thr Ser Ser Val Val Ala
                    245                 250                 255

Gly Met Asp Gln Ala Ala Glu Ser Ser Glu Gly Glu Val Met Ala Ala
                260                 265                 270

Ala Ala Met Gly Ala Val Ala Pro Pro Pro Arg Gln Ala Pro Ile Arg
             275                 280                 285

Ser Thr Tyr Ile Gln Arg Arg Ser Lys Glu Thr Phe Val Asp Val Arg
         290                 295                 300

Ile Val Glu Asp Asp Val Asn Ile Lys Leu Thr Lys Arg Arg Arg Asp
305                 310                 315                 320

Gly Cys Leu Ala Ala Ser Arg Ala Leu Asp Asp Leu Arg Leu Asp
                    325                 330                 335

Leu Val His Leu Ser Gly Gly Lys Ile Gly Asp Cys His Ile Tyr Met
             340                 345                 350

Phe Asn Thr Lys Ile His Ser Gly Ser Pro Val Phe Ala Ser Ala Val
         355                 360                 365

Ala Ser Arg Leu Ile Glu Val Val Asp Glu Tyr
     370                 375

<210> SEQ ID NO 229
<211> LENGTH: 7
<212> TYPE: PRT
<213> ORGANISM: Artificial
<220> FEATURE:
<223> OTHER INFORMATION: Nuclear localization signal from maize Rfr-bHLH

<400> SEQUENCE: 229
```

```
Gly Arg Lys Arg Gly Arg Ala
1               5
```

<210> SEQ ID NO 230
<211> LENGTH: 6
<212> TYPE: PRT
<213> ORGANISM: Artificial
<220> FEATURE:
<223> OTHER INFORMATION: Nuclear localization signal from maize Rf4-bHLH

<400> SEQUENCE: 230

```
Lys Lys Arg Arg Arg Arg
1               5
```

<210> SEQ ID NO 231
<211> LENGTH: 19
<212> TYPE: DNA
<213> ORGANISM: Artificial
<220> FEATURE:
<223> OTHER INFORMATION: bHLH-F primer

<400> SEQUENCE: 231
agtacaccgc cctcatgca                                                19

<210> SEQ ID NO 232
<211> LENGTH: 22
<212> TYPE: DNA
<213> ORGANISM: Artificial
<220> FEATURE:
<223> OTHER INFORMATION: bHLH-R primer

<400> SEQUENCE: 232
ccagctcctg gatgtactcg at                                            22

<210> SEQ ID NO 233
<211> LENGTH: 19
<212> TYPE: DNA
<213> ORGANISM: Artificial
<220> FEATURE:
<223> OTHER INFORMATION: bHLH-probe
<220> FEATURE:
<221> NAME/KEY: misc_feature
<222> LOCATION: (1)..(1)
<223> OTHER INFORMATION: 6FAM label attachment site
<220> FEATURE:
<221> NAME/KEY: misc_feature
<222> LOCATION: (19)..(19)
<223> OTHER INFORMATION: MGBNFQ quencher attachment site

<400> SEQUENCE: 233
acaaagactg atagggcga                                                19

<210> SEQ ID NO 234
<211> LENGTH: 19
<212> TYPE: DNA
<213> ORGANISM: Artificial
<220> FEATURE:
<223> OTHER INFORMATION: INV59F primer

<400> SEQUENCE: 234
cgacgacttg tccgagcag                                                19

<210> SEQ ID NO 235
<211> LENGTH: 15
<212> TYPE: DNA
<213> ORGANISM: Artificial
<220> FEATURE:
<223> OTHER INFORMATION: INV59R primer

<400> SEQUENCE: 235
tgccgtccgt gccct                                                                15

<210> SEQ ID NO 236
<211> LENGTH: 18
<212> TYPE: DNA
<213> ORGANISM: Artificial
<220> FEATURE:
<223> OTHER INFORMATION: INV-probe
<220> FEATURE:
<221> NAME/KEY: misc_feature
<222> LOCATION: (1)..(1)
<223> OTHER INFORMATION: VIC label attachment site
<220> FEATURE:
<221> NAME/KEY: misc_feature
<222> LOCATION: (18)..(18)
<223> OTHER INFORMATION: MGBNFQ quencher attachment site

<400> SEQUENCE: 236
ccgtgtactt ctacctgc                                                             18